US009962436B2

(12) United States Patent
Mond et al.

(10) Patent No.: US 9,962,436 B2
(45) Date of Patent: May 8, 2018

(54) MULTIMERIC FUSION PROTEIN VACCINE AND IMMUNOTHERAPEUTIC

(71) Applicant: The Henry M. Jackson Foundation for the Advancement of Military Medicine, Inc., Bethesda, MD (US)

(72) Inventors: James J Mond, Silver Spring, MD (US); Clifford M. Snapper, Potomac, MD (US); Xinle Cui, Gaithersburg, MD (US)

(73) Assignee: THE HENRY M. JACKSON FOUNDATION FOR THE ADVANCEMENT OF MILITARY MEDICINE, INC., Bethesda, MD (US)

( * ) Notice: Subject to any disclaimer, the term of this patent is extended or adjusted under 35 U.S.C. 154(b) by 320 days.

(21) Appl. No.: 14/416,780

(22) PCT Filed: Jul. 26, 2013

(86) PCT No.: PCT/US2013/052270
§ 371 (c)(1),
(2) Date: Jan. 23, 2015

(87) PCT Pub. No.: WO2014/018858
PCT Pub. Date: Jan. 30, 2014

(65) Prior Publication Data
US 2015/0174237 A1 Jun. 25, 2015

Related U.S. Application Data

(60) Provisional application No. 61/675,948, filed on Jul. 26, 2012.

(51) Int. Cl.
A61K 39/245 (2006.01)
C07K 14/005 (2006.01)
A61K 39/21 (2006.01)
A61K 39/12 (2006.01)
A61K 39/00 (2006.01)

(52) U.S. Cl.
CPC ............ *A61K 39/245* (2013.01); *A61K 39/12* (2013.01); *A61K 39/21* (2013.01); *C07K 14/005* (2013.01); *A61K 2039/53* (2013.01); *A61K 2039/55505* (2013.01); *A61K 2039/55561* (2013.01); *A61K 2039/57* (2013.01); *A61K 2039/70* (2013.01); *C07K 2319/00* (2013.01); *C12N 2710/16234* (2013.01); *C12N 2740/15022* (2013.01); *C12N 2740/15034* (2013.01)

(58) Field of Classification Search
None
See application file for complete search history.

(56) References Cited

U.S. PATENT DOCUMENTS

| 6,432,679 | B1* | 8/2002 | Mond ................. A61K 39/245 424/186.1 |
| 6,749,857 | B1 | 6/2004 | Peters et al. |
| 7,449,188 | B2 | 11/2008 | De Filette et al. |
| 7,541,180 | B2 | 6/2009 | Valiante |
| 7,994,293 | B2 | 8/2011 | Valiante |
| 2005/0003403 | A1* | 1/2005 | Rossi ................. C07K 16/3007 435/6.16 |
| 2008/0260769 | A1 | 10/2008 | Capecchi et al. |
| 2009/0186025 | A1* | 7/2009 | Colaco ................. C07K 14/005 424/134.1 |
| 2010/0098718 | A1 | 4/2010 | Valiante |
| 2011/0293704 | A1* | 12/2011 | Holst ................. A61K 39/0011 424/450 |

FOREIGN PATENT DOCUMENTS

| EP | 1982993 A2 | 10/2008 |
| JP | 2008-263983 A | 11/2008 |
| JP | 2012-509071 A | 4/2012 |
| WO | 2005/014838 | 2/2005 |
| WO | 2010/002818 A2 | 1/2010 |
| WO | 2010/057501 A1 | 5/2010 |
| WO | 01/02440 | 1/2011 |

OTHER PUBLICATIONS

International Search Report dated Dec. 3, 2013 from International Application No. PCT/US2013/052270, pp. 1-12.
De Filette, Marina et al. An Influenza a Vaccine Based on Tetrameric Ectodomain on Matrix Protein 2. The Journal of Biological Chemistry, Apr. 25, 2008, vol. 283, No. 17, pp. 11382-11387.
Fiers, Walter et al. Soluble recombinant influenza vaccines. The Royal Society, Phils. Trans. R. Soc. Land, B (2001) 356, 1961-1963.
Weissenhorn, Winfried et al. Assembly of a rod-shaped chimera of a trimeric GCN4 zipper and the HIV-1 gp41 ectodomain express in *Excherichia coli*. Proc. Natl. Acad. Sci., Jun. 1997, vol. 94, pp. 6065-6069.
Development of a prophylactic vaccine against Epstein-Barr virus (EBV). Uniformed Services University of the Health Sciences, Institute for Vaccine Research, Printed Mar. 27, 2012, pp. 1-5. http://www.usuhs.mil/pat/ivrproject3.html.
(Continued)

Primary Examiner — Agnieszka Boesen
(74) Attorney, Agent, or Firm — MH2 Technology Law Group, LLP

(57) ABSTRACT

The present disclosure provides fusion proteins that incorporate unique mechanisms for multimerizmg antigens to enhance their immunogenicity. The fusion proteins comprise at least two antigens, or other vaccine related proteins, separated by a linker sequence and an oligomerization domain. When expressed, the fusion protein forms a muKimeric protein complex, This approach can be used to muHimeri?.e a single antigen/protein or to create multimers comprising two or more different antigens/proteins. Also provided are nucleic acids encoding the fusion proteins, Yet another aspect is directed to methods of inducing or suppressing an immune response in a subject by administering to the subject a vaccine composition comprising a fusion protein or nucleic acid encoding the fusion protein, optionally without using an adjuvant.

17 Claims, 11 Drawing Sheets

(56) References Cited

OTHER PUBLICATIONS

Supplementary European Search Report dated Mar. 8, 2016 from European Patent Application No. 13823370.5, pp. 1-8.
Cui et al., "A novel tetrameric gp3501-470 as a potential Epstein-Barr virus vaccine", Vaccine, May 9, 2013, vol. 31, No. 30, pp. 3039-3045.
Japanese Office Action dated May 17, 2016 from Japanese Patent Application No. 2015-524466, 6 Pages. (including English translation).
Yang et al., "Highly Stable Trimers Formed by Human Immunodeficiency Virus Type 1 Envelope Glycoproteins Fused with the Trimeric Motif of T4 Bacteriophage Fibritin", Journal of Virology, May 2002, vol. 76, No. 9, pp. 4634-4642.

\* cited by examiner

US 9,962,436 B2

MULTIMERIC FUSION PROTEIN VACCINE AND IMMUNOTHERAPEUTIC

CROSS REFERENCE TO RELATED APPLICATIONS

This patent application is a U.S. National Stage application of PCT/US2013/052270 filed 26 Jul. 2013, which claims priority to U.S. Provisional Application Ser. No. 61/675,948 filed 26 Jul. 2012, the entire disclosures of which are here incorporated herein by reference in their entireties.

GOVERNMENT INTEREST

This invention was made with government support under grant number KM74LJ awarded by the Uniformed Services University and grant number R21AI073627 awarded by the National Institutes of Health. The government has certain rights in this invention.

SEQUENCE LISTING

The instant application contains a Sequence Listing which has been submitted in ASCII format via EFS-Web and is hereby incorporated by reference in its entirety. Said ASCII copy, created on Jul. 25, 2013, is named HMJ-134-PCT-_SL.txt and is 258,258 bytes in size.

BACKGROUND

Induction of humoral or T cell immunity to clinically relevant antigens is often hampered by the weak immunogenicity of these antigens. In order to enhance the immune response, exogenous adjuvants are commonly used. These adjuvants fall into many different categories but they all share the property of stimulating the immune response, in an antigen-nonspecific manner (Schijns, V. E. 2000. Curr. Opin. Immunology 12: 456-463). Thus, their clinical use has been very limited because of the concern of stimulating unwanted inflammatory or autoimmune responses. Many of the newer, more potent adjuvants that stimulate the innate immune system via Toll-like receptors, non-specifically activate macrophages, dendritic cells and other innate immune cells with unwanted pro-inflammatory sequelae (van Duin et al., 2005. Trends Immunol.). Therefore, it would be extremely valuable to devise ways to augment the antigen-specific immune response in the absence of added adjuvants.

Protein aggregates are known to enhance immune responses (Rosenberg, 2006, The AAPS Journal, 8(3):E501-507). For example, protein antigens presented in a highly arrayed structure can induce highly potent antibody responses even in the absence of T helper cells. The mechanism by which protein aggregates mediate such potent antibody responses is not fully understood. However, it is believed that the potency is due, at least in part, to the ability of the multivalent protein to extensively cross link the cell surface immunoglobulins of B cells and activate the B cells.

Several factors can influence a protein aggregate's ability to induce an immune response, including molecular weight and solubility (Rosenberg, 2006, The AAPS Journal, 8(3): E501-507). Lower molecular weight aggregates, such as dimers and trimers generally are not as efficient at inducing immune responses as larger multimers. Multimerization, rather than size, appears to be an important immunogenicity factor because larger sized monomeric proteins are not necessarily more immunogenic than smaller monomeric proteins. In addition, particulate (insoluble) antigens are more rapidly endocytosed by antigen-presenting cells (APCs). The APCs, in turn, process the antigen and present it to T and/or B cells to induce an immune response. Other factors that can influence a protein aggregate's immunogenicity include product origin (foreign versus endogenous), the presence of product contaminants with immunomodulatory activity, the presence of neoepitopes (which may be created with fusion proteins), glycosylation patterns, frequency of administration, route of administration, the host immune status, activity of concomitant immunomodulators, and, for endogenous proteins, the strength of immunologic tolerance to the endogenous protein (Rosenberg, 2006, The AAPS Journal, 8(3):E501-507).

Others have attempted to take advantage of protein aggregation or multimeric targeting strategies in an effort to enhance immune responses. For example, Hultberg et al constructed multimers targeting different epitopes of three different viruses. Llama heavy chain antibody fragments (VHHs) against the trimeric envelope proteins of: 1) Respiratory Syncytial Virus, 2) Rabies virus glycoprotein, and 3) H5N1 Influenza virus were selected from libraries by phage display (Hultberg et al., 2011, PloS ONE 6: e17665). Neutralizing heavy chains recognizing the three different epitopes with affinities in the low nanomolar range were identified for all the three viruses by viral neutralization assays. By fusion with variable linker lengths, multimeric constructs were made that improved neutralization potencies up to 4,000-fold for RSV, 1,500-fold for Rabies virus and 75-fold for influenza H5N1. The multimeric VHH constructs had increased neutralization activity and cross protection potency as compared to their monovalent counterparts, thus demonstrating that multimeric targeting strategies can enhance the potency of anti-viral molecules.

U.S. Pat. No. 6,749,857 describes a fusion protein with a single copy of a truncated flavivirus 80% E protein and a leucine zipper domain fused to the C terminus of the 80% E protein. When expressed in cells, the fusion proteins oligomerize to form a homodimeric polypeptide complex that mimics the homodimeric structure of the naturally occurring flavivirus 80% E protein. This approach was designed to increase the immune potency of the fusion protein by increasing the structural similarity to the native 80% E protein and by increasing the size and antigenic complexity of the immunogen. While the fusion proteins of U.S. Pat. No. 6,749,857 were designed in part to increase the antigenic complexity of the immunogen, the complexity of the construct was limited by a desire to mimic the structure of the native 80% protein. As such, the fusion protein constructs of U.S. Pat. No. 6,749,857 contained only a single copy of the 80% protein and the resulting polypeptide complex formed by the oligomerization of two fusion proteins contained only two copies of the 80% protein, limiting the size of the multimeric antigens formed through this strategy.

Even though protein aggregates are known to enhance immune responses, simple approaches to multimerize proteins in a defined and cost-effective manner for vaccine use, with direct validation of a resultant increase in immunogenicity, have been limited.

Other multi-component constructs have been designed to enhance immune responses by bringing two cells of interest into close proximity. For example, activation of T cells requires two signals. The first signal is initiated by T cell receptor binding to antigenic peptide presented by MHC molecules on antigen presenting cells (APC). The second, costimulatory signal, is mediated via CD28 on the T cell, upon binding to CD80 or CD86 on the APC. To selectively localize costimulatory activity to the surface of tumor cells and enhance activation of tumor-specific T cells, Asano et al. developed bi-specific costimulatory proteins with antibody-like structure (Asano et al., 2008. *J. Immunother.* 31: 752-761). Specifically, within a single polypeptide chain they assembled the IgV-like, CD28-binding domain of human CD86 together with hinge, CH2 and CH3 domains of human IgG1, and the scFv antibody fragment which recognizes the ErbB2 protooncogene present at high levels on the surface of many human tumor cells. Their results suggest that such multivalent soluble proteins which combine specific targeting to tumor cells with co-stimulatory activity may become useful tools to elicit and/or improve T-cell mediated, tumor-specific immune responses.

Another multi-component vaccine approach was designed to bring two different cell types into close proximity using a construct with components that allow simultaneous targeting of both cells (Asano et al., 2008. *J. Immunother.* 31: 752-761). Asano et al. produced a recombinant bi-specific antibody that co-targeted epidermal growth factor receptor on tumor cells and CD3 on T cells. The bi-specific and bi-valent IgG-like antibodies showed stronger binding to each target cell than did the monovalent diabody. The bi-specific construct mediated tumor cell cytotoxicity that was 10 times that of the monovalent constructs. Further the Fc portion of the bi-specific construct further enhanced cytotoxicity via binding to Fc receptors on blood mononuclear cells for antibody-dependent cytotoxicity (ADCC). The growth-inhibition effects of this construct were superior to the approved therapeutic antibody cetuximab, which recognizes the same epidermal growth factor receptor antigen.

Miyata et al developed a multi-component vaccine strategy to enhance immune responses by creating genetic fusion proteins to target the antigen to specific APCs (Miyata et al., 2011, *Infect. Immun.* 79: 4260-4275). The fusion complex was composed of three physically linked molecular entities: 1) a vaccine antigen, 2) a multimeric α-helical coiled-coil core, and 3) an APC-targeting ligand linked to the core via a flexible linker. Immunization of mice with the tri-component complex as compared to the antigen only, induced an enhanced antibody response that conferred increased protection against lethal *Plasmodium yoelii* infection.

New and improved constructs for enhancing immune responses are needed, particularly constructs that can be used to enhance immune responses in the absence of added adjuvant.

SUMMARY

The present disclosure provides new and improved strategies for enhancing an immune response. These improved strategies involve fusion proteins that incorporate unique mechanisms for multimerizing antigens to enhance their immunogenicity. One mechanism for multimerizing antigens is using a linker sequence to separate two antigens in the fusion protein. Without intending to be bound by any theory, it is believed that such a linker sequence can allow the two antigens, whether they be the same or different, to undergo conformational folding and form a dimer or higher order multimer. Another mechanism for multimerizing antigens is using an oligomerization domain, such as a leucine zipper dimerization domain, a T4 bacteriophage fibritin motif trimerization domain, or a tetramerization domain. Combined with the linker sequence, the oligomerization domain permits the further multimerization of an antigen (e.g., tetramer, hexamer, octamer, etc). This approach can be used to multimerize a single antigen or to create multimers comprising two or more different antigens.

This multimerization strategy can also be used to multimerize two or more proteins of interest, such as two or more vaccine-related proteins. Thus, another aspect is directed to a fusion protein comprising a first protein, a linker sequence, a second protein, and an oligomerization domain, where the linker sequence joins the first protein to the second protein and wherein the first and second proteins are vaccine related proteins or peptides, such as a vaccine target protein, an adjuvanting protein, a cell surface targeting domain, a molecule that mediates immune suppression, or a cell surface target domain that binds to an activated cell.

Another aspect is an isolated nucleic acid encoding the fusion protein or oligomerized fusion protein. Yet another aspect is directed to methods of inducing an immune response in a subject by administering to the subject a vaccine composition comprising a fusion protein or nucleic acid encoding the fusion protein, where the fusion protein induces an immune response in the subject. In certain embodiments, the vaccine composition is used to induce an immune response in the subject without using an adjuvant.

BRIEF DESCRIPTION OF THE DRAWINGS

The accompanying drawings, which are incorporated in and constitute a part of this specification, illustrate certain embodiments, and together with the written description, serve to explain certain principles of the constructs and methods disclosed herein.

Serum titers of gp350-specific IgG were determined by ELISA. *Significance, p≤0.05.

Figure 3A:
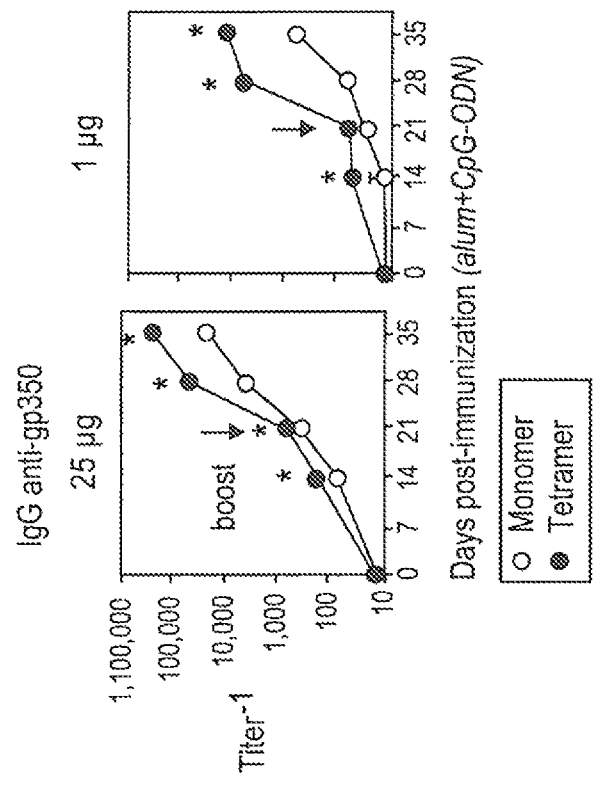
FIG. 3 shows that tetrameric gp350 is markedly more immunogenic than monomeric gp350 protein whether administered in saline or with an adjuvant. DNA vaccination of these constructs also induced heightened immune responses. Mice (5 per group) were immunized i.p. with the indicated doses per mouse, of monomeric or tetrameric gp350 in (FIG. 3A) alum or (FIG. 3B) alum+CpG-ODN, and boosted in a similar manner on day 21. Mice (7 per group) were immunized in the abdominal skin with two tandem deliveries of 0.5 mg 1-3 µm-diameter gold particles coated with 1.0 µg DNA vaccine for a total dose of 4.0 µg DNA. Mice were boosted in a similar manner on week 4. Serum titers of gp350-specific IgG were determined by ELISA at the indicated times (FIG. 3C). Sera from tetramer-immunized mice: "A" and "B" (day 35, 25 µg dose) and "C" (week 6) were analyzed for serum titers of IgG isotypes (FIG. 3D). *Significance, p≤0.05 between tetramer and monomer.
Figure 5:
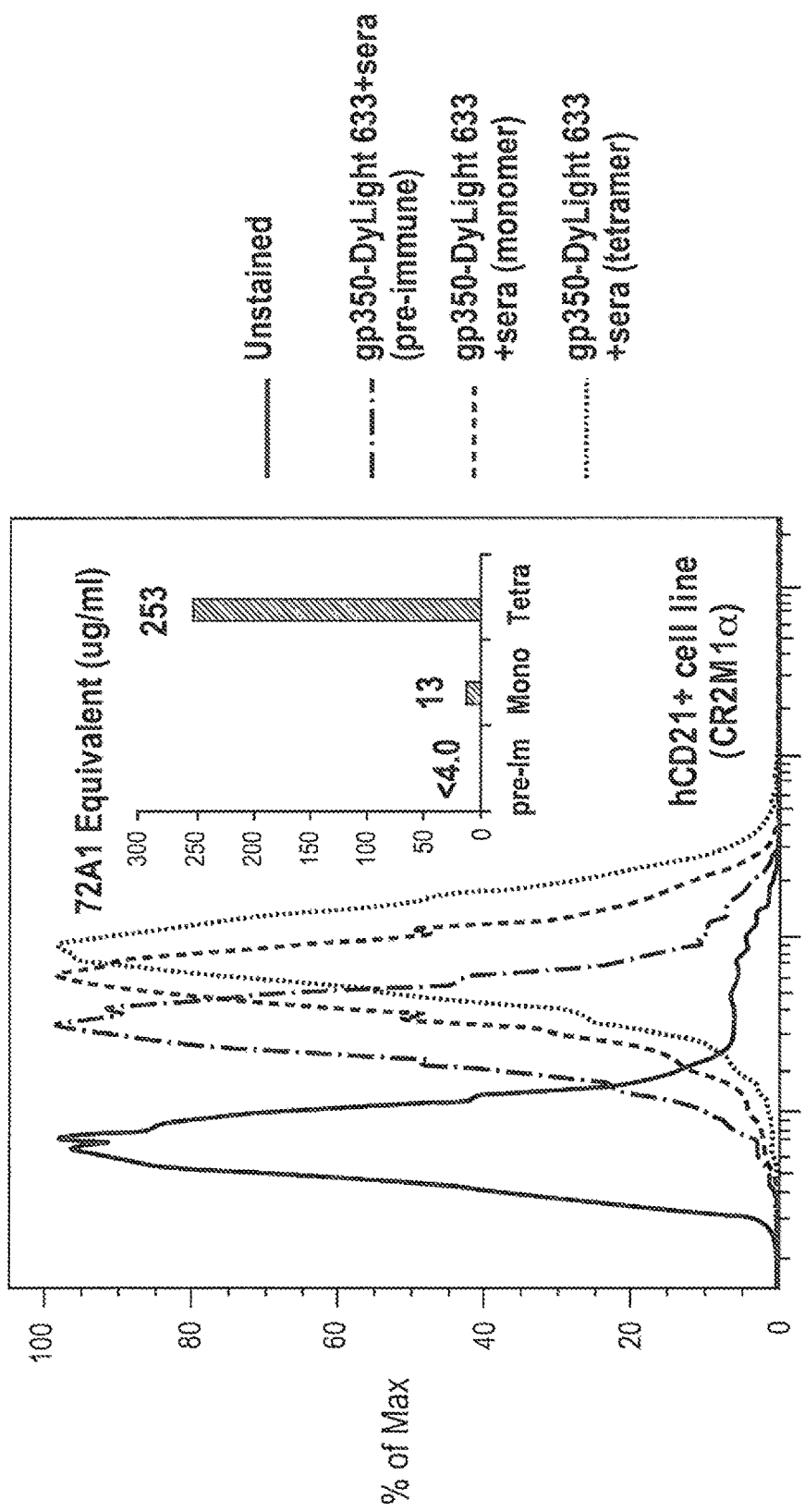

FIG. 5 shows that immunization of mice with tetrameric gp350 protein induces markedly higher levels of neutralizing gp350-specific antibodies relative to monomer. 25 µl of pooled mouse serum (5 mice each) from naïve or immunized mice (day 35, 25 µg monomeric or tetrameric gp350/mouse in alum, see FIG. 3A), were incubated with 2.5 µl of DyLight 633-labeled gp350 monomer. CR2M1α cells were then stained with these mixtures and analyzed by flow cytometry. Various concentrations of 72A1 mAb (neutralizing gp350-specific IgG) were used instead of serum to create a standard curved for quantitation.

Figures 6A, 6B:
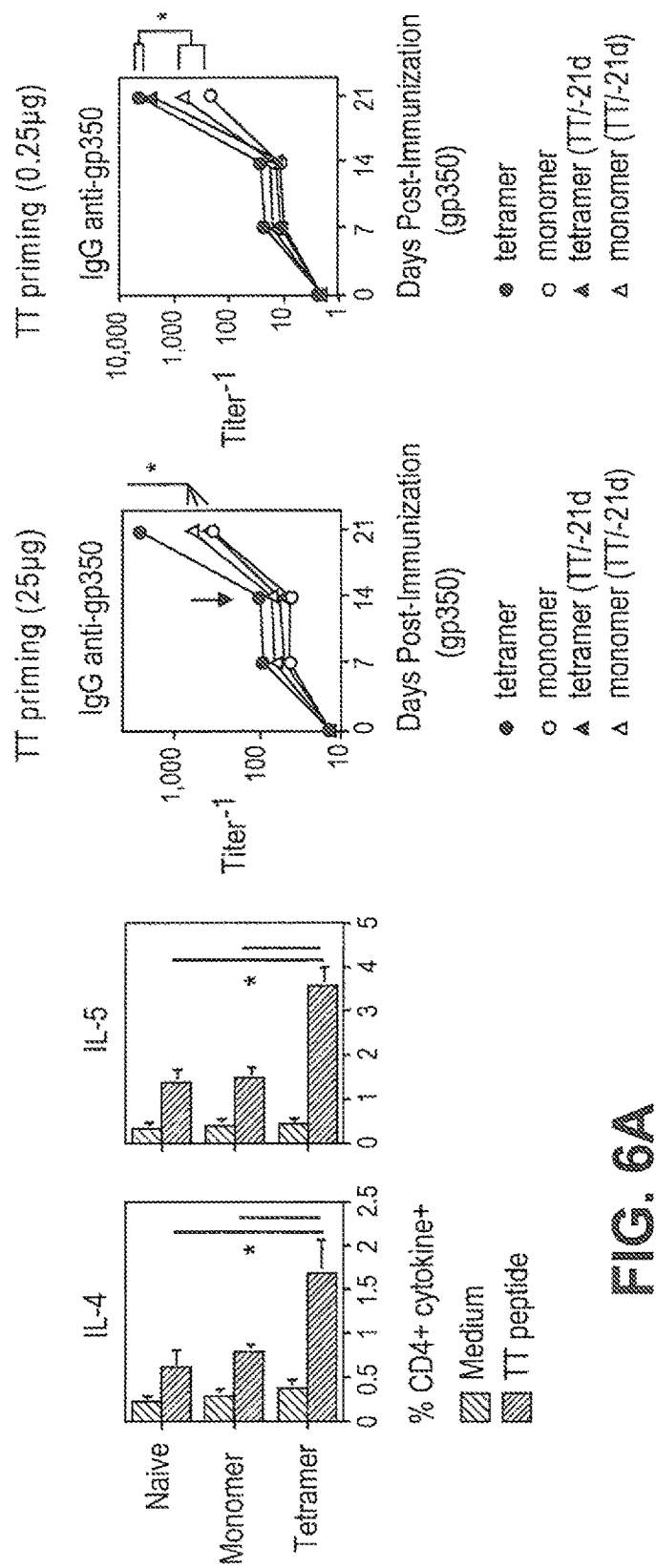

FIGS. 6A-B show that priming with TT protein inhibited the gp350-specific IgG response to tetrameric, but not monomeric gp350. For FIG. 6A, mice (5 per group) were immunized with 25 µg/mouse of monomeric or tetrameric gp350 in alum. Spleen cells were harvested from each mouse on day 21 and separately cultured for 5 h in medium containing 10 U/ml mIL-2+/−5 µg/ml of $P_2$ and $P_{30}$ TT-specific peptides. Golgi Stop was added 1 h after initiation of culture. Cells were then stained for cytoplasmic IL-4 or IL-5 and analyzed by flow cytometry. The percentage of gated CD4+ cells staining positively for each cytokine is illustrated in FIG. 6A. *Significance, p≤0.05. For FIG. 6B, Mice (5 per group) were immunized with 25 µg/mouse or 0.25 µg/mouse of whole TT in alum for 14 days. Mice were then challenged with 25 µg of tetrameric or monomeric gp350 in alum and similarly boosted 14 days later. Serum titers of gp350-specific IgG were determined by ELISA. *Significance, p≤0.05.

Figures 7A, 7B, 7C:
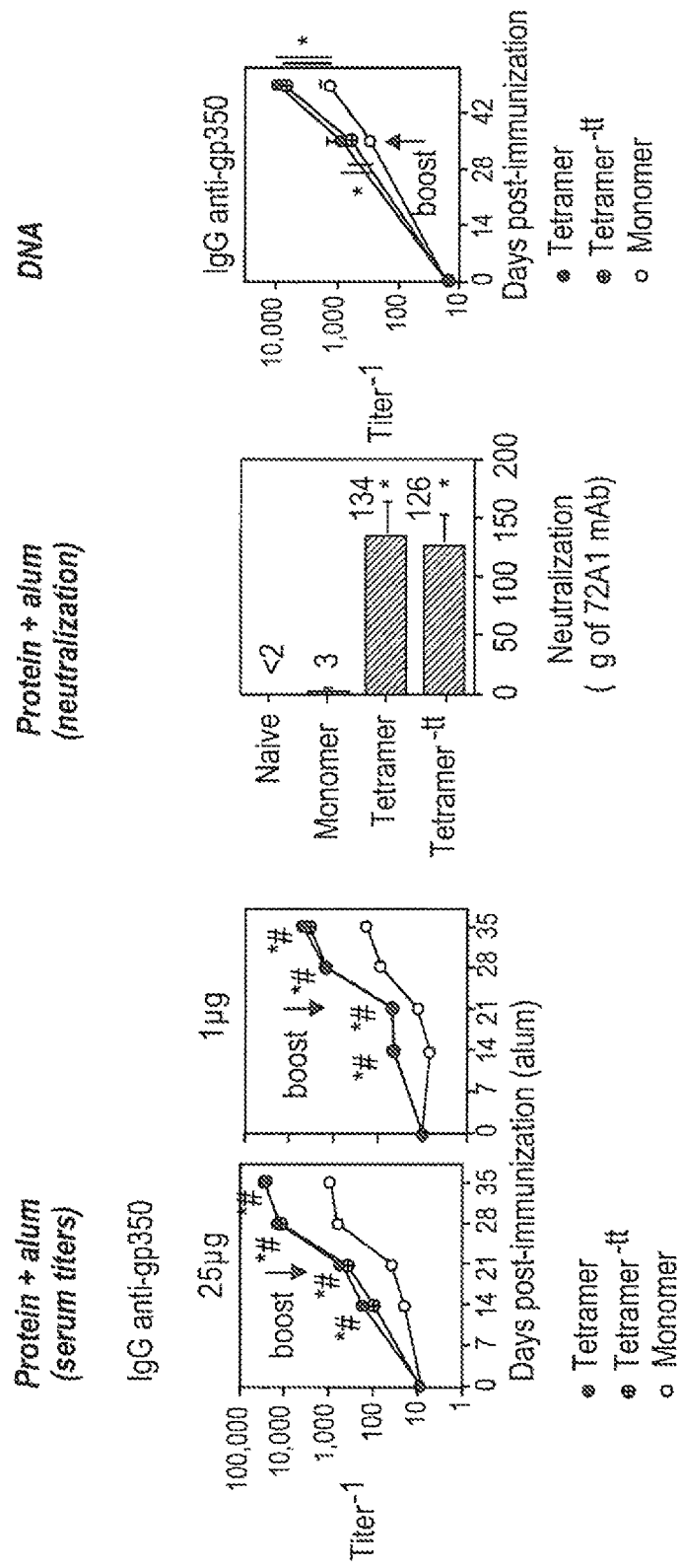

FIG. 7 shows that the TT-specific T cell epitopes in tetrameric gp350 do not contribute to the gp350-specific IgG response in naïve mice. In FIG. 7A, mice (5 per group) were immunized with monomeric gp350 protein, tetrameric gp350 containing TT epitopes ("tetramer"), or tetrameric gp350 without TT epitopes ("tetramer$^{-tt}$") at either 25 µg or 1.0 µg per mouse in alum, and boosted in a similar manner on day 21. Serum titers of gp350-specific were measured by ELISA (FIG. 7A). *Significance, p≤0.05 between tetramer and monomer; #Significance, p≤0.05 between tetramer$^{-tt}$ and monomer. FIG. 7B shows gp350-specific neutralization titers of sera from "A" (25 µg/mouse, day 35 as described in FIG. 5); *Significance, p≤0.05 between tetramer or tetramer$^{-tt}$ versus monomer. FIG. 7C shows DNA immunization with plasmids encoding monomer, tetramer, and tetramer-$^{tt}$ as described in FIG. 3C; *Significance, p≤0.05 between tetramer or tetramer$^{-tt}$ versus monomer.

Figure 8:
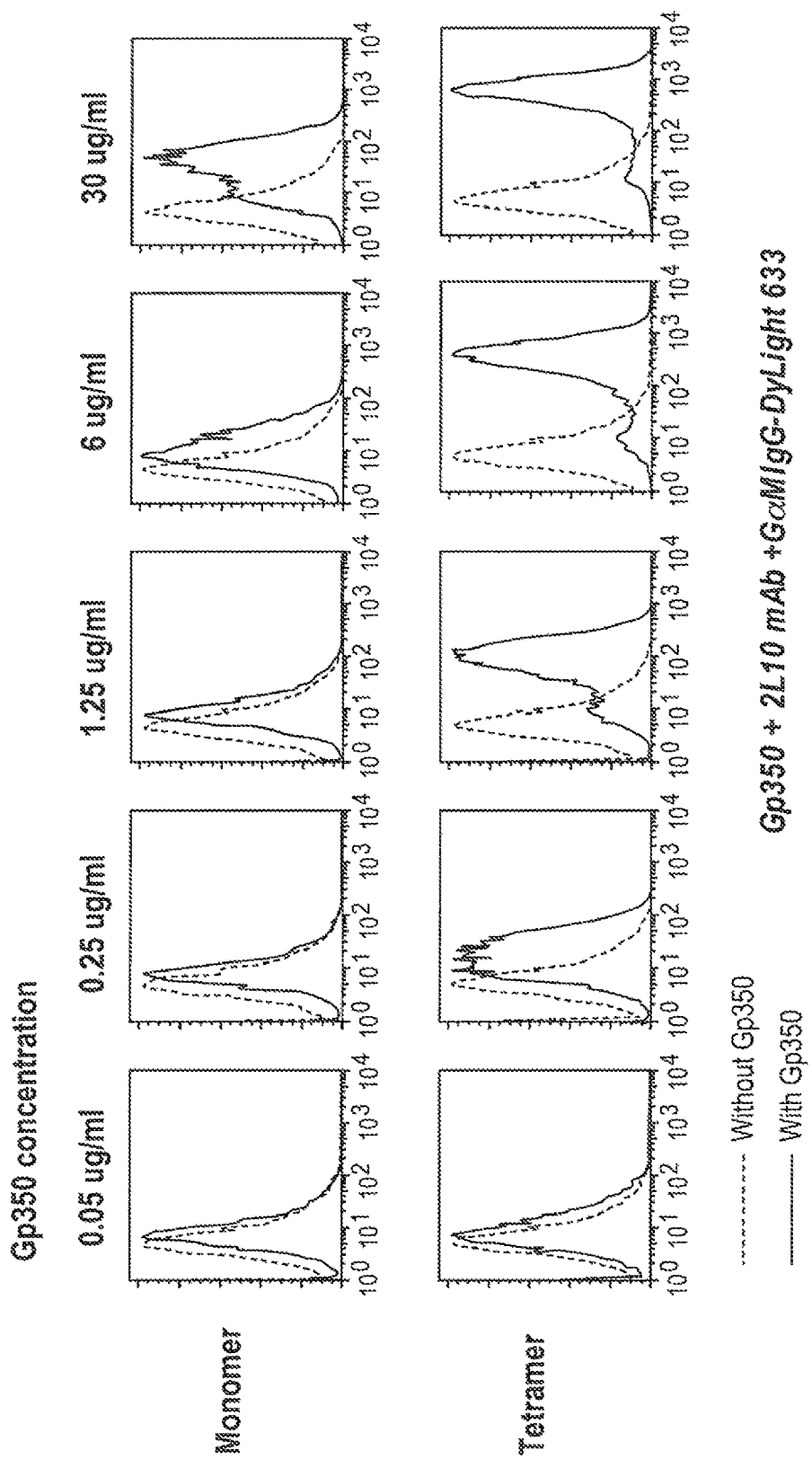

FIG. 8 shows that the tetrameric gp350 binds more avidly to human CD21 than monomer. CR2M1α cells were incubated for 30 min on ice with gp350 monomer or tetramer (0.05-30 µg/ml), washed, then incubated further with 2L10 mAb (mouse IgG1 anti-gp350 mAb) for 30 min. Cells were then washed, followed by staining with DyLight 633-labeled goat anti-mouse IgG. Cells were analyzed by flow cytometry. Broken line: CR2M1α cells without gp350; solid line: with gp350.

Figure 9:
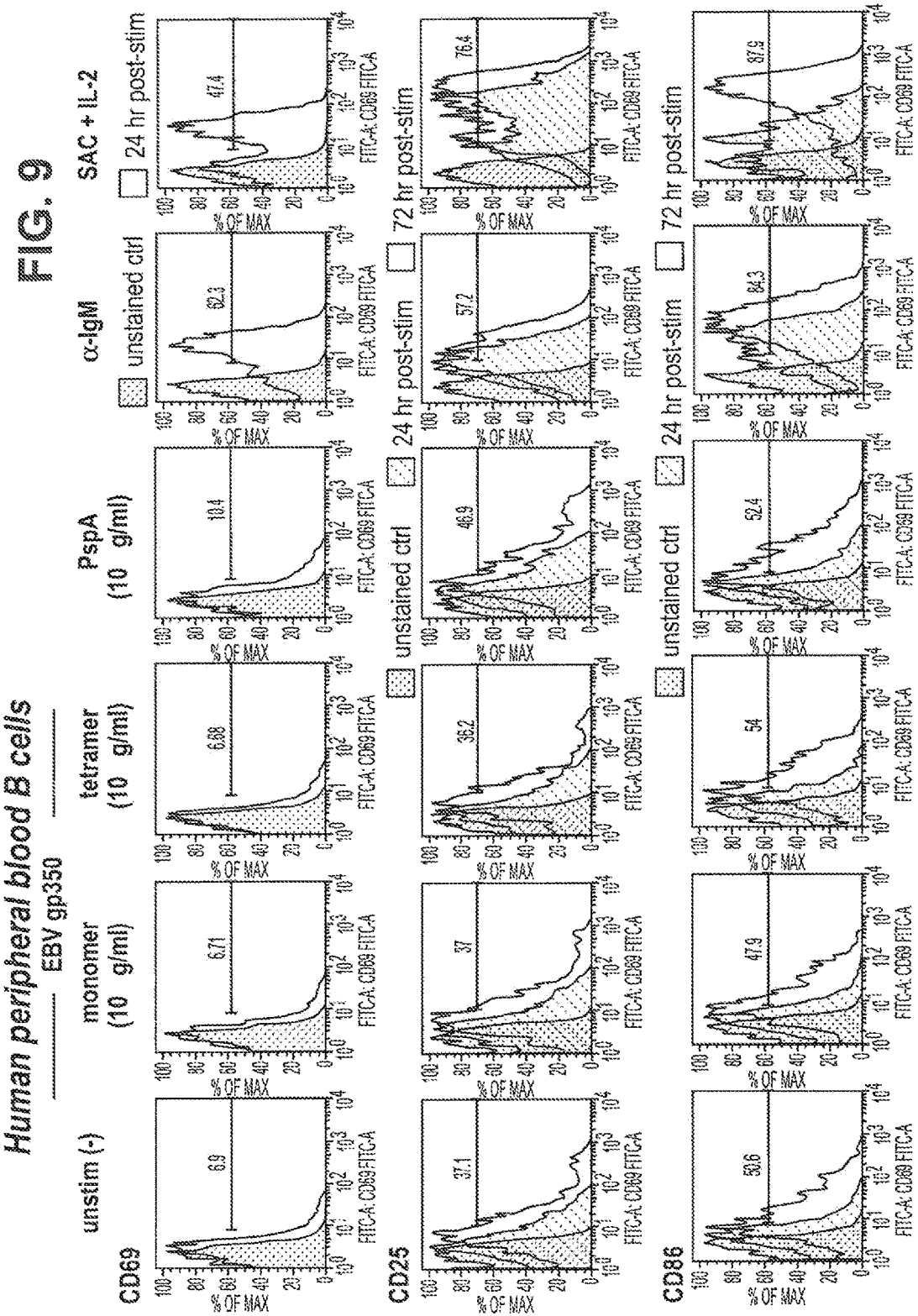

FIG. 9 shows that neither monomeric nor tetrameric gp350 polyclonally activates human B cells. Purified peripheral blood human B cells were cultured for 24 or 72 h with monomeric or tetrameric gp350 (10 µg/ml) recombinant PspA (10 µg/ml), goat anti-human IgM F(ab')$_2$ (20 µg/ml), or (SAC, 1:100 dilution)+recombinant human IL-2 (200 IU/ml). Cells were then stained with PE-conjugated anti-CD69 mAb (24 h post-stimulation) or PE-conjugated anti-CD25 mAb+FITC-conjugated anti-CD86 mAb (72 h post-stimulation) and analyzed by flow cytometry.

Figure 10:
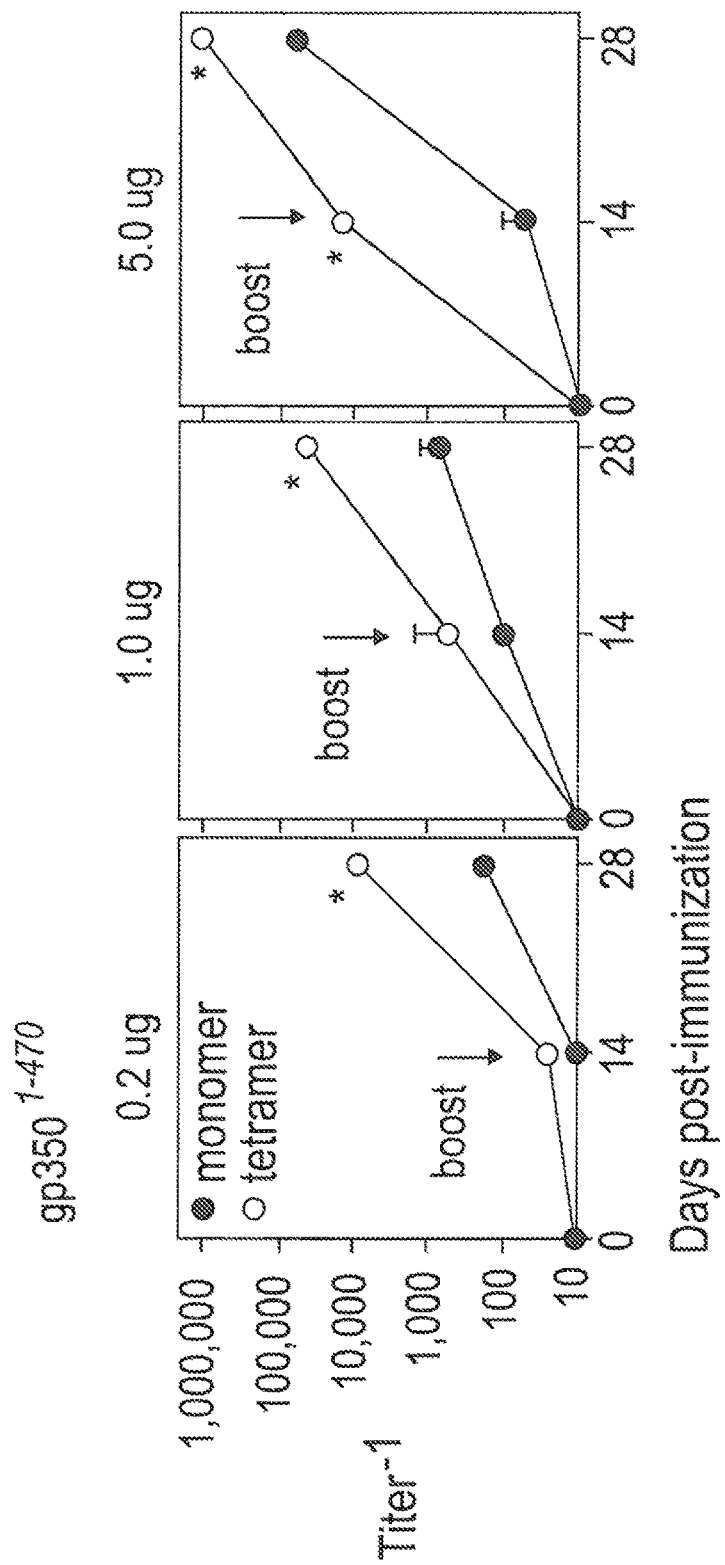

FIG. 10 shows that immunization of rabbits with tetrameric gp350 protein (0.2 µg, 1.0 µg, or 5.0 µg) induces markedly higher levels of neutralizing gp350-specific antibodies relative to monomer.

DETAILED DESCRIPTION

It is to be understood that the following detailed description is provided to give the reader a fuller understanding of certain embodiments, features, and details of aspects of the invention, and should not be interpreted as a limitation of the scope of the invention.

Definitions

In order that the present invention may be more readily understood, certain terms are first defined. Additional definitions are set forth throughout the detailed description.

The term "antibody" as used in this disclosure refers to an immunoglobulin or an antigen-binding fragment thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including; $IgG_1$, $IgG_2$, $IgG_3$, $IgG_4$, IgM, $IgA_1$, $IgA_2$, IgD, and IgE. By way of example, the light chain constant region can be kappa or lambda.

The terms "antigen-binding domain" and "antigen-binding fragment" refer to a part of an antibody molecule that comprises amino acids responsible for the specific binding between the antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant." Antigen-binding domains and antigen-binding fragments include Fab (Fragment antigen-binding); a F(ab')$_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) Proc. Natl. Acad. Sci. USA 85:5879-5883); a Fd fragment having the two $V_H$ and $C_H1$ domains; dAb (Ward et al., (1989) *Nature* 341:544-546), and other antibody fragments that retain antigen-binding function. The Fab fragment has $V_H$-$C_H$1 and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a sc$F_v$ can be constructed. The sc$F_v$ contains a flexible polypeptide that links (1) the C-terminus of $V_H$ to the N-terminus of $V_L$, or (2) the C-terminus of $V_L$ to the N-terminus of $V_H$. A 15-mer (Gly$_4$Ser)$_3$ peptide (SEQ ID NO:3) may be used as a linker, but other linkers are known in the art. These antibody fragments are obtained using conventional techniques known to those with skill in the art, and the fragments are evaluated for function in the same manner as are intact antibodies.

The term "fusion protein" refers to a protein translated from a nucleic acid transcript generated by combining a first nucleic acid sequence that encodes a first protein and at least a second nucleic acid that encodes a second protein, where the fusion protein is not a naturally occurring protein. The nucleic acid construct may encode two or more proteins that are joined in the fusion protein.

The term "adjuvanting protein" refers to a protein that enhances the immune system's response to an antigen. An adjuvanting protein may accelerate, prolong, or enhance antigen-specific immune responses when used in combination with specific antigens. Exemplary adjuvanting proteins include, but are not limited to, flagellin, a heat shock protein, a toll like receptor ligand, or fragments or derivatives thereof that retain the adjuvanting property.

The term "cell surface targeting domain" refers to any moiety that will direct an antigen, vaccine, or specific cell to another specific cell type by binding to a specific cell surface receptor. Exemplary cell surface targeting domains, include, but not limited to, an antibody, or antigen-binding fragment thereof.

The term "cellular activation domain" refers to any moiety that can either specifically or non-specifically bind to a cell and induce cellular activation. Exemplary cellular activation domains include, but are not limited to, CD40 on B cells and CD28 on T cells.

The term "molecule mediating immune suppression" or "molecule that mediates immune suppression" refers to a molecule that upon binding to a cell induces suppression of cellular activation at any stage of activation including for example proliferation, differentiation, or secretion. Exemplary molecules that mediate immune suppression include, but are not limited to, B-7, CTLA-4, PD-1, Lag-3, Tim-3, CD200:CD200R, 2B4, CD160, PIR-B, BTLA, and GP49b.

The term "pharmaceutically acceptable carrier" or "pharmaceutically acceptable excipient" means solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art.

The term "isolated," when used in the context of a polypeptide or nucleic acid refers to a polypeptide or nucleic acid that is substantially free of its natural environment and is thus distinguishable from a polypeptide or nucleic acid that might happen to occur naturally. For instance, an isolated polypeptide or nucleic acid is substantially free of cellular material or other polypeptides or nucleic acids from the cell or tissue source from which it was derived. The term also refers to preparations where the isolated polypeptide or nucleic acid is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The terms "polypeptide," "peptide," and "protein" are used interchangeably herein to refer to polymers of amino acids.

Fusion Proteins.

The present disclosure relates to a new strategy for multimerizing protein antigens in vaccine-related or other immunotherapeutic constructs. The strategy involves creating nucleic acid constructs with oligomerization motifs and a linker sequence separating two of more antigens such that the encoded fusion protein can form a dimeric, trimeric, tetrameric, hexameric, heptameric, or octameric complex from a single nucleic acid construct. This strategy was tested first with a nucleic acid construct encoding two copies of a truncated EBV gp350 protein separated by a linker and a leucine zipper oligomerization domain. To enhance the immunogenicity of the construct, two potent T cell epitopes derived from the tetanus toxoid were included because it was believed that they would be necessary to recruit sufficient T cell help. With the leucine zipper domain, this construct formed a tetrameric gp350 complex when expressed. Compared to the traditional monomeric gp350, the tetramer showed an approximately 25-50-fold higher immunogenicity for specific antibody production both in the presence of weak and strong exogenous adjuvants. Surprisingly, however, the tetramer containing the tetanus toxoid T cell epitopes actually induced immune suppression in animals previously immunized with tetanus toxoid, a potential problem if used clinically. Based on these results, another nucleic acid construct was prepared without the tetanus toxoid epitopes. This construct encoded two copies of the truncated EBV gp350 protein separated by a linker and a leucine zipper oligomerization domain. The construct without the tetanus toxoid epitopes induced gp350-specific antibody responses that were comparable to the antibody responses induced by the construct containing the tetanus toxoid epitopes, unexpectedly showing that the tetanus toxoid epitopes were not required to achieve optimal immunogenicity in unprimed animals and in fact could be suppressive.

This strategy for multimerizing proteins can be exploited with proteins other than EBV gp350/220 proteins, including other viral, bacterial, parasitic, autoimmune, and tumor antigens. This platform can be used to create multimeric fusion proteins comprising multiple copies of a single antigen of interest, like an EBV gp350/220 antigen. For example, a homodimer, homotrimer or tetramer can be created using two, three, or four copies of the same antigen with a dimerization, trimerization or tetramerization domain. When the oligomerization domains associate together, the construct will form a tetramer (if a dimerization domain is used) comprising four copies of the same antigen, a hexamer (if a trimerization domain is used) comprising six copies of the same antigen, or an octamer comprising eight copies of the same antigen (if a tetramerization domain is used).

Alternatively, this platform can be used to create multimeric fusion proteins comprising two or more different antigens of interest. For example, a heterodimer can be created with a first antigen linked to a second different, antigen (or a heterotrimer comprising two or three different antigens). When the oligomerization domains associate together, the construct will form a tetramer (if a dimerization domain is used) that is dimeric for both the first and second antigen, a hexamer (if a trimerization domain is used in the construct) that is dimeric for at least the first and second antigen or trimeric for the first, second, and third antigen, or an octamer (if a tetramerization domain is used). Alternatively a trimeric protein can be formed if the original protein is presented in monomeric form in association with the trimerization domain.

One aspect is directed to a fusion protein comprising a first antigen, a linker sequence, a second antigen, and an oligomerization domain, wherein the linker sequence joins the first antigen to the second antigen and wherein the fusion protein does not include a tetanus toxoid protein. In one embodiment, the first and second antigens are the same. In another embodiment, the first and second antigens are different. The first and second antigens can be viral antigens, bacterial antigens, parasite antigens, autoimmune antigens, or tumor antigens. In one embodiment, the first and second antigens comprise a polypeptide and/or a polysaccharide. In one embodiment, the fusion protein forms a multimeric protein when expressed in a host cell. In another embodiment, the first, second, and third antigens do not occur naturally as a multimeric protein.

The fusion protein may optionally further comprise a third protein and a second linker sequence, where the second linker sequence joins the second antigen to the third antigen, the first antigen, or the oligomerization domain. In other embodiments, the fusion protein comprises four or more proteins and additional linkers. In one embodiment, the fusion protein forms a multimeric protein when expressed in a host cell. In another embodiment, the first and second antigens do not occur naturally as a multimeric protein.

In certain embodiments, the oligomerization domain is a dimerization domain. In other embodiments, the oligomerization domain is a trimerization or tetrameric domain. In one embodiment, the dimerization domain is a leucine zipper domain, including but not limited to a yeast GCN4 leucine zipper domain or a derivative thereof. In another embodiment, the trimerization domain is a T4 bacteriophage fibritin motif or a eukaryotic GNC4 transcription factor motif or a derivative thereof. In other embodiments, the tetrameric domain is a modified eukaryotic GCN4 transcription factor motif or a derivative thereof. In embodiments with two antigens, the oligomerization domain can be located at the N terminus of the fusion protein before the first antigen, at the C terminus of the fusion protein after the second antigen, or between the first and second antigens. In embodiments where the fusion protein further comprises a third protein, the oligomerization domain can be located at the N terminus of the fusion protein before the first antigen, at the C terminus of the fusion protein after the third antigen, between the first and second antigens, or between the second antigen and the third protein. In embodiments where the fusion protein comprises four or more proteins, the oligomerization domain can be located at the N terminus of the fusion protein before the first antigen, at the C terminus of the fusion protein after the last antigen, or between any antigens in the fusion protein.

In one embodiment, the first and second antigen is an EBV antigen, including, but not limited to, a gp350/220 antigen, gH, gL, gB, or gp42. In one embodiment, the fusion protein comprises a homodimer or homotrimer of EBV gp350/220, gH, gL, gB, or gp42. In another embodiment, the fusion protein comprises a heterodimer or heterotrimer of EBV antigens selected from gp350/220, gH, gL, gB, or gp42, such as a heterodimer of gH and gL, gB and gp42, gp350/220 and gB, gp350/220 and gp42, or a heterotrimer of gH, gL, and gB; gH, gL, and gp42; gp350/220, gH, and gL; or gp350/220, gB and gp42.

In another embodiment, the first and second antigen is a CMV antigen, including, but not limited to gB, gL, gH, or pp65. In yet another embodiment, the first antigen is an EBV antigen, including, but not limited to a gp350/220 antigen, and the second antigen is a CMV antigen, including, but not limited to gB, gL, gH, or pp65. In one embodiment, the fusion protein comprises a homodimer or homotrimer of gB, gL, gH, or pp65. In another embodiment, the fusion protein comprises a heterodimer or heterotrimer of CMV antigens selected from gB, gL, gH, and pp65, such as a heterodimer of gB and gL, gB and gH, gB and pp65, gL and gH, gL and pp65, or gH and pp65 or a heterotrimer of gB, gL, and gH, gB, gL, and pp65, gB, gH, and pp65, or gL, gH, and pp65.

In yet another embodiment, the first antigen is an EBV antigen, including, but not limited to a gp350/220 antigen, gH, gL, gB, or gp42, and the second antigen is a CMV antigen, including, but not limited to gB, gL, gH, or pp65. In one embodiment, the first antigen is a gp350/220 antigen and the second antigen is a CMV gB, gL, gH, or pp65.

In another embodiment, the first antigen is an EBV antigen, including, but not limited to a gp350/220 antigen, gH, gL, gB, or gp42, and the second antigen is an HIV antigen, including, but not limited to, Env (envelope protein, including, but not limited to gp160, gp140, gp120, and gp41gp140, gp120, or gp41), Gag (capsid protein), Pol (polymerase protein), Tat, Vif, Vpu, Vpr, Rev and Nef. Of course, these specific viral antigens are exemplary. In one embodiment, the first antigen is a gp350/220 antigen and the second antigen is an HIV Env (envelope protein, including, but not limited to gp160, gp140, gp120, and gp41gp140, gp120, or gp41), Gag (capsid protein), Pol (polymerase protein), Tat, Vif, Vpu, Vpr, Rev, or Nef. Given the disclosure of this application, one of skill in the art could substitute any antigen of interest into the fusion protein constructs described herein. Additional viral, bacterial, parasitic, autoimmune, and tumor antigens are discussed in more detail in other sections of the application.

Another aspect is directed to a fusion protein comprising a first protein, a linker sequence, a second protein, and an oligomerization domain, wherein the linker sequence joins the first protein to the second protein and wherein the first and second proteins are vaccine related proteins, such as a vaccine target protein, an adjuvanting protein, a cell surface targeting domain, a molecule that mediates immune suppression, or a cellular activating domain.

In one embodiment the fusion protein comprises a first protein, a linker sequence, a second protein, and an oligomerization domain, wherein the linker sequence joins the first protein to the second protein and wherein the first protein is a viral, bacterial, parasitic, autoimmune, tumor antigen, or other protein antigen and the second protein is an adjuvanting protein or comprises a cell surface targeting domain. In certain embodiments, the second protein is an adjuvanting protein, such as flagellin or a heat shock protein, or a toll like receptor (TLR) ligand. In certain embodiments, the cell surface targeting domain is specific for an antigen presenting cell, including, but not limited to a macrophage, a dendritic cell, or a B lymphocyte. In another embodiment, the first protein is a viral, bacterial, parasitic, autoimmune, or tumor antigen, the second protein comprises a cell surface targeting domain, and the fusion protein further comprises a third protein, wherein the third protein comprises a cellular activating domain. In this way, the fusion protein could be used to simultaneously target an antigen to a specific cell and activate the specific cell.

In another embodiment, the fusion protein comprises a first protein, a linker sequence, a second protein, and an oligomerization domain, wherein the linker sequence joins the first protein to the second protein and wherein the first protein comprises a first cell surface targeting domain and the second protein comprises a second cell surface targeting domain, wherein the first and second cell surface targeting domains target different cells. In this way, the fusion protein could be used to bring different types of cells into close proximity to each other, such as a natural killer cell or cytotoxic T lymphocyte and a tumor cell. In one embodiment, the first cell surface targeting domain binds to a ligand on a natural killer cell.

In another embodiment, the fusion protein comprises a first protein, a linker sequence, a second protein, and an oligomerization domain, wherein the linker sequence joins the first protein to the second protein and wherein the first protein is a molecule that mediates immune suppression and the second protein is a cell surface target domain that binds to an activated cell. In one embodiment, the molecule that mediates immune suppression binds to the Fc receptor of an antibody (e.g., Fc gamma receptor, Fc alpha receptor, or Fc epsilon receptor) and the cell surface target domain that binds to an activated cell binds to a ligand on a mast cell. In one embodiment, the Fc receptor is an Fc gamma receptor. In this way, the fusion protein construct could be used to suppress the activation of specific cells, for example, during an allergic reaction.

In yet another embodiment, the fusion protein comprises a first protein, a linker sequence, a second protein, and an oligomerization domain, wherein the linker sequence joins the first protein to the second protein and wherein the first and second proteins are HIV proteins. In one embodiment, the first and second proteins are selected from Env (envelope protein, including, but not limited to gp160, gp140, gp120, and gp41gp140, gp120, or gp41), Gag (capsid protein), Pol (polymerase protein), Tat, Vif, Vpu, Vpr, Rev and Nef. In one embodiment, the first HIV protein is gp120 and the second HIV protein is gp41 and the oligomerization domain is a trimerization domain. In certain embodiments, the first and second proteins are HIV proteins, such as gp120 and gp41, the oligomerization domain is a trimerization domain, and the fusion protein further comprises a third protein and a second linker sequence and optionally, a fourth protein and a third linker sequence. In one embodiment, the third protein is an EBV gp350/220 antigen. In another embodiment, the third protein and fourth protein are EBV gp350/220 antigens.

In certain embodiments, the oligomerization domain is a dimerization domain. In other embodiments, the oligomerization domain is a trimerization domain or tetrameric domain. In one embodiment, the dimerization domain is a leucine zipper domain, including but not limited to a yeast GCN4 leucine zipper domain or a derivative thereof. In another embodiment, the trimerization domain is a T4 bacteriophage fibritin motif or a eukaryotic GNC4 transcription factor motif or a derivative thereof. In other embodiments, the tetrameric domain is a modified eukaryotic GNC4 transcription factor motif or a derivative thereof.

In embodiments with two proteins, the oligomerization domain can be located at the N terminus of the fusion protein before the first protein, at the C terminus of the fusion protein after the second protein, or between the first and second proteins. In embodiments with three proteins, the oligomerization domain can be located at the N terminus of the fusion protein before the first protein, at the C terminus of the fusion protein after the third protein, between the first and second proteins, or between the second and third proteins. In embodiments where the fusion protein comprises four or more proteins, the oligomerization domain can be located at the N terminus of the fusion protein before the first antigen, at the C terminus of the fusion protein after the last antigen, or between any antigens in the fusion protein.

Antigens.

As used in this application, "antigen" means a protein or fragment thereof or a polysaccharide linked to a protein carrier that, when expressed in an animal or human cell or tissue, is capable of triggering an immune response. The protein or fragment thereof may be glycosylated or non-glycosylated. Examples include, but are not limited to, viral proteins, bacterial proteins, parasite proteins, autoimmune proteins, and tumor proteins. The antigen may be a wild-type protein, a truncated form of that protein, a mutated form of that protein or any other variant of that protein, in each case able to contribute to immune responses upon expression in the animal or human host to be vaccinated. In certain embodiments, the antigen is a polysaccharide, such as an antigenic polysaccharide from a pathogenic bacterium, that is linked to a protein carrier comprising a glycosylation consensus sequence, as described, for example, in the following published U.S. patent applications, the disclosures of which are hereby incorporated by reference in their entirety: US2011/0097357 and US2011/0274720.

The viral pathogens from which the viral antigens are derived include, but are not limited to: Orthomyxoviruses, such as influenza virus; Retroviruses, such as RSV, HTLV-I, and HTLV-II, Herpesviruses such as Epstein Barr Virus (EBV); cytomegalovirus (CMV) or herpes simplex virus; Lentiviruses, such as human immunodeficiency virus 1 (HIV-1) and HIV-2; Hepdnavirus, such as hepatitis B virus (HBV); Flavivirus, such as dengue fever virus; Rhabdoviruses, such as rabies virus; Picornaviruses, such as Poliovirus; Poxviruses, such as vaccinia virus; Rotavirus; and Parvoviruses, such as Adeno-Associated Viruses (AAV).

Examples of viral antigens can be found in the group including, but not limited to, the Human Immunodeficiency Virus (HIV) antigens Rev, Pol, Nef, Gag, Env, Tat, mutant derivatives of Tat, such as Tat-531-45, T- and B-cell epitopes of gp120, chimeric derivatives of HIV-1 Env and gp120, such as a fusion between gp120 and CD4gp41, a truncated or modified HIV-1 Env, such as gp140 or derivatives of HIV-1 Env and/or gp140. Other examples are EBV envelope glycoproteins, such as Gp350/220; CMV antigens, such as gB, gL, gH, or pp65; hepatitis B surface antigen; rotavirus antigens, such as VP4 and VP7; influenza virus antigens, such as hemagglutinin, neuraminidase, M2, or nucleoprotein; flavivirus antigens, such as non-structural protein NS1; and herpes simplex virus antigens such as thymidine kinase. The EBV Gp350/220 antigen is discussed in further detail below.

Examples of bacterial pathogens from which the bacterial antigens may be derived include, but are not limited to, *Streptococcus* spp. (including *S. pneumoniae*), *Enterococcus* spp., *Shigella* spp., *Salmonella* spp., *Mycobaterium* spp., *Clostridium* spp., *Rickettsia* spp., *Helicobacter pylori* spp., *Escherichia coli* spp., *Pseudomonas* spp., *Listeria* spp., *Legionella pneumonia, Borellia burgdorferi, Corynebacterium diphtheria, Bordetella pertussis, Chlamydia trachomitis, Haemophilus influenza, Neisseria meningitidis, Vibrio cholera, Listeria monocytogenes*, or *Bacillus anthracus*.

Examples of protective antigens of bacterial pathogens include the pneumolysin, PsaA, PspC, histidine triad proteins, and pilus proteins of *Streptococcus pneumoniae*; the somatic antigens of enterotoxigenic *E. coli*, such, as the CFA/I fimbrial antigen and the nontoxic B-subunit of the heat-labile toxin; pertactin of *Bordetella pertussis*, adenylate cyclase-hemolysin of *B. pertussis*, fragment C of tetanus toxin of *Clostridium tetani*, OspA of *Borellia burgdorferi*, protective paracrystalline-surface-layer proteins of *Rickettsia prowazekii* and *Rickettsia typhi*, the listeriolysin (also known as "Llo" and "Hly") and/or the superoxide dismutase (also known as "SOD" and "p60") of *Listeria monocytogenes*, urease of *Helicobacter pylori*, and the receptor-binding domain of lethal toxin and/or the protective antigen of *Bacillus anthracus*.

The parasitic pathogens from which the parasitic antigens are derived include, but are not limited to: *Plasmodium* spp. such as *Plasmodium falciparum*, *Trypanosome* spp. such as *Trypanosoma cruzi*, *Giardia* spp. such as *Giardia intestinalis*, *Boophilus* spp., *Babesia* spp. such as *Babesia microti*, Entamoeba spp. such as Entamoeba histolytica, Eimeria spp. such as Eimeria maxima, Leishmania spp., Schistosome spp., Brugia spp., Fascida spp., Dirofilaria spp., Wuchereria spp., and Onchocerea spp.

Examples of protective antigens of parasitic pathogens include the circumsporozoite (CS) or Liver Stage Specific (LSA) antigens LSA-1 and LSA-3 of Plasmodium spp. such as those of P. bergerii or P. falciparum, or immunogenic mutants thereof; the merozoite surface antigen of Plasmodium spp., the galactose-specific lectin of Entamoeba histolytica, gp63 of Leishmania spp., gp46 of Leishmania major, paramyosin of Brugia malayi, the triose-phosphate isomerase of Schistosoma mansoni, the secreted globin-like protein of Trichostrongylus colubriformis, the glutathione-S-transferase of Frasciola hepatica, Schistosoma bovis and S. japonicum, and KLH of Schistosoma bovis and S. japonicum.

The fusion protein may also include host antigens, which may be any cellular protein expressed in the recipient cell including, but not limited to, tumor, transplantation, and autoimmune antigens. Examples of such antigens include, but are not limited to, prostate-specific antigen, mucin-1 (MUC1), gp100, HER2, AE37, E75, GP2, TAG-72, carcinoembryonic antigen (CEA), melanoma associated antigen 1 (MAGE-1), tyrosinase, CD3, and IAS beta chain.

Epstein Barr Virus.

Epstein Barr virus (EBV), also known as human herpesvirus 4, is a major, global source of morbidity and mortality, responsible for such pathologic entities as Burkitt lymphoma, nasopharyngeal carcinoma, infectious mononucleosis, a subset of Hodgkin's disease, and the lymphoproliferative syndrome in immunosuppressed patients [1-3]. EBV has a double stranded, linear DNA genome. The nucleotide sequence of the EBV genome (SEQ ID NO:15) and the amino acid sequences of the viral proteins encoded thereby are known and set forth under the NCBI Reference Number NC_009334, Version NC_009334.1, GI:139424470, which sequences are hereby incorporated by reference.

In the developing world, EBV seroconversion typically occurs in infancy, whereas in developed countries it is more likely contracted in adolescence. Infectious mononucleosis typically occurs only in this latter group [3]. The major human reservoir for latent EBV and EBV transmission is the resting memory B lymphocyte [4]. EBV is dependent upon the gp350-CD21 binding event for viral entry into the B cell [5, 6], an event that is critical for infectivity and B cell neoplastic transformation [2]. Gp350 is the major EBV outer membrane glycoprotein, while CD21, also known as complement receptor type 2 (CR2), is a receptor on the surface of B cells that binds to iC3b complement protein. Sera from patients with active EBV infection contain antibody that prevent EBV entry into B cells ("neutralizing" antibody). Adsorption of these sera with gp350, eliminates most of this neutralizing activity [7], indicating that gp350 serves as the major EBV antigen to which a protective humoral immune response is directed.

A number of studies have demonstrated that immunization of non-human primates with a subunit gp350 vaccine in adjuvant protects against experimental EBV-induced lymphoma or EBV replication. Thus, purified native gp350, injected into cottontop marmosets (CTM), in association with liposomes, ISCOM's, or muramyl dipeptide, protected against EBV-induced lymphoma [8, 9]. Recombinant gp350 in alum or muramyl dipeptide was similarly protective [10, 11]. Common marmosets also showed decreased viral replication after EBV challenge following immunization with recombinant gp350 in alum [12]. Non-human primate studies using gp350 expressed by adenoviral or vaccinia viral vectors have similarly shown protection against experimental EBV-induced lymphoma or EBV replication in CTM or common marmosets [13-15].

A pilot study in humans has also suggested a potential role for gp350 vaccination in host protection against EBV. In a study by Gu et al [16] a single dose of gp350/220 expressed by vaccinia virus (VV) was give by scarification to 1-3 year olds who were EBV-seronegative, and VV-seronegative. These children developed neutralizing antibodies to EBV (1:40-1:160). Whereas 10/10 unvaccinated controls became infected at 16 months of follow-up, only 39 vaccinated children became infected at this time. More recently, Phase I/II studies were conducted in which healthy EBV-seronegative adults were immunized with a recombinant monomeric gp350 protein in alum +/− monophosphoryl lipid A [17, 18]. Following 3 doses, up to 82% of subjects had detectable neutralizing serum anti-gp350 antibody titers. The vaccine demonstrated an efficacy of 78.0% in preventing the development of infectious mononucleosis but not in preventing asymptomatic EBV infection. Finally, an additional phase I trial of recombinant monomeric gp350 protein in alum given to children with chronic kidney disease demonstrated only a minority of subjects developing detectable neutralizing serum anti-gp350 titers [19].

A monomeric protein, as used in phase I/II human clinical trials assessing gp350-induced IgG responses, is by itself a relatively weak immunogen relative to proteins that are expressed in a multimeric manner or that are aggregated [20-25]. Without intending to be bound by any theory, increased immunogenicity of multimeric proteins is most likely due, at least in part, to their more avid binding to, and crosslinking of the B cell receptor followed by more potent signaling and enhanced uptake of antigen by the B cell.

Gp350/220.

The EBV glycoprotein gp350 and the related splice variant gp220 are responsible for attachment of EBV with high affinity to CR2 on B cells. Antibodies to gp350/220 that block EBV binding neutralize B-cell infection. gp350/220 is a highly glycosylated single-pass membrane protein. As a result of alternative splicing, the viral glycoprotein appears in two forms, with approximate masses of 350 and 220 kDa. The 200 kDa splice form lacks residues 500-757 of the full length gp350. Both gp350 and gp220 retain the CR2 binding domain at the amino terminus. A truncated version of gp350/220 having amino acids 1-470 of gp350 retains the ability to bind CR2 and can inhibit the binding of EBV to CR2 [29]. In addition, portions of the gp350/220 protein between amino acids 21-26 or between amino acids 372-378 of the gp350 sequence have been linked to CR2 binding. Tanner et al, Cell 203-213 (1987) and Nemerow et al. 61:1416-20 (1987). Thus, the term gp350/220 protein or gp350/220 antigen refers to the full length gp350 or gp220 proteins as well as fragments or modified versions thereof that retain the ability to bind the CR2.

The amino acid and nucleic acid sequence of gp350, set forth in GenBank under Accession Number M10593, Version M10593.1, GI 330360, is hereby incorporated by reference. The amino acid sequence of gp350 is:

```
                                                    (SEQ ID NO: 1)
MEAALLVCQY  TIQSLIHLTG  EDPGFFNVEI  PEFPFYPTCN  VCTADVNVTI   50

NFDVGGKKHQ  LDLDFGQLTP  HTKAVYQPRG  AFGGSENATN  LFLLELLGAG  100

ELALTMRSKK  LPINVTTGEE  QQVSLESVDV  YFQDVFGTMW  CHHAEMQNPV  150

YLIPETVPYI  KWDNCNSTNI  TAVVRAQGLD  VTLPLSLPTS  AQDSNFSVKT  200

EMLGNEIDIE  CIMEDGEISQ  VLPGDNKFNI  TCSGYESHVP  SGGILTSTSP  250

VATPIPGTGY  AYSLRLTPRP  VSRFLGNNSI  LYVFYSGNGP  KASGGDYCTQ  300

SNIVFSDEIP  ASQDMPTNTT  DITYVGDNAT  YSVPMVTSED  ANSPNVTVTA  350

FWAWPNNTET  DFKCKWTLTS  GIPSGCENIS  GAFASNRTFD  ITVSGLGTAP  400

KTLIITRTAT  NATTTTHKVI  FSKAPESTTT  SPTLNTTGFA  DPNTTTGLPS  450

STHVPTNLTA  PASTGPTVST  ADVTSPTPAG  TTSGASPVTP  SPSPWDNGTE  500

SKAPDMTSST  SPVTTPTPNA  TSPTPAVTTP  TPNATSPTPA  VTTPTPNATS  550

PTLGKTSPTS  AVTTPTPNAT  SPTLGKTSPT  SAVTTPTPNA  TSPTLGKTSP  600

TSAVTTPTPN  ATGPTVGETS  PQANATNHTL  GGTSPTPVVT  SQPKNATSAV  650

TTGQNHITSS  STSSMSLRPS  SNPETLSPST  SDNSTSHMPL  LTSAHPTGGE  700

NITQVTPASI  STHHVSTSSP  EPRPGTTSQA  SGPGNSSTST  KPGEVNVTKG  750

TPPQNATSPQ  APSGQKTAVP  TVTSTGGKAN  STTGGKHTTG  HGARTSTEPT  800

TDYGGDSTTP  RPRYNATTYL  PPSTSSKLRP  RWTFTSPPVT  TAQATVPVPP  850

TSQPRFSNLS  MLVLQWASLA  VLTLLLLLVM  ADCAFRRNLS  TSHTYTTPPY  900

DDAETYV                                                    907
```

The amino acid sequence of gp220, set forth in GenBank under Accession Number M10593, Version M10593.1, GI 330360, and hereby incorporated by reference, is:

```
                                                    (SEQ ID NO: 2)
MEAALLVCQY  TIQSLIHLTG  EDPGFFNVEI  PEFPFYPTCN  VCTADVNVTI   50

NFDVGGKKHQ  LDLDFGQLTP  HTKAVYQPRG  AFGGSENATN  LPLLELLGAG  100

ELALTMRSKK  LPINVTTGEE  QQVSLESVDV  YFQDVFGTMW  CHHAEMQNPV  150

YLIPETVPYI  KWDNCNSTNI  TAVVRAQGLD  VTLPLSLPTS  AQDSNFSVKT  200

EMLGNEIDIE  CIMEDGEISQ  VLPGDNKFNI  TCSGYESHVP  SGGILTSTSP  250

VATPIPGTGY  AYSLRLTPRP  VSRFLGNNSI  LYVFYSGNGP  KASGGDYCIQ  300

SNIVFSDEIP  ASQDMPTNTT  DITYVGDNAT  YSVPMVTSED  ANSPNVTVTA  350

FWAWPNNTET  DFKCKWTLTS  GTPSGCENIS  GAFASNRTFD  ITVSGLGTAP  400

KTLTITRTAT  NATTTTWKVI  FSKAPESTTT  SPTLNTTGFA  DPNTTTGLPS  450

STHVPTNLTA  PASTGPTVST  ADVTSPTPAG  TTSGASPVTP  SPSPWDNGTE  500

STPPQNATSP  QAPSGQKTAV  PTVTSTGGKA  NSTTGGKHTT  GHGARTSTEP  550

TTDYGGDSTT  PRPRYNATTY  LPPSTSSKLR  PRWTPTSPPV  TTAQATVPVP  600

PTSQPRFSNL  SMLVLQWASL  AVLTLLLLLV  MADCAFRRNL  STSHTYTTPP  650

YDDAETYV                                                   700
```

EBV gH, gL, gB, and gp42.

EBV is an enveloped virus that gains entry into host cells by fusing its own lipid membrane with the host cell membrane. EBV can infect both B cells and epithelial cells. The minimal requirement for viral fusion with B cells includes EBV glycoproteins gH, gL, gB, and gp42. For infection of B cells, gp42 binds to the host cell MHC class II molecules to trigger viral cell membrane fusion. On the other hand, for infection of epithelial cells, gp42 is not required. Rather, the EBV gH, gL, and gB proteins are sufficient for viral fusion with epithelial cells. EBV gH/gL exists as a noncovalently associated complex. EBV gL can be expressed independently of gH, but in order for EBV gH to fold properly and traffic to the cell surface, gL must also be present.

The amino acid sequence of EBV gH is:

```
                                                      (SEQ ID NO: 16)
MQLLCVFCLV LLWEVGAASL SEVKLHLDIE GHASHYTIPW TELMAKVPGL      50

SPEALWREAN VTEDLASMLN RYKLIYKTSG TLGIALAEPV DIPAVSEGSM     100

QVDASKVHPG VISGLNSPAC MLSAPLEKQL FYYIGTMLPN TRPHSYVFYQ     150

LRCHLSYVAL SINGDKFQYT GAMTSKFLMG TYKRVTEKGD EHVLSLIFGK     200

TKDLPDLRGP FSYPSLTSAQ SGDYSLVIVT TFVHYANFHN YFVPNLKDMF     250

SRAVTMTAAS YARTVLQKLV LLEMKGGCRE PELDTETLTT MFEVSVAFFK     300

VGHAVGETGN GCVDLRWLAK SFFELTVLKD IIGICYGATV KGMQSYGLER     350

LAAVLMATVK MEELGHLTTE KQEYALRLAT VGYPKAGVYS GLIGGATSVL     400

LSAYNRHPLF QPLHTVMRET LFIGSHVVLR ELRLNVTTQG PNLALYQLLS     450

TALCSALEIG EVLRGLALGT ESGLFSPCYL SLRFDLTRDK LLSMAPQEAM     500

LDQAAVSNAV DGFLGRLSLE REDRDAWHLP AYKCVDRLDK VLMIIPLINV     550

TFIISSDREV RGSALYEAST TYLSSSLFLS PVIMNKCSQG AVAGEPRQIP     600

KIQNFTRTQK SCIFCGFALL SYDEKEGLET TTYITSQEVQ NSILSSNYFD     650

FDNLHVHYLL LTTNGTVMEI AGLYEERAHV VLAIILYFIA FALGIFLVHK     700

IVMFFL                                                    706
```

The amino acid sequence of EBV gL is:

```
                                                      (SEQ ID NO: 17)
MRTVGVFLAT CLVTIFVLPT WGNWAYPCCH VTQLRAQHLL ALENISDIYL      50

VSNQTCDGFS LASLNSPKNG SNQLVISRCA NGLNVVSFFI SILKRSSSAL     100

TGHLRELLTT LETLYGSFSV EDLFGANLNR YAWHRGG                  137
```

The amino acid sequence of EBV gB is:

```
                                                      (SEQ ID NO: 18)
MTRRRVLSVV VLLAALACRL GAQTPEQPAP PATTVQPTAT RQQTSFPFRV      50

CELSSHGDLF RFSSDIQCPS FGTRENHTEG LLMVFKDNII PYSFKVRSYT     100

KIVTNILIYN GWYADSVTNR HEEKFSVDSY ETDQMDTIYQ CYNAVKMTKD     150

GLTRVYVDRD GVNITVNLKP TGGLANGVRR YASQTELYDA PGWLIWTRYT     200

RTTVNCLITD MMAKSNSPFD FFVTTTGQTV EMSPFYDGKN KETFHERADS     250

FHVRTNYKIV DYDNRGTNPQ GERRAFLDKG TYTLSWKLEN RTAYCPLQHW     300

QTFDSTIATE TGKSIHFVTD EGTSSFVTNT TVGIELPDAF KCIEEQVNKT     350

MHEKYEAVQD RYTKGQEAIT YFITSGGLLL AWLPLTPRSL ATVKNLTELT     400

TPTSSPPSSP SPPAPPAARG STSAAVLRRR RRDAGNATTP VPPAAPGKSL     450

GTLNNPATVQ IQFAYDSLRR QINRMLGLDA RAWCLEQKRQ NMVLRELTKI     500

NPTTVMSSTY GKAVAAKRLG DVISVSQCVP VNQATVTLRK SMRVPGSETM     550

CYSRPLVSFS FINDTKTYEG QLGTDNEIFL TKKMTEVCQA TSQYYFQSGN     600

EIHVYNDYHH FKTIELDGIA TLQTFISLNT SLIENIDFAS LELYSRDEQR     650

ASNVFDLEGI FREYNFQAQN IAGLRKDLDN AVSNGRNQFV DGLGELMDSL     700

GSVGQSITNL VSTVGGLFSS LVSGFISFFK NPFGGMLILV LVAGVVILVI     750

SLTRRTRQMS QQPVQMLYPG IDELAQQHAS GEGPGINPIS KTELQAIMLA     800
```

```
                                           -continued
LHEQNQEQKR AAQRAAGPSV ASRALQAARD RFPGLRRRRY HDPETAAALL   850

GRAETEF                                                 857
```

The amino acid sequence of EBV gp42 is:

```
                                                 (SEQ ID NO: 19)
MVSFKQVRVP LFTAIALVIV LLLAYFLPPR VRGGGRVSAA AITWVPKPNV    50

EVWPVDPPPP VNFNKTAEQE YGDKEIKLPH WTPTLHTFQV PKNYTKANCT   100

YCNTREYTFS YRERCFYFTK KKHTWNGCFQ ACAELYPCTY FYGPTPDILP   150

VVTRNLNAIE SLWVGVYRVG EGNWTSLDGG TFKVYQIFGS HCTYVSKFST   200

VPVSHHECSF LKPCLCVSQR SNS                               223
```

Modified gp350/220 polypeptides that bind to CR2 include naturally-occurring or synthetically programmed variant polypeptides substantially identical to either the gp350 or gp220 polypeptides SEQ ID Nos: 1 and 2), but which have an amino acid sequence different from that of gp350 or gp220 because of one or more deletions, insertions or substitutions. Some gp350/220 variant sequences have already been identified by sequencing the DNA of different strains of EBV, and are readily available to one of ordinary skill in the art (Beisel et al., J. Viriol. 1985, 54(3):665-74). Similarly, modified gH, gL, gB, and gp42 polypeptides include naturally-occurring or synthetically programmed variant polypeptides substantially identical to either the pH, gL gB, or gp42 polypeptides (e.g., SEQ ID Nos: 16, 17, 18, or 19), but which have an amino acid sequence different from that of gH, gL, gB, or gp42 because of one or more deletions, insertions or substitutions.

The variant amino acid sequence preferably is at least 60%, 65%, 70%, or 80%, identical to a gp350/220 polypeptide of SEQ ID Nos. 1 or 2 or a gH, gL, gB, or gp42 polypeptide of SEQ ID Nos. 16, 17, 18, or 19, more preferably at least 85% identical, still more preferably at least 90% identical, and most preferably at least 95% identical. The percent identity can be determined, for example, by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

Variant polypeptides can be obtained by mutation of nucleotide sequences encoding the gp350/220, gH, gL, gB, or gp42 polypeptides. Alterations of the amino acid sequence can occur naturally, or be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (Gene 42:133, 1986); Bauer et al. (Gene 37:73, 1985); Craik, (BioTechniques, Jan. 12-19, 1985); Smith et al. (Genetic Engineering: Principles and Methods, Plenum Press, 1981); Kunkel (Proc. Natl. Acad. Sci. USA 82:488, 1985); Kunkel et al. Methods in Enzymol. 154:367, 1987); and U.S. Pat. Nos. 4,518,584 and 4,737,462, all of which are incorporated by reference.

Oligomerization Domain.

Oligomerization domains are polypeptides that cause polypeptides comprising them to oligomerize, i.e., to form covalent and/or non-covalent associations with another polypeptide comprising a corresponding oligomerization domain. Thus, two or more polypeptides are "oligomerized" if they are bound to each other via their oligomerization domains. Any oligomerization domain known in the art can be used. Examples include leucine zipper domains and fibritin domains. The polypeptides in an oligomer can have identical polypeptide sequences, similar polypeptide sequences or different polypeptide sequences.

Homodimerization and homo-oligomerization refer to the association of the same polypeptide components to form dimers or oligomers. Heterodimerization and hetero-oligomerization refer to the association of different polypeptides to form dimers or oligomers. Homo-oligomers thus comprise an association of multiple copies of a particular polypeptide, while hetero-oligomers comprise an association of copies of different polypeptides. "Oligomerization," "oligomerize," and "oligomer," with or without prefixes, are intended to encompass "dimerization," "dimerize," and "dimer." Thus, in one embodiment, the oligomerization domain is a dimerization domain that mediates the self-association of two fusion proteins. In another embodiment, the oligomerization domain is a trimerization domain that mediates the self-association of three fusion proteins. In another embodiment, the oligomerization domain is a tetramerization domain that mediates the self-association of four fusion proteins. In one embodiment, the trimerization domain is fibritin motif or a eukaryotic GCN4 transcription factor motif or derivative thereof.

In one embodiment, the oligomerization domain comprises a leucine zipper domain. Leucine zipper domains are peptides that promote oligomerization of the proteins in which they are found. Leucine zippers were originally identified in several DNA-binding proteins (Landschulz et al., Science 240:1759, 1988), and have since been found in a variety of different proteins. Among the known leucine zippers are naturally occurring peptides and derivatives thereof that dimerize or trimerize. For example, the yeast GCN4 leucine zipper can be used to dimerize polypeptides of interest [27, 28]. Other examples of leucine zipper domains suitable for producing soluble multimeric proteins are described in PCT application WO 94/10308, and the leucine zipper derived from lung surfactant protein D (SPD) described in Hoppe et al. FEBS Lett. 344:191, 1994. The use of a modified leucine zipper that allows for stable trimerization of a heterologous protein fused thereto is described in Fanslow et al., Semin. Immunol, 6:267, 1994.

In yet another embodiment, the oligomerization domain is a fibritin trimerization motif, particularly a bacteriophage fibritin trimerization motif, more particularly a fibritin trimerization domain from bacteriophage T4 or phage RB69 or phage AR1 or a derivative thereof. The T4 fibritin trimerization domain and variants thereof are described in U.S. Pat. No. 6,911,205; U.S. Pat. No. 8,147,843, and WO 01/19958, which are hereby incorporated by reference in their entirety.

Linker Sequences.

Linker sequences are used in the fusion proteins to separate different components of the fusion protein. Thus, the amino terminal end of the linker sequence is joined by a peptide bond to a first polypeptide and the carboxy terminal end of the linker sequence is joined by a peptide bind to a second polypeptide. The first or second polypeptide may be an antigen, an oligomerization domain, an adjuvanting protein, a cell surface targeting domain, a molecule that mediates immune suppression, or a cellular activation domain. Such a linker sequence joins the first polypeptide and the second polypeptide, in contrast to a first polypeptide and a second polypeptide that are joined together without an intervening polypeptide sequence. Thus, the linker sequence can join two antigens, an antigen and an oligomerization domain, an antigen and an adjuvanting protein, an antigen and a cell surface targeting domain, an antigen and a molecule that mediates immune suppression, and an antigen and a cellular activation domain, an adjuvanting protein and an oligomerization domain, etc. It is understood that the linker sequence is not a sequence that naturally separates a first and second polypeptide, if the first and second polypeptide happen to naturally exist in combination together.

In one embodiment, the linker sequence is a polypeptide having 5-25 amino acids, particularly a length of 6, 7, 8, 9, 10, 11, 12, 13, 14, 15, 16, 17, 18, 19 or 20 amino acids. In another embodiment, the linker sequence is a polypeptide having 10-25 amino acids. The linker sequence preferably comprises glycine and serine amino acids. In one embodiment, the linker sequence is 15 amino acids in length and has the amino acid sequence $(Gly_4Ser)_3$(SEQ ID NO:3).

Other suitable peptide linkers are those described in U.S. Pat. Nos. 4,751,180, 4,935,233, and 5,073,627, each of which is hereby incorporated by reference in its entirety. A DNA sequence encoding a desired linker sequence may be inserted between, and in the same reading frame as, for example, DNA sequences encoding the first and second polypeptide using conventional techniques known in the art. For example, a chemically synthesized oligonucleotide encoding the linker may be ligated between sequences encoding the first and second polypeptide.

Nucleic Acids, Cloning and Expression Systems.

The present disclosure further provides isolated nucleic acids encoding the disclosed fusion proteins. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The present disclosure also provides constructs in the form of plasmids, vectors, phagemids, transcription or expression cassettes which comprise at least one nucleic acid encoding a fusion protein or a portion thereof. The disclosure further provides a host cell which comprises one or more constructs as above.

Also provided are methods of making the fusion proteins encoded by these nucleic acids. The fusion proteins may be produced using recombinant techniques. The production and expression of recombinant proteins is well known in the art and can be carried out using conventional procedures, such as those disclosed in Sambrook et al., *Molecular Cloning: A Laboratory Manual* (4th Ed. 2012), Cold Spring Harbor Press. For example, expression of the fusion protein may be achieved by culturing under appropriate conditions recombinant host cells containing the nucleic acid encoding the fusion protein. Following production by expression a fusion protein may be isolated and/or purified using any suitable technique, then used as appropriate.

Systems for cloning and expression of a polypeptide in a variety of different host cells are well known in the art. Any protein expression system compatible with the constructs disclosed in this application may be used to produce the disclosed fusion protein.

Suitable vectors can be chosen or constructed, so that they contain appropriate regulatory sequences, including promoter sequences, terminator sequences, polyadenylation sequences, enhancer sequences, marker genes and other sequences as appropriate.

A further aspect of the disclosure provides a host cell comprising a nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, elcetroporation and transfection using bacteriophage. These techniques are well known in the art. See e.g., Current Protocols in Molecular Biology, Ausubel et al, eds., John Wiley & Sons (2010). DNA introduction may be followed by a selection method (e.g., antibiotic resistance) to select cells that contain the vector.

Vaccine Compositions.

The fusion proteins and nucleic acids encoding the same that are described in this application provide an improved platform for developing a vaccine that achieves enhanced immunogenicity in a subject.

Thus, one aspect is directed to a composition comprising the nucleic acid encoding the fusion protein or the fusion protein, at least one pharmaceutically acceptable excipient, and optionally an adjuvant (hereinafter referred to as "vaccine composition"). In certain embodiments, the vaccine composition does not include an adjuvant.

The pharmaceutically acceptable excipient can be chosen from, for example, diluents such as starch, microcrystalline, cellulose, dicalcium phosphate, lactose, sorbitol, mannitol, sucrose, methyl dextrins; binders such as povidone, hydroxypropyl methylcellulose, dihydroxy propylcellulose, and sodium carboxylmethylcellulose; and disintegrants such as crospovidone, sodium starch glycolate, croscarmellose sodium, and mixtures of any of the foregoing. The pharmaceutically acceptable excipient can further be chosen from lubricants such as magnesium stearate, calcium stearate, stearic acid, glyceryl behenate, hygrogenated vegetable oil, glycerine fumerate and glidants such as colloidal silicon dioxide, and mixtures thereof. In some embodiments, the pharmaceutically acceptable excipient is chosen from microcrystalline cellulose, starch, talc, povidone, crospovidone, magnesium stearate, colloidal silicon dioxide, sodium dodecyl sulfate, and mixtures of any of the foregoing. The excipients can be intragranular, intergranular, or mixtures thereof.

The vaccine composition can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form. After formulation, the vaccine composition can be incorporated into a sterile container which is then sealed and stored at a low temperature (e.g., 4° C.), or it can be freeze dried.

The vaccine composition can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as for example, sodium, potassium, ammonium, calcium, or ferric hydroxides, and such organic bases as isopropylamine, trimethylamine, 2-ethylamino ethanol, histidine, procaine, and the like.

The vaccine conaposition can optionally comprise agents that enhance the protective efficacy of the vaccine, such as adjuvants. Adjuvants include any compound or compounds that act to increase an immune response to an antigen delivered by the fusion protein, thereby reducing the quantity of fusion protein (or nucleic acid encoding the same) necessary in the vaccine, and/or the frequency of administration necessary to generate a protective immune response. Adjuvants can include for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) Curr. Opin. Immunol. 12:456), Mycobacterialphlei (M. phlei) cell wall extract (MCWE) (U.S. Pat. No. 4,744,984), M. phlei DNA (M-DNA), and M. phlei cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonium bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-α), interleukin-2 (IL-2), and granulocyte macrophage-colony stimulating factor (GM-CSF), or combinations thereof.

The vaccine composition can be prepared using techniques well known to those skilled in the art including, but not limited to, mixing, sonication and microfluidation. The adjuvant can comprise from about 10% to about 80% (v/v) of the vaccine composition, more preferably about 20% to about 50% (v/v), and more preferably about 20% to about 30% (v/v), or any integer within these ranges.

The vaccine composition can be administered to any animal, and preferably is a mammal such as a human, mouse, rat, hamster, guinea pig, rabbit, cat, dog, monkey, cow, horse, pig, and the like. Humans are most preferred.

Administration of the vaccine composition can be by infusion or injection (e.g., intravenously, intramuscularly, intracutaneously, subcutaneously, intrathecal, intraduodenally, intraperitoneally, and the like). The vaccine composition can also be administered intranasally, vaginally, rectally, orally, intratonsilar, or transdermally. Additionally, the vaccine composition can be administered by "needle-free" delivery systems.

The effective amount of the vaccine composition may be dependent on any number of variables, including without limitation, the species, breed, size, height, weight, age, overall health of the patient, the type of formulation, or the mode or manner or administration. The appropriate effective amount can be routinely determined by those of skill in the art using routine optimization techniques and the skilled and informed judgment of the practitioner and other factors evident to those skilled in the art. Preferably, a therapeutically effective dose of the vaccine composition described herein will provide the therapeutic preventive benefit without causing substantial toxicity to the subject.

The vaccine composition can be administered to a patient on any schedule appropriate to induce and/or sustain an immune response against EBV Gp350/220 or any other protein of interest. For example, patients can be administered a vaccine composition as a primary immunization as described and exemplified herein, followed by administration of a secondary immunization, or booster, to bolster and/or maintain protective immunity.

The vaccine administration schedule, including primary immunization and booster administration, can continue as long as needed for the patient, for example, over the course of several years, to over the lifetime of the patient. The frequency of primary vaccine and booster administration and dose administered can be tailored and/or adjusted to meet the particular needs of individual patients, as determined by the administering physician according to any means suitable in the art.

The vaccine composition may be administered prophylactically (before exposure to the antigen or pathogen of interest) or therapeutically (after exposure to the antigen or pathogen of interest).

Methods of Inducing or Suppressing an Immune Response.

In another aspect, the vaccine composition comprising the fusion protein (or nucleic acid encoding the same) can be used in a method of inducing or suppressing an immune response. The immune response can be induced in a naïve subject who has not previously been exposed to EBV, CMV, or HIV (or some other foreign pathogen). Alternatively, the immune response can be induced or suppressed in a subject who has been previously exposed to EBV, CMV, or HIV (or some other foreign pathogen) and used to enhance an existing immune response.

In one embodiment, the method of enhancing or suppressing an immune response comprises administering to a subject a vaccine composition comprising a fusion protein, as described in this application, wherein the fusion protein induces or suppresses an immune response against an antigen in the fusion protein in the subject. In another embodiment, the method of enhancing or suppressing an immune response comprises administering to a subject a vaccine composition comprising a nucleic acid construct that encodes a fusion protein, as described in this application, wherein the fusion protein is expressed in the subject and induces or suppresses an immune response against an antigen in the fusion protein in the subject.

In these methods of inducing or suppressing an immune response, the immune response can be measured using routine methods in the art, such as those disclosed in this application. These routine methods include, but are not limited to, measuring an antibody response, such as an antibody response directed against a protein encoded by the recombinant vector, and measuring cellular proliferation, including, for example, by measuring tritiated thymidine incorporation or cytokine (e.g., IFN-γ) production.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

To test whether protein multimerization can provide a cost-effective and reproducible means for enhancing immune responses to target antigens of interest, a recombinant nucleic acid plasmid was designed to encode a fusion protein comprising a first and second antigen, separated by a linker sequence and an oligomerization domain. In the test construct prepared to validate the system, two identical gp350 sequences are separated by a (Gly$_4$Ser)$_3$ (SEQ ID NO:3) linker to allow for proper protein folding [26], followed by a *Saccharomyces cerevisiae* GCN4 leucine zipper sequence [27, 28] to mediate self-association of the gp350 dimer, and thus formation of a tetrameric gp350. Immunization of mice with either the plasmid DNA itself or the resulting tetrameric protein results in markedly higher titers of gp350 specific IgG relative to the gp350 monomer, even in the presence of a strong adjuvant. Most importantly, the gp350 subunits that comprise the tetrameric protein are conformationally intact and elicit serum titers of neutralizing antibody that are more than 19-fold higher than that induced by monomer. These data strongly suggest a promising, new prophylactic EBV vaccine for future clinical testing, as well as a more general approach to enhance the immunogenicity of other proteins of vaccine interest.

Materials and Methods

Construction of plasmids for production of monomeric and tetrameric gp350.

A gp350 cDNA fragment encoding amino acids 1-470 was cloned by PCR amplification of the DNA isolated from a recombinant baculovirus that expressed the truncated gp350 [29]. The following primer set was used:

forward 5'-CACCATGGAGGCAGCCTTGCTTGT-3' (SEQ ID NO:4) and reverse 5'-AGATCTTTAGGATACAGTGGGGCCTGT GC-3 (SEQ ID NO:5), denatured at 94° C. for 30 sec, annealed at 52° C. for 30 sec, extended at 68° C. for 2 min, total 25 cycles. The cDNA fragment was inserted into the pENTR/SD/D-TOPO directional cloning vector (Invitrogen, Grand Island, N.Y.) and verified by sequencing.

Gp350 Monomer Construct:

To make the construct expressing gp350 monomer, PCR amplification was performed under the conditions as described above using the primer sets designated GF1: 5'-GCCACCATGGAGACAGACACACTCCTGC-TATGGGTACTGCTGCTC TGGGTTCCAGGTTC-CACTGGTGACGCCGGCCCAGCCGGCCAG-GCGCGCGCGCCGT ACGAAGCTCGCCCTT-3' (SEQ ID NO:6) and GR6: 5'-TCAATGGTGATGGTGAT-GATGGGTCGGATACAGTCGGGGCCTGT-3' (SEQ ID NO:7). GF1 contained an IgGκ leader sequence and GR6 contained the sequence coding for a His$_6$ tag (SEQ ID NO:14). The PCR product was cloned into the pOptiVEC-TOPO vector (Invitrogen), and verified by sequencing.

Gp350 Tetramer Construct with TT Epitopes:

The construct expressing gp350 tetramer was made by creating two separate gp350 units: gp350F1R1 and gp350F2R5, followed by ligating the two units together. The gp350F1R1 was made via PCR using the primer sets GF1 (as above) and GR1: 5'-CCATCGATGGCTAGCTAGCG-GTGATACAGTGGGGCCTGT-3' (SEQ ID NO:8). GR1 contained a linker sequence (Gly$_4$Ser)$_3$ (SEQ ID NO:3) and sequences specific for the restriction enzymes Nhe I and Cla I. The PCR product was cloned into the pOptiVEC-TOPO vector, and was verified by sequencing, Gp350F2R5 contained sequences encoding the universal tetanus toxoid (TT)-specific CD4+ T cell epitopes P$_2$ and P$_{30}$ [30], a leucine zipper [27, 28] and a His6 tag (SEQ ID NO:14), and was created by 3 rounds of PCR, adding the coding sequences sequentially. The first 2 rounds of PCR were done using the same forward primer designated GF: 5'-ATGGAGGCAGC-CTTGCTTGT-3' (SEQ ID NO:9) and reverse primers GR2: 5'-TCAACCAAAAGCTAACGGTAAAATTATTAAATTT-TAGTTCAGTTATACCT ATAAATTTAGAATTTGCTTT-TATATACTGGGTGGATACAGTGGGGCCTGT-3' (SEQ ID NO:10) and GR3: 5'-TTTTTGCTCAACAGCTCTTC-CACTTTATCTTCCAGCTGTTTCATG CGTTCTAAAT-GACTAGCAGATACTTTAGGAACCCTCAAC-CAAAAGCTAACGGTA A-3' (SEQ ID NO:11), respectively. The last PCR was performed using the forward primer designated GF2: 5'-CTAGCTAGC GGT GGC GGA GGG AGT GGT GGC GGA GGG AGC GGT GGC GGA GGG AGT ATGGAGGACAGCCTTGCTTGT-3' (SEQ ID NO:12) and reverse primer GR5: 5'-CCATCGATTCAATG-GTGATGGTGATGATGGCTAGTGCGTTCGCCCAC-CACGC TTTTCAGACGCGCCACTTCGTTTTCCAGAT-GATAGTTTTTGCTCAACAGCTCTTC C-3' (SEQ ID NO:13). GF2 and GR5 contained the sequences for the restriction enzymes Nhe I and Cla I, respectively. The PCR product was cloned into the PCRII-TOPO vector (Invitrogen), and was verified by sequencing. The plasmids gp350F1R1 and gp350F2R5 were digested with Nhe I and Cla I, the fragments containing gp350 were gel-purified and ligated with T4 DNA ligase at 4° C. overnight, followed by transformation of "Top 10 f" *E. coli* (Invitrogen) with the ligation mixture. Two clones were selected for further study following verification by sequencing.

Gp350 Tetramer Construct without TT Epitope.

The plasmid was constructed using a similar approach as described above, but the sequences encoding $P_2$ and $P_{30}$ were deleted.

Transfection of Chinese Hamster Ovary (CHO) Cells (Clone DG44).

DG44 cells were maintained in "CD DG44" medium (Invitrogen), and $2\times10^7$ cells were used for transfection. 30 µg of gp350 monomeric or tetrameric constrict was resuspended in 1.2 ml "OptiPro SFM" medium after linearization with PvuI, followed by adding 30 µl of "FreeStyle Max Reagent", mixed gently and incubated for 10 min at room temperature. The DNA-Freestyle Max Reagent complex was slowly added into the flask containing $2\times10^7$ DG44 cells with gentle shaking. The cells were incubated at 37° C., 5% $CO_2$ for 48 hours. Cells were centrifuged at 1,200 rpm and maintained in "CD OptiCHO" serum-free medium. Methotrexate (MTX, Sigma, St. Louis, Mo.) was used to select high recombinant protein-secreting cells, with the concentration of MTX gradually increased from 50 nM to 4 µM.

CHO Culture in Hollow Fiber Bioreactors and Purification of Recombinant gp350 Proteins.

After MTX selection, gp350 monomer- and tetramer-expressing CHO cells were loaded into "Fibercell" cartridges ("C2008" [5 kD MW cut-off] and "C2011" [20 kD MW cut-off], respectively, FiberCell Systems, Inc., Frederick, Md.), and concentrated supernatants were collected daily. Supernatants were further concentrated by centrifugation at 3,000 rpm for 30 min using a "Centriprep Centrifugal Filter Unit", 30,000 MW cut-off (Thermo Scientific, Waltham, Mass.). Affinity purification was performed using a cobalt column (Thermo Scientific), according to manufacturer's instructions. Briefly, concentrated supernatants were mixed with an equal volume of equilibration buffer, and added to the cobalt purification column. The column was incubated with gentle agitation for 60 min at 4° C. and washed 3× with washing buffer. The gp350 recombinant proteins were eluted with elution buffer and analyzed by electrophoresis on 3-8% NuPAGE Tris-Acetate Mini Gels, under denaturing or native conditions, and stained with Simple Blue (Invitrogen). The gp350 proteins were also transferred onto nitrocellulose membranes and analyzed by Western Blot using anti-His antibody (Invitrogen). Gp350 proteins were further analyzed by immunoblotting with the g350-specific mAb, 72A1 [31], incubated overnight at 4° C. The nitrocellulose membranes were then incubated with HRP-labeled goat anti-mouse IgG, followed by development with chemiluminescent substrate (Thermo Scientific) for 10 min, and signal was detected on X-ray film. The 72A1 B cell hybridoma was a kind gift from Dr. Jonathan Hannan (University of Edinburgh, Edinburgh, UK). 72A1 mAb was purified on a protein G column from culture supernatant.

Mice.

Female BALB/c mice, purchased from the National Cancer Institute (Frederick, Md.) were used at 7-10 weeks of age for all protein immunizations. Female BALB/c mice purchased from Harlan Laboratories (Indianapolis, Ind.), were used at 4-6 weeks of age for all plasmid DNA vaccinations. These studies were conducted in accordance with the principles set forth in the *Guide for Care and Use of Laboratory Animals* (Institute of Laboratory Animal Resources, National Research Council, revised 1996), and were approved by the Uniformed Services University of the Health Sciences and the University of Washington Institutional Animal Care and Use Committees.

Antigens and Immunizations.

Purified pneumococcal capsular polysaccharide, type 14 (PPS14) was purchased from ATCC (Manassas, Va.). Gp350-PPS14 and TT-PPS14 conjugates were synthesized in a similar fashion, as previously described [32]. The molar ratios of gp350 and TT to PPS14 were about 8:1. Alum (Allhydrogel 2%) was obtained from Brenntag Biosector (Denmark). A stimulatory 30 mer CpG-containing oligodeoxynucleotide (CpG-ODN) was synthesized as previously described [33]. Mice were immunized i.p. with conjugates adsorbed on 13 µg of alum mixed with 25 µg of CpG-ODN. Monomeric and tetrameric Gp350 proteins were injected i.p. in alum +/− CpG-ODN. Serum samples for ELISA assay were obtained from blood taken from the tail vein.

Particle-Mediated Epidermal Delivery (PMED).

Mice were vaccinated by particle-mediated epidermal delivery (PMED) in the abdominal skin using the Powder-Ject XR-1 DNA vaccine delivery system as previously described [34]. Each immunization consisted of two tandem deliveries of 0.5 mg 1-3 µm-diameter gold particles coated with 1.0 µg DNA vaccine for a total dose of 4.0 µg DNA, formulated as previously described [34]. DNA vaccines were administered by PMED at a helium pressure of 350 psi at zero and four weeks.

Measurement of Serum Titers of Antigen-Specific IgG and IgG Isotypes by ELLSA.

Immulon 4 ELISA plates (Dynex Technologies, Inc., Chantilly, Va.) were coated (50 µL/well) with monomeric gp350, TT, or PPS14 (5 µg/ml) in PBS overnight at 4° C. Plates were washed 3× with PBS+0.1% Tween 20 and were blocked with PBS+1% BSA for 1 h at 37° C. Threefold dilutions of serum samples, starting at a ⅟₅₀ serum dilution, in PBS+1% BSA were then added overnight at 4° C. and plates were washed 3× with PBS+0.1% Tween 20. Alkaline phosphatase-conjugated polyclonal goat anti-mouse IgG, IgG3, IgG1, IgG2b, or IgG2a Abs (SouthernBiotech, Birmingham, Ala.) (200 ng/ml final concentration) in PBS+1% BSA were then added, and plates were incubated at 37° C.

for 1 h. Plates were washed 5× with PBS+0.1% Tween 20. Substrate (p-nitrophenyl phosphate, disodium; Sigma) at 1 mg/ml in TM buffer (1 M Tris+0.3 mM $MgCl_2$, pH 9.8) was then added for color development. Color was read at an absorbance of 405 nm on a Multiskan Ascent ELISA reader (Labsystems, Finland).

Measurement of Serum Gp350-Specific Neutralizing Antibody.

Gp350 monomeric protein was labeled with Dylight 633 (Thermo Scientific). 25 µl of mouse serum from naïve or immunized mice, were incubated with 2.5 µl of DyLight 633-labeled gp350 monomer, for a final concentration of monomer of 1 µg/ml, for 30 min at room temperature. A pellet of $5×10^5$ CR2M1α cells was resuspended in the serum gp350 monomer mixture for 30 min on ice, washed 3× with 0.5% BSA-PBS, and fixed in 4% para-formaldehyde. The CR2M1α cell line was made by transfecting the K562 human erythroleukemia line with human CD21 [35]. To create a standard curve, varying concentrations of 72A1 mAb (final concentrations of 1-256 µg/ml) were incubated with Dylight 633-labeled monomeric gp350 (final concentration of 1 µg/ml) for 30 min at room temperature, followed by incubation with $5×10^5$ CR2M1α cells as described above. CR2M1α cells were then analyzed on a BD LSRII Flow Cytometer Cell Analyzer.

Detection of Intracellular IL-4 and IL-5 by Flow Cytometry.

Spleen cells were isolated from mice, 21 d following i.p. immunization with gp350 monomer or tetramer in alum, and cultured for 5 h in 6-well plates at $2×10^6$ cells/well in 1 ml of RPMI-1640+10% fetal calf serum, containing 10 U/ml mIL-2 and 5 µg/ml of $P_2$ and $P_{30}$ TT-specific peptides. Golgi Stop (BD Biosciences, San Jose, Calif.) was added 1 h after initiation of culture. Cells were then stained with FITC-rat IgG2b anti-mouse CD4 (clone GK1.5) in the presence of rat IgG2b anti-mouse CD16/CD32 (clone 2.4G2) for 30 min on ice. Cells were washed, fixed, and permeabilized using cytofix/cytoperm solution (BD Biosciences). Following washing 2× in perm/wash buffer, cells were incubated with APC-labeled rat IgG2b anti-mouse IL-4 (clone BVD4-ID11) or PE-labeled rat IgG1 anti-mouse IL-5 (clone TRFK5) for 30 min on ice, followed by washing twice in perm/wash buffer. Cells were analyzed on a BD LSRII Flow Cytometer Cell Analyzer, using FlowJo software.

Binding of Monomeric and Tetrameric Gp350 Proteins to Human CD21.

CR2M1α cells were incubated for 30 min on ice with gp350 monomer or tetramer (0.05-30 µg/ml), washed 3× with 0.5% BSA-PBS and incubated further with mouse anti-gp350 mAb (2L10, Thermo Scientific) for 30 minutes. 2L10 mAb binds to a non-neutralizing epitope on gp350, distinct from the neutralizing epitope recognized by 72A1 [36, 37]. Cells were then washed 3× in 0.5% BSA-PBS, followed by incubation with DyLight 633-labeled goat anti-mouse IgG. Cells were fixed in 4% paraformaldehyde and analyzed on a BD LSRII Flow Cytometer Cell Analyzer.

Analysis of Human B Cell Activation.

Peripheral blood mononuclear cells (PBMC) were isolated by Ficoll-Hypaque (Roche, Indianapolis, Ind.) density gradient centrifugation from donor buffy coats (Blood Bank, National Institutes of Health, Bethesda, Md.) and washed twice in 1× PBS. B cells were purified from a starting population of $3×10^8$ PBMC by magnetic bead cell separation (B cell isolation kit II, Miltenyi Biotec, Auburn, Calif.), yielding >94% purified CD19+ B cells as assessed by flow cytometry. Sorted B cells were resuspended at $1×10^6$ cells/ml in complete RPMI 1640 medium (Lonza, Walkersville, Md.) containing 10% fetal calf scram (FCS, Lonza), 2 mM glutamine, and 100 U/ml each of penicillin and streptomycin (Invitrogen). B cells were aliquoted (0.5-$1×10^6$ cells/well) in a 24 well plate and incubated for 24 or 72 h in a 37° C. incubator (5% $CO_2$) with monomeric or tetrameric gp350 (10 µg/ml), recombinant PspA (10 µg/ml), goat anti-human IgM F(ab')$_2$ (Jackson ImmunoResearch, West Grove, Pa., 20 µg/ml), or protein A from heat killed *Staphylococcus aureus* Cowan strain I (SAC, Sigma, St. Louis, Mo., 1:100 dilution)+recombinant human IL-2 (Peprotech, Rocky Hill, N.J., 200 IU/ml), Upregulation of cell surface activation markers was subsequently measured by staining cells with PE-conjugated anti-CD69 mAb (24 h post-stimulation) or PE-conjugated anti-CD25 mAb+FITC-conjugated anti-CD86 mAb (72 h post-stimulation). All antibodies were purchased from BD Biosciences. Cells ($3×10^5$) were incubated with 5 µl of each antibody in 100 µl FACS buffer (1× PBS, 1% FCS, 0.1% sodium azide) for 30 min, washed in 2 ml FACS buffer, and collected on an LSR II flow cytometer (Becton Dickinson, Franklin Lakes, N.J.). Data analysis was performed using FlowJo software (TreeStar, Ashland, Oreg.).

Statistics.

Serum titers of antigen-specific Ig were expressed as the geometric means±SEM of the individual serum titers. Percentages of CD4+ T cells expressing cytoplasmic IL-4 or IL-5 were expressed as the arithmetic means+/−SEM of the individual samples. Significance was determined by the Student t test. p-values of ≤0.05 were considered statistically significant.

Figure 1:
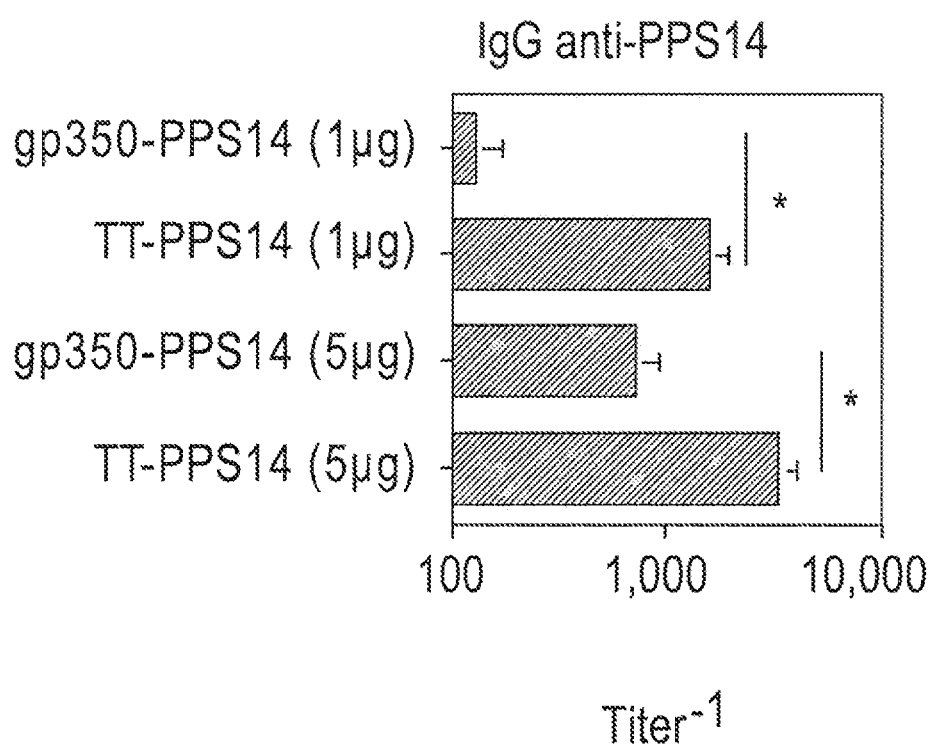
FIG. 1 shows that tetanus toxoid is a more potent carrier protein than gp350 for a pneumococcal polysaccharide conjugate vaccine. Mice were immunized i.p. with gp350-PPS14 or TT-PPS14 at 1 or 5 µg/mouse (5 mice per group) in alum+CpG-ODN, and boosted in a similar fashion on day 14. PPS14-specific IgG titers were measured by ELISA from sera obtained on day 21. *Significance, p≤0.05 between gp350-PPS14 and TT-PPS14.
Figure 2:
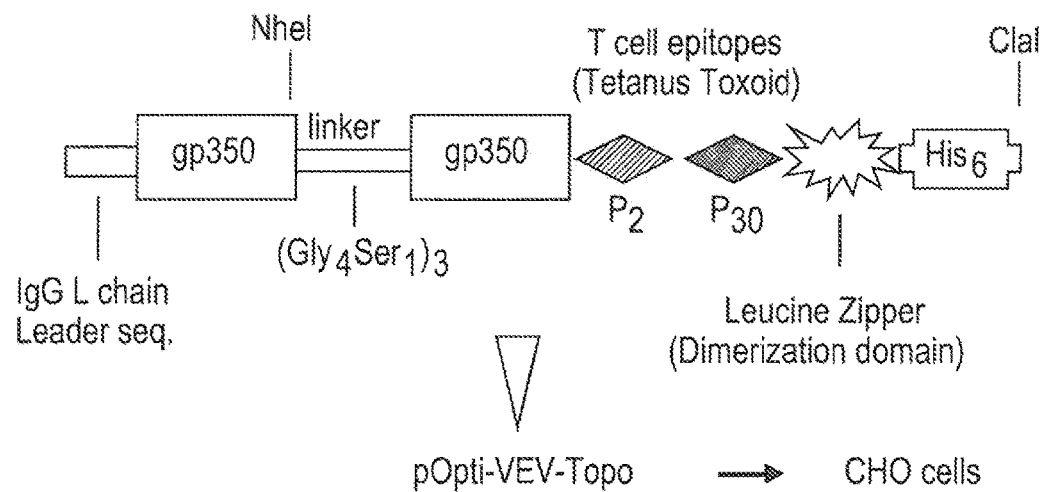
FIG. 2 shows a DNA plasmid map for production of tetrameric gp350 containing TT-specific CD4+ T cell epitopes. "(Gly$_4$Ser$_1$)$_3$" disclosed as SEQ ID NO: 3 and "His$_6$" disclosed as SEQ ID NO: 14, as well as production of a tetrameric gp350 protein containing TT-specific CD4+ T cell epitopes by SDS-PAGE (denatured) and PAGE (native) gels developed with 72A1 mAb.
Figure 2:
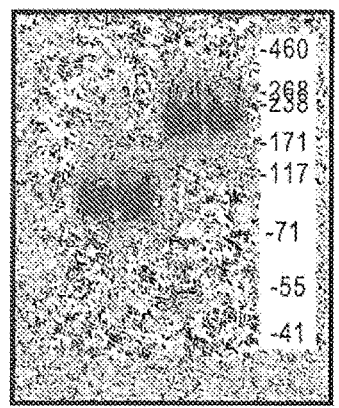
Figure 2:
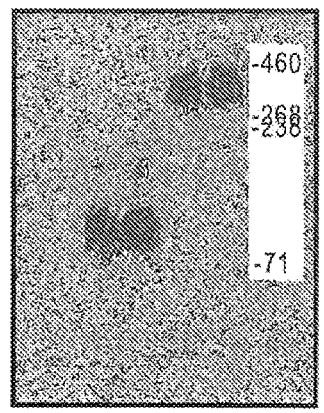

Example 1: DNA Plasmid and Production of a Tetrameric Gp350 Protein Containing TT-Specific CD4+ T Cell Epitopes Optimal antibody responses to protein antigens require both dominant B and T cell epitopes. Although the EBV gp350 envelope protein is a potential target for an antibody-based prophylactic EBV vaccine, the relative strength and dominance of its T cell epitopes are unknown. Highly immunogenic carrier proteins, such as tetanus toxoid (TT), are utilized in polysaccharide conjugate vaccines to recruit CD4+ T cell help for the associated IgG anti-polysaccharide response. Initially, it was believed that adding TT to the EBV construct would help enhance and optimize the antibody response to the gp350 proteins. This initial belief was reinforced with early experiments comparing the relative ability of gp350 versus TT to promote an IgG response specific for pneumococcal polysaccharide, serotype 14 (PPS14), and thus indirectly to recruit CD4± T cell help. Mice were immunized i.p, with either 1 or 5 μg of gp350-PPS14 or TT-PPS14 in alum+CpG-ODN as adjuvant and similarly boosted on day 14. Serum titers of PPS14-specific IgG, measured on day 21, were significantly higher using TT-PPS14 relative to gp350-PPS14 using either 1 or 5 μg of conjugate (FIG. 1), strongly suggesting that TT contained more potent CD4+ T cell epitopes.

Multimerization of proteins can confer increased immunogenicity [21, 22, 25, 38, 39]. Therefore, a DNA construct that would direct the production of a tetrameric g350 was designed. EBV neutralizing antibody, required for a successful prophylactic vaccine, is specific for the conformational epitope of gp350 that mediates binding to CD21 on human B cells, mediating EBV entry. Thus, proper folding of the individual gp350 molecules in the tetramer was considered important. Given the known properties of TT as a potent inducer of CD4 T helper cells and the data illustrated in FIG. 1, two universal human TT-specific CD4+ T cell epitopes ($P_2$ and $P_{30}$) [30] were introduced into the construct to maximize recruitment of T cell help for the gp350-specific IgG response. The construct design is illustrated in FIG. 2A. Specifically, an IgG light chain leader sequence was introduced 5' to facilitate protein secretion, followed by two identical gp350 sequences separated by a $(Gly_4Ser)_3$ linker (SEQ ID NO:3) to allow for proper protein folding [26]. Sequences encoding $P_2$ and $P_{30}$ were introduced 3' to the second gp350 followed by a *Saccharomyces cerevisiae* GCN4 leucine zipper sequence [127, 28] to mediate self-association of the gp350 dimer, and thus formation of a tetrameric gp350. A $His_6$ tag (SEQ ID NO:14) was positioned 3' of the leucine zipper for purposes of purification. A DNA construct encoding a monomeric gp350 lacking TT-specific epitopes was also produced for comparison.

To produce protein, Chinese hamster ovary (CHO) cells were stably transfected with either tetrameric or monomeric gp350 DNA, and high-producing CHO cells were selected using increasing concentrations of methotrexate in the culture medium. Protein was purified from culture supernatant and detected by SDS-PAGE (denaturing) and PAGE (native) using the gp350-specific 72A1 mAb that recognizes the CD21-binding, conformational epitope [31] (FIG. 2B). Under denaturing conditions, in which leucine zipper binding is disrupted, a single band of about 200 Kd was observed for the resulting gp350 dimer, whereas under native conditions a single band representing intact tetrameric gp350 of about 400 Kd was detected. In both cases, monomeric gp350 was detected as an approximately 100 Kd band. Of note, under denaturing conditions the concentration of 72A1 mAb required for development of a detectable band was 10-fold higher than that necessary under native conditions, likely reflecting loss of gp350 conformation in the former.

Example 2: Tetrameric Gp350 is Markedly More Immunogenic than Monomeric Gp350 Protein, Even in the Presence of a Strong Adjuvant and Following DNA Vaccination The relative ability of tetrameric versus monomeric gp350 to induce a gp350-specific IgG response was determined. Mice were injected i.p. with 25, 1.0, or 0.2 μg of tetrameric or monomeric gp350 per mouse in the presence of alum adjuvant and boosted in a similar fashion on day 21. Serum titers of gp350-specific IgG were measured by ELISA on the indicated days (FIG. 3A). Tetrameric gp350 induced 18-fold higher secondary serum gp350-specific IgG titers relative to monomeric gp350 at the higher dose (25 μg). Tetrameric gp350 at 1.0 μg induced serum titers that were comparable to mice receiving 25 μg of monomer, whereas tetramer at a dose of 0.2 μg/mouse elicited a barely detectable gp350-specific IgG response (data not shown). Thus, tetrameric gp350 exhibited about 25-fold higher immunogenicity on a per weight basis relative to monomer. In marked contrast to tetramer, monomer induced a barely detectable gp350-specific IgG response at 1.0 μg.

Figure 3B:
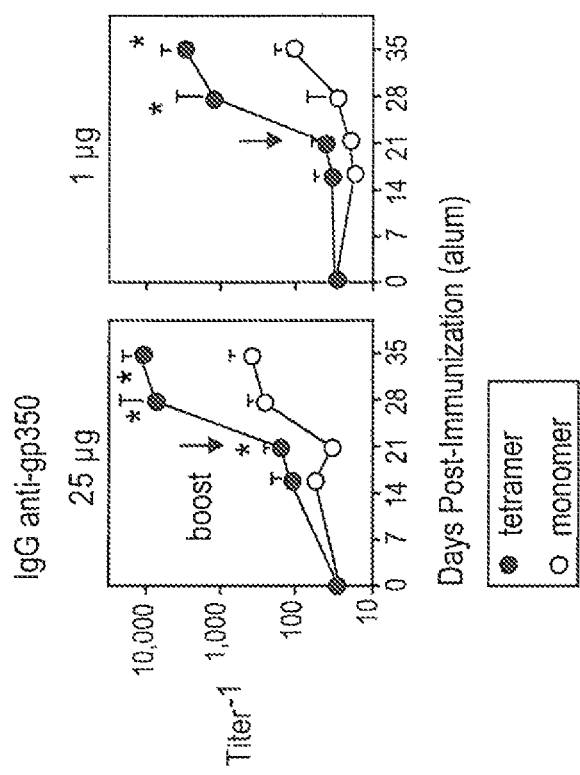

Next the effects of an adjuvant more potent than alum were tested to determine whether the differences observed between the immunogenicity of tetrameric and monomeric gp350 would still be manifest in the presence of the more potent adjuvant. Mice were immunized i.p. with 25 or 1.0 μg of tetrameric or monomeric gp350 per mouse in the presence of alum and 25 μg of a stimulatory 30-mer CpG-containing oligodeoxynucleotide (CpG-ODN), a ligand for Toll-like receptor (TLR)9 [40]. Addition of CpG-ODN to alum resulted in a 21-fold enhancement in the secondary serum gp350-specific IgG titers in response to 25 μg of tetrameric gp350 relative to that observed using only alum as adjuvant (FIG. 3B). Similarly, CpG-ODN enhanced the response to 25 μg of monomeric gp350 by 54-fold. Nevertheless, at the 25 μg dose, tetrameric gp350 still induced 11-fold higher gp350-specific IgG titers relative to 25 μg of monomer. Of note, in the presence of alum+CpG-ODN, 1 μg of tetrameric gp350 induced responses that were comparable to mice receiving 25 μg of monomer. Even at the lower and much weaker immunogenic dose of 1 μg, tetrameric gp350 induced 21-fold higher serum titers of gp350-specific IgG relative to monomer. Thus, tetrameric gp350 is markedly more immunogenic than monomeric gp350 even in the presence of a relatively strong adjuvant.

Figures 3C, 3D:
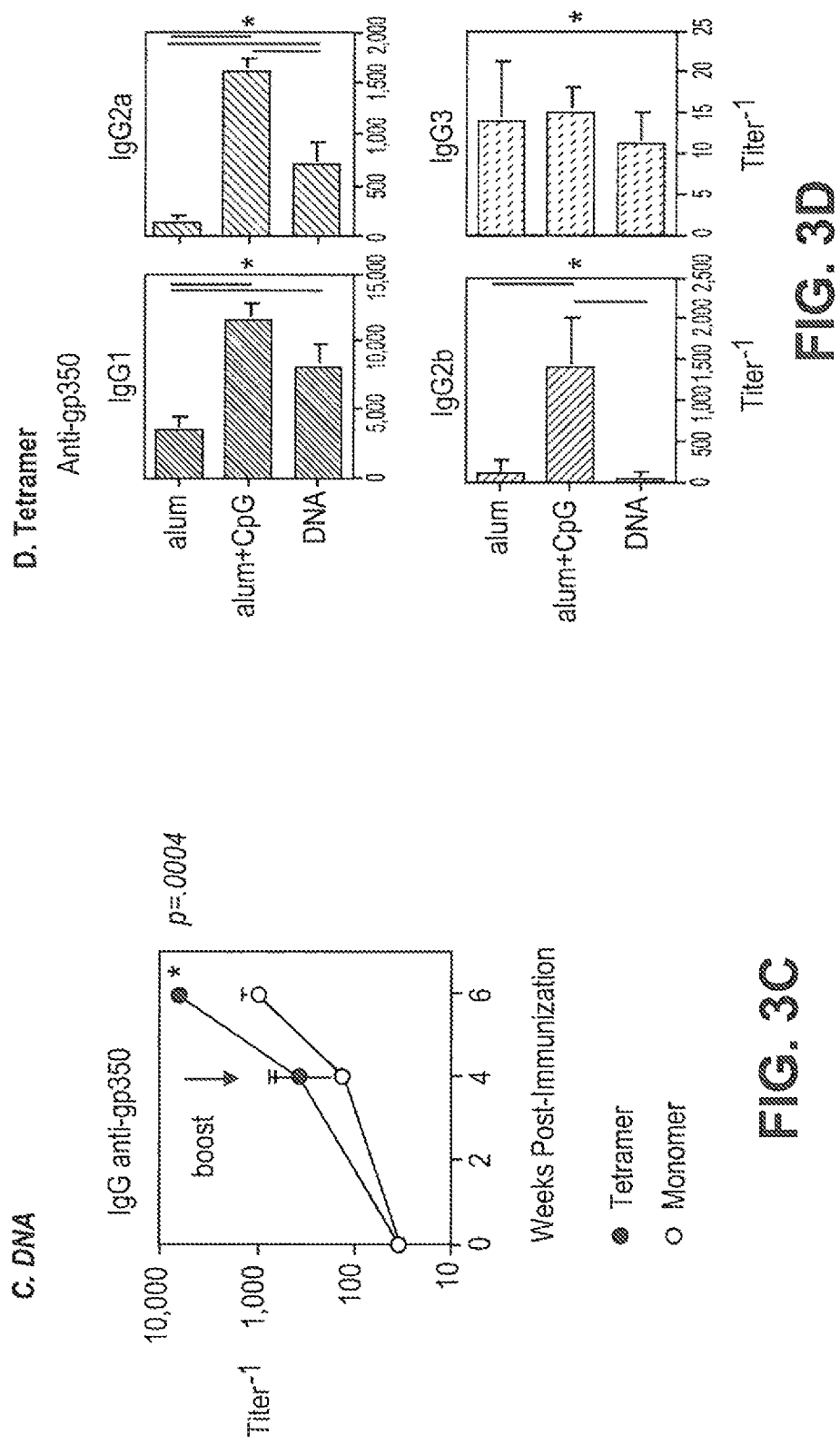

Vaccination with plasmid DNA may confer a number of advantages over protein immunization [41], including the ability to elicit both humoral and cell-mediated immunity in a safe and cost-effective manner. Thus, the level of induction of gp350-specific IgG following primary immunization, and boost at 4 weeks, of equal amounts of DNA encoding monomer versus tetramer was compared. DNA was introduced into the epidermis on microscopic gold particles (i.e. particle-mediated epidermal delivery [PMED]) [42, 43]. Primary immunization with either plasmid induced minimal serum titers of gp350-specific IgG by 4 weeks (FIG. 3C). However, upon boosting, both plasmids induced a significant gp350-specific IgG response by week 6. Of note, the secondary gp350-specific IgG response to the DNA encoding tetrameric gp350 was 8-fold higher (p=0.0004) than that elicited by DNA encoding the monomer. Analysis of serum gp350-specific IgG isotype titers for tetrameric gp350 protein in alum+/−CpG-ODN (25 μg dose) and DNA encoding tetrameric gp350 were compared (FIG. 3D). As anticipated, gp350 protein in alum alone elicited a primarily IgG1 response. Addition of CpG-ODN significantly boosted the gp35 0-specific IgG1 response over that seen with alum alone, and further induced scrim titers of gp350-specific IgG2b and IgG2a. DNA vaccination induced serum titers of gp350-specific IgG1 and IgG2a comparable to and lower (about 3-fold), respectively, to that observed for gp350 protein in alum+CpG-ODN, whereas no detectable IgG2b was observed in response to DNA (FIG. 3D). Minimal titers of gp350-specific IgG3 were produced in response to any of the 3 immunization groups.

Example 3: The Enhanced gp350-Specific IgG Response Requires Both Priming and Boosting with the Tetrameric Form of gp350

Figure 4:
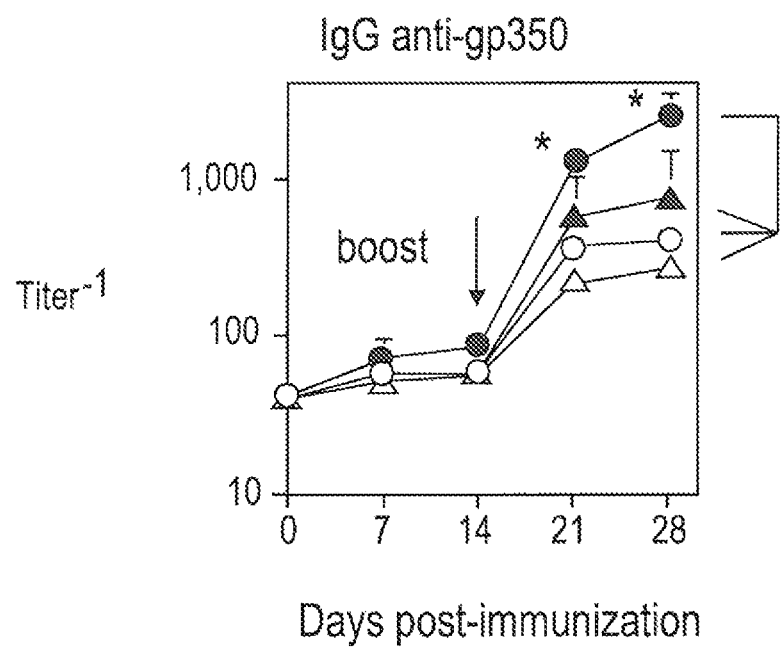
FIG. 4 shows that the enhanced gp350-specific IgG response requires both priming and boosting with tetrameric gp350. Mice (5 per group) were primed and boosted as indicated with tetrameric or monomeric gp350 in alum.

The stimulatory requirements for elicitation of a T cell-dependent secondary response are typically less stringent than that for induction of a primary [44, 45]. The substantially higher secondary gp350-specific IgG responses observed following priming and boosting with tetrameric gp350 relative to monomer, could have been caused by the tetrameric gp350 during the primary and/or secondary immunization. To determine this, four groups of mice were established in which various combinations of priming and boosting with tetrameric and monomer gp350 were performed, using alum as adjuvant. As illustrated in FIG. 4, only both priming and boosting with tetrameric gp350 resulted in significantly higher secondary serum titers of gp350-specific IgG relative to priming and boosting with monomer.

Example 4: Immunization with Tetrameric gp350 Protein Induces Markedly Higher Levels of Neutralizing gp350-Specific Ig Relative to Monomer Binding of EBV gp350 to CD21 is necessary for viral entry into the B cell. [5, 6], an event that is critical for infectivity and B cell neoplastic transformation [2]. Thus, elicitation of antibody that blocks this interaction (i.e. "neutralizing" antibody) [7] may serve as the basis for an effective prophylactic EBV vaccine [17, 18]. In this regard, a gp350-specific mAb was previously produced (clone 72A1), that can specifically block gp350 binding to human CD21 [31]. To measure the amount of neutralizing antibody in sera from gp350-immunized mice, an erythroleukemia cell line transfected with human CD21 (CR2M1α) was used. Initially, monomeric gp350 was directly labeled with the fluorochrome DyLight 633 and mixed with varying amounts of 72A1 mAb prior to incubation with CR2M1α cells. A standard neutralization curve was generated that related the amount of 72A1 mAb added with a fixed amount of gp350-DyLight 633, and the subsequent mean fluorescence intensity (MFI) of staining of CR2M1α cells. Monomeric gp350-DyLight 633 was then mixed with undiluted pre-immune sera or sera from mice following priming and boosting with 25 µg of tetrameric or monomeric gp350 and subsequently incubated with CR2M1α cells. As illustrated in FIG. 5, pre-immune sera contained <4.0 µg/ml of 72A1 mAb-equivalents of neutralizing activity. Whereas, monomeric gp350 induced 13 µg/ml of neutralizing activity, tetramer induced 253 µg/ml, a 19-fold greater level of activity than monomer. Of interest the difference in neutralizing activity between sera obtained from monomer—versus tetramer-immunized mice closely mirrored the difference observed for total (neutralizing and non-neutralizing) serum titers of gp350-specific IgG (see FIG. 3). These data indicate that tetrameric gp350 is a more effective EBV vaccine candidate than monomeric gp350, the latter already shown to be safe, and to have partial efficacy in reducing the incidence of infectious mononucleosis in phase I/II clinical trials [17, 18].

Example 5: Priming with TT Protein can Inhibit the gp350-Specific IgG Response to Tetrameric, but not Monomeric gp350

Two universal TT-specific TT epitopes were introduced into the tetrameric gp350 vaccine with the expectation that this would contribute to the enhancement of the gp350-specific IgG response relative to monomeric gp350. In this regard, children typically receive TT as a vaccine for protection against *Clostridium tetani*, and thus are likely to have TT-primed CD4+ T cells. It has been demonstrated that pre-immunization of mice with TT suppressed a subsequent antibody response to synthetic peptides conjugated to TT [46] and that this was due to clonal dominance [47] and required CD4+ T cells for its induction [48]. Thus, it was first determined whether tetrameric gp350 primed TT-specific CD4+ T cells in vivo, and if initial priming of mice with whole TT protein would impact on the subsequent gp350-specific IgG response to tetramer. Mice were immunized with 25 µg of tetrameric or monomeric gp350 in alum. On day 21 spleen cells were isolated and cultured with the $P_2$ and $P_{30}$ TT peptides, followed by flow cytometric analysis of gated CD4+ T cells for intracytoplasmic expression of IL-4 and IL-5. CD4+ T cells from mice primed with tetrameric gp350, but not monomer-primed or naïve mice, exhibited a significant increase in CD4+ T cells expressing cytoplasmic IL-4 and IL-5 following elicitation with TT peptide in vitro, but not in the presence of medium alone (FIG. 6A). This indicated that tetrameric gp350 primed TT-specific CD4+ T cells in vivo. Next, naive mice were immunized with 25 µg of whole TT protein in alum, with boosting in a similar fashion on day 14, resulting in readily detectable serum titers of TT-specific IgG by day 21 (data not shown). TT-primed and non-primed mice were then immunized with 25 µg of monomeric or tetrameric gp350 in alum and boosted in a similar fashion 14 days later. Non-primed mice immunized with tetrameric gp350 elicited a significantly higher gp350-specific IgG response relative to monomer (FIG. 6B), as demonstrated earlier (FIG. 3A). However, in TT-primed mice, the gp350-specific IgG response was inhibited in response to tetrameric, but not monomeric, grp350, so that no significant difference in serum titers was observed between the two groups. Utilizing a 100-fold lower dose of TT that induced about 3-fold lower secondary serum titers of TT-specific IgG than that observed using 25 µg of TT for priming (data not shown), no inhibition was observed, and no enhancement, of the gp350-specific IgG response to tetramer (FIG. 6C). The TT-specific IgG antibodies elicited in response to TT did not bind tetrameric gp350 as indicated by ELISA assay (data not shown), consistent with $P_2$ and $P_{30}$ being T cell, and not B cell, epitopes. Thus, TT priming, in a dose-dependent fashion, can result in inhibition of an antibody response to a protein antigen containing TT-specific T cell epitopes, consistent with earlier reports [46-48].

Example 6: The TT-Specific T Cell Epitopes in Tetrameric gp350 do not Contribute to the gp350-Specific IgG Response in Naïve Mice To determine the extent, if any, to which the TT epitopes contributed to the more potent immunogenicity of tetrameric versus monomeric gp350 in naïve mice, a new DNA plasmid was constructed in which the TT-specific T cell epitopes were deleted in the DNA encoding tetrameric TT (referred to as "tetramer$^{-tt}$"). The new plasmid was validated by sequencing, and immunoelectrophoresis of CHO cell-expressed protein using 72A1 mAb. A new set of mice were immunized with 25 or 1.0 µg of monomer, tetramer, or tetramer$^{-tt}$ in alum and boosted in a similar fashion on day 21. As illustrated in FIG. 7A, the tetramer and tetramer$^{-tt}$ induced dose-dependent gp350-specific IgG responses that were not significantly different from each other, but that were each about 25-fold higher than that elicited by monomer at each of the two doses. Again, in contrast to the robust gp350-specific IgG responses observed with 1 µg of tetramer or tetramer$^{tt}$, 1 µg of monomer induced a barely detectable response. Similarly, tetramer and tetramer$^{-tt}$ elicited a similar gp350-specific neutralizing antibody response at the 25 µg dose, that was each greater than 40-fold higher than that elicited by monomer (FIG. 7B). Finally, immunization with plasmid DNA encoding tetramer and tetramer$^{-tt}$ elicited gp350-specific IgG responses that were similar, but about 8-fold higher than that observed using plasmid DNA encoding monomeric gp350 (FIG. 7C). These data strongly suggest that the marked enhancement in the gp350-specific IgG response to tetrameric versus monomeric gp350 is based exclusively on protein multimerization, and not to the provision of stronger T cell epitopes.

Example 7: Tetrameric Gp350 Binds More Avidly to Human CD21 than Monomer

The capacity of B cells to bind cognate antigen via their B cell receptor (BCR) and present the resulting peptide/

MHC-II to CD4+ T cells is a critical event in the evolution of a T cell-dependent humoral immune response. In this regard, multimerization of antigen may boost immunogenicity, at least in part, by promoting more avid BCR binding to specific B cells. Gp350 is a ligand for human, although not mouse, CD21. Thus, human CD21, expressed by the CR2M1α, was used as a surrogate for BCR binding to gp350, to compare the efficiency of binding of tetrameric versus monomeric gp350. To accomplish this, CR2M1α cells were incubated with increasing concentrations of unlabeled monomer or tetramer (0.05-30 μg/ml), followed by unlabeled 2L10 mAb (mouse IgG1 anti-gp350). This mAb binds to gp350 at a site distinct from the CD21-binding site, and hence is not blocked upon gp350/CD21 binding. This was followed by staining with DyLight 633-labeled goat anti-mouse IgG and analysis by flow cytometry. Incubation of CR2M1α cells with increasing concentrations of monomeric and tetrameric gp350 resulted in a dose-dependent progressive increase in MFI staining in both cases (FIG. 8). Of note, staining using 1.25 μg/ml of tetrameric gp350 resulted in an MFI equivalent to 30 μg/ml of monomeric gp350, suggesting about 24-fold greater binding avidity of tetramer versus monomer. This degree of difference in apparent avidity of binding is similar to that observed for induction of gp350-specific IgG and neutralizing antibody in response to tetramer versus monomer. These data are consistent with the notion that greater BCR binding to tetrameric gp350 by gp350-specific B cells may account, at least in part, for its greater immunogenicity in vivo.

Example 8: Neither Monomeric Nor Tetrameric gp350 Polyclonally Activates Human B Cells Purified, recombinant gp350 has been shown to upregulate IL-6 mRNA synthesis in human B cells in a CD21-dependent manner [49]. This suggests that tetrameric gp350, which is predicted to induce CD21 crosslinking on human B cells, could potentially act as a polyclonal B cell activator, with possible unwanted side-effects when used as a vaccine. To determine this, purified peripheral blood human B cells were incubated with 10 μg/ml of monomeric or tetrameric gp350, or a negative control protein (pneumococcal surface protein A [PspA]). As positive controls we used anti-IgM antibody or SAC+IL-2 for B cell activation. As illustrated in FIG. 9, neither monomeric nor tetrameric gp350, not PspA, unregulated the activation markers CD69 (at 24 hrs) or CD25 (at 24 or 72 hrs), nor the costimulatory molecule CD86 (at 24 or 72 hrs). In contrast, anti-IgM or SAC+IL-2 strongly upregulated all 3 of these markers. Further, in contrast to anti-IgM or SAC+IL-2, neither monomeric nor tetrameric gp350 induced increases in B cell size (data not shown). These data are consistent with a previous report demonstrating that aggregated or latex-bound C3dg, which crosslink CD21, lack the ability to directly trigger G1 entry by resting human B cells [50]. These data strongly suggest that a tetrameric gp350 vaccine will not induce polyclonal B cell activation in vivo.

Example 9: Tetrameric Gp350 Immunization in a Permissive Rabbit Model

The rabbit, in contrast to the mouse, is a permissive model for EBV infection, and thus ideal for pre-clinical testing of an EBV vaccine [67]. This likely reflects, in part, our own observation that rabbit B cells, in contrast to mouse B cells, bind gp350, most likely by binding to B cell CD21. Thus, flow cytometric analysis using Dylight-labeled gp350 and FITC-anti-rabbit IgM mAb to stain B cells was conducted to determine whether gp350 binds to rabbit B cells. Both peripheral blood and splenic B cells, isolated from New Zealand white rabbits, showed strong double staining. No staining was observed using a negative control, Dylight-labeled pneumococcal surface protein A (PspA) (data not shown).

Next a series of dose response immunization studies of tetrameric versus monomeric gp350 were performed to determine the relative immunogenicity of monomeric gp350 and tetrameric gp350 in rabbits. Rabbits (4 per group) were immunized s.c. with 5.0, 1.0, or 0.2 μg of monomeric or tetrameric gp350 in alum and boosted in a similar fashion on day 14. Sera were collected at day 0, 14, and 28 for measurement of gp350-specific IgG titers by ELISA (FIG. 10). As illustrated, tetrameric gp350 was markedly more immunogenic than monomeric gp350 at all doses. The difference in serum titers of gp350-specific IgG between tetramer and monomer in the rabbit were up to 100-fold, compared to the ~20-fold differences observed in the mouse. Since co-crosslinking of CD21 and the B cell receptor (BCR) induce synergistic B cell signaling, tetrameric gp350 may also act as an intramolecular adjuvant in rabbits (and by extension humans).

Example 10: Construction of Other EBV Multimeric Constructs

EBV infection and persistence is critically dependent upon viral entry into B cells and nasopharyngeal epithelial cells. B cell infection involves initial binding of EBV gp350 to B cell CD21 followed by binding of EBV gp42 to B cell MHC class II molecules. This results in viral fusion and entry mediated by EBV heterodimer and gB. Epithelial cell infection by EBV also involves gH/gL and gB, but not gp350 or gp42. The multimerization technique described in this application has been used to produce an EBV gH/gL heterodimer with a trimerization domain. The multimerization techniques can be similarly used to produce multimeric gB or gp42 constructs.

Discussion:

In this study, a tetramer of the EBV envelope protein gp350 was created by constructing a plasmid in which two copies of a truncated gp350, containing the CD21-binding neutralization epitope, were separated by a linker, to allow for conformational folding. This dimeric gp350 underwent further dimerization to form a tetramer following translation within transfected CHO cells, via homotypic binding of 3' leucine zipper motifs. This protein multimerization strategy resulted in a marked enhancement in elicitation of gp350-specific IgG, including neutralizing antibody, relative to monomeric gp350. Enhanced immunogenicity of tetrameric versus monomeric gp350 was observed following direct immunization with plasmid, or with protein in the presence of even a strong adjuvant such as alum+CpG-ODN. Tetrameric gp350 bound much more efficiently to human CD21 but did not polyclonally activate human B cells. Furthermore, when the immunogenicity of the multimeric construct was tested in the permissive rabbit model, the difference in serum titers of gp350-specific IgG between tetramer and monomer in the rabbit were up to 100-fold, compared to the 20-fold differences observed in the mouse. Thus, these data support the value of testing tetrameric gp350 in clinical trials for its potential to elicit more protective immunity against such EBV-mediated diseases as infectious mononucleosis, and perhaps neoplastic transformation, as opposed to monomeric gp350 used in previous, small-scale human studies

[16-19]. These data also support the use of this multimerization strategy to enhance humoral immune responses to other proteins of vaccine interest, in a reproducible and cost-effective manner.

Multimerization of proteins/peptides has been shown to enhance their immunogenicity. Thus, a plasmid encoding green fluorescent protein (GFP) fused to a long polyglutamine tail that mediates aggregation, induced significantly higher serum GFP-specific Ig titers and enhanced GFP-specific CD8+ CTL activity following prime/boost immunization in mice, relative to non-aggregating GFP [21]. Multimerization of bovine serum albumin (BSA) by covalent attachment of BSA or haptenated BSA to dextran at a ratio of 20-30 BSA2×10$^6$ MW dextran resulted in strong enhancements in elicited murine serum titers of BSA- or hapten-specific IgG1, respectively, relative to unconjugated protein [25]. Rabbits immunized with glutathione S-transferase (GST) fusion proteins with increasing copy number of a peptide epitope (M2e) of the influenza virus M2 protein elicited M2e-specific IgG in response to GST-(M2e)$_8$ with an average affinity constant ($K_A$) of up to two orders of magnitude greater than that induced by GST-(M2e)$_1$ [20]. Covalent attachment of increasing copy number of peptides onto virus-like particles (VLPs) resulted in a positive correlation between epitope density and the magnitude of the peptide-specific murine IgG, although not IgM, response following immunization [23]. Higher epitope densities also allowed for efficient IgG responses in the absence of complement receptor type 2 (CD21). An unwanted consequence of protein multimerization has been absented with the use of therapeutic proteins such as human growth hormone, intravenous immune globulin (IVIG), human serum albumin, human interleukin-2, and human interferon-β in which aggregated proteins within the preparation preferentially induced immune responses, including neutralizing antibody that decreased therapeutic efficacy [22, 24]. Finally, alum, a commonly used adjuvant in clinical vaccines, itself forms aggregates that trap antigen at the site of injection [15]. Of note, in this study, tetrameric gp350 in alum with or without additional adjuvanting with CpG-ODN was nevertheless markedly more immunogenic than monomeric gp350 delivered in the same adjuvants. Although direct evidence in vivo is limited, and without intending to be bound by any theory, the increased immunogenicity of multimeric proteins likely arises from more efficient activation of complement, enhanced binding to the BCR, more efficient BCR-mediated signaling, enhanced B cell uptake and presentation of protein-derived peptide to CD4+ T cells and/or enhanced trapping of multimeric proteins on the surface of follicular dendritic cells [24, 52].

The presence of strong CD4+ T cell, in addition to B cell, epitopes is important for robust T cell-dependent (TD) IgG responses to protein antigens. In this regard, TT was shown to be a significantly more potent carrier protein than gp350 for eliciting a TD IgG response specific for a pneumococcal polysaccharide, as part of a conjugate vaccine. This strongly suggested that TT contained more potent CD4+ T cell epitopes than gp350 for delivery of helper function to B cells. Accordingly, the initial gp350 tetramer design incorporated two known universal TT-specific CD4+ T cell epitopes. However, the data in this study unexpectedly show that not only did the TT epitopes not contribute to the immunogenicity of the tetramer in naïve mice, but they actually mediated inhibition of antibody responses in TT-primed mice. This latter observation was relevant in light of the widespread use of TT as a clinical vaccine. In this regard, it has been demonstrated that pre-immunization of mice with TT suppressed a subsequent antibody response to synthetic peptides conjugated to TT [46] and that this was due to clonal dominance [47] and required CD4+ T cells for its induction [48]. However, it is possible that inclusion of other universal human CD4+ T cell epitopes such as N19 [53, 54] or PADRE [55, 56] might prove more successful.

EBV gp350 binds to human (and rabbit), but not mouse, CD21 [57]. Physiologically, CD21 expressed on B cells and follicular dendritic cells (FDC) binds the complement fragment C3d that in association with antigen, promotes immunogenicity [26, 58, 59]. This likely occurs via co-crosslinking of BCR and CD21, leading to highly synergistic B cell signaling [60], and trapping of antigen via CD21 on FDC to promote germinal center formation [61]. A previous study further demonstrated that gp350 could potentially substitute for C3d as an adjuvant, by promoting human B cell signaling via BCR/CD21 co-crosslinking [62]. Enhancement of antigen-specific antibody responses via C3d, involves at least 2 copies of C3d per molecule of antigen. Thus, in humans, gp350-specific B cells binding to tetrameric but not monomeric, gp350 via a single BCR would potentially have access to 2-3 gp350 molecules for CD21 binding, that could facilitate specific BCR/CD21 co-crosslinking and synergistic B cell signaling. In light of this data demonstrating a marked increase in the efficiency of binding of tetramer versus monomer to human CD21, we predict that tetrameric gp350 will also bind to specific BCR, as well CD21-expressing human FDC with greater avidity than monomeric gp350. Collectively, these observations strongly suggest that gp350, expressed as a tetramer, will act as both a molecular adjuvant as well as a specific target antigen for a clinical EBV vaccine. Importantly, tetrameric gp350 by itself did not polyclonally activate human B cells, thus obviating concerns for unwanted non-specific immune stimulation in vivo.

The molecular strategy described herein for creating tetrameric gp350 could also be applied to boost humoral immune, responses to other proteins of vaccine interest, including other EBV proteins, such as gH/gL, gp42, and gB. Further, gp350 might be of value as a molecular adjuvant for another target protein, through creation of a heterodimer linked to a leucine zipper for dimerization, or a trimerization motif such as the T4 bacteriophage fibritin (FT) [63] or the eukaryotic GCN4 transcription factor motif (GCN4) [64]. Finally, heterodimers comprising a target protein and an additional protein possessing adjuvant activity, such as flagellin [65], or for example to an scFv fragment that targets an antigen-presenting cell or innate receptor [66], may generate additional, highly immunogenic multimeric proteins for vaccination.

REFERENCES

The following references are cited in the application and provide general information on the field of the invention and provide assays and other details discussed in the application. The following references are incorporated herein by reference in their entirety.

[1] Cohen J I. The biology of Epstein-Barr virus: lessons learned from the virus and the host. Current opinion in immunology 1999 August; 11(4):365-70.
[2] Thorley-Lawson D A. EBV the prototypical human tumor virus—just how bad is it? J Allergy Clin Immunol 2005 August; 116(2):251-61; quiz 62.
[3] Vetsika E K, Callan M. Infectious mononucleosis and Epstein-Barr virus. Expert Rev Mol Med 2004 Nov. 5; 6(23):1-16.

[4] Babcock G J, Decker L L, Volk M, Thorley-Lawson D A. EBV persistence in memory B cells in vivo. Immunity 1998 September; 9(3):395-404.

[5] Tanner J, Weis J, Fearon D, Whang Y, Kieff E. Epstein-Barr virus gp350/220 binding to the B lymphocyte C3d receptor mediates adsorption, capping, and endocytosis. Cell 1987 Jul. 17; 50(2):203-13.

[6] Tanner J, Whang Y, Sample J, Sears A, Kieff E. Soluble gp350/220 and deletion mutant glycoproteins block Epstein-Barr virus adsorption to lymphocytes. Journal of virology 1988; 62(12):4452-64.

[7] Thorley-Lawson D A, Poodry C A. Identification and isolation of the main component (gp350-gp220) of Epstein-Barr virus responsible for generating neutralizing antibodies in vivo. Journal of virology 1982 August; 43(2):730-6.

[8] Morgan A J, Epstein M A, North J R. Comparative immunogenicity studies on Epstein-Barr virus membrane antigen (MA) gp340 with novel adjuvants in mice, rabbits, and cotton-top tamarins. J Med Virol 1984; 13(3): 281-92.

[9] Morgan A J, Allison A C, Finerty S, Scullion F T, Byars N E, Epstein M A, Validation of a first-generation Epstein-Barr virus vaccine preparation suitable for human use. J Med Virol 1989 September; 29(1):74-8.

[10] Finerty S, Tarlton J, Mackett M, Conway M, Arrand J R, Watkins P E, et al. Protective immunization against Epstein-Barr virus-induced disease in cottontop tamarins using the virus envelope glycoprotein gp340 produced from a bovine papillomavirus expression vector. J Gen Virol 1992 February; 73 (Pt 2):449-53.

[11] Finerty S, Mackett M, Arrand J R, Watkins P E, Tarlton J, Morgan A J. Immunization of cottontop tamarins and rabbits with a candidate vaccine against the Epstein-Barr virus based on the major viral envelope glycoprotein gp340 and alum. Vaccine 1994 October; 12(13):1180-4.

[12] Cox C, Naylor B A, Mackett M, Arrand J R, Griffin B E, Wedderburn N. Immunization of common marmosets with Epstein-Barr virus (EBV) envelope glycoprotein gp340: effect on viral shedding following EBV challenge. J Med Virol 1998 August; 55(4):255-61.

[13] Mackett M, Cox C, Pepper S D, Lees J F, Naylor B A, Wedderburn N, et al. Immunisation of common marmosets with vaccinia virus expressing Epstein-Barr virus (EBV) gp340 and challenge with EBV. J Med Virol 1996 November; 50(3):263-71.

[14] Ragot T, Finerty S, Watkins P E, Perricaudet M, Morgan A J. Replication-defective recombinant adenovirus expressing the Epstein-Barr virus (EBV) envelope glycoprotein gp340/220 induces protective immunity against EBV-induced lymphomas in the cottontop tamarin. J Gen Virol 1993 March; 74 (Pt 3):501-7.

[15] Morgan A J, Mackett M, Finerty S, Arrand J R, Scullion F T, Epstein M A. Recombinant vaccinia virus expressing Epstein-Barr virus glycoprotein gp340 protects cottontop tamarins against EB virus-induced malignant lymphomas. J Med Virol 1988 June; 25(2):189-95.

[16] Gu S Y, Huang T M, Ruan L, Miao Y H, Lu H, Chu C M, et al. First EBV vaccine trial in humans using recombinant vaccinia virus expressing the major membrane antigen. Dev Biol Stand 1995; 84:171-7.

[17] Sakai E M, Hoppenbrouwers K, Vandermeulen C, Moutsehen M, Leonard P, Moreels A, et al. Recombinant gp350 vaccine for infectious mononucleosis: a phase 2 randomized, double-blind, placebo-controlled trial to evaluate the safety, immunogenicity, and efficacy of an Epstein-Barr virus vaccine in healthy young adults. The Journal of infectious diseases 2007 Dec. 15; 196(12): 1749-53.

[18] Moutschen M, Leonard P, Sokal E M, Smets F, Haumont M, Mazza P, et al. Phase I/II studies to evaluate safety and immunogenicity of a recombinant gp350 Epstein-Barr virus vaccine in healthy adults. Vaccine 2007 Jun. 11; 25(24):4697-705.

[19] Rees L, Tizard E J, Morgan A J, Cuhitt W D, Finerty S, Oyewole-Eletu T A, et al. A phase I trial of epstein-barr virus gp350 vaccine for children with chronic kidney disease awaiting transplantation. Transplantation 2009 Oct. 27; 88(8):1025-9.

[20] Liu W, Chen Y H. High epitope density in a single protein molecule significantly enhances antigenicity as well as immunogenicity: a novel strategy for modern vaccine development and a preliminary investigation about B cell discrimination of monomeric proteins. European journal of immunology 2005 February; 35(2):505-14.

[21] Ilyinskii P O, Thoidis G, Sherman M Y, Shneider A. Adjuvant potential of aggregate-forming polyglutamine domains. Vaccine 2008 Jun. 19; 26(26):3223-6.

[22] van Beers M M, Jiskoot W, Schellekens H. On the role of aggregates in the immunogenicity of recombinant human interferon beta in patients with multiple sclerosis. J Interferon Cytokine Res 2010 October; 30(10):767-75.

[23] Jegerlehner A, Storni T, Lipowsky G, Schmid M, Pumpens P, Bachmann M F. Regulation of IgG antibody responses by epitope density and CD21-mediated costimulation. European journal of immunology 2002 November; 32(11):3305-14.

[24] Rosenberg A S. Effects of protein aggregates: an immunologic perspective, AAPS J 2006; 8(3):E501-7.

[25] Lees A, Finkelman F, Inman J K, Witherspoon K, Johnson P, Kennedy J, et al. Enhanced immunogenicity of protein-dextran conjugates: I. Rapid stimulation of enhanced antibody responses to poorly immunogenic molecules. Vaccine 1994 October; 12(13):1160-6.

[26] Dempsey P W, Allison M E, Akkaraju S, Goodnow C C, Fearon D T. C3d of complement as a molecular adjuvant: bridging innate and acquired immunity. Science 1996 Jan. 19; 271(5247):348-50.

[27] Czenvinski M, Siegel D L, Moore J S, Spitalnik P F, Spitalnik S L, Construction of bacteriophage expressing mouse monoclonal Fab fragments directed against the human MN glycophorin blood group antigens. Transfusion 1995 February; 35(2):137-44.

[28] O'Shea E K, Rutkowski R, Kim P S. Evidence that the leucine zipper is a coiled coil. Science 1989 Jan. 27; 243(4890):538-42.

[29] Sarrias M R, Franchini S. Canziani G, Argyropoulos E, Moore W T, Sahu A, et al. Kinetic analysis of the interactions of complement receptor 2 (CR2, CD21) with its ligands C3d, iC3b, and the EBV glycoprotein gp350/220. J Immunol 2001 Aug. 1; 167(3):1490-9.

[30] Valmori D, Pessi A, Bianchi E, Corradin G. Use of human universally antigenic tetanus toxin T cell epitopes as carriers for human vaccination. J Immunol 1992 Jul. 15; 149(2):717-21.

[31] Hoffman G J, Lazarowitz S G, Hayward S D. Monoclonal antibody against a 250,000-dalton glycoprotein of Epstein-Barr virus identifies a membrane antigen and a neutralizing antigen. Proceedings of the National Academy of Sciences of the United States of America 1980 May; 77(5):2979-83.

[32] Khan A Q, Lees A, Snapper C M. Differential regulation of IgG anti-capsular polysaccharide and antiprotein responses to intact *Streptococcus pneumoniae* in the presence of cognate CD4+ T cell help. J Immunol 2004 Jan. 1; 172(1):532-9.

[33] Sen G, Flora M, Chattopadhyay G, Klinman D M, Lees A, Mond J J. et al. The critical DNA flanking sequences of a CpG oligodeoxynucleotide, but not the 6 base CpG motif, can be replaced with RNA without quantitative or qualitative charges in Toll-like receptor 9-mediated activity. Cell Immunol 2004 November-December; 232(1-2): 64-74.

[34] Pertmer T M, Eisenbraun M D, McCabe D, Prayaga S K, Fuller D H, Haynes J R. Gene gun-based nucleic acid immunization: elicitation of humoral and cytotoxic T lymphocyte responses following epiderinal delivery of nanogram quantities of DNA, Vaccine 1995; 13(15): 1427-30.

[35] Carel J C, Frazier B, Ley T J, Holers V M. Analysis of epitope expression and the functional repertoire of recombinant complement receptor 2 (CR21CD21) in mouse and human cells. J Immunol 1989 Aug. 1; 143(3):923-30.

[36] Nemerow G R, Houghten R A, Moore M D, Cooper N R. Identification of an epitope in the major envelope protein of Epstein-Barr virus that mediates viral binding to the B lymphocyte EBV receptor (CR2). Cell 1989 Feb. 10; 56(3):369-77.

[37] Nemerow G R, Cooper N R. Early events in the infection of human B lymphocytes by Epstein-Barr virus: the internalization process. Virology 1984 Jan. 15; 132 (1):186-98.

[38] Zaborsky N, Brunner M, Wanner M, Himly M, Karl T, Schwarzenbacher R, et al. Antigen aggregation decides the fate of the allergic immune response. S Immunol 2010 Jan. 15; 184(2):725-35.

[39] Fradkin A R, Carpenter J F, Randolph T W. Immunogenicity of aggregates of recombinant human growth hormone in mouse models, J Pharm Sci 2009 September; 98(9):3247-64.

[40] Hemmi H, Takeuchi O, Kawai T, Kaisho T, Sato S, Sanjo H, et al. A Toll-like receptor recognizes bacterial DNA, Nature 2000; 408(6813):740-5.

[41] Ferraro B, Morrow M P, Hutnick N A, Shin T H, Lucke C E, Weiner D B. Clinical applications of DNA vaccines: current progress, Clinical infectious diseases: an official publication of the Infectious Diseases Society of America 2011 Aug. 1; 53(3):296-302.

[42] Yager E J, Dean H H, Fuller D H. Prospects for developing an effective particle-mediated DNA vaccine against influenza. Expert review of vaccines 2009 September; 8(9):1205-20.

[43] Roy M J, Wu M S, Barr L J, Fuller J T, Tussey L G, Speller S, et al. Induction of antigen-specific CD8+ T cells, T helper cells, and protective levels of antibody in humans by particle-mediated administration of a hepatitis B virus DNA vaccine. Vaccine 2000 Nov. 22; 19(7-8): 764-78.

[44] Luqman M, Bottomly K. Activation requirements for CD4+ T cells differing in CD45R expression. J Immunol 1992 Oct. 1; 149(7):2300-6.

[45] Ronchese F, Hausmann B. B lymphocytes in vivo fail to prime naive T cells but can stimulate antigen-experienced T lymphocytes. The Journal of experimental medicine 1993 Mar. 1; 177(3):679-90.

[46] Schutze M P, Leclerc C, Jolivet M, Audibert F, Chedid L. Carrier-induced epitopic suppression, a major issue for future synthetic vaccines. J Immunol 1985 October; 135 (4):2319-22.

[47] Schutze M P, Deriaud E, Przewlocki G, LeClerc C. Carrier-induced epitopic suppression is initiated through clonal dominance. J Immunol 1989 Apr. 15; 142(8):2635-40.

[48] Leclerc C, Schutze M P, Deriaud B, Przewlocki G. The in vivo elimination of CD4+ T cells prevents the induction but not the expression of carrier-induced epitopic suppression. J Immunol 1990 Sep. 1; 145(5):1343-9.

[49] D'Addario M, Libermann T A, Xu J, Ahmad A, Menezes J. Epstein-Barr Virus and its glycoprotein-350 upregulate IL-6 in human B-lymphocytes via CD21, involving activation of NF-kappaB and different signaling pathways. Journal of molecular biology 2001; 308(3): 501-14.

[50] Bohnsack J F, Cooper N R. CR2 ligands modulate human B cell activation. J Immunol 1988 Oct. 15; 141 (8):2569-76.

[51] Shirodkar S, Hutchinson R L, Perry D L, White J L, Hem S L. Aluminum compounds used as adjuvants in vaccines. Pharmaceutical research 1990 December; 7(12):1282-8.

[52] Bachmann M F, Jennings G T. Vaccine delivery: a matter of size, geometry, kinetics and molecular patterns. Nature reviews Immunology 2010 November; 10(11): 787-96.

[53] Baraldo K, Mori E, Bartoloni A, Norelli F, Grandi G, Rappuoli R, et al. Combined conjugate vaccines: enhanced immunogenicity with the N19 polyepitope as a carrier protein. Infection and immunity 2005 September; 73(9):5835-41.

[54] Falugi F, Petracca R, Mariani M, Luzzi E, Mancianti S, Carinei V, et al. Rationally designed strings of promiscuous CD4(+) T cell epitopes provide help to *Haemophilus influenzae* type b oligosaccharide: a model for new conjugate vaccines. European journal of immunology 2001 December; 31(12)3816-24.

[55] del Guercio M F, Alexander J, Kubo R T, Arrhenius T, Maewal A, Appella E, et al. Potent immunogenic short linear peptide constructs composed of B cell epitopes and Pan DR T helper epitopes (PADRE) for antibody responses in vivo. Vaccine 1997 March; 15(4):441-8.

[56] Alexander J, del Guercio M F, Maewal A, Qiao L, Fikes J, Chesnut R W, et al. Linear PADRE T helper epitope and carbohydrate B cell epitope conjugates induce specific high titer IgG antibody responses. J Immunol 2000 Feb. 1; 164(3):1625-33.

[57] Martin D R, Yuryev A, Kalli K R, Fearon D T, Ahearn J M. Determination of the structural basis for selective binding of Epstein-Barr virus to human complement receptor type 2. The Journal of experimental medicine 1991 Dec. 1; 74(6):1299-311.

[58] Test S T, Mitsuyoshi J, Connolly C C, Lucas A H. Increased immunogenicity and induction of class switching by conjugation of complement C3d to pneumococcal serotype 14 capsular polysaccharide. Infection and immunity 2001 May; 69(5):3031-40.

[59] Ross T M, Xu Y, Bright R A, Robinson H L. C3d enhancement of antibodies to hemagglutinin accelerates protection against influenza virus challenge. Nature immunology 2000 August; 1(2):127-31.

[60] Fearon D T, Carter R H. The CD19/CR2/TAPA-1 complex of B lymphocytes: linking natural to acquired immunity. Annual review of immunology 1995; 13:127-49.
[61] Allen C D, Cyster J G, Follicular dendritic cell networks of primary follicles and germinal centers: phenotype and function. Semin Immunol 2008 February; 20(1):14-25.
[62] Goeckeritz B E, Lees A, Vos Q, Tsokos G C, Kuhlbusch K, Mond J J. Enhanced and sustained activation of human B cells by anti-immunoglobulin conjugated to the EBV glycoprotein gp350. European journal of immunology 2000; 30(3):969-73.
[63] Bower J F, Yang X, Sodroski J, Ross T M. Elicitation of neutralizing antibodies with DNA vaccines expressing soluble stabilized human immunodeficiency virus type I envelope glycoprotein trimers conjugated to C3d. Journal of virology 2004 May; 78(9):4710-9.
[64] Zhang P F, Cham F, Doug M, Choudhary A, Bouma P, Zhang Z, et al. Extensively cross-reactive anti-HIV-1 neutralizing antibodies induced by gp140 immunization. Proceedings of the National Academy of Sciences of the United States of America 2007 Jun. 12; 104(24):10193-8.
[65] McSorley S J, Ehst B D, Yu Y, Gewirtz A T. Bacterial flagellin is an effective adjuvant for CD4(+) T cells in vivo. J Immunol 2002 Oct. 1; 169(7):3914-9.
[66] Tunheim G, Thompson K M, Fredriksen A B, Espevik T, Schjetne K W, Bogen B. Human receptors of innate immunity (CD14, TLR2) are promising targets for novel recombinant immunoglobulin-based vaccine candidates. Vaccine 2007 Jun. 11; 25(24):4723-34.
[67] Okuno K, et al., Epstein-Barr virus can infect rabbits by the nanasa or peroral route: an animal model for natural primary EBV infection in humans. J. Med. Virol. 2010 82: 977.

What is claimed:

1. A fusion protein comprising a first antigen, a linker sequence, a second antigen, and an oligomerization domain,
   wherein the linker sequence is a polypeptide having 5 to 25 amino acids and wherein the linker sequence joins the first antigen to the second antigen,
   wherein the first and second antigens are herpesvirus antigens,
   wherein the fusion protein does not include a tetanus toxoid protein, and wherein the fusion protein is capable of inducing an enhanced immune response in a subject in comparison to a fusion protein in the absence of the linker and/or the oligomerization domain and
   wherein the first and second antigens are cytomegalovirus (CMV) antigens selected from gB, gL, gH, or pp65 antigens; or
   wherein the first and second antigens are Epstein Barr Virus (EBV) antigens selected from Gp350/220, gB, gL, or gH antigens.

2. The fusion protein of claim 1, wherein the first and second antigens are EBV Gp350/220 antigens.

3. The fusion protein of claim 1, wherein the fusion protein forms a multimeric protein complex when expressed in a host cell.

4. The fusion protein of claim 1, wherein the first and second antigens do not occur naturally as a multimeric protein complex.

5. The fusion protein of claim 1, wherein the oligomerization domain is a dimerization domain, a trimerization domain, or a tetramerization domain.

6. The fusion protein of claim 5, wherein the dimerization domain is a GCN4 yeast leucine zipper domain or a derivative thereof.

7. The fusion protein of claim 5, wherein the trimerization domain is a T4 bacteriophage fibritin motif or a eukaryotic GNC4 transcription factor motif or a derivative thereof.

8. The fusion protein of claim 1, wherein the oligomerization domain is located at the C terminus or N terminus of the fusion protein.

9. The fusion protein of claim 1, wherein the linker sequence is between 10-25 amino acids.

10. The fusion protein of claim 1, wherein the linker sequence comprises glycine and serine amino acids.

11. The fusion protein of claim 1, wherein the antigens are EBV antigens and the first EBV antigen is gL and the second EBV antigen is gH, wherein the oligomerization domain is a trimerization domain, and wherein the fusion protein forms a multimeric protein complex when expressed in a host cell.

12. The fusion proteins of claim 11, wherein the linker sequence is between 10-25 amino acids.

13. The fusion protein of claim 1, wherein the first and second antigens are EBV Gp350/220 antigens, wherein the oligomerization domain is a dimerization domain, and wherein the fusion protein forms a multimeric protein complex when expressed in a host cell.

14. The fusion protein of claim 13, wherein the linker sequence is between 10-25 amino acids.

15. The fusion protein of claim 1, wherein the antigens are CMV antigens and the first CMV antigen is gL and the second CMV antigen is gH, wherein the oligomerization domain is a trimerization domain, and wherein the fusion protein forms a multimeric protein complex when expressed in a host cell.

16. The fusion protein of claim 15, wherein the linker sequence is between 10-25 amino acids.

17. A fusion protein consisting of a first herpesvirus antigen, a linker sequence, a second herpesvirus antigen, and an oligomerization domain,
   wherein the linker sequence is a polypeptide having 5 to 25 amino acids and wherein the linker sequence joins the first antigen to the second antigen, wherein the fusion protein does not include a tetanus toxoid protein, wherein the fusion protein is capable of inducing an enhanced immune response in a subject in comparison to a fusion protein in the absence of the linker and/or the oligomerization domain, wherein the oligomerization domain is a dimerization domain or a trimerization domain, and wherein the fusion protein forms a multimeric protein complex when expressed in a host cell.

* * * * *

SEQUENCE LISTING

```
<160> NUMBER OF SEQ ID NOS: 19

<210> SEQ ID NO 1
<211> LENGTH: 907
<212> TYPE: PRT
<213> ORGANISM: Epstein-Barr virus

<400> SEQUENCE: 1

Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
            115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255
```

```
Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
        290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
        370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
        435                 440                 445

Pro Ser Ser Thr His Val Pro Thr Asn Leu Thr Ala Pro Ala Ser Thr
        450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Lys Ala Pro Asp Met Thr Ser Ser Thr Ser Pro
            500                 505                 510

Val Thr Thr Pro Thr Pro Asn Ala Thr Ser Pro Thr Pro Ala Val Thr
        515                 520                 525

Thr Pro Thr Pro Asn Ala Thr Ser Pro Thr Pro Ala Val Thr Thr Pro
        530                 535                 540

Thr Pro Asn Ala Thr Ser Pro Thr Leu Gly Lys Thr Ser Pro Thr Ser
545                 550                 555                 560

Ala Val Thr Thr Pro Thr Pro Asn Ala Thr Ser Pro Thr Leu Gly Lys
                565                 570                 575

Thr Ser Pro Thr Ser Ala Val Thr Thr Pro Thr Pro Asn Ala Thr Ser
            580                 585                 590

Pro Thr Leu Gly Lys Thr Ser Pro Thr Ser Ala Val Thr Thr Pro Thr
        595                 600                 605

Pro Asn Ala Thr Gly Pro Thr Val Gly Glu Thr Ser Pro Gln Ala Asn
        610                 615                 620

Ala Thr Asn His Thr Leu Gly Gly Thr Ser Pro Thr Pro Val Val Thr
625                 630                 635                 640

Ser Gln Pro Lys Asn Ala Thr Ser Ala Val Thr Thr Gly Gln His Asn
                645                 650                 655

Ile Thr Ser Ser Ser Thr Ser Ser Met Ser Leu Arg Pro Ser Ser Asn
            660                 665                 670
```

```
Pro Glu Thr Leu Ser Pro Ser Thr Ser Asp Asn Ser Thr Ser His Met
            675                 680                 685

Pro Leu Leu Thr Ser Ala His Pro Thr Gly Gly Glu Asn Ile Thr Gln
        690                 695                 700

Val Thr Pro Ala Ser Ile Ser Thr His His Val Ser Thr Ser Ser Pro
705                 710                 715                 720

Glu Pro Arg Pro Gly Thr Thr Ser Gln Ala Ser Gly Pro Gly Asn Ser
                725                 730                 735

Ser Thr Ser Thr Lys Pro Gly Glu Val Asn Val Thr Lys Gly Thr Pro
            740                 745                 750

Pro Gln Asn Ala Thr Ser Pro Gln Ala Pro Ser Gly Gln Lys Thr Ala
        755                 760                 765

Val Pro Thr Val Thr Ser Thr Gly Gly Lys Ala Asn Ser Thr Thr Gly
770                 775                 780

Gly Lys His Thr Thr Gly His Gly Ala Arg Thr Ser Thr Glu Pro Thr
785                 790                 795                 800

Thr Asp Tyr Gly Gly Asp Ser Thr Thr Pro Arg Pro Arg Tyr Asn Ala
                805                 810                 815

Thr Thr Tyr Leu Pro Pro Ser Thr Ser Ser Lys Leu Arg Pro Arg Trp
            820                 825                 830

Thr Phe Thr Ser Pro Pro Val Thr Thr Ala Gln Ala Thr Val Pro Val
        835                 840                 845

Pro Pro Thr Ser Gln Pro Arg Phe Ser Asn Leu Ser Met Leu Val Leu
        850                 855                 860

Gln Trp Ala Ser Leu Ala Val Leu Thr Leu Leu Leu Leu Leu Val Met
865                 870                 875                 880

Ala Asp Cys Ala Phe Arg Arg Asn Leu Ser Thr Ser His Thr Tyr Thr
                885                 890                 895

Thr Pro Pro Tyr Asp Asp Ala Glu Thr Tyr Val
            900                 905

<210> SEQ ID NO 2
<211> LENGTH: 658
<212> TYPE: PRT
<213> ORGANISM: Epstein-Barr virus

<400> SEQUENCE: 2

Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140
```

```
Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
            165                 170                 175

Gln Gly Leu Asp Val Thr Leu Pro Leu Ser Leu Pro Thr Ser Ala Gln
        180                 185                 190

Asp Ser Asn Phe Ser Val Lys Thr Glu Met Leu Gly Asn Glu Ile Asp
    195                 200                 205

Ile Glu Cys Ile Met Glu Asp Gly Glu Ile Ser Gln Val Leu Pro Gly
210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Thr Pro Pro Gln Asn Ala Thr Ser Pro Gln Ala
            500                 505                 510

Pro Ser Gly Gln Lys Thr Ala Val Pro Thr Val Thr Ser Thr Gly Gly
        515                 520                 525

Lys Ala Asn Ser Thr Thr Gly Gly Lys His Thr Thr Gly His Gly Ala
    530                 535                 540

Arg Thr Ser Thr Glu Pro Thr Thr Asp Tyr Gly Gly Asp Ser Thr Thr
545                 550                 555                 560
```

```
Pro Arg Pro Arg Tyr Asn Ala Thr Thr Tyr Leu Pro Pro Ser Thr Ser
            565                 570                 575

Ser Lys Leu Arg Pro Arg Trp Thr Phe Thr Ser Pro Val Thr Thr
        580                 585                 590

Ala Gln Ala Thr Val Pro Val Pro Pro Thr Ser Gln Pro Arg Phe Ser
        595                 600                 605

Asn Leu Ser Met Leu Val Leu Gln Trp Ala Ser Leu Ala Val Leu Thr
        610                 615                 620

Leu Leu Leu Leu Leu Val Met Ala Asp Cys Ala Phe Arg Arg Asn Leu
625                 630                 635                 640

Ser Thr Ser His Thr Tyr Thr Thr Pro Pro Tyr Asp Asp Ala Glu Thr
                645                 650                 655

Tyr Val

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caccatggag gcagccttgc ttgt                                            24

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agatctttag gatacagtgg ggcctgtgc                                       29

<210> SEQ ID NO 6
<211> LENGTH: 114
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gccaccatgg agacagacac actcctgcta tgggtactgc tgctctgggt tccaggttcc     60
actggtgacg cggcccagcc ggccaggcgc gcgcgccgta cgaagctcgc cctt          114

<210> SEQ ID NO 7
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 7
tcaatggtga tggtgatgat gggtggatac agtggggcct gt                         42

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccatcgatgg ctagctagcg gtggatacag tggggcctgt                            40

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atggaggcag ccttgcttgt                                                  20

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcaaccaaaa gctaacggta aaattattaa attttagttc agttatacct ataaatttag      60
aatttgcttt tatatactgg gtggatacag tggggcctgt                           100

<210> SEQ ID NO 11
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttttgctca acagctcttc cactttatct tccagctgtt tcatgcgttc taaatgacta      60
gcagatactt taggaaccct caaccaaaag ctaacggtaa                           100

<210> SEQ ID NO 12
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctagctagcg gtggcggagg gagtggtggc ggagggagcg gtggcggagg gagtatggag      60
gcagccttgc ttgt                                                       74
```

<210> SEQ ID NO 13
<211> LENGTH: 108
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 13
ccatcgattc aatggtgatg gtgatgatgg ctagtgcgtt cgcccaccag cttttttcaga    60 cgcgccactt cgtttttccag atgatagttt ttgctcaaca gctcttcc    108

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
    6xHis tag

<400> SEQUENCE: 14

His His His His His His
1               5

<210> SEQ ID NO 15
<211> LENGTH: 172764
<212> TYPE: DNA
<213> ORGANISM: Human herpesvirus 4

<400> SEQUENCE: 15
agaatttgtc ttgctctatt caccgttact tttcttcttg cccgttctct ttcttagtat    60
gaatccagta tgcctgcctg taattgttgc gccctacctg ttttggctgg cggctattgc   120
cgcctcgtgt ttcacggcct cagttagtac cgttgtgacc gccaccggct tggccctctc   180
acttctactc ttggcagcag tggccagctc atatgccgct gcacaaagga aactgctgac   240
accggtgaca gttcttactg cggttgtcac ttgtgagtac acacgcacca tttacaatgc   300
atgatgttcg tgagattgat ctgtctctaa cagttcactt cctctgcttt tctcctcagt   360 cttttgcaatt tgcctaacat ggaggattga ggacccacct tttaattctc ttctgtttgc   420
attgctggcc gcagctggcg gactacaagg catttacggt tagtgtgcct ctgtgatgga   480
atgcaggttt gacttcatat gtatgccttg gcatgacgtc aactttactt ttatttcagt   540
tctggtgatg cttgtgctcc tgatactagc gtacagaagg agatggcgcc gtttgactgt   600
ttgtggcggc atcatgtttt tggcatgtgt acttgtcctt atcgtcgacg ctgttttgca   660
gctgagtccc ctccttggag ctgtaactgt ggtttccatg acgctgctgc tactggcttt   720
cgtcctctgg ctctcttcgc caggggggcct aggtactctt ggtgcagccc ttttaacgtt   780
ggcagcaggt aagccacacg tgtgacattg cttgcctttt tgccacatgt tttctggaca   840
caggactaac catgccatct ctgattatag ctctggcact gctagcgtca ctgattttgg   900
gcacacttaa cttgactaca atgttccttc tcatgctcct atggacactt ggtaagtttt   960 ccccttcctttt aactcattac ttgttctttt gtaatcgcag ctctaacttg gcatctcttt  1020
tacagtggtt ctcctgattt gctcttcgtg ctcttcatgt ccactgagca agatccttct  1080
ggcacgactg ttcctatatg ctctcgcact cttgttgcta gcctccgcgc taatcgctgg  1140
tggcagtatt ttgcaaacaa acttcaagag tttaagcagc actgaattta cccagtgaa  1200 gtatctattt gttactcctg tttagttgaa gaaaacaagc tattggattg taacacacat  1260

```
tttacgcttt gttccttaga tttgttctgc atgttattac tgattgtcgc tggcatactc   1320
ttcattcttg ctatcctgac cgaatggggc agtggaaata aacatacgg tccagttttt   1380 atgtgcctcg gtggcctgct caccatggta gccggcgctg tgtggctgac ggtgatgact   1440
aacacgcttt tgtctgcctg gattcttaca gcaggattcc tgattttcct cattggtaag   1500
tgtgacacca acaggtgttg ccttgttatg tcaccgttct gacacatgac ttacatgggt   1560
ttggcttttg taggctttgc cctctttggg gtcattagat gctgccgcta ctgctgctac   1620
tactgcctta cactggaaag tgaggagcgc ccaccgaccc catatcgcaa cactgtataa   1680
aggtaagtat tattaaattt tagagacact atcacgtgta acttgacgtg caaggatgga   1740 ggatagggc agggaaacgc aaatgccggt tgcccggtat gggggcccgt ttattatggt   1800
aaggctcttc gggcaagatg gagaggcaaa catacaggag caaaggctat atgagctact   1860
ctctgacccc cgctccgcgc tcggcctaga cccggggccc ctgattgctg agaacctgct   1920
gctagtggcg ctgcgtggca ccaacaacga tcccaggcct cagcgtcagg agagggccag   1980
agaactggcc ctcgttggca ttctactagg aaacggcgag cagggtgaac acttgggcac   2040
ggagagtgcc ctggaggcct caggcaacaa ctatgtgtat gcctacggac cagactggat   2100
ggcaaggcct tccacatggt ccgcggaaat ccagcaattc ctgcgactcc tgggcgccac   2160
gtacgtgctt cgcgtggaga tgggcaggca gtttggcttc gaggtgcata aagccggcc   2220 ctccttccgt cagttccagg ccatcaatca tcttgtcctg tttgacaacg cccttcgcaa   2280
gtacgattcc ggccaggtgg cggcgggctt ccagagggcc cttctggtgg ccgggccaga   2340
gaccgctgac acgaggccgg acctccgcaa gctgaatgag tgggtgtttg gtggcagggc   2400
tgctggtggc agacagctgg ccgacgagct aaagatcgtg tccgcgctgc gagacactta   2460
ctcgggccac ttggtccttc agcccacgga gacccttgac acatggaagg tgttgagcag   2520
ggacacacga accgctcata gtttggagca cggattcatt catgccgcgg ggaccatcca   2580
ggccaactgc ccacagctgt ttatgagacg ccagcacccc ggcctctttc ccttcgttag   2640
tgcaatagca tcatcgctgg gctggtacta ccagaccgcc accggccccg gagcagatgc   2700
cagggcggcg gccggcgtc aacaggcctt tcagaccagg cgggcggctg aatgccatgc   2760
caaaagcggg gtgccggtcg tggccggctt ctataggacc atcaacgcca cgctcaaggg   2820
aggagagggc ctacagccca ctatgtttaa cggggagctg ggggccatca agcaccaggc   2880
acttgacact gtgaggtatg actacggcca ctatctcata atgttggggc cattccagcc   2940
atggagcgga ctgacggccc ctccgtgccc ttacgccgaa agttcatggg cacaggcgg   3000 cgtgcagacg gccctcgagc tgttctcggc cctgtacccg gccccgtgca tctcgggcta   3060
cgcgcgcccc ccgggcccca gtgctgtgat cgagcatctg gggtccctag tcccaaaggg   3120
gggtctgctg ttgtttctgt ctcacctacc ggatgatgtt aaggacgggc tcggagaaat   3180
ggggccggcc agggccacgg gacctggaat gcagcagttt gtcagcagct acttcctcaa   3240
ccccgcctgt tccaacgtct tcattacagt gaggcagcga ggggaaaaga tcaacggccg   3300
taccgtcctc caagcgctcg gacgcgcatg cgatatggca ggctgccagc actatgtgct   3360
gggctccacg gttccctcg gtggactcaa cttgtcaac gacctggcgt ccccggtttc   3420
caccgccgag atgatggatg atttctctcc cttcttcacc gtggagttc cccgattca   3480 agaggagggc gcacgttctc cggtacccctt agatgtggac gagagcatgg acatctctcc   3540
gtcttacgag ttgccctggc tctcgctgga gtcatgcctc acaagcatcc tgtcacaccc   3600
```

```
caccgtggga agcaaggagc acttggtcag gcacacggac agggtcagcg gaggacgcgt    3660
ggcacagcag cccggggtag gtcccctgga cctgccgctg gcggactacg ccttcgttgc    3720
ccacagtcag gtctggacca ggcccggtgg ggctcctccc ttgccctatc gtacctggga    3780
tcgaatgaca gagaagctgc ttgtctccgc aaagcccggc ggagagaacg ttaaggtttc    3840
aggtaccgtg attacattgg gagaacaggg gtacaaagtg tcgttggatc tgagggaggg    3900
aaccaggctg gcaatggctg aggcgctgct gaatgcagca tttgcccccaa tcttggatcc    3960 ggaagacgtc ttgctcaccc tgcatctaca cctggatccg cgccgggcag acaactcggt    4020
cgtgatggag gctatgacgg cggcgagtga ctacgcgcgt ggcctgggcg tgaagctgac    4080
ctttggctcg gcctcctgcc ccgagaccgg ctcgtccgcc tccagcttca tgactgtggt    4140
ggcctctgtc tccgcccag gggaattctc gggtcctctg atcacgccag tgcttcagaa    4200
gacgggcagt ctcctgattg cggtgcgttg cggggatggc aagatccagg gagggtcgct    4260
gtttgagcag ctcttagcg acgtggccac gaccccacgg gcgcccgagg cgttgtctct    4320
gaagaatctc ttccgggcag tccagcagct ggtcaagagc ggcatcgtgc tgtcagggca    4380
tgacatcagc gacgggggcc tggtgacctg cctggtggag atggccctgg ccgggcagcg    4440
gggagtgacc atcactatgc cggtggcctc cgactacctc ccggagatgt ttgcagagca    4500
ccccggcctg gtgtttgagg tggaggagcg cagcgtgggt gaggtgctgc agaccctgcg    4560
ctccatgaac atgtacccgg cagtcctcgg tcgagtgggc gagcaaggtc cagatcaaat    4620
gtttgaggtg cagcacggcc cagagacggt gttgcgccag tcgctgcgcc tgctgctggg    4680
aacctggtcc tcctttgcca gcgagcagta cgagtgcctg cgaccagatc ggattaaccg    4740
gtccatgcac gtttccgact acggctataa cgaagcactg gcagtctccc cgttgacagg    4800
aaagaatctc agcccacgcc ggctggtgac agagcctgac ccacgatgtc aggtggccgt    4860
gctatgcgcc ccgggcacca ggggccatga agcctcctg gcggccttca cgaatgccgg    4920
atgcctgtgc cgacgggtgt tcttcgcga ggttaggac aacacgttcc tcgacaagta    4980
cgtgggtctg gccatcggag gagttcatgg ggccagggac tctgccctgg caggccgtgc    5040
caccgtggcg ctgattaatc gttccccccgc cctgcgtgac gctattctaa agttcctcaa    5100
caggccagat acgttctcgg tggccttggg ggagctgggg gtgcaagttt tggctggcct    5160
gggggccgtg gggtcaacag ataatccacc cgccccctggc gtggaagtta atgtccagag    5220
atcacctctg attctggccc ccaacgcctc tggcatgttt gagtcccgct ggctgaacat    5280
tagcatcccg gcgaccacca gctctgtcat gctgcgtggc ctccggggct gcgtcctgcc    5340
ttgttgggtg caaggctcgt gcctgggcct gcaatttact aacctcggga tgccatatgt    5400
tttgcagaat gccaccagac tcgcctgcca cttccacagc aatggcacgg acgcctggcg    5460
ctttgctatg aattatccaa gaaaccccac ggagcagggc aacattgcag ggctctgttc    5520
acgcgatggt cgtcatctgg ctctcctgtg tgaccctca cttgtacag acttttggca    5580 atgggagcac attccccccg cctttgggca ccccacgggg tgctcccct ggacacttat    5640 gtttcaagca gctcacctat ggtcactcag gcacggtcgc cctccgagt gaccagtcac    5700 cttccagact atgcatacac tgaatttagc ctgatattgt ccccccgagcc ccgggcccag    5760 ccctcctcag aaaactctgc atggagaagc tggacgtgaa ccttcccccc cccccgacc    5820 tgtgtgctgt atttacaaac actacaataa acccaatgtg caaatgtggt ttgtatggct    5880
actttgtgtt cctaaaaat gcaacaatag aagtggaaac cctcagtcac gggacattaa    5940
cctcaaccac aaaatggggg ttggagaaag taaccacata tactggagat gattcatggg    6000
```

```
ctgggggttc ccggacaata cacccatctg gagttcaact taattacatg gtagataaat     6060
taagagtccc tcctcaccac tcgaaactat ggcagacatt ctataagata acgaggagag     6120
atgaggtgag ggcagaggac attgggcagg tgtgggccac ggggcagctg gccatatccc     6180
ccgcaccaca gaagtgtaag caaagtgaag ggctcggaag gcaggcgggg cctagcaatg     6240
tcacagctaa atgcccacca gggcacacac tcaagcgggg tctcggagct cctaggtcag     6300
accacgaaag gtcagcctgc aaggtggatg gcgtgttttc tgaggttatc cccgctacgt     6360
gcagtgctgg gtgagagaga ccctagaatg tgtcgaaatg accaagcgtc cccgcagcgg     6420
ggctcccaac acgggttccc agagagggta aagaggggg ccataaagcc cagggtgtaa     6480
aacaccgacc gcgccaccag atggcacacg tgggggaaat gagggttagc ataggcaacc     6540
cccgcctaca caccaactat agcaaacccc gccccgtcac ggtgacgtag tctgtcttga     6600
ggagatgtag acttgtagac actgcaaaac ctcaggacct acgctgccct agaggttttg     6660
ctagggagga gacgtgtgtg gctgtagcca cccgtcccgg gtacaagtcc cgggtggtga     6720
ggacggtgtc tgtggttgtc ttcccagact ctgctttctg ccgtcttcgg tcaagtacca     6780
gctggtggtc cgcatgtttt gatccaaact ttagttttag gatttatgca tccattatcc     6840
cgcagttcca cctaaacggg gcttaacgtt gcatcccaga agatgcacac gtaaccccgc     6900
ctacaaccgt gacgtggctg tttaccagca tatatagagt tacggttcac tacatcaaac     6960
aggacagccg ttgccctagt ggtttcggac acaccgccaa cgctcagtgc ggtgctaccg     7020
acccgaggtc aagtcccggg ggaggagaag agaggcttcc cgcctagagc atttgcaagt     7080
caggattctc taatccctct gggagaaggg tattcggctt gtccgctgtt ttttgtggc     7140 tagttttgca cccacaacat gtaagggccc gctaccccta caacacaaaa caaactatct     7200
ccactaacca tccttttgcc aatcaattct gtgacgggt ttcctggaca cccagtctta     7260
gttcaggtag acacccagtt atgcagtgcc accaattcca accatttta aacctcctgg     7320 aattctatca ttaaacggca tgcaggaaaa ggacaagcag cgaaaattca cgcccccttg     7380
ggaggtggcg gcatatgcaa aggatagcac tcccactcta ctactgggta ttatatgctg     7440
actgtatatg cattaggata gcatatgcta cccagatata gattaggata gcatatgcta     7500
cccggatata gattaggata gcatatacta cccaaataga gattaggata gcatatgcta     7560
cccaaataga gattaggata gcatatgcta cccggatata gattaggata gcatatacta     7620
cccaaataga gattaggata gcatatgcta cccaaataga gattaggata gcatatgcta     7680
cccggatata gattaggata gcatatgcta cccaaataga gattgggata gcatatgcta     7740
cccggatata gattaggata gcatatgcta cccaaataga gattaggata gcatatgcta     7800
cccggatata gattaggata gcatatgcta cccaaataga gattgggata gcatatgcta     7860
tcctaatctc tatctgggta gcatatacta tcctaatctc tatatgggta gcatatgcta     7920
tcctaatcta tatctgggta gcatatacta tcctaatctc tatatgggta gcatatgcta     7980
tcctaatcta tatctgggta gcatatgcta tccatcgcaa cattagccca ccgtgctctc     8040
aacgacctcg tgaatatgag gaccaacaac cctgtgcttg gcgctcaggc gcaagtgtgt     8100
gtaacttgtc ttccagatcg cagcaatcgc gcccctatct tggcccgccc acctactat     8160 gcaggtattc cccggggtgc cattagtggt tttgtgggca agtggtttga ccgcagtggt     8220
tagcggggtt acaatcagcc aagttattac acccttagtt tacagtccaa aaccgcaggg     8280
cggcgtgtgg gggctgacgc gtgcccccac tccacaattt caaaaaaaag agtggccact     8340
```

```
tgtctttgtt tatgggcccc attggcgtgg agccccgttt aattttcggg ggtgttagag    8400
acaaccagtg gagtccgctg ctgtcggcgt ccactctctt tcccttgtt acaaatagag     8460 tgtaacaaca tggttcacct gtcttggtcc ctgcctggga cacatcttaa taaccccagt    8520
atcatattgc actaggatta tgtgttgccc atagccataa attcgtgtga gatggacatc    8580
cagtctttac ggcttgtccc caccccatgg atttctattg ttaaagatat tcagaatgtt    8640
tcattcctac actagtattt attgcccaag gagtttgtga gggttatatt ggtgtcatag    8700
cacaatgcca ccactgaacc ccccgtccaa attttattct gggggcgtca cctgaaacct    8760
tgttttcgag cacctcacat acaccttact gttcacaact cagcagttat tctattagct    8820
aaacgaagga gaatgaagaa gcaggcgaag attcaggaga gttcactgcc cgctccttga    8880
tcttcagcca ctgcccttgt gactaaaatg gttcactacc ctcgtggaat cctgatccca    8940
tgtaaataaa accgtgacag ctcatggggt gggagatatc gctgttcctt aggacccttt    9000
tactaaccct aattcgatag catatgcttc ccgttgggta acatgtgcta ttgaattagg    9060
gttagtctgg atagtatatg ctactacccg ggaagcatat gctacccgtt tagggttaaa    9120 aaggggggcct tataaacact cttgctaacg ccctcttgag ggtccgctta tcggtagcta    9180
cacaggcccc tctgattgac gttggtgtag cctcccatag tcttcctggg ccctggggag    9240
gtacatgtcc cccagcattg gtgtaagagc ttcaaccaag agttacacat aaaggcaatg    9300
ttgtgttgca gtccacagac tgcaaagtct gcttcaggat gaaagccact cagtgttggc    9360
aaatgtgcac atccatttat aaggatgtca actacagtca gagaaccccct ttgtgtttgg    9420 tccccccccc gtgtcacatg tggaacaggg cccagttggc aagttgtacc aaccaactga    9480
agggattaca tgcactgccc cgcgggaaat acgtcctacc caggaacccg aaacagtgtt    9540
tcccagaagc tgtaaaaata gaacgccctg gaactgcccc actgtgcaat gcagcttta     9600 gccatgccat gctctataaa tcacttccct atctcaggta ggcctgcaca ccttaggtat    9660
ggagcgaagg ttagtggtca ctctgcagtg cctggtgctg cttacctgg cacctgagtg     9720 tggaggtaca gaccaatgtg acaattttcc ccaaatgttg agggacctaa gggatgcctt    9780
cagtcgtgtt aaaaccttt tccagacaaa ggacgaggta gataaccttt tgctcaagga     9840
gtctctgcta gaggacttta agggctacct tggatgccag gccctgtcag aaatgatcca    9900
attctacctg gaggaagtca tgccacaggc tgaaaaccag gaccctgaag ccaaagacca    9960
tgtaaattct ttgggtgaaa atctaaagac cctacggctc cgcctgcgca ggtgccacag   10020
gttcctgccg tgtgagaaca agagtaaagc tgtggaacag ataaaaaatg cctttaacaa   10080
gctgcaggaa aaaggaattt acaaagccat gagtgaattt gacatttta ttaactacat     10140 agaagcatac atgacaatta aagccaggtg ataattccat accctggaag caggagatgg   10200
gtgcatttca ccccaacccc ccctttcgac tgtcatttac aataaaatga aacctttat     10260 tcttgattgc ctcttgtgtt cttgccgccc aggtaccttc ctgtgttctc cccacgggaa   10320
aaagaatagc ttctgcagaa ggccattgac gcaagttttg cccgtgggga ttacccgacc   10380
cggccactta cagcacattt tgttctaggt ccatcttagg agcccgggcc agcattctat   10440
cagcttaacg ggaagagaag tggggagggc actcgcccac taaccttaac acctgcagcc   10500
tacaaaagta cactagctgt ttgctctatt cgccactaga gaccgccaag atgcgaaact   10560
gcaggcccgg gccaggcct tgtagggcag acggttaggc tgacaagggg acaagtgtgg    10620
caggtgggcg gaaggggca caagaatgac ggcgaaactg gaccacgtc caccccgccc     10680 tcaagcgtcc gggagccagg cggttcggtt aaggagggcg gccttgcgaa caatcattag   10740
```

```
tagctaccaa caagggcccc cagatgcccc ccaccagtca ccccggccgt gtccactcac   10800
atattccact cttatttta aattaatgtg tcccaattag aaacccaagc gcagaaatta   10860
gttgagaggc tagtgtttta acatgcacc ctaggccagc cagagataat gtcacaagac   10920
tatcaagttg gtgtaaacac gccgtgggaa aaaattatg gttcagtgcg tcgagtgcta   10980
tctttggaac agtagaaaat tgaaccttgt tggcgggaga aggcataacg ccttatctgg   11040
gaggagcgac ggattatagc caataagaga gctcaagacg cagggctcgc aaagtatagt   11100
ggccccgtgg gaccttagag gtggagcaac gtctaaagtg gtaataacac caggcggggc   11160
tgggcaaagg ggtcctacgg gcgggattaa ttacgccttg cttacgcaag ctcagttaat   11220
tcgcccacga cttgaaaaat gtagcccta accaattggc ggcccctaag ggggggacta   11280
aggtcccact acaaaaactc tgtgttctgc tgcaaatttt agataagatg gcatagagac   11340
aaggacaccg aagaccccca gagccctcat cgcagggttc ttaccatgcg gccatgtagg   11400
cccacttaac actacaagac ctacgcctct ccattcatca tgtaacccac aaatcatcta   11460
aaccgtaagt ctaagggcct cctgaggttt tctcaggagg ccctaatgta taattaatca   11520
tgcatttgat tttaaaaaag taggttacac tcattttagg ccagacttta tttgcagatt   11580
aataatttat gtgattctcc ttccctctag gactgaagaa acagcctcct gcacgtgagc   11640
atgtatctga ataattatt atgtcataag tgtaatgatt agaaagtcat aaacccactt   11700
cccttttacat gaatctgggc actgaatttt ggggtacttc taaagactaa cgtgttcgat   11760
ttcggggtca cttccccttt tataagtgtg tgaacagtga tttcagtaaa acctaagaga   11820
tattggtgt cacttccgca ttttaagttt cagaaaattt taaaattaaa attgaaattt   11880
ctctcaaaat aattccaatg aaaacttcaa agaatcttat gtatgtaatt cttttgccc   11940
aaactgggct tcagatgcct tctattgcac tctcacaaaa acattctgga cacatgtgcc   12000
agacgcctgg gcctctaagg ccctcgggtc ccctggacc ccggcctcag caaccctgct   12060
gctccctcc tgccacccca gcctcccccc ctccccgtcc cccttcgctc cttatcctcc   12120
cccggtcccc agtagggccg cctgccccc tgcacccagt acctgcccct cttggccacg   12180
cacccgggc caggccacct tagacccggc caagccccat ccctgaagac ccagcggcca   12240
ttctctctgg taacgagcag agaagaagta gaggcccgcg gccattgggc ccagattgag   12300
agaccagtcc aggggcccga ggttggagcc agcgggcacc cgaggtccca gcacccggtc   12360
cctccgggg gcagagacag gcagggcccc ccggcagctg ccccgagga ggcgcccgga   12420
gtggggccgg tcggctgggc tggccgagcc cgggtctggg aggtctgggg tggcgagcct   12480
gctgtctcag gaggggcctg gctccgccgg gtggccctgg ggtaagtctg ggaggcagag   12540
ggacggccta ggcccgggga agtggagggg gatcgcccgg gtctctgttg gcagagtccg   12600
ggcgatcctc tgagacccct cgggcccgga cggccgccct cggcccccca gacagacccc   12660
agggtctcca gcagggtcc ggcatctcca ggggcagcag gctcaccacc acaggccccc   12720
cagacccggg tctcggccag ccgagccgac cggccccgcg ccgggcgcct cctcggagcc   12780
agccccgggg gttggttctg cccctctctc tgtccttcag aggaaccagg gacctcgggc   12840
accccagagc ccctcgggcc cgcctccagg cgccctcctg gtctccgctc ccctctgagc   12900
cccgttaaac ccaaagaatg tctgagggga gccaccctcg gggcccaggc cccagagtcc   12960
agaggtcagg ggcacctcag ggtgcctccc cgggtcccag gccagccgga gggacccgg   13020
cagcccgggc ggccccagag gccggttcct cgccccttcc ccgggcttca gagcccaggg   13080
```

```
tgtccccag aagggaccct aggcgtcccc tctcctcccc tccaggcccg agcctctccc    13140
tcgcggagag gggcctcttc gagccctcaa gtccagtccc accgagaccc gagtggcccg    13200 gatccccac cggcccttct cttcccct actcctctcc aaccttcgct ccaccctaga      13260
ccccagcttc tggcctcccc gggtccacca ggccagccgg agggaccccg gcagcccggg    13320
cgagtcgcct tccctctccc ctggcctctc cttcccgcct cccacccgag cccctcagc    13380 ttgcctcccc accgggtcca tcaggccggc cggaggacc ccggcggccc ggtgtcagtt     13440 cccctgcag ccgcccagtc tctgcctcca ggcaagggcg ccagctttc tcccccagc      13500 ctgaggccca ggctcctgtg cactgtctgt aaagtccagc ctcccacgcc cgtccacggc    13560
tcccaggccc agccccgtcc accctcccc acgttggaca ggccctctgt ccacccgggc     13620
catccccgcc cccctgtgtc caccccagtc ccgtccaggg gggactttat gtgacccttg   13680
ggcctggctc cccatagact cccatgtaag cctgcctcga gtaggtgcct ccagagcccc    13740
ttttgccccc ctggcggccc agcccgaccc ccgggcgccc ccaaactttg tccagatgtc    13800
caggggtccc cgagggcgag gcccagcccc ctcccgcccc tgtccactgc cccggtcccc    13860
ccagaagccc ccaaaagtag aggctcaggc catgcgcgcc ctgtcaccag gcctgccaaa    13920
gagccagatc taaggccggg agaggcagcc ccaaagcggg tgcagtaaca ggtaatctct    13980
ggtagtgatt tggacccgaa atctgacact ttagagctct ggaggacttt aaaactctaa   14040
aaatcaaaac tttagaggcg aatgggcgcc attttgtccc cacgcgcgca taatggcgga    14100
cctaggccta aaaccccag gaagcgggtc tatggttggc tgcgctgctg ctatctttag     14160
aggggaaaag aggaataagc ccccagacag gggagtgggc ttgtttgtga cttcaccaaa    14220
ggtcagggcc caaggggggtt cgcgttgcta ggccaccttc tcagtccagc gcgtttacgt   14280
aagccagaca gcagccaatt gtcagttcta gggagggga ccactgcccc tggtataaag     14340
tggtcctgca gctatttctg gtcgcatcag agcgccagga gtccacacaa atgtaagagg   14400
gggtcttcta cctctcccta gccctccgcc ccctccaagg actcgggccc agtttctaac   14460 tttttccct tccctccctc gtcttgccct gcgcctgggg ccaccttcat caccgtcgct     14520
gactccgcca tccaagccta ggggagaccg aagtgaagtc cctggaccag ccggccgg     14580 gccccccggt atcgggccag aggtaagtgg actttaattt tttctgctaa gcccaacact   14640
ccaccacacc caggcacaca ctacacacac ccaccgtct cagggtcccc tcggacagct     14700
cctaagaagg caccggtcgc ccagtcctac cagagggggc caagaaccca gacgagtccg    14760
tagaagggtc ctcgtccagc aagaagagga ggtggtaagc ggttcacctt caggggtaag   14820
taacctgacc tctccagggc tcacataaag ggaggcttag tatacatgct tcttgctttt   14880
cacaggaacc tgggggctag tctgggtggg tttaggctgc ctcaagttgc atcagccagg    14940
gcttcatgcc ctcctcagtt ccctagtccc cgggcttcag gcccctccg tccccgtcct     15000 ccagagaccc gggcttcagg ccctgcctct cctgttaccc ttttagaacc acagcctgga    15060
cacatgtgcc agacgcctgg gcctctaagg ccctcgggtc ccctggacc ccggcctcag     15120 caaccctgct gctcccctcc tgccacccca gcctcccccc ctcccgtcc ccttcgctc     15180 cttatcctcc cccggtcccc agtagggcg cctgccccc tgcacccagt acctgccct     15240 cttggccacg caccccgggc caggccacct tagacccggc caagcccat ccctgaagac     15300 ccagcggcca ttctctctgg taacgagcag agaagaagta gaggcccgcg gccattgggc   15360
ccagattgag agaccagtcc aggggcccga ggttggagcc agcggcacc cgaggtccca    15420 gcacccggtc cctccggggg gcagagacag gcagggcccc ccggcagctg gccccgagga    15480
```

```
ggcgcccgga gtggggccgg tcggctgggc tggccgagcc cgggtctggg aggtctgggg    15540
tggcgagcct gctgtctcag gaggggcctg gctccgccgg gtggccctgg ggtaagtctg    15600
ggaggcagag ggacggccta ggcccgggga agtggagggg gatcgcccgg gtctctgttg    15660
gcagagtccg ggcgatcctc tgagaccctc cgggcccgga cggccgccct cggccccca    15720
gacagacccc agggtctcca ggcagggtcc ggcatctcca ggggcagcag gctcaccacc    15780
acaggccccc cagacccggg tctcggccag ccgagccgac cggccccgcg ccgggcgcct    15840
cctcggagcc agccccggg gttggttctg cccctctctc tgtccttcag aggaaccagg    15900
gacctcgggc accccagagc ccctcggccc gcctccagg cgccctcctg gtctccgctc    15960
ccctctgagc cccgttaaac ccaaagaatg tctgagggga gccaccctcg ggcccaggc    16020
cccagagtcc agaggtcagg ggcacctcag ggtgcctccc cgggtcccag gccagccgga    16080
gggaccccgg cagcccgggc ggccccagag gccggttcct cgcccctttcc ccgggcttca    16140
gagcccaggg tgtccccccag aagggaccct aggcgtcccc tctcctcccc tccaggcccg    16200
agcctctccc tcgcggagag gggcctcttc gagccctcaa gtccagtccc accgagaccc    16260
gagtggcccg gatcccccac cggcccttct ctttccccct actcctctcc aaccttcgct    16320
ccaccctaga ccccagcttc tggcctcccc gggtccacca ggccagccgg agggaccccg    16380
gcagcccggg cgagtcgcct tccctctccc ctggcctctc cttcccgcct cccacccgag    16440
cccctcagc ttgcctcccc accgggtcca tcaggccggc cggagggacc ccggcggccc    16500
ggtgtcagtt cccctgcag ccgcccagtc tctgcctcca ggcaagggcg ccagcttttc    16560
tcccccagc ctgaggccca ggctcctgtg cactgtctgt aaagtccagc ctcccacgcc    16620
cgtccacggc tcccaggccc agcccgtcc accctccc cacgttggaca ggccctctgt    16680
ccacccgggc catccccgcc ccctgtgtc caccccagtc ccgtccaggg gggactttat    16740
gtgacccttg ggcctggctc cccatagact cccatgtaag cctgcctcga gtaggtgcct    16800
ccagagcccc ttttgccccc ctggcggccc agcccgaccc ccgggcgccc ccaaactttg    16860
tccagatgtc caggggtccc cgagggcgag gcccagcccc ctcccgcccc tgtccactgc    16920
cccggtcccc ccagaagccc ccaaaagtag aggctcaggc catgcgcgcc ctgtcaccag    16980
gcctgccaaa gagccagatc taaggccggg agaggcagcc ccaaagcggg tgcagtaaca    17040
ggtaatctct ggtagtgatt tggacccgaa atctgacact ttagagctct ggaggacttt    17100
aaaactctaa aaatcaaaac tttagaggcg aatgggcgcc atttgtccc cacgcgcgca    17160
taatggcgga cctaggccta aaaccccag gaagcgggtc tatggttggc tgcgctgctg    17220
ctatctttag aggggaaaag aggaataagc ccccagacag gggagtgggc ttgtttgtga    17280
cttcaccaaa ggtcagggcc caaggggggtt cgcgttgcta ggccaccttc tcagtccagc    17340
gcgtttacgt aagccagaca gcagccaatt gtcagttcta ggggaggggga ccactgcccc    17400
tggtataaag tggtcctgca gctatttctg gtcgcatcag agcgccagga gtccacacaa    17460
atgtaagagg gggtcttcta cctctcccta gccctccgcc cctccaagg actcgggccc    17520
agtttctaac ttttcccct tccctcccctc gtcttgccct gcgcctgggg ccaccttcat    17580
caccgtcgct gactccgcca tccaagccta ggggagaccc aagtgaagtc cctgaccag    17640
cccggccgg gcccccggt atcgggccag aggtaagtgg actttaattt tttctgctaa    17700
gcccaacact ccaccacacc caggcacaca ctacacacac ccaccgtct cagggtcccc    17760
tcggacagct cctaagaagg caccggtcgc ccagtcctac cagaggggggc caagaaccca    17820
```

```
gacgagtccg tagaagggtc ctcgtccagc aagaagagga ggtggtaagc ggttcacctt   17880
caggggtaag taacctgacc tctccagggc tcacataaag ggaggcttag tatacatgct   17940
tcttgctttt cacaggaacc tgggggctag tctgggtggg tttaggctgc ctcaagttgc   18000
atcagccagg gcttcatgcc ctcctcagtt ccctagtccc cgggcttcag gcccctccg    18060 tccccgtcct ccagagaccc gggcttcagg ccctgcctct cctgttaccc ttttagaacc   18120
acagcctgga cacatgtgcc agacgcctgg gcctctaagg ccctcgggtc ccctggacc    18180 ccggcctcag caaccctgct gctcccctcc tgccacccca gcctccccccc ctcccgtcc   18240 cccttcgctc cttatcctcc cccggtcccc agtagggccg cctgccccccc tgcacccagt   18300 acctgcccct cttggccacg caccccgggc caggccacct tagacccggc caagcccat    18360 ccctgaagac ccagcggcca ttctctctgg taacgagcag agaagaagta gaggcccgcg   18420
gccattgggc ccagattgag agaccagtcc aggggcccga ggttggagcc agcgggcacc   18480
cgaggtccca gcacccggtc cctcgggggg gcagagacag gcagggcccc ccggcagctg   18540
gccccgagga ggcgcccgga gtggggccgg tcggctgggc tggccgagcc cgggtctggg   18600
aggtctgggg tggcgagcct gctgtctcag gaggggcctg gctccgccgg gtggccctgg   18660
ggtaagtctg ggaggcagag ggacggccta ggcccgggga agtggagggg gatcgcccgg   18720
gtctctgttg gcagagtccg ggcgatcctc tgagaccctc cgggcccgga cggccgccct   18780 cggccccccca gacagacccc agggtctcca ggcagggtcc ggcatctcca ggggcagcag   18840
gctcaccacc acaggccccc cagacccggg tctcggccag ccgagccgac cggccccgcg   18900
ccgggcgcct cctcggagcc agcccccggg gttggttctg ccctctctc tgtccttcag    18960 aggaaccagg gacctcgggc accccagagc ccctcgggcc cgcctccagg cgccctcctg   19020
gtctccgctc ccctctgagc cccgttaaac ccaaagaatg tctgagggga gccaccctcg   19080
gggcccaggc cccagagtcc agaggtcagg ggcacctcag ggtgcctccc cgggtcccag   19140
gccagccgga gggaccccgg cagcccggc ggccccagag gccggttcct cgccccttcc    19200
ccgggcttca gagcccaggg tgtcccccag aagggaccct aggcgtcccc tctcctcccc   19260
tccaggcccg agcctctccc tcgcggagag gggcctcttc gagccctcaa gtccagtccc   19320
accgagaccc gagtggcccg gatcccccac cggcccttct ctttcccccct actcctctcc   19380 aaccttcgct ccaccctaga ccccagcttc tggcctcccc gggtccacca ggccagccgg   19440
agggaccccg gcagcccggg cgagtcgcct tccctctccc ctggcctctc cttcccgcct   19500
cccacccgag cccctcagc ttgcctcccc accgggtcca tcaggccggc cggagggacc    19560
ccggcggccc ggtgtcagtt cccctgcag ccgcccagtc tctgcctcca ggcaagggcg    19620
ccagcttttc tcccccagc ctgaggccca ggctcctgtg cactgtctgt aaagtccagc    19680
ctcccacgcc cgtccacggc tcccaggccc agcccgtcc accctcccc acgttggaca     19740 ggccctctgt ccaccggc catccccgcc ccctgtgtc cacccagtc cgtccaggg        19800 gggactttat gtgacccttg ggcctggctc cccatagact cccatgtaag cctgcctcga   19860
gtaggtgcct ccagagcccc ttttgccccc ctggcggccc agcccgaccc ccgggcgccc   19920
ccaaactttg tccagatgtc cagggtccc cgagggcgag gccagcccc ctcccgcccc     19980 tgtccactgc cccggtcccc ccagaagccc ccaaaagtag aggctcaggc catgcgcgcc   20040
ctgtcaccag gcctgccaaa gagccagatc taaggccggg agaggcagcc ccaaagcggg   20100
tgcagtaaca ggtaatctct ggtagtgatt tggacccgaa atctgacact ttagagctct   20160
ggaggacttt aaaactctaa aaatcaaaac tttagaggcg aatgggcgcc attttgtccc   20220
```

```
cacgcgcgca taatggcgga cctaggccta aaaccccag gaagcgggtc tatggttggc   20280
tgcgctgctg ctatctttag aggggaaaag aggaataagc ccccagacag gggagtgggc   20340
ttgtttgtga cttcaccaaa ggtcagggcc caaggggtt cgcgttgcta ggccaccttc   20400
tcagtccagc gcgtttacgt aagccagaca gcagccaatt gtcagttcta ggaggggga   20460
ccactgcccc tggtataaag tggtcctgca gctatttctg gtcgcatcag agcgccagga   20520
gtccacacaa atgtaagagg gggtcttcta cctctccta gccctccgcc cctccaagg   20580
actcgggccc agtttctaac ttttttcct tccctccctc gtcttgccct gcgcctgggg   20640
ccaccttcat caccgtcgct gactccgcca tccaagccta ggggagaccg aagtgaagtc   20700
cctggaccag cccggcccgg gcccccggt atcgggccag aggtaagtgg actttaattt   20760
tttctgctaa gcccaacact ccaccacacc caggcacaca ctacacacac ccaccgtct   20820
cagggtcccc tcggacagct cctaagaagg caccggtcgc ccagtcctac cagaggggc   20880
caagaaccca gacgagtccg tagaagggtc ctcgtccagc aagaagagga ggtggtaagc   20940
ggttcacctt caggggtaag taacctgacc tctccaggc tcacataaag ggaggcttag   21000
tatacatgct tcttgctttt cacaggaacc tggggctag tctgggtggg tttaggctgc   21060
ctcaagttgc atcagccagg gcttcatgcc ctcctcagtt ccctagtccc cgggcttcag   21120
gcccctccg tcccgtcct ccagagaccc gggcttcagg ccctgcctct cctgttaccc   21180
ttttagaacc acagcctgga cacatgtgcc agacgcctgg gcctctaagg ccctcgggtc   21240
cccctggacc ccggcctcag caaccctgct gctccctcc tgccaccca gcctcccccc   21300
ctccccgtcc cccttcgctc cttatcctcc cccggtcccc agtagggccg cctgccccc   21360
tgcacccagt acctgccccct cttggccacg caccccgggc caggccacct tagacccggc   21420
caagcccat ccctgaagac ccagcggcca ttctctctgg taacgagcag agaagaagta   21480
gaggcccgcg gccattgggc ccagattgag agaccagtcc aggggcccga ggttggagcc   21540
agcgggcacc cgaggtccca gcacccggtc cctccggggg gcagagacag gcagggcccc   21600
ccggcagctg gccccgagga ggcgcccgga gtggggccgg tcggctgggc tggccgagcc   21660
cgggtctggg aggtctgggg tggcgagcct gctgtctcag gaggggcctg gctccgccgg   21720
gtggccctgg ggtaagtctg ggaggcagag ggacggccta ggcccgggga agtggagggg   21780
gatcgcccgg gtctctgttg gcagagtccg ggcgatcctc tgagaccctc cgggcccgga   21840
cggccgccct cggccccca gacagacccc agggtctcca ggcagggtcc ggcatctcca   21900
ggggcagcag gctcaccacc acaggccccc cagacccggg tctcggccag ccgagccgac   21960
cggccccgcg ccgggcgcct cctcggagcc agcccccggg gttggttctg cccctctctc   22020
tgtccttcag aggaaccagg gacctcgggc accccagagc ccctcgggcc cgcctccagg   22080
cgccctcctg gtctccgctc ccctctgagc cccgttaaac ccaaagaatg tctgagggga   22140
gccaccctcg gggcccaggc cccagagtcc agaggtcagg ggcacctcag ggtgcctccc   22200
cgggtcccag gccagccgga gggaccccgg cagcccgggc ggcccagag gccggttcct   22260
cgccccttcc ccgggcttca gagcccaggg tgtcccccag aagggaccct aggcgtcccc   22320
tctcctcccc tccaggcccg agcctctccc tcgcggagag gggcctcttc gagccctcaa   22380
gtccagtccc accgagaccc gagtggcccg gatcccccac cggcccttct ctttccccct   22440
actcctctcc aaccttcgct ccaccctaga cccagcttc tggcctcccc gggtccacca   22500
ggccagccgg agggaccccg gcagcccggg cgagtcgcct tccctctccc ctggcctctc   22560
```

```
cttcccgcct cccacccgag cccccctcagc ttgcctcccc accgggtcca tcaggccggc   22620
cggagggacc ccggcggccc ggtgtcagtt cccccctgcag ccgcccagtc tctgcctcca   22680
ggcaagggcg ccagctttc tcccccage ctgaggccca ggctcctgtg cactgtctgt      22740
aaagtccagc ctcccacgcc cgtccacggc tcccaggccc agccccgtcc acccctcccc    22800
acgttggaca ggccctctgt ccacccgggc catccccgcc ccctgtgtc caccccagtc     22860 ccgtccaggg gggactttat gtgacccttg ggcctggctc cccatagact cccatgtaag    22920
cctgcctcga gtaggtgcct ccagagcccc ttttgccccc ctggcggccc agcccgaccc   22980
ccgggcgccc ccaaactttg tccagatgtc caggggtccc cgagggcgag gcccagcccc   23040
ctcccgcccc tgtccactgc cccggtcccc ccagaagccc ccaaaagtag aggctcaggc   23100
catgcgcgcc ctgtcaccag gcctgccaaa gagccagatc taaggccggg agaggcagcc   23160
ccaaagcggg tgcagtaaca ggtaatctct ggtagtgatt tggacccgaa atctgacact    23220
ttagagctct ggaggacttt aaaactctaa aaatcaaaac tttagaggcg aatgggcgcc   23280
attttgtccc cacgcgcgca taatggcgga cctaggccta aaaccccag gaagcgggtc    23340 tatggttggc tgcgctgctg ctatctttag aggggaaaag aggaataagc ccccagacag   23400
gggagtgggc ttgtttgtga cttcaccaaa ggtcagggcc caaggggtt cgcgttgcta    23460 ggccaccttc tcagtccagc gcgtttacgt aagccagaca gcagccaatt gtcagttcta   23520
gggaggggga ccactgcccc tggtataaag tggtcctgca gctatttctg gtcgcatcag   23580
agcgccagga gtccacacaa atgtaagagg gggtcttcta cctctcccta gccctccgcc   23640
ccctccaagg actcgggccc agtttctaac ttttccccct tccctccctc gtcttgccct   23700
gcgcctgggg ccaccttcat caccgtcgct gactccgcca tccaagccta ggggagaccg   23760
aagtgaagtc cctggaccag cccggccggg gcccccggt atcgggccag aggtaagtgg    23820
actttaattt tttctgctaa gcccaacact ccaccacacc caggcacaca ctacacacac    23880
ccacccgtct cagggtcccc tcggacagct cctaagaagg caccggtcgc ccagtcctac   23940 cagaggggc caagaaccca gacgagtccg tagaagggtc ctcgtccagc aagaagagga    24000
ggtggtaagc ggttcacctt caggggtaag taacctgacc tctccagggc tcacataaag   24060
ggaggcttag tatacatgct tcttgctttt cacaggaacc tgggggctag tctgggtggg   24120
tttaggctgc tcaagttgc atcagccagg gcttcatgcc ctcctcagtt ccctagtccc    24180
cgggcttcag gcccctccg tccccgtcct ccagagaccc gggcttcagg ccctgcctct    24240
cctgttaccc ttttagaacc acagcctgga cacatgtgcc agacgcctgg gcctctaagg    24300
ccctcgggtc cccctggacc ccggcctcag caaccctgct gctcccctcc tgccacccca   24360 gcctccccc ctccccgtcc cccttcgctc cttatcctcc cccggtcccc agtagggccg     24420 cctgccccc tgcacccagt acctgcccct cttggccacg caccccgggc caggccacct   24480
tagacccggc caagcccat ccctgaagac ccagcggcca ttctctctgg taacgagcag    24540
agaagaagta gaggcccgcg gccattgggc ccagattgag agaccagtcc aggggcccga   24600
ggttggagcc agcgggcacc cgaggtccca gcacccggtc cctccggggg gcagagacag   24660
gcagggcccc ccggcagctg gccccgagga ggcgccggga gtggggccgg tcggctgggc   24720
tggccgagcc cgggtctggg aggtctgggg tggcgagcct gctgtctcag gagggggcctg   24780 gctccgccgg gtggccctgg ggtaagtctg ggaggcagag ggacggccta ggcccgggga   24840
agtggagggg gatcgcccgg gtctctgttg gcagagtccg ggcgatcctc tgagacccctc   24900 cgggcccgga cggccgccct cggcccccca gacagacccc agggtctcca ggcagggtcc   24960
```

```
ggcatctcca ggggcagcag gctcaccacc acaggccccc cagacccggg tctcggccag    25020
ccgagccgac cggccccgcg ccgggcgcct cctcggagcc agcccccggg gttggttctg    25080
cccctctctc tgtccttcag aggaaccagg gacctcgggc accccagagc ccctcgggcc    25140
cgcctccagg cgccctcctg gtctccgctc ccctctgagc cccgttaaac ccaaagaatg    25200
tctgagggga gccaccctcg gggcccaggc cccagagtcc agaggtcagg ggcacctcag    25260
ggtgcctccc cgggtccagg ccagccggag ggaccccggg cagcccgggc ggccccagag    25320
gccggttcct cgccccttcc ccgggcttca gagcccaggg tgtcccccag aagggaccct    25380
aggcgtcccc tctcctcccc tccaggcccg agcctctccc tcgcggagag gggcctcttc    25440
gagccctcaa gtccagtccc accgagaccc gagtggcccg gatccccac cggcccttct     25500 ctttccccct actcctctcc aaccttcgct ccacccctaga ccccagcttc tggcctcccc   25560
gggtccacca ggccagccgg agggaccccg gcagcccggg cgagtcgcct tccctctccc    25620
ctggcctctc cttcccgcct cccacccgag cccctcagc ttgcctcccc accgggtcca     25680
tcaggccggc cggagggacc ccggcggccc ggtgtcagtt cccctgcag ccgcccagtc     25740 tctgcctcca ggcaagggcg ccagctttc tccccccagc ctgaggccca ggctcctgtg     25800
cactgtctgt aaagtccagc ctcccacgcc cgtccacggc tcccaggccc agcccgtcc     25860 accctcccc acgttggaca ggccctctgt ccaccgggc catccccgcc ccctgtgtc       25920 caccccagtc ccgtccaggg gggactttat gtgacccttg ggcctggctc cccatagact    25980
cccatgtaag cctgcctcga gtaggtgcct ccagagcccc ttttgccccc ctggcggccc    26040
agcccgaccc ccgggcgccc ccaaactttg tccagatgtc caggggtccc cgagggcgag    26100
gcccagcccc ctcccgcccc tgtccactgc cccggtcccc ccagaagccc ccaaaagtag    26160
aggctcaggc catgcgcgcc ctgtcaccag gcctgccaaa gagccagatc taaggccggg    26220
agaggcagcc ccaaagcggg tgcagtaaca ggtaatctct ggtagtgatt tggacccgaa    26280
atctgacact ttagagctct ggaggacttt aaaactctaa aaatcaaaac tttagaggcg    26340
aatgggcgcc attttgtccc cacgcgcgca taatggcgga cctaggccta aaaccccag     26400 gaagcgggtc tatggttggc tgcgctgctg ctatctttag aggggaaaag aggaataagc    26460
ccccagacag gggagtgggc ttgtttgtga cttcaccaaa ggtcagggcc caaggggggtt   26520 cgcgttgcta ggccaccttc tcagtccagc gcgtttacgt aagccagaca gcagccaatt    26580
gtcagttcta gggaggggga ccactgcccc tggtataaag tggtcctgca gctatttctg    26640
gtcgcatcag agcgccagga gtccacacaa atgtaagagg gggtcttcta cctctcccta   26700
gccctccgcc ccctccaagg actcgggccc agtttctaac ttttctccccct tccctcccctc 26760 gtcttgccct gcgcctgggg ccaccttcat caccgtcgct gactccgcca tccaagccta   26820
ggggagaccg aagtgaagtc cctggaccag cccggcccgg gccccccggt atcgggccag    26880
aggtaagtgg actttaattt tttctgctaa gcccaacact ccaccacacc caggcacaca    26940
ctacacacac ccacccgtct cagggtcccc tcggacagct cctaagaagg caccggtcgc    27000
ccagtcctac cagaggggc caagaaccca gacgagtccg tagaagggtc ctcgtccagc     27060
aagaagagga ggtggtaagc ggttcacctt caggggtaag taacctgacc tctccagggc    27120
tcacataaag ggaggcttag tatacatgct tcttgctttt cacaggaacc tgggggctag    27180
tctgggtggg tttaggctgc ctcaagttgc atcagccagg gcttcatgcc ctcctcagtt    27240
ccctagtccc cgggcttcag gccccctccg tccccgtcct ccagagaccc gggcttcagg    27300
```

```
ccctgcctct cctgttaccc ttttagaacc acagcctgga cacatgtgcc agacgcctgg   27360
gcctctaagg ccctcgggtc ccctggacc ccggcctcag caaccctgct gctccctcc     27420 tgccacccca gcctccccc ctcccgtcc cccttcgctc cttatcctcc cccggtcccc     27480
agtagggccg cctgccccc tgcacccagt acctgcccct cttggccacg caccccgggc    27540
caggccacct tagacccggc caagcccat ccctgaagac ccagcggcca ttctctctgg    27600
taacgagcag agaagaagta gaggcccgcg gccattgggc ccagattgag agaccagtcc   27660
aggggcccga ggttggagcc agcgggcacc cgaggtccca gcacccggtc cctccggggg   27720
gcagagacag gcagggcccc ccggcagctg gccccgagga ggcgcccgga gtggggccgg   27780
tcggctgggc tggccgagcc cgggtctggg aggtctgggg tggcgagcct gctgtctcag   27840 gagggcctg gctccgccgg gtggccctgg ggtaagtctg ggaggcagag ggacggccta    27900
ggcccgggga agtggagggg gatcgcccgg gtctctgttg gcagagtccg ggcgatcctc   27960
tgagaccctc cggggcccga cggccgccct cggcccccca gacagacccc agggtctcca   28020
ggcagggtcc ggcatctcca ggggcagcag gctcaccacc acaggccccc cagacccggg   28080
tctcggccag ccgagccgac cggccccgcg ccgggcgcct cctcggagcc agccccggg    28140 gttggttctg cccctctctc tgtccttcag aggaaccagg gacctcgggc accccagagc   28200
ccctcgggcc cgcctccagg cgccctcctg gtctccgctc ccctctgagc cccgttaaac   28260
ccaaagaatg tctgagggga gccacccctcg gggcccaggc cccagagtcc agaggtcagg   28320
ggcacctcag ggtgcctccc cgggtcccag gccagccgga gggaccccgg cagcccgggc   28380
ggccccagag gccggttcct cgcccctccc ccgggcttca gagcccaggg tgtcccccag   28440
aagggaccct aggcgtcccc tctcctcccc tccaggcccg agcctctccc tcgcggagag   28500
gggcctcttc gagccctcaa gtccagtccc accgagaccc gagtggccg gatcccccac    28560 cggcccttct ctttccccct actcctctcc aaccttcgct ccaccctaga ccccagcttc   28620
tggcctcccc gggtccacca ggccagccgg agggaccccg gcagcccggg cgagtcgcct   28680
tccctctccc ctggcctctc cttcccgcct cccacccgag cccctcagc ttgcctcccc    28740 accgggtcca tcaggccggc cggagggacc ccggcggccc ggtgtcagtt ccccctgcag   28800
ccgcccagtc tctgcctcca ggcaagggcg ccagcttttc tcccccagc ctgaggccca    28860 ggctcctgtg cactgtctgt aaagtccagc ctcccacgcc cgtccacggc tccaggccc    28920 agccccgtcc acccctcccc acgttggaca ggccctctgt ccacccgggc catcccgcc    28980 cccctgtgtc caccccagtc ccgtccaggg gggactttat gtgacccttg ggcctggctc   29040
cccatagact cccatgtaag cctgcctcga gtaggtgcct ccagagcccc ttttgccccc   29100
ctggcggccc agcccgaccc ccgggcgccc ccaaactttg tccagatgtc caggggtccc   29160
cgagggcgag gcccagcccc ctcccgcccc tgtccactgc cccggtcccc ccagaagccc   29220
ccaaaagtag aggctcaggc catgcgcgcc ctgtcaccag gcctgccaaa gagccagatc   29280
taaggccggg agaggcagcc ccaaagcggg tgcagtaaca ggtaatctct ggtagtgatt   29340
tggacccgaa atctgacact ttagagctct ggaggacttt aaaactctaa aaatcaaaac   29400
tttagaggcg aatgggcgcc attttgtccc cacgcgcgca taatggcgga cctaggccta   29460 aaaccccccag gaagcgggtc tatggttggc tgcgctgctg ctatctttag aggggaaaag   29520
aggaataagc cccagacag gggagtgggc ttgtttgtga cttcaccaaa ggtcagggcc    29580
caagggggtt cgcgttgcta ggccaccttc tcagtccagc gcgtttacgt aagccagaca   29640
gcagccaatt gtcagttcta gggaggggga ccactgcccc tggtataaag tggtcctgca   29700
```

```
gctatttctg gtcgcatcag agcgccagga gtccacacaa atgtaagagg gggtcttcta    29760
cctctcccta gccctccgcc ccctccaagg actcgggccc agtttctaac ttttttcccct   29820 tccctccctc gtcttgccct gcgcctgggg ccaccttcat caccgtcgct gactccgcca    29880
tccaagccta ggggagaccg aagtgaagtc cctggaccag cccggcccgg ccccccggt     29940 atcgggccag aggtaagtgg acttttaattt tttctgctaa gcccaacact ccaccacacc   30000
caggcacaca ctacacacac ccacccgtct cagggtcccc tcggacagct cctaagaagg    30060
caccggtcgc ccagtcctac cagagggggc caagaaccca gacgagtccg tagaagggtc    30120
ctcgtccagc aagaagagga ggtggtaagc ggttcacctt caggggtaag taacctgacc    30180
tctccagggc tcacataaag ggaggcttag tatacatgct tcttgctttt cacaggaacc    30240
tgggggctag tctgggtggg tttaggctgc ctcaagttgc atcagccagg gcttcatgcc    30300
ctcctcagtt ccctagtccc cgggcttcag gccccctccg tccccgtcct ccagagaccc    30360
gggcttcagg ccctgcctct cctgttaccc ttttagaacc acagcctgga cacatgtgcc    30420
agacgcctgg gcctctaagg ccctcgggtc ccctggacc ccggcctcag caaccctgct     30480 gctccctcc tgccacccca gcctccccc ctccccgtcc cccttcgctc cttatcctcc      30540
cccggtcccc agtagggccg cctgccccc tgcacccagt acctgcccct cttggccacg     30600
caccccgggc caggccacct tagacccggc caagccccat ccctgaagac ccagcggcca    30660
ttctctctgg taacgagcag agaagaagta gaggcccgcg gccattgggc ccagattgag    30720
agaccagtcc aggggcccga ggttggagcc agcgggcacc cgaggtccca gcacccggtc    30780 cctccgggggg gcagagacag gcagggcccc ccggcagctg gccccgagga ggcgcccgga   30840
gtggggccgg tcggctgggc tggccgagcc cgggtctggg aggtctgggg tggcgagcct    30900
gctgtctcag gaggggcctg gctccgccgg gtggccctgg ggtaagtctg ggaggcagag    30960
ggacggccta ggcccgggga agtggagggg gatcgcccgg gtctctgttg gcagagtccg    31020
ggcgatcctc tgagaccctc cgggcccgga cggccgccct cggcccccca gacagacccc    31080
agggtctcca ggcagggtcc ggcatctcca ggggcagcag gctcaccacc acaggccccc    31140
cagacccggg tctcggccag ccgagccgac cggcccgcg ccgggcgcct cctcggagcc     31200
agccccgggg gttggttctg cccctctctc tgtccttcag aggaaccagg gacctcgggc    31260
accccagagc ccctcgggcc cgcctccagg cgccctcctg gtctccgctc ccctctgagc    31320
cccgttaaac ccaaagaatg tctgagggga gccaccctcg gggcccaggc cccagagtcc    31380
agaggtcagg ggcacctcag ggtgcctccc cgggtcccag gccagccgga gggacccgg     31440 cagcccgggc ggcccagag gccggttcct cgcccttcc ccgggcttca gagcccaggg     31500 tgtccccag aagggaccct aggcgtcccc tctcctcccc tccaggcccg agcctctccc     31560
tcgcggagag gggcctcttc gagccctcaa gtccagtccc accgagaccc gagtggcccg    31620 gatccccac cggcccttct ctttccccct actcctctcc aaccttcgct ccaccctaga    31680
ccccagcttc tggcctcccc gggtccacca ggccagccgg agggaccccg gcagcccggg    31740
cgagtcgcct tccctctccc ctggcctctc cttcccgcct cccacccgag ccccctcagc    31800
ttgcctcccc accgggtcca tcaggccggc cggagggacc ccggcggccc ggtgtcagtt    31860 cccctgcag ccgcccagtc tctgcctcca ggcaagggcg ccagcttttc tccccccagc     31920
ctgaggccca ggctcctgtg cactgtctgt aaagtccagc ctcccacgcc cgtccacggc    31980
tcccaggccc agcccgtcc accctcccc acgttggaca ggccctctgt ccacccggc      32040
```

```
catccccgcc ccctgtgtc cacccagtc cgtccaggg gggactttat gtgacccttg    32100
ggcctggctc cccatagact cccatgtaag cctgcctcga gtaggtgcct ccagagcccc    32160
ttttgccccc ctggcggccc agcccgaccc ccgggcgccc ccaaactttg tccagatgtc    32220
caggggtccc cgagggcgag gcccagcccc ctcccgcccc tgtccactgc cccggtcccc    32280
ccagaagccc ccaaaagtag aggctcaggc catgcgcgcc ctgtcaccag gcctgccaaa    32340
gagccagatc taaggccggg agaggcagcc ccaaagcggg tgcagtaaca ggtaatctct    32400
ggtagtgatt tggacccgaa atctgacact ttagagctct ggaggacttt aaaactctaa    32460
aaatcaaaac tttagaggcg aatgggcgcc attttgtccc cacgcgcgca taatggcgga    32520
cctaggccta aaaccccag gaagcgggtc tatggttggc tgcgctgctg ctatctttag    32580
aggggaaaag aggaataagc ccccagacag gggagtgggc ttgtttgtga cttcaccaaa    32640
ggtcagggcc caaggggggtt cgcgttgcta ggccaccttc tcagtccagc gcgtttacgt    32700
aagccagaca gcagccaatt gtcagttcta ggggaggggga ccactgcccc tggtataaag    32760
tggtcctgca gctatttctg gtcgcatcag agcgccagga gtccacacaa atgtaagagg    32820
gggtcttcta cctctcccta gccctccgcc cctccaagg actcgggccc agtttctaac    32880 ttttttcccct tccctccctc gtcttgccct gcgcctgggg ccaccttcat caccgtcgct    32940
gactccgcca tccaagccta ggggagaccg aagtgaagtc cctggaccag cccggcccgg    33000
gccccccggt atcgggccag aggtaagtgg actttaattt tttctgctaa gcccaacact    33060
ccaccacacc caggcacaca ctacacacac ccaccgtct cagggtcccc tcggacagct    33120
cctaagaagg caccggtcgc ccagtcctac cagagggggc caagaaccca gacgagtccg    33180
tagaagggtc ctcgtccagc aagaagagga ggtggtaagc ggttcacctt caggggtaag    33240
taacctgacc tctccagggc tcacataaag ggaggcttag tatacatgct tcttgctttt    33300
cacaggaacc tgggggctag tctgggtggg tttaggctgc ctcaagttgc atcagccagg    33360
gcttcatgcc ctcctcagtt ccctagtccc cgggcttcag gccccctccg tccccgtcct    33420
ccagagaccc gggcttcagg ccctgcctct cctgttaccc ttttagaacc acagcctgga    33480
cacatgtgcc agacgcctgg gcctctaagg cctcgggtc cccctggacc ccggcctcag    33540
caaccctgct gctcccctcc tgccacccca gcctccccc ctcccgtcc ccttcgctc    33600 cttatcctcc cccggtcccc agtagggccg cctgccccc tgcacccagt acctgcccct    33660
cttggccacg caccccgggc caggccacct tagacccggc caagcccat ccctgaagac    33720 ccagcggcca ttctctctgg taacgagcag agaagaagta gaggcccgcg gccattgggc    33780
ccagattgag agaccagtcc aggggcccga ggttggagcc agcgggcacc cgaggtccca    33840
gcacccggtc cctccggggg gcagagacag gcagggcccc ccggcagctg gccccgagga    33900
ggcgcccgga gtgggccgg tcggctgggc tggccgagcc cgggtctggg aggtctgggg    33960
tggcgagcct gctgtctcag gaggggcctg gctccgccgg gtggccctgg ggtaagtctg    34020
ggaggcagag ggacggccta ggcccgggga agtggagggg gatcgcccgg gtctctgttg    34080
gcagagtccg ggcgatcctc tgagaccctc cgggcccgga cggccgccct cggcccccca    34140
gacagacccc agggtctcca ggcagggtcc ggcatctcca ggggcagcag gctcaccacc    34200
acaggccccc cagacccggg tctcggccag ccgagccgac cggcccgcg ccgggcgcct    34260 cctcggagcc agccccgggg gttggttctg ccctctctc tgtccttcag aggaaccagg    34320
gacctcgggc acccccagagc ccctcggccc cgcctcagg cgcctcctg gtctccgctc    34380 ccctctgagc cccgttaaac ccaaagaatg tctgagggga gccacctcg ggcccaggc    34440
```

```
cccagagtcc agaggtcagg ggcacctcag ggtgcctccc cgggtcccag gccagccgga    34500
gggaccccgg cagcccgggc ggcccagag gccggttcct cgccccttcc ccgggcttca     34560
gagcccaggg tgtcccccag aagggaccct aggcgtcccc tctcctcccc tccaggcccg    34620
agcctctccc tcgcggagag gggcctcttc gagcccaa gtccagtccc accgagaccc     34680
gagtggcccg gatcccccac cggcccttct cttcccccct actcctctcc aaccttcgct    34740
ccaccctaga ccccagcttc tggcctcccc gggtccacca ggcagccgg agggaccccg     34800 gcagcccggg cgagtcgcct tccctctccc ctggcctctc cttcccgcct cccacccgag    34860 cccccctcagc ttgcctcccc accgggtcca tcaggccggc cggagggacc ccggcggccc   34920
ggtgtcagtt cccctgcag ccgcccagtc tctgcctcca ggcaagggcg ccagcttttc     34980
tccccccagc ctgaggccca ggctcctgtg cactgtctgt aaagtccagc ctcccacgcc    35040
cgtccacggc tccaggccc agccccgtcc acccctcccc acgttggaca ggccctctgt     35100
ccacccgggc catccccgcc ccctgtgtc caccccagtc ccgtccaggg gggactttat     35160
gtgacccttg ggcctggctc cccatagact cccatgtaag cctgcctcga gtaggtgcct    35220
ccagagcccc ttttgccccc ctggcggccc agcccgaccc ccgggcgccc ccaaactttg    35280
tccagatgtc caggggtccc cgagggcgag gcccagcccc ctcccgccca agctgctttg    35340
attcctggga tattttgggg aatggtgtta actttctccc cttgtatttg ctattcaatc    35400
aacctgattc cccctgctca tacctccact cacaaccaag ccactacggc cacgtccaca    35460
acctcccgca caggtaagtg cttttccatt tttagcccca gccccgcctc tataagttct    35520
aggcaaacct ccaatcacca gccaccttcc aatgtagtct cttagagagt ggctgctacg    35580
cattagcgag agatttgacc cacacccagt agccacccga cgccaatctg tctacataga    35640
agaagaagag gatgaagact aagtcacagg cttagccagg tgatttgtga atttcagttt    35700
atttactttc ttccaatcaa gctttcccag cctccgcttc tcaggtccca gttatgggtt    35760
ttccatgggg gacctagtat ccgttctatt agattaactc gcaagatact aaaattaacc    35820
aaggtcagcc caagtgacgc gtgttatgcc aggctgccca ccctgaggat ttcccccaaa    35880
aatgggctgt tagtagggtc ctcctacccc ctctttaggc caggtgtgtt attttgttgt    35940
gttagtgcta tgtaatgtgt tgccgccagg tggcagcttg tttgtagatg tgcagcgccc    36000
cttaatggta ggtctgcttt agggctgcca ggtggcgcaa actaggatta attcacctgt    36060 atcccttttcc ctccacccgc agtaactcag cgctggcgtg tgacgtggtg taaagttttg   36120
cctgaacctg tggttgggca ggtacatgcc aacaaccttc taagcacccg cgcttgtgtt    36180
ttgctttatc tgctgccatc atgcctacat actatcttgc gttacatggg ggacagtcat    36240
ataatctaat tgttgacact gatatgtctg gaaacccgtc actctccgta attcccacga    36300
atccttacca ggaacaacta tcaaataatc cattaattca actacaaatc gttgtcgggg    36360
aaaacactgg ggcacccgca ccgcccaac caccccccc accccctcca cctcctccac      36420
ctgagcgcag ggatgcctgg acacaagagc ccttaccact ggatatgaat cccctgggca    36480
gtgacgccag tcaaggccct ctggcatctt ccataagaat gctttgcatg gctcaatacc    36540
ttcttagaaa cgcacggggc caacaaggcc ttcttaggcc actaggacca caaacacgct    36600
ctcaggtcac cttggaacgt caacctgtcc acaaccctcg ccaggaggca cccatcattt    36660
tgttacagag tcccgcgccc ccccgattca caccagtgcc catggtagcc ttaggacata    36720
ctcttcaacc cacaccacca ccaaggccta ctcttcctca acccagaata ccactgataa    36780
```

```
taccaccaag gcatactaat caaccagcca caacaccacc cacggcgcca caaaggctca    36840
cactagggca tcaactaagt ctaccaccgc atcctccccc gcatcagagc accccacatt    36900
gtagttctga tagtacagga ctccctccac ctcccacatc ttacagcatt ccttctatga    36960
cattatcccc cgaaccattg ccgccaccag cagcaccagc accccccctt ccaggtgtca    37020
tttatgacca acaagcactt cctccaactc cagggccacc atggtggcca cctgtccgcg    37080
accccacgcc aaccactcag actccaccaa caaatacgaa acagggcccg gaccagggcc    37140
agggaagggg caggtggcgg ggcaggggca gaagcaaggg caggggcaga atgcacaaac    37200
ttcctgaacc acggagacca gggccagaca cttccagtcc tagtatgcct caattaagtc    37260
cggttgtcag tcttcatcag ggacaggggc ctgagaactc accaaccccc ggcccgtcta    37320
cggccggccc cgtctgtaga gtgacaccct cagcaacccc tgacatttca ccaatacatg    37380
aaccagagtc ctctgatagt gaagaacccc cctttctctt ccccagtgat tggtatcctc    37440
caacgttaga acctgcagaa ttagatgaaa gttgggaggg cattttttgaa acaacagaat    37500
ctcatagctc tgatgaagag aatgtagggg ggcctagtaa aagacctcgc acctccactc    37560
agtaaaagac cttactctct ccagtaatca atgtatccca ataaatgtt aatgattttg       37620
ttcttaacta ttgacccgcc tgtcattcta ttaattaaac aagggaagct atgtttagct    37680
attccaccaa cactgcacca atggacagcc aaaattggtg ccttgctcac agctcttttt    37740
gccagtggct tacagcccag taggcagctc agaaaagttt agctattcca ccaacccggc    37800
cccaatgaat gcttgccaaa attggggcct tgctctcagc actttgccag cgacttatag    37860
catggtaggc cgctcaactc ggcctgtctt actgccagc ctactctcca cttccagtcc     37920
atgttcgcac tcctatgcat ttccttccct cccactttta tcccagtccc aacccaaaac    37980
cacacacaac acatagaatt gttagtttaa acagtttatt gatacatggc tgcttttagc    38040
ctaattgtgt attgctctcg ttgccaaaac ctggtgtaag ggccggcacc cgcaacatgg    38100
ggaaaacata accgccgcca tcccatgggg agggtagagg cggttgacat gtaggtgagt    38160
agtgtaagaa gcatggcgaa gtagacaggt tacttttaga gtgtagtgta cagggccggg    38220
cgcaacagtg ccaccaaccc ggggtctgag cattccatgg gcagcaggga cactgcacta    38280
ccgccaggtc caggggcagc cggggttcct ggcgctccgg ggggcagcca ggcggccgcc    38340
ggtgggtccg ctgggccgct gccccgctcc gggtggggggg tggccccgct gggcaccgct    38400
gcgccgccgc caggtccagg ggcagccggg gttcctggcg ctccggggc agccgggcgg    38460
ccgcggtgg gtccgctggg ccgctgcccc gctccgggtg ggggtggcc ccgctgggca     38520
ccgctgcgcc gccgccaggt cctggggcag ccggggttcc tggcgctccg ggggcagccg    38580
ggcggccgcc ggtgggtccg ctgggccgct gccccgctcc gggtgggggg tggccccgct    38640
gggcaccgct gcgccgccgc caggtcctgg ggcagccggg gttcctggcg ctccggggc    38700
agccgggcgg ccgccggtgg gtccgctggg ccgctgcccc gctccgggtg ggggtggcc    38760
ccgctgggca ccgctgtgcc gccgccaggt cctgggcag ccggggttcc tggcgctccg    38820
ggggcagccg gcggccgcc ggtgggtccg ctgggccgct gccccgctcc gggtgggggg   38880
tggccccgct gggcaccgct gcgccgccgc caggtccagg ggcagccggg gttcctggcg    38940
ctccggggc agccgggcgg ccgccggtgg gtccgctggg ccgctgcccc gctccgggtg    39000
gggggtggcc ccgctgggca ccgctgcgcc gccgccaggt cctggggcag ccggggttcc    39060
tggcgctccg ggggcagccg gcggccgcc ggtgggtccg ctgggccgct gccccgctcc    39120
gggtgggggg tggccccgct gggcaccgct gcgccgccgc caggtcctgg ggcagccggg    39180
```

```
gttcctggcg ctccgggggc agccgggcgg ccgccggtgg gtccgctggg ccgctgcccc   39240
gctccgggtg gggggtggcc ccgctgggca ccgctgcgcc gccgccaggt ccaggggcag   39300
ccggggttcc tggcgctccg ggggcagccg ggcggccgcc ggtgggtccg ctgggccgct   39360
gccccgctcc gggtgggggg tggccccgct gggcaccgct gcgccgccgc caggtcctgg   39420
ggcagccggg gttcctggcg ctccgggggc agccgggcgg ccgccggtgg gtccgctggg   39480
ccgctgcccc gctccgggtg gggggtggcc ccgctgggca ccgctgtgcc gccgccaggt   39540
cctggggcag ccggggttcc tggcgctccg ggggcagccg ggcggccgcc ggtgggtccg   39600
ctgggccgct gccccgctcc gggtgggggg tggccccgct gggcaccgct gcgccgccgc   39660
caggtccagg ggcagccggg gttcctggcg ctccgggggc agccgggcgg ccgccggtgg   39720
gtccgctggg ccgctgcccc gctccgggtg gggggtggcc ccgctgggca ccgctgcgcc   39780
gccgccaggt cctggggcag ccggggttcc tggcgctccg ggggcagccg ggcggccgcc   39840
ggtgggtccg ctgggccgct gccccgctcc gggtgggggg tggccccgct gggcaccgct   39900
gcgccgccgc caggtcctgg ggcagccggg gttcctggcg ctccactgca cctggaatgc   39960
agggtggggg cgtggtcccc tggacccccag ccccgccgat ccctccccca gggcgtaccc   40020
ggcttgcctg gttctggggc tcctctgggg gtcgctgcat ccgccggtag ggttcgaatg   40080
ggcgtggtcc gcttgctctg ctggcccggt acgcctggat tgccggctgg gggctggggt   40140
cccgggacgc cccctccctg ctcccacccg gttccctccc ccagggcgtg ccccgcttgc   40200
ctggtcctgg agctcatccg gggatgctgc atccgctagt ccgacctggg tgggtgcggt   40260
ccgctggccc caccctgggg gtcgccgccg ggtctgctgg tccggtgcac ctgaaaggca   40320
gggggggggc agtgagggag gggcgtggtc ctgggacccc gcgccgactg gcagggggtc   40380
cccatggcac aggcctaggg gtccagggggg cagccgcggc ccagcgcgcc ccgttcacgg   40440
gggaggaccg cggccgagcc accagggggcc cggcggggggt gggggggtgcg ctcccaggcc   40500 ggaccctggt gccaggcagg gaccccgcgc caccccgcttc atgggggggg aggccgccgc   40560
aaggacgccg ggccggctgg gaggtgtgca cccccccgagc gtctggacga cgctggcgag   40620
ccgggccggc tcgccttctt ttatcctctt tttgggggtct ctgtgtaata cttttaaggtt   40680 tgctcaggag tgggggcttc ttattggtta attcaggtgt gtcattttag cccgttgggt   40740
ttcattaagg tgtgtcacca ggtggtggt acctggaggt tattctattg ggataacgag   40800
aggaggaggg gctagaggtc cgcgagattt ggggtaggcg gagcctcagg agggtcccct   40860
ccatagggtt gaaccaggag ggggaggatt gggctccgcc ccgatatacc tagtgggtgg   40920
agcctagagg taggtatcca tagggttcca ttatcctgga ggtatcctaa gctccgcccc   40980
tatataccag gtgggtggag ctaggtagga ttcagctagg ttcctactgg ggtacccccc   41040
taccctacct taaggtgcgc caccccttcct ccttccgttt taatggtaga ataacctata   41100
ggttattaac ctagtggtgg aatagggtat tgcagctggg tatataccta taggtatata   41160
gaacctagag gaagggaacc ctatagtgta atccctcccc ccctaccccc ccctccctt   41220 acggttgcct gagcccatcc cccaccccag caccccgggg tgacgtggca ccccgcgtgc   41280
cttactgact tgtcaccttt gcacatttgg tcagctgacc gatgctcgcc acttcctggg   41340
tcatgacctg gcctgtgcct tgtcccgtgg acaatgtccc tccagcgtgg tggctgcctt   41400
tgggatgcat cactttgagc cactaagccc cgttgctcg ccttgcctgc ctcaccatga   41460
cacactaagc ccctgctaat ccatgagccc cgcctttagg aagcaccacg tcccggggac   41520
```

```
ggaagggggac ttggggtgat tttctatgtg ggggtggaaa tatgagcaag aataaggacg   41580
gctccttatt aacctgatca gccccggagt tgcctgtttc atcactaacc ccgggcctga   41640
agaggttgac aagaagggtc aaggtttcgt ctgtgtgttg aagggcaggg gctgttgggt   41700
gcatctggaa cggcttacct cgggtaactg tttgccatta aaaggttggg gattaggttt   41760
agccccttta gctgccattt cgaaccgggg tgtgcagatg caggtctccg ggtgggcagg   41820
cagtacgaga tgtcacgttg tgttgtcttt cctcccaccc ctgtcctggc tgtggcaaat   41880
gcgaccctca tagagttgtg tttcaggtct gtgtcctgtt ttgcggtggg ttatttcccc   41940
cctcagtgtt cgccagctta tttccccagt ccccacgtac tggggcctgt ggacacctga   42000
gggagcggcc gttggtgggc atgtgttgga attgctccca ccctcaattt tcgcttgcct   42060
tcttcccttg ttaacctgat agcatagcct ctaggtttcc ttgtaggtct gtttgggttt   42120
gttggttcac gtggtgctaa cttgaatttt ttggttttct agttccctct taattacatt   42180
tgtgccagat cttgtagagc aagatggcct attcaacaag ggagatactg ttagccctgt   42240
gtatacggga cagtcgtgtg catggaaatg gtaccctgca tcctgtgttg gagctagcag   42300
caagagaaac acctctccgc ctttcgccag aggacactgt agttctgcgt tatcatgtgt   42360
tgcttgagga gataattgaa cgaaattcag agacatttac agaaacttgg aacagattta   42420
taacacacac cgaacatgtg gacctggatt ttaactcagt attttttagag atatttcacc   42480 gtggagaccc aagccttggg cgcgcgttgg cctggatggc ctggtgcatg catgcctgca   42540
ggacattgtg ttgtaaccag tctactcctt actatgttgt ggacctgtca gttcgtggga   42600
tgttagaagc cagcgaaggc ctggatggtt ggattcatca acagggcggc tggtctacat   42660
taattgaaga caacattcct ggatccagaa ggtttagctg gactttgttt cttgctggac   42720
tgactttgag tctgttagtt atatgtagtt atttatttat ctccagagga agacactaat   42780
ctatacattt tctcagcact ttatatgaat cagggtcatt gggcctgcgg ggaactgagc   42840
cagtaggata ttaggcaagg gtgacacagt gcccatgcat tataatttaa ccaaacagtg   42900
gtcgtgagtt ttaggccggc catgggggct tacaagaata acatgccaat gacccggccc   42960
ccacttttaa attctgttgc agcagatagc tgatacccaa tgttatcttt tgcggcagaa   43020
attgaaagtg ctggccatat ctacaattgg gtgtcctagg tgggatatac gcctgtggtg   43080
ttctaacggg aagtgtgtaa gcacacacgt aatttgcaag cggtgcttca cgctcttcgt   43140
taaaataaca caaggacaag atactaaaga aataactgag gtgagtgtgg aagatgggga   43200
atactatgtg ttatgttaac gggtgagagc ctatactgca gcccagactc ggggggagga   43260
ggaaatggta agagttatac tctacttatc ttttttgaca ctacatttaa ctgttatgta   43320
acaatgtttg cttattttca tgttcaataa acgctatgtt aatgatgaag aacctgtgtt   43380
ctttggaagt gggcccaatg gggtagtagg ttttgggagg gtgccgtgct agatatttca   43440
actgccacag accccatttt gtcccacctg ttaccacatt ctaggtcctg catccagtgg   43500
gccaggtgtc tcaccatggc tctttctagg tggataccac agtccaggcc cccaaggcta   43560
ccgtgctaat tacctcctca tgtccacccc caccctgtgt tactgtcgcc tgattatcct   43620
ggcttagcag cctccaagtt ttacaagacg tcccattgcc ctgcccttgg tccaagtctc   43680
gcctgttttc agcagcctgt tgtagcctgc ccccaagttt cgcaggtttc ccccatgctt   43740
ccacccgtta acccaatagc atgacagcca atccaacacg aggcaagttt taagagttaa   43800
aagcaactac tgtttatttt ccaaaatgag ctgggtatag ttgatgatct gtaggcgcag   43860
ctcatcccca cattccaggt ccttgatggc ctcgtagatg gcatcttcgt cgacattgac   43920
```

```
agccttctca tataccgtgt ctctggggct gacctttata cagaaggcgt cccctactag   43980
gtccacggcc agctcgtagg tggggcctat gttttcacat aacagtttca agcaggtctc   44040
tgggatgtga agggaggtgc cctggagcag gagatgcatg attaggcgcc cttttccatt   44100
tgtgctgaag atggggcaga tggtgccaca aaagtgtccg gtgaccaggt aagcgtagag   44160
aaggctgggt tgggaaagtc cagcctttac tgcactggga gagctgctga gcagagacac   44220
atagaaggtc ttgttgggta ttatcttgtg gacattgttg aagaaggaga gctgggtgga   44280
gctaaactcc tgaggcacat gaacctggga cctattgatg cagatctcgc agtgagaccc   44340
cagagtcagg ctgtggccga agggagacag gcgaaggcag cgcccggggg agagagtgca   44400
cagtgacagt gggagaaaca cggcctctga gacatgtatg ggggtgttca tctcacgcag   44460
aaaatctttg cccagctcaa agttggcaga gattcccctg aagaagtccc gtagtgaaaa   44520
atgggatctg tctacaccat gtctggtgtg ccgggaacat attgatcggg ccacactgcc   44580
aaccctttcc attcttccca gctctgagcg agattttcca cacctggaca ccgacttcac   44640
gctatgcgcc gaggcctttg aaggccgtgta gtttctgtgg tgcggatgca ttaggcggcg   44700
caatgcggga tctgccggtc gctgttggcg tgcattcacg gcatctgggg tgaccggggc   44760
catcgggttt acttttcaca cgtagacctg ggaagtttga taggactgta ccaggtcaag   44820
gccgtggatg cgcaggacca cgtccagttc cttagtgaca tccacgagga ttgttttgcc   44880
cactctggcc acttgtgtgg atttaaatat gtacacaagc gtaattaacg agtcacagac   44940
cccctgttcc agattctgac cggctgcaag cgctgcctta aaggcctgga agctgggtgg   45000
gtaaatctga ccaaacagca cgctcggatt cgtgatgctg tggttgatgg cacacagggg   45060
gtcgcagaac aggtgcttgt ggaagtcttg cggggtgcac atctgcagcc aggcccttag   45120
cctggggcat ggcacatcca gcagcgtgtt ttgggtcttg atgaggaaca cgatcctgtc   45180
taggattttg atgttgttgc cgaacgagtc aagaatcagg ctcttgaagc ggtcaagggt   45240
gtccttggcg tccgggtggg ccccgaggct ctcgcagagt gggcagatgg tccgtgaggc   45300
attcttgtgc cttagtccaa acatgggggc caggaggcag gggccctgcg aatggtcgcc   45360
agcctccggt ctggtgatgg ccaggccaa ctccgccagc tcatcgccgc tgtattccgc   45420
gtttaaaccg atagcatggt ggcctggccc cccgagcagg tccgtcccct gccacgtacc   45480
taatagtagt ccacagtagt cggccttggt tgtaatttta ggagagagtc ctcccttttc   45540
ggccctgaga aatggatgct gaactcggtt tctggtaggc aggtggcagc acagggcggt   45600
gtacaggccc ctgccgacgt cccctgggac atcctgggaa tctttgcagg ttctgggtcc   45660
agggagggta agaaaagtgg gggtggttct gggccacatg gacttgaagc agaagttggc   45720
cggggactgg ccggtgagga tggatttcag aaactccaat ttgtagtagc cgaggttggc   45780
atttctaatc atgtcagaag aggacacagg gaggaagcac cggcaaatgt aaaagtgaag   45840
ctggatgtca atggcaagaa tcctggaggg catgaagagg gaatccaacc ccccggccat   45900
ggggaagtat tttatcagga tgtgtaaaaa gtccatgcct gtgatgaggc tagagatcca   45960
ggctcgtggg gcatttagac agtagtagca gagcagggca tagtcctcaa agaaggccac   46020
gggggcatct gagtgattga ccagggtgtc gagcagatca caaactcggc aggtgctggc   46080
tggagagagg gactcgtagg tgtggacgag tggtgggtag gctatgcctt cttccgcgtt   46140
ggctggaaga taggagtggg ccatcaaaag gccgactgcc tcgaactggc ttttcagatt   46200
gtccacggtc cagggcacaa agtcctccat ctttggagtt ctgcccgcga tctgtgccac   46260
```

```
ctctgttacg ccactcctcg tgagggggca gctggacagt cttttttccgg tcaggggggtt    46320 tggctcgttt gcgctcgtga ctttgtgagc catgacacat ctgggtggca aggtgaggtc    46380
ttctgggttt ttaataccgg ggtcggcacc agtttctggg acaccgccac aaggacaagg    46440
tgggctagca agttctcgag tctacgaaga ctccggggggc agtcttttga gtttctcgcc    46500
tatgatccac cccaatctcg cccccctaat tgcgccatct gcctacgcga ggctgaacct    46560
cctgaatcac tgcatctttc ttgaggcgtt taaagaagag aatagtggcc agggcctcgg    46620
tggggtccag cgtgaggtct tatttttgaa aagggatatt ataaaacagg tcattgctcg    46680
gattgtggca gccgatagca ccctagatct agtgaatcat ggcgagcccg aagagaggc    46740 tcctagacga gctcaataac ttaattgtgt catttctgtg tgactctggg tctctggaag    46800
tggagagatg ctccggggcg catgtgttct ccagggcag ctcccaaccc ctctgcaccg    46860
tgaagctgcg ccacggacag atttaccacc tggagtttgt ctacaagttc ctggcccttta    46920 agctgaagaa ctgcaactac ccttcctcgc ccgtgtttgt gatatccaac aacggcctgg    46980
ccaccaccct gaggtgcttt ttgcacgagc cgtcgggtct cagatcgggc cagagcggcc    47040
cttgcctggg tctctcaacg gatgttgacc taccaaagaa ctccatcatt atgctgggcc    47100
aggatgactt cattaagttc aaaagcccc tggtcttccc tgctgagctt gatctcctga    47160
aatctatggt ggtctgccgg gcctacatca cggaacaccg gacgacgatg cagtttctgg    47220
tgtttcaggc cgccaacgcc cagaaggcct cgcgggtcat ggatatgatt agtgatatgt    47280
ctcagcaact gtctcggtct ggtcaagtcg aggatacggg cgccagagtc acaggtggag    47340
gaggtcccag gcctggcgtc acgcactcgg ggtgtcttgg ggactcacac gttaggggggc    47400 gcggtggttg ggacttggat aacttttcag aagctgagac cgaagacgag gcgagttacg    47460
ctccttggag ggacaaagac tcgtggtcgg aatccgaggc ggcgccgtgg aagaaggaac    47520
tcgtgaggca ccccatccgc aggcaccgga cacgcgagac tcgccgtatg cgcgggagcc    47580
attcacgggt ggaacacgtg cccccccgaga ccccgggagac ggtggtgggg ggagcatggc    47640
gttattcttg gcgcgccaca ccttatctgg cacgggtgct ggctgtcacg gccgtggccc    47700
tgctcctgat gtttctgagg tggacctgac gttgcaggcc cttggggagc ggggggttctc    47760 caggctcctg gatctgggggc tggcctgcct ggatctgagc tatgtggaaa tgagggaatt    47820
tgtggtttgg ggcaggcccc cagcttctga ggcggctgtg gcctctacgc caggctcgct    47880
tttccgaagc cactcgtccg cctactggtt gtcggaggtg gagaggcccg gggggcctttgt    47940 ccgctgggcc aggtcacaga ccagcccctc atccctgacc ctcgcgcccc atcttggccc    48000
gtccctcttg tcccttttcag tggtcaccgg tggtgggtgt ggagccgtgg ccttttgcaa    48060
cgcctttttc ctagcttatt ttttggttgt gcggtctgtt ttccccgcgt tttccgatag    48120
aatagctgcc tggatctgcg cccagtcccc tttctgcgaa acacccgggg ccgtggccag    48180
gggttaccga ggcctcgtga agaggttctt ggcattcgtg tttgagcgta gtagctatga    48240 ccccccccttg ttgaggcaaa actctaggcc tgtgagcgc tgctttgcca tcaagaatta    48300
tgtcccgggc ctggactcac aaaagctgtgt gacggtcccg agcttctccc gctgggccca    48360
gtctcacgcc agcgagctcg atccccggga gattcgcgac agagttacac cagcgactgc    48420
accttcgttc gtggctgatc atgcctcggc tctattggcc tccctccaga agaaggcctc    48480
cgacaccccc tgtgggaatc ccattcagtg gatgtggtac cgcctgttgg taaactcgtg    48540
cctgaggagt gcccactgtc ttctgcctat acctgccgtc tctgaggggg ggagaaagac    48600
gggcgggggc gtaggggagg atctcgtggg ggccgggggg ccctgcctga gccgggatgt    48660
```

```
tttcgtggcg atcgtaagcc gcaatgttct ctcgtgtctg ctgaacgtgc ctgccgcggg   48720
tccccgggcc tacaagtgtt tcagatccca cgcctccaga ccggtgtctg gcccggatta   48780
ccctcccttg gccgtgtttt gcatggactg cggttactgc ttgaactttg gaaagcagac   48840
aggtgtagga ggcaggctca attcctttag acccactctc cagttttatc cccgtgacca   48900
gaaggagaag catgtgctga cctgccatgc cagcggccgt gtgtactgct ccaactgcgg   48960
ctctgcggcg gtgggctgcc agaggctggc tgagccaccg agcgcccgct cgggctggcg   49020
gccccgaatc cgggcagtgc tgccgcacaa cgcggcctac gagctcgacc gtggctcccg   49080
cctcttggat gccatcatcc cctgcttggg acccgaccgc acttgcatgc ggccggtggt   49140
cctgcggggg gtgacggtca ggcagctcct gtatttaact ttgcggacag aggccagagc   49200
cgtttgctcc atctgtcagc aacgccaagc tccagaggac gcccgcgacg agcctcacct   49260
gttctcctcc tgtttagagg tagaattgcc acctggtgag cggtgtgcgg gctgccgtct   49320
ctatcagacg cgttatggca cgccggctgc ccaagcccac cctccagggg aggctggagg   49380
cggattttcc agacagtccc ctgcttccta aatttcaaga gctgaaccag aataatctcc   49440
ccaatgatgt ttttcgggag gctcaaagaa gttacctggt atttctgaca tcccagttct   49500
gctacgaaga gtacgtgcag aggactttg gggtgcctcg gcgccaacgc gccatagaca   49560
agaggcagag agccagtgtg gctgggctg gtgctcatgc acaccttggc gggtcatccg   49620
ccacccccgt ccagcaggct caggccgccg catccgctgg gaccggggcc ttggcatcat   49680
cagcgccgtc cacggccgta gcccagtccg cgacccctc tgtttcttca tctattagca   49740
gcctccgggc cgcgacttcg ggggcgactg ccgccgcctc cgccgccgca gctgtcgata   49800
ccgggtcagg tggcggggga caaccccaag acaccgcccc gcgcgggca cgtaagaaac   49860 agtagagggc acgaaacatg gtgtatgcac tttattaata aacaattaca gatacaaaaa   49920
cttgagtctc tcgaggtctg cgatgaggcg gtgggtggaa cgctccagct tgcggcgaag   49980
ctggctcacg aagcgagaca gtactcggct agcctgacta agggtgaggc tataacgcag   50040
gtcctgttcc ggggcggcgg tggatagaga ggaggggat ccggagggga ccactaggtc   50100
gccggaggtc gaccctcctg tcaccacctc cctgataatg tcttcaatag acagaaattg   50160
ggtgaccact gagggagtgt tccacagtaa tgttgtctgg tcgctagatg gcgcgggtga   50220
ggccacgctt tgcgaaaacg aaagtgcttg aaaaggcgcg ggatagcgtg cgctaccgga   50280
tggcgggtaa tacatgctat ccttacattt tggcattttg ggcagctggg aggcggcgga   50340
tgggggtgct tcttttcgca cggtgtatgt ttggggaccc gcatgccggt actgggatag   50400
gcgcacctcg ggccgcgcgc caggctccga ccggaatgc attgggggca atgggattgc   50460 ggggggattgt tgctgtctgc tcctgacagg agagacacg cgcggcggag atgcagccga   50520
cggcggggcc gcggtgggct gcccccgagg acgggcgccg gccgccagcg ccccgtggc   50580 ctttggcacg ggcctggcac ccaccgcttt aattgtgggg gtgggcaggg cagctgcatc   50640
ttggggcctt tgtgcttgcg ttttttgggg gcgcggtgcc aatgcaccaa ctgggtgtg   50700 cgccggggcg gccaagccgg accccagggc gggtgcctgg gggatgggaa agccggacgg   50760
cgcttctccc gggtcgaacg ctggagtagc ggaggctgct gcgccggcgg ccaccacggg   50820 cgcacgggt cgcagcccga cggccgtggg gaggcgggtg gcggagggcc gaatctccgc   50880
ggcttcttcc cggccccccct gctgtttctt ctcccgttgc atgatagaat ggccataggg   50940
tgggtcctga gaggaggctt gtgtgtcctg gggctggagc ccaaaagtcg ttaaagacgc   51000
```

```
tgctgatggt gtgggagcta tgcctcccgt cgactggccg ggcttgtagg gggctgaggg    51060
tggataactg ggcttctgtg aaggcaccaa ccctggaatc tggatggtat gtttcttctg    51120
tgaccccgag gcagtcgatg gtgtagagtt tggagacaat gtgtagacga tgggcccttg    51180
ttcagaagcc cagggacttg agggggggctg ttgtggtgct ggttggggaa ggagctccag    51240
ggaatctttg ggccatggcc ttggggaggt tcccggagac cggtctgggc tctcggaagc    51300
cctcgtttcg gccccgaaat agggccttgc catcaatcgg gggcctggga gagtgatggg    51360
ggcggccaat cccggggtaa ctgtcacgtc cggggggag gaggtaggag acagccagtc    51420
cctgggcctg ccaggggcca ccttctctaa gaggggctc tgtgggctgg gagggccaga    51480
ggcctcagat tcagcagtag tgctcccctc ttccccctgg tccgtctccc ctcctcccaa    51540
ctgctggagc cggtcggagg aggccggggt gttatctgct gactgaaacc cgtccccgct    51600
gaccagtccg tgccccaccc ttgggggaa accggagaac agctcctgga cgttgcgtgg    51660
attcggggga agctggtatc caaccggcag tggaggatct tcgtgctcgt agaaggaggg    51720
gttgagtaca tcggtcggcc atcgtgaggc cccggccgcg ttaaagtaga actgcacgtc    51780
cggcagattg tgccgatagg tgaaacactt ccagatgatg ttttttctgt tggccaggat    51840
ggccacggtg gggggcctgg cctccttagg tttggcggcc ctggcctcgg tgagaagctc    51900
gcgtagccac acggcctggc gtgcaaagat ggacatctct ggctcgaaag actcggagta    51960
gccgtccagg tcctgcagaa aattcagcga gatggtctcc accagggacc ggaagggctc    52020
agagtgcccg tcgcagtaga ggaggggagc aacgaccctg acctgtccca gggtcttcag    52080
gttaaacaga tattgagagg agacaaagag agttaggggc cgaccgagga aggccgccgc    52140
cacggccgcc tcaaaaacgg agacggggat ggtgtcaccg gagcccctct taggaccggt    52200
aatgggagtg ccataaggca taagatttct cagggcccgg ccgtaacgg tgccgtagga    52260 agacgggggtt tcgcggggga cctcgagtcc ctccgccctg gggagctctt ctccgcgtgt    52320
ataggcctgc ttcacaaagt cgcgcaggta gtcctgaaat gcgaccgggc cctccagcgg    52380
gcgcaatgag tgccagagct gctgaagggc ctcgggggcg aagcaccggc gtgcgaggag    52440
cagcatgcag gctcgggcgc gggccgtact ttggttgtgg accaggccca agaactcggg    52500
gtgcggccag agggcggccc gggtatccat ctcctcccag gcgtcctgga agaagatgaa    52560
gccggtgggt ggaccggcga tgcggtggcg ggtgaggcgg cgcgcgtctt ccccgtcgtt    52620
gctgccgcgg gtggttgagg gcatgccccc cctcccggag gctggactcc tgaccagcct    52680
gtaggtgagg accgagtccg acaggaggtc tcccaaaccc ccatctctcg ctagagccga    52740
gaccaggccg agtcctgcgt agaacgatgg ggcgcccagg aaggcggcag cgtaggccgg    52800
atgtgtgccg accagcagcg ccatcatctc ccgttgttcc aatagaataa cttcccggtc    52860
tgtggccggg gctggataag gggggtgatt cctagaggcg atgagactgg cgtgcgctaa    52920
aagcgtcatg gccacaatgg ggttgtctgc caggtcttcc atcagggctt tgggcgcaga    52980
gacgtattcc cgaagcagct ccccggcgtt ggactccacg tcgggccagg tgtcccagta    53040
ggagtcggcg gcggcggcgc tgaggcgggc ggaagctaca ctggccaggg ttcttctcct    53100
cctctcttgg tcatcctgcg ggggaccaat agcttggggg cgtccggctg gggtcaggga    53160
aaaggcctct gggttctcca gcacggtggg catgacatat tccagaaagt tgtggtagac    53220
ggggatgtag ttgagcggct cctgggtgtc tgcggagacg taggccgggt taaggggggtc    53280 gcagggagac tctgtttcca gccagagggt gccggcgtat ttcgcggcc ctgccgccgc    53340 cagaaattgt gcccgccggg tcggggctcc attgccccat ccagttggtg gtgccgaaat    53400
```

```
cgtgatgagg aggggcaggt tgttggtcaa gggatgctta acgaaaacgg taggctgggc   53460
ggtctcgtaa aaagccagga aactctgctt ggccgaggca tagcgcagca gcttgtcctt   53520
gaggagtgca tactgggagc cagccgaggc cccaagcgcc aggcccctgg cagcctccac   53580
cacgatcttg agctggcgcg ggtcggtgtg gcccctggcc tgggtgacca gatcctgcag   53640
cgttccctgc agctgggact cttcctgggc ctcctggatg atggcctcca gtcgggagag   53700
gcgccttttc cagtctgcga cggtctcctt gccccccgcg acccgcttgg ggtccaacgt   53760
ggccagagcc aacctcagct cctccatgcc atccatggag ttctgggcca tgccctcgac   53820
ttccaggagc cgtgttagct catgaatttc accgtcagcc gcagcggcta ggttcagcca   53880
ggcacccaca cccccagcta aggccagggc tccttcggaa agaccccgca ctgcctcgca   53940
gatgccccgg atccacttgg cggctgccag ggatttccgg tagggccacg agccgttccc   54000
ggccgctgcc cgggccaggg cggcctcgag gggagcctgg acaggggctt tgggcgggga   54060
ggggagcagg ctccggagtt catcgtcggg ggcttcgtcg cgtgacctgg agaggacggc   54120
ctccagagcc gtgtgaaagc cccgccgagt gcttgccgcc atctcgtggg ccttcgccat   54180
cagggtctgg ctctccccgga cctgctcttc cagcgcccgg acctcggccg cctcggcctc   54240
ggtcagcagc tctgagaaga agtcccccgt ggcctggagg agatcgtccc gctctcgcct   54300
tgtcagcagc tggggcttct taggccagag cgccgagtcc gaggccagcc tgggcggggc   54360
ggttgcctgg gggatagttg gaggaggagg caggttagcc tggcctgggt cattagtggc   54420
ttcgggtagc gtccgatcca cgtactcgct cacgatggcc gtcagggcag cctcggctga   54480
tcgtcttttt tccagaagcc cggccagccc ccgctcgtac tccgcgtagg gggcctccag   54540
atccgtgttg accaccgctg atttcatgtc cggggactgc agggcctggc gcgtctgcgc   54600
gagggccgaa cggatggcat cggccgccgt cctggcacga aagagggccc cggccgcttc   54660
ctccgctcct cgccctcctc ctccttcttt ggcggtagcc gcggggggtgg cgggccaagc   54720 gtccagtctg gccagagggc cggtctcgat ctccgtgaac cagccgggtt ccacggcctc   54780
cattctctcc gccgcaccac catcgtccac gagcagggat cgcagtctct ccctcctcac   54840
cctcgttatt cccaatagca tagcggcaag gatctgtgtg agggagtcca agatgtccgt   54900
gtttctggct actgccgccg ctgctgccgc ggctgagtcc gtattgtctg gcagcaggga   54960
ggccagcagg gtgttccagt catcgggcga agtgggagcg ggctctgggc gtgccccag   55020 cgccttccta attctggccc aggcctcatt cgcctctcgc gctcgccgct cccgcctctc   55080
cttgtcttcc tgttctcgga gcttctcctt ttccttgcgc ccggtctcca taagctgccg   55140
cagcttcttc tcatactgtc gcttgagctc tttgttgggg gcagtgtcca gaaaggcctc   55200
gagctgttcc tcggtggcgg gcttaaagcc ttcggcctcc aggcgccagg cctgcacctc   55260
cttctgtctg agctgatcgt tgttgttatt cttcaatttc tgcaggtaac ttaggaagcg   55320
tttcttgagc ttccctggga tgagcgtttt ggagagctga ttctgcagcc cagagagtag   55380
tctcagggca tcctctggag cctgacctgt gaccgtcgca tcatagaccg ccagtagacc   55440
tgggagcaga ttcaccgccg cggccgtctc ctttaaggtg ctgtgagtag caaaattctg   55500
caaggccact aggcgcgctg gctccagcgt cagccggttg cccatctcga atgtgtgcag   55560
ggcctctgag accatggggt ccaggatgcg gtcaatgcca tcctgcacct cagggtcaag   55620
gaccggcaag tcacgataga ggtggtctat gctctcctcg aaggaggcaa tgtagttatc   55680
gatggtgtag aaggtgatgg atttcaggat gttcatcagg tacttttttgg agcggacaat   55740
```

```
ctgctgtata gtgtcacgta ggcggatgta cgtggggttc tttgcggccc cgactatcga   55800
ccctgcattt gcgatgtact tttctatgac gggatggtg agggccgcgg tgtcggccag    55860
tggtggcgtg gcttcggggt tgtcgtggtt ggcgggtgtc gcagagggag aggcgggaga    55920 gatggggcg cctggggccg aggccacacc ggccaggccc aacattgcct cgatgtcgtc     55980
caggatggtg cggaggcgct tttcgttttc tctggtggtc tcgagctcct tctgtttttt   56040
cgcgactgtc tcaaactctg aagggggggc aatgctgggg tcgtcctcct caactcgctc    56100 cagggccag gggataccgc tcatatcact aagggcggtg cccaggtaga ggagctcgcg     56160
atagtcccat tcaatggacg tgtaccggat gtttaggaga ggcagggagg cgatgatctg    56220
gcatgtgtgc cgcaggtgtg tcaggaggtc gtcaaaatcc atcaccgttg ggaggcttgg    56280
gtcctcaagg taggagagat aatcggaggc cgccgaggcc accttgtccc tgatgtccgc    56340
cgtacacctg cgcacgtgca gggccgcatt cttggaccgg acgggcacgt tgtggacaaa    56400 gggggcact gaggcggcgg gaggggcccc atactctatc gctgtcaaca gcgccaaaaa     56460
gcggacgtcc tcctcatcta ccccagcctg ttgtctggcc acggccgttc gggcggcctc    56520
cgccagggat aggaggcgct tccagctctc gtcgtccagg accaagggga catccacgtg    56580
cgggcccctg tagatggaat gatcctcggg ttctcctcct ccttcctccc cctcctgatc    56640
tccgcccgag agcaggtcgg tcaggcgtct acgggccgcc tccaggtcaa attttccgtc    56700
gccgctctcg gccagctggg gaatttcagc cagcatctta gcaccggcat ctacacggac    56760
cgcgtccttc gtggccaggg acggcaggca ggcctccagc tttgcggcca ggtgctcatg    56820
gaactctccc gctcttccct tgttttctga tagcatgttt gcgaggtttt ggatgttaag    56880
ttcggaagtg agcagttgct ccaggtccag cgtggggacc tgcagatgtc ccgaccagtc    56940
ctttaagaat tccagcagat ttagcacagc cgatcggtcc ctactcctta ttagcccctg    57000
ctcgaggacc actgtcacaa gaagatagtc tatcatgctc aaggcatctg cctctggcac    57060
ttccctgtta gaggccgggt cgtagacgat ggcctgttcc tggtaggtat gtccggctat    57120
tctcgcaatg ttgctctcga ggggcacaaa gtccatctca ggagtctcta tgtcaaaggt    57180
ggtctgatag tattggctcc tggcggtgtc cagtgtgatg gggacgtgg gggcactgga     57240 tcccgattcc aggctgttgg agaacacttc atcttcaaac atgtcttcat cctctgtggt    57300
ggggatatcg gaggctaagt cgctctccgc ttcttcagag tcggacatgg ataggaaagg    57360
ctcctctagg tcagacaggt agcggacgag gccagaaccc ccagatgcat catccccaaa    57420
ggagggctgc tgcccgaagg gaggtgatgg ggatatctcc gttccagccc tgtcagcggc    57480
cgagggattg ttttttctg gttcgagtgt cgtggctgat ggtgggagct gctgagcatg     57540
aggaggagcc ggggtagctg atggcagggg ctgctgctga ggaggaagag gagaaggagc    57600
ccgggcggct gacggcgggg gctgctgctg aggaagaagt ggagagggag ccggggcggc    57660
tgattgcggg ggctgctgct gagttggagg aggagaagga gccggggcgg ctgattgcgg    57720
gggctgctgc tgagttggag gaggagaaag agtcgtggcg gtgggggctg ctgctgcagt    57780
cggggaaggg gatggggtgg tcagagggat ttctgggttc gagggagctg cctgtggcag    57840
agggatgggt atttgcaaag ggaggcgagg agatggagtg actgaaggag cgatagttga    57900
gactggcgcg gggcggggtg tcggggaggc gggtggtgat tggtgaggga tggggattac    57960 tggagggga aggcgagctg ctgaaggggg gcgatgggc ggaacgtggg tgcgtggcag      58020
ctgatcatcc tctgtgtcag tggtggagga cagagggagg cggcggccgg aggtgggctt    58080
cttgtggggg ctatctttgc ccaatcccctt tttcctcttg ggagtctgag gcgctgcgcc    58140
```

```
gcccgacgcc cttggtggcg tggagggagc ggggaccccg ggggtgtgac ctaggccggg     58200 gatgggatg aagaggggag ggctggaggc cggggccgcg gaggccgggg ccgcggaggc      58260
cggggccgcg gaggccgggg ccgcagaggc cggggccgca gaggccgggg ccgcggaggc    58320
cggggccgca gaggccgggg ccgcagaggc cggggccgca gaggccggag acgacggcg     58380 ggagttggtc tttgcaggac tatacctggc ggcagggaat gagtcggatg tgaaagatcg    58440
agagggcagt ggcctgaggt tatacggtat tattcgccgt tcaaacggta gcatgacggg    58500
agggctgcta tcagcaccgg gcgtccccgc cgcctcccca tcactggaca caagctcggg    58560
ccccaccagg tcaaagccgc tgccgttggc ctcataaaag tcatacacgc catagtgttc    58620
cagcataaag atgcggggt cctctgtctc aaaggcctcg ggtagaaaat agagatgcac    58680
gcaagtgtac tgggcccctg gtgccccac gtactgcagg atgtcgtgcg cataggtgct      58740
gactctgaca tgggcggggg tgcccggggc cgcatccttc tggcagtggg ggtcaaacaa   58800
gtagaaggag ccatctgtct cgatgatgat ggccccgcg tagatgtcgc agatgtagag     58860
gatgaactgg gccaccccgt tgtaactgcc gtgcaggacc tcggccaggg actgaacaac    58920
tgccgagttt gcgatctggg cagggaatag gacgaggcca aagatctccg ccgagcggta    58980
tatgtgcacg cgcccaccgc ccctcaggac cacggagctg ggcacgtccg tcaactgggc    59040
catctcgtgc cccttgagga tgccgctctg gcgcatgagg gcatccagcc gcgcccctc     59100 gtccaggacc tcgtccagct cagggcggga ggtcagggg cggccggcca ggaagctctt     59160
gaccaggtag aggacgcagt tgctgacgca ctggatgccg gcaaagcggc caaacttgca    59220
gtgggcctgg ttgcacgagg ccgtgcctag gatgcggagg gccgagcctc cactcccgcc    59280 cccggggca ttcacatcca tggtcctgat tccgcgcacg gggccggttc ccgggtgcg     59340 ctggctttgc ccccagtcgc cgttactcat cttcggcggt ggggcgggga ggacgccttg    59400 tcgccccct tctggtccgg ggtcttacgc ggctggcggc ggcagccgcc gagagataag    59460
gggggtacgt gtgtgcctcc gcctctcctc tgtctgggcc ccgccgccg cttgcccgcc      59520 ttgaaggaga gggggtagtc cgcggactgc gtctgcgggg gcaggaggtc tcaaccttct     59580
gggctcgggc cgcggtgtcg atatccgatg gcctttccct gtcttcctcg tatgctcctt    59640
ctcctcctcc tcccggcacg cccctgagat ctgcctcccc tccctctccc tcgtcctggt    59700
cggaaaagtc tgaggaggag aaggagaatg ggaggagtc caaaacgca cgccacctgc     59760 cgtgggcgg tggtgacagg tcccggctgg ccggcgctt gctcgcgttc ctgccgttac      59820
ccaggagaat ggccgcgagt ttttggcgg ggaggatgcg gaatggcggg gcgtttgtc     59880 ccacgggtga gggggaatcg tcggttaggg ccggcacgag gtggtgggtc tggacccggg    59940
ccgtgcgagc aaaggcggcg agaaccgagg ggcttctggg ggtgactgtg atctgttccg    60000
gatttaggtc catggcgggt gtgtatgttt taataggggt ggtctctggc gcggcaggat    60060
gatggtcgag gacgtccacc agggccttgc agatgctctt gcctagatac aggatgtcgt    60120
ccatgctgag gggaggtggg gtgtctgctc ccccctgcgg aagccgcctg ggtgcgggg     60180 tgaagacagg tggtgggcgg gcgtctcgcc ggactatggc ctcggcacgc tcggcgtcga    60240
tggcgggtgg ctggaacagg cgggcgaatg tgtaatcccg gaaccggtag gcgacgctgc    60300
gcctgagggc gccgtcagg ctgtatccca gctccagggc gtgctccacc cgctcgttga     60360
gctcctcgag atccggacgc aggggctcgc tggtgtgggc ccagaggggg tgatccgcga    60420
tgccccggct ctccctgagg gccggcacca ggaggcgcct tctgagggtg gccgtgtcgg    60480
```

```
ccgtggccag ggcccacctg gcggcggcgt cccggcacac atcctggatg ccctccacga   60540
cgctctttag cgtctggagg tccgtggagt agtggcgggg ggaggatgaa acgctctttt   60600
ccttcaccgc taccaccgcc tcctcctcct cttccgtcgc cagagggatc tgcaccctcc   60660
cggtctctgc gtcgtacagg agcgggcggg agcacagcct ccaagctgcc cccgtcaagc   60720
gcgagatgtc ctccgagagg gtctcacccg agaccagaaa gcggcgggtg gccaggccca   60780
acgactccgc cgtcgtgctg tatctcaggg tgaagaggag tgaaaagagg gaggtggggcc  60840 aggcaagcgg tggtgcttcc gccgcccgct ctgaagctga gatagtctcg gagatgatgc   60900
ctgagacctc tcggacggcg tccatgatcc taaggactgc gtcgtgggac gacagccccc   60960
aggggccccc gccctcttcg tcttctgcac cctcggctcc tgcgtccccg gccttgcctt   61020 cccctctaa gttgaggggg cgcagtccga ccgcctgggg ggactcccca ggcatcggag   61080 gggcccgtc atagatctcc cagacggtgg cgtatatgag ctcgagagga cggcgggccc   61140
gggtcagctc gggggaaggg agggccaggt cgctgccgaa ggagaccagc cagcgcaggg   61200 cggcagaga gcgggttttg ggcagctcgt tggagaggac ccggcgaagg gcgggccaga   61260
tttggaactc gatgaaggcg gccgggaaga aggggctgcg gacataggcc ggatccgcgc   61320
gcgccgtttg gccggccctc agggaccggc agtatgcctc gacgtctgtc cgcggggccg   61380
ccgccaccgc cgccgtccac tgccttctcc cctgctcgcc ggggagtagg gggggcttac   61440
aggggagggc cggagccggg gcggggcct gccacaggcg gctgtagcgg acccatagca   61500
gagacctgag gagttcggat gaaaggtccc ccgccacctg ctcatactcg gccgcgggag   61560
gagggacgat gaagatgcgc agaggggtta cggcgtccca agggtccgcc gccgccccca   61620
cacccacagc cgtcgcggcg ggggcggcgg cgggcgtaga ggggccgctg gtgcgccggg   61680
ctcgtctgtc cacggcctcg gcctccgccc tcaggtaggc cgcccgggcc acacgggcga   61740
agcggctcgt ggggctcgcg gtgggcagca gtcggaaaaa gtgcagggca aagcccgata   61800
gactctctag gagggcggcg gtggcctcga gccacctcca ccgcgagcgg gacacccggg   61860
gcacagaggc cagcatcatg gcgtagtccc ccgccacggt ctcgttgagc ccggccgaga   61920
gcagaaccgt ggccacctgc tcgatggcgg ctggagagaa ggatgcccgg ctccccgccg   61980
cctcctgcac acgagcggcc agggcctcca tctctgccgc catcccggcc aggaaggcct   62040
cgatgaccga gtctgggacg ccgtaagtct ggtcccagag cagggcctcg tacacatagt   62100
cgtaaaagag ggcccctgag ggctccaaaa gccggagccg ggcggcgtca aaggccagga   62160
cgggcacagc cgcgacgggg ggcgtttgtc ccccgctggc ctccgcgtac acgcccagga   62220
tctctaccgc ccgccgccgg gccagggca gtgaggccac cacgctggaa agtgactcgg   62280
ggcggtgaaa gagaccgcca ccgccgcttt cttcaccctc tccccgccg gccccgcccc   62340 cactgtgctc caccagctcc acggccatgg ccttgatgtc cgcggccgtg ggctgaccct   62400
gccctgcagc cgcccagggg tagcggttgg tctccgcgta tacggtgacc agccatctcc   62460
ccagcgtcgt tttcgccgcg ttaaaagcgt agaatgacag cccctcccgc gggaaggcgt   62520
cccaccgggc cagataagtg tcggccacca gctcttccac gaaggcaaag gtggccgttg   62580
ggccagagac cgcgagcacc tccccgctgc cctcttcgat gatgcgccgg tacgtggccg   62640
ccagggcccg ggtctctgcg atgagccgag agccgtccag cggatcgtcg gtggccggag   62700
aggctgtcgt ggggggcagt gaggaggcca gcacgtccag ggccgcctcc agatggccga   62760
ggccgaagct gcgcctggaa aaggaggccg cccggagtag gtagtaggcg tggtggcgga   62820
ggaccgccgc cgggtaagcg tggccgctca tgagggtgag agtatttaaa aaatcgcgca   62880
```

```
ccagcaccgg ctgggccaaa tctcccagtc caaagatccc cagctccaga ggcatcagcg   62940
cgcgcaggcg ggcagcgggg tcgtccccag acagcagcaa ctgacgcgtc acgcgggcga   63000
gccccccgtc cacctctgcc aggggcggct gggcgtctgc ccctccgcta ccgccgccgc   63060
tgtcactctc catagcggac gccatgaagg tccaggggtc cgtcgatcgc cgccgtctgc   63120
aacgccgaat cgcggggctg ctgccccctc cggcccggcg tctaaatatt tcccgggggt   63180
ccgaattcac gcgggacgtt cgtgggctgg ttgaggaaca cgcgcaggcc tcctcgctga   63240
gtgcggcggc cgtctggcgc gcagggctgc tggccccggg ggaggtggcg gtcgccgggg   63300
gtggcagtgg agggggagc ttcagctggt ctggtggcg gccgccagtc tttggggact   63360
ttctgataca cgccagctcc ttcaacaacg ccgaggcaac tggaacgccc cttttccaat   63420
tcaagcagag tgacccgttc tcgggcgtcg acgcggtatt cactcctctc tcccgttta   63480 tcctaatgaa tcacggccgg ggtgtagccg cccgggtcga gcaggtggg ggcctgacgc   63540 ggatggccaa cctgctgtac gacagccccg caaccctggc tgacctggtc ccggactttg   63600
ggcggctggt ggccgaccgc cgcttccaca acttcatcac ccctgtgggc ccctggtgg   63660 agaatataaa gagcacctat ctgaataaaa tcaccacggt ggtccacggg cctgtggtca   63720
gcaaggccat ccctcgcagc accgtcaagg tgacggtgcc ccaggaggcc tttgtggatc   63780
tggacgcgtg gctctccggc ggcgccgggg gtggcggtgg aggatgcttc gtcgggggc   63840 tgggcctgca gccgtgcccc gccgatgcgc gcctctatgt cgctctgacc tatgaggaag   63900
ccgggccgcg gtttacgttt ttccagtcgt cccgcggcca ctgtcagatc atgaatatct   63960 taagaatta ttactcacca tccatcatgc accgctacgc tgtggtccag cccctacata   64020
tagaggagct gaccttcggg gcggttgcct gtctggggac atttagtgct actgacggtt   64080
ggaggaggtc tgccttcaat taccgtggct ctagcctccc cgtggtggag attgacagct   64140
tttattccaa cgtctctgac tgggaggtga ttctctagac ttaacgggag gaaacaggag   64200
gaggaggggg acaagagcac aaaagtggtt cagtggacac ccaccacaca gcatggcaac   64260
gaccagtcat gttgagcatg agctcctctc caaattgatt gatgagttaa aggtcaaggc   64320
caactcagac cccgaggctg atgtcctggc agggcgcctg ctccaccgcc ttaaggccga   64380
gtcagttaca cacacagtag ccgaatatct ggaggtcttc tctgacaaat tctacgatga   64440
ggaattcttc cagatgcacc gggatgagct ggagacccga gtctctgctt tcgcgcagag   64500
cccggcctac gagcgcatcg tctccagcgg ctacctgtcg gccctgcgct actatgacac   64560
ctatctgtat gtggggcgca gcgggaagca ggagagtgtg cagcactttt acatgcggtt   64620
agccggcttc tgtgcctcaa ccacctgcct ctacgcgggt ctcagggcag ccctgcagcg   64680
ggccaggccg gagattgaga gtgacatgga ggtgtttgat tactactttg agcacctaac   64740
ctcccagacg gtgtgctgct ccacgccctt tatgcgcttt gccggggtgg aaaactccac   64800
tctggccagc tgcatcctca ccacccccga cctcagctcc gagtgggacg tgacccaggc   64860
cctctatagg cacctggggc gctacctctt tcagcgagcc ggggtgggtg tagggtgac   64920 gggggctggc caggatggga aacacatcag cctcctgatg aggatgatca acagccacgt   64980
ggagtaccac aactacggct gcaagcggcc ggtcagcgtg gcggcctaca tggagccctg   65040
gcacagccag attttcaagt ttttggaaac gaagctgccg gagaaccacg agaggtgccc   65100
gggcatcttt acgggctct tgtcccga gctcttcttc aagcttttta gggacactcc   65160
ctggtcggac tggtacctgt ttgaccccaa ggacgccggg gacctggaga ggctctacgg   65220
```

```
ggaggagttt gagcgcgagt actatcggct ggtgacagcg ggcaagtttt gtgggcgggt   65280
ctccatcaag tccctgatgt tctctatcgt caactgcgcc gtcaaggccg gcagcccctt   65340
catccttttg aaggaggcct gcaacgccca cttttggcgc gacctgcagg gcgaggccat   65400
gaacgctgcc aacctgtgcg ccgaggtgct gcagccctcg aggaagtctg tggccacctg   65460
caatctggcc aacatctgcc tcccgcgctg cctggtgaat gcgcctctgg cggtgcgggc   65520
acagcgggcc gacacgcagg gggatgaact cctgctggcc ctcccctcgac tctcagtcac   65580 cctacctgga gaggggcag tcggtgatgg attctcgcta gcccgcctca gagatgccac   65640
ccagtgtgcc acctttgtgg tggcctgctc cattcttcag ggatccccca cttatgattc   65700
cagggatatg gcctccatgg gcctcggggt gcagggcctg gccgatgtct ttgcggacct   65760
gggctggcag tacactgacc ctccctctcg ctcgttaaac aaggaaatat tcgaacatat   65820
gtactttacg gccctctgca ccagtagtct gattggactt cacaccagga agatttttcc   65880
gggtttcaaa cagagcaagt atgccggggg gtggtttcac tggcacgatt gggcaggaac   65940
agacctttct attcccaggg aaatttggtc tcgcctctct gaacgcattg tgaggaatgg   66000
gcttttcaat tcacagttta tcgccctgat gcccacctca ggctgtgccc aggtgacggg   66060
ctgttcggac gccttctacc ccttctatgc caatgcgtcc accaaggtca ccaacaagga   66120
ggaggccctt aggccaaacc ggtcttttttg gcgtcatgtg cgtctggatg acagggaagc   66180
tttgaatctt gtcgggggcc gtgtctcctg cctcccggag gctctgcggc agcgctacct   66240
gcgtttccaa acggccttg attacaacca ggaggacctg attcagatgt cccgggacag   66300 ggccccctt gtgaccagga gccaatctca cagcctgtttt ttgcgtgagg aagatgccgc   66360
gcgggccagc acgctagcca acctactggt gcgcagctac gagctgggcc tgaagactat   66420
catgtactat tgtcgcattg agaaggccgc cgatctgggg gtgatggagt gtaaggccag   66480
cgcggctctg tcggtgccgc gggaggaaca gaatgagcgg agtcccgctg agcagatgcc   66540
gcctcgtccc atgaaccggg cgcaggttgc ggggccggtt gacatcatga gcaagggccc   66600
aggggaggga ccaggtgggt ggtgtgtgcc cggggggattg gaagtgtgct ataagtaccg   66660
tcagctcttc tcagaggatg atctgttgga gactgacggt tttactgaac gagcctgtga   66720
atcttgccaa taaacgttta ttgccatgtc caagttgttg tacgtgcgtg atcatgaggg   66780
ctttgcctgc ctaacggtcg aaacccaccg caaccgctgg ttcgcggctc acattgtcct   66840
caccaaggac tgcgggtgtc tcaagctact caatgagagg gacttggagt tttacaagtt   66900 cctcttttacg ttcctggcca tggccgagaa gcttgtgaac tttaacattg atgaactggt   66960
caccagcttc gagagccacg acattgatca ctactacacc gagcagaagg ccatggagaa   67020
cgtccacggg gagacttatg ctaacatttt aaacatgctc tttgatgggg acagggcggc   67080
gatgaacgcc tacgcagagg ccatcatggc cgacgaggcc ctgcaagcca gatttcctg   67140 gctccgtgac aaggtggcgg ccgccgtcac cctgccggag aagattcttg tgttcctgct   67200
gattgaaggc atcttcttca ttagctcctt ctacagcata gccctgctgc gggtccgggg   67260
cctaatgcct ggcatctgcc tggccaataa ctacataagt agggatgagc tgctccacac   67320
ccgcgctgcc tccctgttat acaatagcat gacagccaag gctgaccgac caagggccac   67380
ctggatccag gagctgtttc gcactgcggt ggaggtagag actgccttca tcgaggctcg   67440
tggagagggg gttaccttgg tggatgtgcg agccataaag cagtttctgg aggccacggc   67500
cgatcgcatc ctgggtgaca ttggtcaggc tcccttgtat ggcacaccac cccccaagga   67560
ctgcccgctc acctacatga ctagcatcaa gcaaactaat ttctttgagc aagagagttc   67620
```

```
cgattacacc atgctggtgg tagatgacct ttgagtcagg gtggctactt gctcaggttt   67680
ctgggcataa attctcctgc ctgcctctgc tctggtacgt tggcttctgc tgctgcttgt   67740
gatcatggaa accactcaga ctctccgctt taagaccaag gccctagccg tcctgtccaa   67800
gtgctatgac catgcccaga ctcatctcaa gggaggagtg ctgcaggtaa accttctgtc   67860
tgtaaactat ggaggccccc ggctggccgc cgtggccaac gcaggcacgg ccgggctaat   67920
cagcttcgag gtctcccctg acgctgtggc cgagtggcag aatcaccaga gcccagagga   67980
ggccccggcc gccgtgtcat ttagaaacct tgcctacggg cgcacctgtg tcctgggcaa   68040
ggagctgttt ggctcggctg tggagcaggc ttccctgcaa ttttacaagc ggccacaagg   68100
gggttcccgg cctgaatttg ttaagctcac tatggaatat gatgataagg tgtccaagag   68160
ccaccacacc tgcgccctga tgccctatat gcccccggcc agcgacaggc tgaggaacga   68220
gcagatgatt gggcaggtgc tgttgatgcc caagacggct tcctcgttgc agaagtgggc   68280
acgccagcaa ggctcaggcg gcgttaaggt gacactcaat ccggatctct acgtcaccac   68340
gtatacttct ggggaggcct gcctcaccct agactacaag cctctgagtg tggggccata   68400
cgaggccttc actggccctg tggccaaggc tcaggacgtg ggggccgttg aggcccacgt   68460
tgtctgctcg gtagcagcgg actcgctggc ggcggcgctt agcctctgcc gcattccggc   68520
cgttagcgtg ccaatcttga ggttttacag gtctggcatc atagctgtgg tggccggcct   68580
gctgacgtca gcggggggacc tgccgttgga tcttagtgtt attttattta accacgcctc   68640
cgaagaggcg gccgccagta cggcctctga gccagaagat aaaagtcccc gggtgcaacc   68700
actgggcaca ggactccaac aacgcccag acatacggtc agtccatctc cttcacctcc   68760
gccacctcct aggacccta cttgggagag tccggcaagg ccagagacac cctcgcctgc   68820
cattcccagc cactccagca acaccgcact ggagaggcct ctggctgttc agctcgcgag   68880
gaaaaggaca tcgtcggagg ccaggcagaa gcagaagcac cccaagaaag tgaagcaggc   68940
ctttaacccc ctcatttaac accatgttct cgtgcaagca gcacctgtcc ctgggggcct   69000
gtgtcttctg tctcggcctc ctggccagca cccccttcat ttggtgcttt gtctttgcca   69060
acctgctctc tctggagatc ttctcaccgt ggcagacaca cgtgtacagg cttggattcc   69120
cgacggcatg cctaatggcc gtcctctgga cgctggtacc cgccaagcac gcggtgaggg   69180
ccgtcactcc agccatcatg ctgaatattg ccagcgcctt gatcttcttc tcccttagag   69240
tctactcgac cagcacgtgg gtttctgccc cctgtctctt tctggccaac ctgcctctct   69300
tatgcctgtg gccccggctg gccatcgaga ttgtttacat ctgcccggct atacaccaaa   69360
ggttctttga acttgggttg ctcttggcct gcaccatctt tgccctgtcc gtggtctcca   69420
gggccctgga ggtgtcggct gtcttcatgt ctccattttt catctttctg gctttgggct   69480
ctggaagcct ggccggtgct cggcgtaacc agatttacac ctcgggtctc gagcggagac   69540
gcagcatttt ctgcgcccgg ggagatcatt cggtggcatc cctgaaggag accctccata   69600
aatgcccgtg ggatctgctg gccatctctg ccttgaccgt tcttgtcgtc tgtgtgatga   69660
ttgtgttgca tgtgcacgca gaggtgttct ttggactctc tagataccctg cccctctttc   69720 tctgtggggc gatggcctcc ggggggctgt acctgggcca ttccagcatc attgcatgtg   69780
tcatggccac cctctgcacc ctgtcatctg ttgtggtata tttcctccat gaaacccttg   69840
gacccctggg caagaccgtg ctgtttatct caatctttgt ctattacttt agcggggtag   69900
cggccctgag cgcagctatg cgctacaagc ttaagaagtt tgtgaacgga cccctggtcc   69960
```

```
atctccgtgt ggtatacatg tgctgttttg tctttacttt ttgtgaatat ctgttggtga   70020
cattcattaa atcctaacga ccggagtcct gtctctttgt gttcttgggg gacttgagtt   70080
agctgtcttt cctcttatta cattgggcta acgggaggaa atgaacccag ggtggcagt   70140 ggatggggtc atttatgggc aaaactcaca ggacatgttt ggggagttag cattggcgtc   70200
gggaaacaca gctctggcag ttataaccgc accagctaac aggacatgtt tgggggagtt   70260
ggcattggcg tcaggagaca cggctctgtc agttatcacc gtaccatgag tgccatgtgt   70320
gtccagtgcc taatcaccgt tcctcatttt gtgtgcctcc tcaaatgttc cagaagtcgg   70380
ccacagggga ggtggctgaa ttagggcctt ttccctcatt cccccatgag acccacgtgg   70440
caggcctagg ggctacattc gcctcccacg tttcccttcg cgtgaggcat ccgatatgac   70500
tgaattttcg cagtctcttt tccctcttcc cttgttattc ccatagaatt acagtgaggt   70560
tacacaggtg gagattcagt ttaaccattt attgatttaa tccaggaaca aaaaacagtc   70620
ctagtgaccc agtgcccgga gagagaatgg ccctgacaag tcggctgcat gatgcacttc   70680
ggcagtcacg tgtgtgagtc tccacggcct ctgtcaaaag ggagcttagc gtgccagggt   70740
tgtaattctt gatgtagtgg cccaggaatt caacttcatc gtgtctccgt ctgcagttgg   70800
cgttaatgta ggctggggct actgccgcat atgctgccaa gagacagagg ggctgcttca   70860
catatgagct gctcagggtc tccaccacct tgttttgacg ggccgtggca caggtgatgt   70920
agaagagttg cttcacaaag ttgtagtctc gcgtgttagg aaggaagcag ggtgccagct   70980
ctttgagctt ggtcaggatc accttgctaa gactcatggc gcaggccagg aggatgtctt   71040 ccgcggggagc taggggcagg tcgccgtggt aggtgatctc ctggagccaa agatggtct   71100 cttctagcat ggccaccagg gtgcagagcc ccgcgttctg gatcgcctgc atgcgtgcat   71160
ccagccatgt gtccttgttg gttgacttgg tgaaaaactc acgtagtgtc ttgtagctcc   71220
tgcgcagctc gtgtctgggt tgcactttct gccaggctcc aatctctgga tgggcggcca   71280
ccgccagcat cgactgtagg aacgggtctt ggatgggctc tagggtcaga gaggccaggg   71340
ggctgggcaa ggtgacaaat gtaatcttgg agacaggctt aaccagactc atgtcaaacc   71400
acggtttgtt gggcaggggc ctctggctgc gttcttgcct cgcctgcttc cttgtgctcc   71460
tgccggcccc tcgagattct gaccggggac ctctggttgc tctgttgctt cggggagctc   71520
ttggagacct cggtgctcta ggcaccctgg gggcccttgg ggctctgggc gctcttgctc   71580
ccgggggcag gtgtcggcgc ttgccataac tttcatcggt gcagccatgg acctctccgc   71640
gtcgcctttt gtggcctctg gtgtaagagg agttgccagt ctcctccttc tcgtcctcgt   71700
ccctgcacag gggtgagcga tgcaatgtga ctgtcttgtc ctgtaggtcc cacttctttc   71760
tgggaatcac aaacgatgcc gaggtagggg ttatgaccac gctggagggc cgtgcaggta   71820
tggtgtgggc cggagttgga tcttcatcct cctcctctga ggatgaaatc tctccatctg   71880
tggagtgttc ttcgctgccc tccataggggt ccatatcgca gtctgtgttg gtgtctgaga   71940
ccgcttcgag ttccagaatg tggctctctg cagaggggag acaaaggtg gagactgcct   72000 tgagcacctc tgtctcaggc accggatgcc cccggctcca cggccccggc cactggccgg   72060
tgtagcttct tacctgcggg atcctcgttg gaggaaatgc tgctagttcg ggagagtctc   72120
tgagaaggaa ccatcttgtc tgtctctacg acgggctagc tgggatgtag tgctgtcttg   72180
actggcctca gccctatttta tgattctgga ggcgggcacg ctgatggaga atgggcggt   72240 cggttgattg gccccacagc gaccggcgaa gcactgactc atgaaggtga ccgtgatggc   72300
ctgtgatgtg tagtagagta ccagaaacac cctcacattc ttggagctgg ccctgtgggt   72360
```

-continued

```
atgcctcagg cacgcaaagt tcctgccccg ggcatggcac acctgaacta agtttggccc      72420
ggtttgctca aacgtgacat ggagaaactg ggggaatttg tcttctggca cagctgttgc      72480
cagggtgctc atgagcgagg gccagatgca ggagctgacc caggcgacga gatccaggcc      72540
cagatgtccc tctatcatgg cgcagacatt ctccacggtg gggggcaggg tctcgcgggt      72600
cctctggatt agatagtcac gcccatcatc cgcgatgtgg tagcagaagg ttttgggggc      72660
cggccagccc acgtgcagtg agtgatgtaa gaggttttga atgttgaggg cattcttaac      72720
atagctgtgc ttgtcttcct cttccggatg acagacaaag aggcgcagct gccggctaag      72780
accaccgccc ctgtccacct tgtaggtatg cggcagccgg atgcaccgcc cggcgtgata      72840
cacgccgctg tcaaaaagcg gggcccaat ctctttgatc ttgtgacgca tgcggcgcag       72900
gcaggccgtt aggcccatga gcttctgcag cacagacaca aacccttgta ctgcgcttgt      72960
tcccacaata gcatggcctc taggtagggg ggtgatgacg cgaaagccca gttttcccgt      73020
gcatatgcaa aaggggagca catcttccat attatccggg tcggcgggtg acaagctga       73080
tttgaaaaaa tagactgggt gggccctgga cactggaccc aggcggcgca tgaggcgcag      73140
tacctcacgc cgcacggtcc ggcacaggtc atagatttcc tccagcgacc aggggcccc      73200
cttgatcttt agatccaggt ccaggaccag gttgcagacc ggaagccggg gattaaagta      73260
ttcatgccgg gagacaaaga gctgctcgct caggctgttc tgtgaatagt acactggggt      73320
gtaggagagg gccctggtga gacacgtgtc tgggaggcgg cagttggtcg gggtggagac      73380
gacctccgcc aggtgggacg agaagggtc agcggctgtc attacaaagt agtgcctgtc       73440
tgcaaaatgg cagaggaaga ccggtagccg ctgcacccct cgaaggacgg tgggtgggag      73500
gaattgttcc ttgggattcc actggccccg gcaggtggcc tggccggcca agcatagaaa      73560
cccttgaagc gtgggggggt atgtgggacc ctcatccgcg tgccagcgcg cgagctccac      73620
cagctcccgg gccacgtcca cactgagccc ggcccaagcc cgcatgagtc cgtcatcggg      73680
gtcggggtcc cacgtgtatg gggccggggg ctccatgcgg atttcagct gctggacacg       73740
cacatgctca gccaggtaag tctcccgggt gaagtaggtg cgcatgtgct ccgcaaagcc      73800
cctgtccagg agcgagggga gcacgacgcc ccccgaaggc agacacccaa tttctcccac      73860
gctcgttaac tgagagtatc gcttaaaggt tccctcgttg aagcactgtg cgtgggccaa      73920
atagacgtag cgcacgagat cggccgaggc caggggaagg cgcccctgt aggcgtctat       73980
cgtccttgcc acagcgcgga tctctcgtga gtcccgccgc agcttctcgt gtgcaaagtg      74040
ggcaaaagcc tcggtctgct ccgcccatgc cgaggagcca aagacctccc ccagctcggc      74100
cagggacgtg acggcggcca ggctctgacc agactcggaa gtaaatagct ccgtgaggtg      74160
cgccagggtc tcaatcgtac aaggaatgcc ccaaaaatag taagcagccg tgactagcac      74220
gaactgggcc tcgtgggagc caaaggtgct aatgaaccac ctggccgaga tgttaacgcg      74280
gtagatgcgg cgcagacagc ccacgatctt gggacgcagc cacgccacgc ggcctctggc      74340
atcccctgt ggctgcttct tagcgctcag tgtgagcagt tccacgaggg gcgtgagcga       74400
gcgcagggcc cccgcgcgat ctaggtaggt ggatagacgg tccgcggtga gcggcgtgag      74460
gccgcgcagg aaggggaagg cctcctccgc cggcaggtgc agcgtcagaa ccaggccgca      74520
gcggctctgt gaggtcagcc gcttcttggg caggtgaagc tgcagttcca cgagagaacc      74580
cgccacgtgg tggaggggcg aggcgttgtg gcacaaacaa aacaggcgga agccctcgtc      74640
aggccgcgag aggatggcat cgaggatggc ctccgcaatg tcagtgtttg aggccacaag      74700
```

```
ggccttgatg acgacggggg cggacattat ttaagaccgg gaggccccaa cggcgggcta    74760
aacagaacga tggccttcta tctcccagac tggtcgtgct gcgggctctg gctctttggc    74820
cggcccagga atagatacag ccagctccct gaggagccgg agacctttga gtgcccggac    74880
cgctggcgag ccgagataga tctgggcctg cccctggtg tgcaggtggg agatttgcta    74940
agaaatgagc agacgatggg ctcactgaga caggtttatt tgctcgccgt tcaagccaat    75000
agcatcacgg atcacctgaa gcgctttgac gccgtccgcg tccctgagag ctgtcgtggg    75060
gtggtggagg cccaggtggc caagcttgag gccgtgcgct cagtcatctg gaataccatg    75120
atctctctgg ctgtaagcgg catcgagatg gacgagaatg ggctcaaggc cctgctggac    75180
aaacaggctg gcgacagcct ggccctgatg gagatggaga aggtggccac ggcgctcaag    75240
atggacgaga ccggtgcctg ggcgcaagag atctcggccg ttgtctcatc ggtgaccgcc    75300
ccctcagcct cggccccttt catcaactcc gcctttgagc ccgaggtgcc cacccccgtc    75360
cttgcaccgc ctcccgtggt gcggcagccg gagcactctg ggcccacgga gctcgcgtta    75420
acgtagcaac cagactccac accaaataaa cattttattg gtaaaacaag ggatatgaag    75480
gtgtcattga cccgaggatc caaacccccct cccctgtctc ccctcgagcg cctcgctcag    75540
cccactatca cccatggcca ggcccggcac ctcctcgaag gcgcagctgg cccacctaaa    75600
gagagatctg gggccaagga cccccgcgtc actgtggggg ctgtagaagg aggtgaggtg    75660
gtgcttgtga aggtaaacaa gctgacagaa gcgccggtac ttgttaagga acacggtctg    75720
gtcactaaag ttggtcaggc tgacgtccac cccaccccgg cgccacctgc agggcttcac    75780 tagaatacccc tgcatggcca ggcccgacct gccaaagatt gtcggcctgt ggtgagggat    75840
agaagggggg ggcacggtga gtgtcactga cacggtctga tgggggaaga gggccaggtc    75900
ctttggcaaa gagacgtcca ggcccacgtc cccggggtac tgggggtggt tgatgggacc    75960
cttgtcctcc tccatctggg gggtggcata tctgaaggca gccaggtgga ttttgagctc    76020
cgatggacgc agcgtggagt tgtagcgccg ctgattctgg aggattagcc ggagttcccc    76080
cgtgtagccg ggatcgatga tgccaacatg agacgtgacc ggacgggagg tgctgcccca    76140
cagcatgagc ccatgaccct cgggtgggcg ggcatagagg cctaggtcca cagttgtggt    76200
cttcatcggg cgcagcagga tggtggtctt gttgaccaag gtgagccgcc ctacactagc    76260
ctgctggagc aacagcttgt cattctggaa ggctagcgt atgtgtggac aggcctccat    76320
ggtgatgatc taacagacag ggacggcggc gctatatata agagcccaag acccggctct    76380
ctttactgcg aaatggggaa ggtcctaaga aagccgtttg caaaggctgt gccactgctc    76440
ttcctcgccg ccacctggct tctgaccggg gtgctgccgg ccggcgcttc cagtcccaca    76500
aacgcggcgg cggcttccct gactgaagcc caggaccagt tctactccta cacatgtaat    76560
gcggacacat tctcgccttc tttgaccagc tttgcctcca tctgggcact tctgacgctt    76620
gtcttagtca ttatagcctc agccatctac ctgatgtacg tctgctttaa caagtttgtg    76680
aacacgctgc tgacggatta gatggggata tttaaagggg cagcaatcct cggctgtctg    76740
tacttcttct ctgctcgtta aaccaatagc atgtcagctc cacgcaaagt cagattgcct    76800
tctgttaagg ctgttgacat gagcatgaa gacatggccg cccgcctggc tcgcctggag    76860
tctgagaata aggctctgaa gcaacaggtc ctcagggggg gtgcctgtgc ctcgtctacc    76920
tctgttcctt ctgctccagt gcctccgcct gagccgctta cagctcgaca gcgagaggta    76980
atgattacga aggccacggg ccgtttggcg tctcaggcta tgaagaagat tgaagacaag    77040
gtgcggaaat cagttgacgg tgtaactacc cgcaatgaaa tggaaaatat attgcaaaat    77100
```

```
ctgaccctcc gcattcaagt atctatgttg ggtgcaaaag gccaacccag ccctggtgag    77160
ggaacacgac cacgagaatc aaacgaccct aacgccaccc gacgtgcccg ctcccgctcc    77220
cggggacgtg aagcaaagaa agtgcaaatt tctgattaat aaatctttat tgactttata    77280
cataggtctc ggcgtcatca tatggtgggg tggtgtaggt atgggatgtc gacaagttac    77340
gcctgaaggc gcagtccgcc atgaccagca gcagcagaag ggtcagcaca gccagagagg    77400
cccactgcag tactagcatg gagaggtttg agaatctggg ctgggacgtt ggcgggacag    77460
gcacggtggc ttgggctgtg gtaaccggtg ggctcgtaaa agtccagcgg ggccgcagtt    77520
tgctagaagt gctgggaggt agataggtgg tcgcattgta tctcgttctt ggcgtagttg    77580
aatcaccgcc gtaatctgtg gtgggctctg tacttgtccg ggctccatgt cctgtggtgt    77640
gctttccacc ggtggtagaa ttggcctttc cacctgttga ggtgaccgtg gaaccgccg    77700 tcttttggcc actgggggcc tggggcgacg ttgcattttt gggggcgtg cctttggtga    77760 cattaacctc ccccggtttt gtggatgtgg aactgtttcc agggcctgac gcttggctgg    77820
tggtgcctgg gcggggcgct ggcgaactgg tggacacatg atgtgtgctg gtagaggctg    77880
gtgtcacctg tgttatattt tcaccacctg ttgggtgagc ggaggttagt aaaggcatat    77940
gtgacgttga attgtcactg gtggaggggc tgagtgtctc tgagattgaa ctgggtctca    78000
gtgacatgga agaggttgaa cttgaagtta tgttatgttg gcctgtggta acagcactgg    78060
ttgcattttt tggtgggctg gtaactactg gggtggaact tgttcctcct aatgtgtggt    78120
tggtggtatt tgcctgtgga cttgtttctc ccacggtagg gctggtggca tttgggttg    78180 gggtagtcac tgctgaggtg ggacttgttt ttcccaaggt ggggatggtg gcatttgggg    78240
ttggggtagt cactgctggg gtggggctgg tggcatttgg ggttgggta gtcactgctg    78300 aggtgggact tgttttcc aaggtggggc tggtggcatt tggggttggg gtagtcactg    78360
ctggggtggg gctggtggca tttgggttg gggtagtcac tgctgaggtg gggctggtca    78420 tgtcggggc cttactttct gtgccgttgt cccgtggaga tggacttggt gtcaccggtg    78480
atgcgcctga cgttgtgccg gctggtgttg ggctggtgac atccgcggtg gatacagtgg    78540
ggcctgtgct tgcaggtgcg gtgaggttgg taggcacgtg agtagagctg ggtagacctg    78600
tcgttgtatt gggagcagca atccagttg tattcaaggt aggggaggtg gtggtgctct    78660
cgggtgcctt ggagaatata accttgtggg ttgttgtggt ggcattggta gccgttcgtg    78720
tgataatgag tgtcttgggg gccgtgccaa gacccgagac agtaatgtca aatgtccgat    78780
tgctcgcaaa tgcaccagaa atattttcac aacccgaagg tgtccccgag gtgagagtcc    78840
atttgcactt aaagtcagtt tcagtgttgt ttggccaggc ccaaaaggca gtcactgtaa    78900
catttggcga gtttgcgtcc tcagaagtga ccattggcac tgaataggta gcattgtcac    78960
ccacatatgt gatgtctgtg gtgtttgtcg gcatgtcctg tgaagctgga atctcatcag    79020
agaacacaat gttggactga atgcagtaat ctccccgct cgccttcggt ccattcccag    79080
agtaaaacac gtacagtata ctgttattgc caagaaatcg tgacactgga cgtggtgtca    79140
gacgcaggct gtatgcatac cctgtaccag gtattgggt ggccacggga ctcgttgatg    79200
tgagaattcc gccgctggga acatggctct cgtatccact gcaggtgatg ttaaatttgt    79260
tgtctccggg cagaacttgt gaaatttcgc catcctccat aatacactca atatctatct    79320
cattaccgag catttctgtt tttacgctga aattcgagtc ttgagctgat gttggcaaac    79380
ttaagggtag cgtgacatcc agcccctgtg cccttactac tgccgttata ttggtagaat    79440
```

```
tacagttatc ccactttatg tatggcactg tttctggtat taggtatact gggttttgca   79500
tttctgcatg gtggcaccac atggtgccaa acacatcttg aaagtagaca tctacagatt   79560
ccaggcttac ttgttgctcc tctccggtgg tgatgttaat tggaagcttc ttagaccgca   79620
tagttagagc caattctcct gcaccaagga gctccagtag aaagagattg gtggcatttt   79680
ctgagccacc aaatgcacct cgaggttggt agacagcctt tgtatggggt gtcagcaggc   79740
caaagtcaag attaagttta tgcttttttgc ccccgacatc gaaattgata gttgcattga   79800
catctgccgt gcaaacattg cacgctgggt aaaatgggaa ttccagaatc tcaacattga   79860
aaaaaccagg atcatcacgc gtgagttgga taaggctctg gatggtgtac tgacacacaa   79920
gcaaggctgc ctccattgtc tcagcaccga tttctaggca gcaccctctt taataggtgc   79980
aaggggggtg cggtgttggt gagtcacact ttcgttgcag acaaaatgga caaggacagg   80040
ccgggtctcc cggccccgga tgacaacata aagaagtac catctacctc gggtgttcag   80100
gaacgggcgt ctgagggaga ttgggaaaat gtcctcatag agatatcaga tagcagctca   80160
gaagaggaag cagaagatgc ccacctggag ccatcccaga ggggtaaaaa gagaaaacgg   80220
gtcgatgatg atgccggtgg ttcagctcca gcacaacacg tgcccccccc tcagctggat   80280 cacccctggtc gagaagccat tctctacagg tttccgctag atttaagaag gtttattcaa   80340
gcaattggag ccgcagctac ggtgagcttc cctatggccc aggtgtgtga tgtgtgtttt   80400
tgcccatcgc acaacaaggt aagtgatttg ttgccgttgg tttcagcacc ccgacacgcg   80460
agccatagac cagttttttcg gatcccagat ttcaaatacc gacctgtacg taatgtatgc   80520
catggccatt cgacaggcca ttagagatcg tcggaggaat ccagcttctc gtagaagtca   80580
ggtcaaatgg agaatgacca ccctggccgc tggttggcct atgggttacc aggcatacag   80640
tagctggatg tacagctaca ccgatcccca ggtgactgcc acgatcatac atctgcaggc   80700
gactcttggg tgcgcaagtg gccgtaggtg tcatgtgacc ttttctgccg gcacctttag   80760
gccgccgcga tgtagtcccg gggatcgcca gtggttgtat gttcagagcc gcgtgggtga   80820
ccttgtgcag agttctaatc catgctacag tattttcttt gactacatgg ccatacatag   80880
gagcctcacg aaaatctggg atgaagtggt aacacctgat cagcgtgtta catttatgga   80940
attcctgggc ttttttgcaac gcacggagtt ggtctacatc aagagctttg tcagctatgc   81000
cttgggcacc actagtatcg aaacaccgtg gatggatgag aatcctagca cagagacggc   81060
acaggcttgg aatgccggct tgctccgggg gcgtgcgtac gggcaagact tgcttagaac   81120
tgaaggagaa catggcgaag gtgctacctg tgaaacacgg gaagaaagtg aggacacaga   81180
gagcgatggg gatgatgaag aacttcctcg tgtagtgtcc agggatggaa ctaagcacag   81240 acgacccctct atattttaa gacgcctgca caggttgctg ttgatgagag cgggcaaagg   81300
aaaggaacgg gccagggaga cactggcgaa ggcccctagg cgcacttatg gcacacctag   81360
gccgccagtt cagaaaccaa gaccagaggt cccgcaaagc tatgagacag ctaccagtca   81420
cgggtcggcg caagtcccag aaccccacc cacccaccca ttacatcagc aacacagcat   81480
ggccccgtgt atggtagctc agaacccacg tgcaccctta ggggaccaac tcccaggtgt   81540
tcctaaagat ggacgagggg cgtgtgcacc ggtacccgcc ctggccgggc ctattgtccg   81600
gccctgggag tcatccctgt tacagtctcc gggaagggcc tttgcacccg ttagcccaca   81660
acccatgcca gtagaacccg tccctgtccc tactgtggca cttgagcgac cagtttgtcc   81720
cgcacctcct gagattgcta tgcagggccc ggggggaacct tctggcatta aacgcacacg   81780
ggagcgttgg aggcccgcac cgtggacgcc aaacccaccc cgctctccca gtcagatgtc   81840
```

```
cgtgcgtgac cgtctggctc gtttgcgtgc tgaggcacag gcccgtcagg ctagtgttga   81900
ggtgcagccc acccagttga cccaagtatc ccctcagcaa ccaatggaga ggccgttgga   81960
accagagcag cagatgttcc ctggttcccc ctttagccag gtcgctgatg ttgcccggga   82020
atctggggta cctgcaatgc agcctcagta ctttgacctc cccttaactc aacccattag   82080
ccagggggca cccgcggccc cgttgagggc tagtatgggc ccggtacctc cggtaccggc   82140
aacacagcca cagtattttg acatcccctt aactgaaccc attaaccagg ggcatccgc   82200 ggcccatttt ctccctcagc aaccaatgga ggggccgttg gtacccgagc ggtggatgtt   82260
ccaaggtgcc accctgagcc agagtgttag gccaggggta gcgcagtcac aatattttga   82320
cctcccctta actcaaccca ttaaccatgg ggcacccgca gcccatttcc tccatcagcc   82380
accaatggag gggccgtggg tacccgagca gtggatgttc caaggtgccc ccctagcca   82440 aggcactgac gtggtccaac atcagctgga tgatttgggg tatccactcc atgatctcaa   82500
ccatcccggg gttccgtgt ctcctgccgt taaccaatat catttcagcc aggctgcctt   82560
tgggttacct attgatgagg atgagagtgg cgagaggtcc gatacctccg agccgtatga   82620
agctcttgat ttgtcaatcc atggcaggcc ctgccctcag gcccccgaat ggcctgttca   82680
aggggagggt ggccaggatg ccaccgaggt tcttgatttg tcaatccatg gcaggccccg   82740
ccctcggacc cccgagtggc ctgttcaagg ggagagtggc cagaatgtca cagaccatga   82800
acctagaagg gtggtggtgt cagctattgt tcacatgtgt caggatgacg agtttccgga   82860
tctacaagat cctccagatg aggcctaagc aaaggtgtag aagtgtgtcc ccctccattc   82920
cacccactga tatacgcccg acaataaagt tgatgatatt gaattccaca cctactcgtg   82980 tttgtgatt tatttcatat tccatgagag agacctcgca tatttgcaga gggtcactga   83040 aacatttat cttaaaacag ttacacctga aaatgaaga aagcgtggct cagcagagca   83100
cagcaagccg atgccggggg ggcatctggc tccgaggacc caccagatta tggagatcaa   83160
ggtaatgtgc aacaggtggg atctgatcct atttcacctg cgattggccc cttttgaactc   83220 tctgcggcca gtgaggatga tcctcaatct gggccagtgg aagagaattt agatgccgct   83280
gcaagagagg aagaggaacc tgatgagcag gagcacaatg tggtgatga tcccttggaa   83340 gtccatactc ggcagcctag atttgtggat gtgaacccaa cgcaggctcc agtgatccaa   83400
ctagtccatg ctgtttatga ttccatgttg gtaagaggca cctagaacat ttccagatgt   83460
ttagcttgga tattttggcc agtcttaatt tattgtcatt ggtttcagca atcggacctc   83520
cggtctctag gcagttttatt ccttgagcaa aacctgaaca tcgaagagtt tatatggatg   83580
tgcatgacag tgcgtcacag atgtcaggcc atcagacaaa aaccattacc gattgataag   83640
cagaggcggt ggaagctcct gtcaccttac agaacctggc gtatgggtta ccgtacgcaa   83700
accctcaatg taaacagttt tgagacaggg ggagataaag tccacccact ccttgtgact   83760
gctacgctag gatgtgaaga gggcctgcgg catgcaataa cttacagtgc tggcattgta   83820
cagctaccac gaatgtcaga ccaaaaccaa aagatagaaa cagccttctt gatggcacgt   83880
cgtgctaggt cactttcggc agaaagatat actttgttct tgatttagt atcctctgga   83940 aacaccctgt atgccatatg gattgggctg gcacgagaa accgagttgc atttgtcgag   84000
tttgtaggat ggctatgtaa gaaggaccac actcatatac gtgaatggtt ccgccagtgc   84060
accgggagac cctcaccatc caagccatgg atgagagcgc atcccgtcgc cgttccttat   84120
gacgatccat taacaagtga ggagactgac ctggcctatg cccgtggact ggccatgagt   84180
```

-continued

```
atcgaggctg ctagactgcc agatgatcca ataattgttg aggatgacga tgaaagtgag    84240
gaaattgaag ataaatgtga taaggatgaa gaggaaagtg gaacggaaga tgttacaagc    84300
ataccgcaaa cactgccgca cagtccaaca gtatacggca ggccctcggt gttttaccga    84360
aagccagata ctaaatcaac caaaaaatgc agggccatag tgactgacct tagtataatc    84420
aaggtcattg aagatgaaca cagaaagaag aagacagcca gaacagagca accaagagcc    84480
aagcctgatt cccctgcccc cacagtggtc cttcggcgac cacccacgca aaaggtgact    84540
ggccctgccg gttcactgag tgtccaggct cagctggagc catggcaacc tttgtcctgg    84600
ccacatgaga caagagttat acttcacgga ccacccacgc agggtgacca agcacacggt    84660
tccatgctag accttcttga aaaggacgac cagcacatgg agcagcaggt tatggcaacc    84720
ctactgccac cagaaccaca ccagcccgg tctgggagaa gagccccttg tgtctacacc    84780
gctgacctag acatagaaag tgatgagccc gccacgtcag agccggttct tgatcagcta    84840
ctgcccgccc caggacttgg acctcttgca attcaaccat taacgtcccc caccacgtct    84900
caactccgca gttcagcacc gagccacgca caaactccat ggccggttac ccacccaagt    84960
cagactccag gtggcccaac gacacagtcc ctggcaccgg aaacagaagc cccgcgccag    85020
tggccaatgc cactgcgacc tatccctctg cacccctttgc ggatgcagcc aatatcattt    85080
aatcctgcag tgagacccac tccccatcag ccacctcagg tggagcccac tttctatcag    85140
tccacttggg tgaaacccc tcaacaatac cagcctcaga tggggcacat tccatatcag    85200
ccccgaccaa cgggtcactc tactatgctc cggcccagt gggcacccac caccatgcag    85260
ccaccaccaa gggcgcccac tcccatgccg ccacctcagg ggccacccac cgctatgcag    85320
aggcctcagg gggcgcccac tcccatgccg ccacctcagg ggacacccac cgccatgcag    85380
aggcctcagg gtgcgcccac tcccatgccg ccacctcagg ggacacccac cgccatgcag    85440
aggcctcagg gtgcgcccac tcccatgccg ccacctcagg ggacacccac cgccatacag    85500
aggcctcagg gtgcgcccac tcccatgccg ccacctcagg ggacacccac cgccatgcag    85560
aggcctcagg gggcgcccac tcccatgccg ccacctcagg ggacacccac cgccatgcag    85620
aggcctcagg gggcgcccac tcccatgccg ccacctcagg ggccacccac cgccatgcag    85680
aggcctcggg gggcgcccac tcccatgccg ccacctcagg ggccacccac cgccatgcag    85740
aggcctcagg gggcgcccac tcccatgccg ccacctcagg ggccacccac cgccatgcag    85800
aggcctcggg gggcgcccac tcccatgccg ccacctcagg ggccacccac cgccatgcag    85860
aggcctcagg gggcgcccac tcccatgccg ccacctcagg ggccacccac cgccatgcag    85920
aggcctcggg gggcgcccac tcccatgccg ccacctcagg ggccacccac cgccatgcag    85980
ctgtcaccaa gggcacttac cggccagaag gggccagcaa agcacattct gcgccagttg    86040
ttaacggggg gcgtcaagag tgggagacca tcacttaagt ttaaggctgc ccttgagcgt    86100
caagccgctg cgggcttgcg accttcacca gggtctggaa cgggtgccaa gattgtgcag    86160
gcacctgttt tctatccacc cgtcctacag cccatacaag ttatgtggca agtgggttcc    86220
tcaaaggccg tggccgcctc aacggtgaca caggcaccca cggaatatac cggggaaagg    86280
aggttagggg ggcctatgtc tcccactgat attccgccgt ctaaacgggt gaagaaaaag    86340
gcctatccag agcgcaagac gccgcatggg gggccctcac actcttccac cgttatgtgg    86400
gagaatgtca gccagggaca acagcagact ctggagtgcg gaggaactga taaacaggaa    86460
aggaacatgt tggggatggg ggacattgca gtttcttccc cttcctcttc tgaaacatcg    86520
aatgatgagt gatttcaacc acgtaacaag aactgggatg aaccctcggg cagtatcaga    86580
```

```
ctgcggggag gggcagtgat aagtcatgac aattttagat gaggtagaca ttttgcatat   86640
tttcagaccc accatggaat catttgaagg agaggggac tctatacagt cacctgacaa   86700
tgcgcgggga gatgatgtac agaatactgg tgagcatatt caggaccccg ggccggggcc   86760
ttcaaccggc ggggcttctg agggattggt gcagaacgag ccggactcaa gagatcaaca   86820
gtcccggggg cagagaaggg gtgatgaaaa cagaggctgg atgcagcgca tcaggcgaag   86880
gcggagaaga cgggccgcat tgtccggcca tcttttagac atggaagaca atgtgccgcc   86940
gtggtttcct ccacacgata tcacaccata tgtcgcaagg aatatcaggg acgctgcctg   87000
ccaggctgtc aaggtgagca tgcctctaac tgggttcatg ggggccatct aaggcccacg   87060
tgtgacccat gtttccatta attttagcac tcgcacctgc aagcgctatc aaacctgata   87120
ctcgatagtg gtttagacac acaacacctc ttgtgcttcg tgatggcagc caggcagcgt   87180
cttcaggaca ttcgacgtgg acccttggtt gtagagggag gtgttggttg cgacattgg    87240 cttctgacat ctcccagccg atcctggtcc atgggatatc gcacagcaac actacgcaca   87300
ttaactcccg tgcctaacag ggttggggct gacagcatca tgttaactgc cacgtttgga   87360
tgccaaaatg gggcactagc tataaacacc ttctccgcca ccgtgtggat accacccct    87420 gctggaccaa gagagcaaga aagatacgct cgggaagccg aggtgcgctt ccttcgtggt   87480
aaatggcaga ggcggttccg aagaatcttt gatttgatag aactgtgtgg ctctctgcac   87540
cacgtctggc aaaacatgct gcagaccgag gagaaccttt tagatttcgt gcgtttcatg   87600
ggtgtcatgt ccagctgcaa tagttcatct gtgaattact ggtttcacaa gacaatcgga   87660
aactttaagc catattaccc gtggaatgca ccacctaatg aaaatccata tcacgcacgg   87720
agaggcataa aagaacaagt aatccagaaa gcatttctaa aggcacaaag acagggttta   87780
tcaatgttag caacgggagg tggacccaga ggtgatgcta ctagtgaaac gagcagcgat   87840
gaggataccg gtagacaggg ttcggatgtg gagctagagt catcggacga tgagctgcca   87900
tatatcgatc ccaacatgga gccagttcag cagaggcccg tcatgtttgt gagccgtgtg   87960
cctgtaagga aaccgaggac actgccgtgg cctacaccca agacgcaccc agtgaagcgc   88020
acaattgtta agacctccta tagatctgat gaggcagaag aagcacagag cacccctgaa   88080
aggccgggcc cttccaaaca accatcagag cccgtggagc ccgcccacac aaccccagcg   88140
gggaggtcaa cggtgattct ccacgaacca cctcgagagc ccgaagctgt ttccttcaag   88200
cctccgccac caccttcccg gaggagaagg ggagcgtgtg ttgtatatga cgatgatatc   88260
atagaggtga ttgatgttga aaccaccgaa gaggagacga cgtcaatgca aagacagcct   88320
ccgctcgggc aacaaccgcc ccccccgtg atttctaccg ggagtgccat gtcttccagt    88380
cacacggatc catcagtaac acagccaagt aagccacatc ggaaacctca agacggattt   88440
caacgttcag gccgacgtca aaaacgagcc atgcctcccc cagtgagtcc ttctgacgct   88500
gggcctcctt ccaccaggcc tcgtgtcatg gcgcctcctt ccaccgggcc tcgtgtcatg   88560
gcgactcctt ccaccgggcc tcgtgacatg gcgcctcctt ccaccgggcc tcgtgacatg   88620
gcgcctcctt ccaccgggcc tcgtgacatg gcgcctcctt ccaccgggcc tcgtgacatg   88680
gcgcctaccg tcgtacatat gtttacgagg gagcgcctgc tcacccagtc caccggccct   88740
gcacctcgga gcttctggga aatgcgggcc ggccgtgatg ctcccaaaat tcaacaagaa   88800
ccaagttcac aacagcagcc agccactcag tctacaccgc cttgccaatc atgggtccca   88860
tctgtctatg tcctcccggc agtggatgct ggtaatgccc agcccctaca aatatcacac   88920
```

```
ttgagctcca tgtcgcccac gcagccgata tcgcatgaag aacaaccccg gtatgaggat   88980
cctgacactc ctctggattt gagtttacat ccagatactg caactctgcc gcccacccag   89040
gatttatacc ctggacgcga ggatctgcag gccacccagg ctccataccc gggatacgag   89100
gagccacggc ccccccaggc tccttttgta ggtgactatg gttttgttca aattccctcg   89160
gctcaatggg agccacaccc ctctcagggc acataccagg gccacattga tccccagctt   89220
ccggctgctc tagatttagg gccagagcag ccccggttcc cacaagatcc atatgtgtat   89280
tccgggggcc aattgtcttc atgtccaggt tatgcaggtc cctggccctc gaggcctcaa   89340
catccaagat ataggcacac cttggcattg tggcctcgag aacccaggca tgggcactct   89400
cagggcccat ggaaaccctg gtcagcacat ctcccacctc agtgggatgg atctgcagga   89460
catgccaggg atcaggtctc ccagttccca catctgcatt cggagacagg cccaccacgt   89520
cttcaacttt catcggtgcc acaggtgctg tacccgcagc cactggtctc atcctctgca   89580
ccatcgtggt catctcccca gccccgagcc ccatacgcc ccattccaac aagattcccc    89640
cctcccccta tgccgttaca agatagcatg gccgtggggt gcgactcatc aggtacagca   89700
tgcccaagca tgccctttgc cagtgattac agtcaaggtg catttacccc actggacatt   89760
aatgccccca cgccaaaaag tcctcgagta gaagaaagtt ctcacggacc cgcccggtgt   89820
tcccaagcta cttctgaagc acaggagatt cttagtgaca attctgagat ctccgtgttc   89880
ccaaaagatg caaagcagac tgactatgat gcatccactg aaagtgagct agattaaggg   89940
gatccaaggt gaccctgtt agctatttga tctttgactg acacataaac atggtttaag     90000
gaatgaacac tcatggtgtg agactggaac tgtactaaat ttgctgacat atgtacaatg   90060
agagccaaaa atttgataaa ccttaaaagt ccccccatct aatgatgtcc agttcccttc   90120
tcccacccct acaccccga cccaaaggga ctcaatggca ttcagatttc tagttaccac    90180
aggtagaata tcgggcgttg gcccataaaa ataagtgcat ggatatagct ctgcacaggc   90240
ttggaaacac ccattccagg tgtgcttctt tttggtgaaa taaaacagc gttctttata    90300 tgaaaatgtg tattctcttg tgttgcagta tgtacagtta gctttggtat agttttggg    90360 tacctgaaac gtgtgcaggg tgggtgtcca atgtggcagt tttatctctt tgtccccata   90420
ctcctgctcg gccgtcttgt taaagttaac cggcggtgga ggatccaccg gccagacctc   90480
tacatttggt ttgggtaccc aggtgatggc cgctgccgac acccgccctc ctcctcttac   90540
cctgggtggc aaaaagtatg ccaggagtag aacaataaca agtgcgatgg cggtaaacaa   90600
tggcaccctc acctgcttaa acgaaaccat ggcaaccact tcaaagagag ccaacaggaa   90660
gatatttatt aatattccat tagtaaacga ggcgtgaagc aggcgtggtt tcaataacgg   90720
gagttagaaa tttaagagat cctcgtgtaa aacatctggt gtccggggga taatggagtc   90780
aacatccagg cttgggcaca tctgcttcaa caggaggcgc agcctgtcat tttcagatga   90840
tttggcagaa gccacctgcg gacaaaaatc aggcgtttag atgggcatt ttatgtttgg    90900 gccattagcc acctgggcat tcgtgttact gtatactgac ctcacggtag tgctgcagca   90960
gatgcttaaa cttggcccgg cattttctgg aagccacccg attcttgtat cgctttatat   91020
ctagttcaga atcacattcc tccagctgcg agcaagggaa tgcgttacta caagtggtgc   91080
ctagtcagtt gaaacaggcc ccaccgtccg ctgccgccct ccttgagccc caccatccgc   91140
tgccaccctc tttgagcccc accgtccgct gccaccctct ttgagcccct tcttaccgat   91200
tctggctgta gtggtttcct tgtacgtcgt gccggggcag ccgctggtgc aggctgtgga   91260
gcaccaatgt ctgctagctg ttgtccttgg ttagccccgg gacaagcaaa caccactgct   91320
```

```
gctgctggtt gaacagtaga attgtctcca ggttgaggtg cttctccccc ggcttggtta    91380
gtctgttgat tctgggttat gtctgagact gggaatagct gaggtgctgc ataagcttga    91440
taagcattct caggagcagg ctgaggggca ggaaaccacg acccagttgg agcggctgaa    91500
acatgatagg cagtgagctg gccttgtggc agaggctctg gcagcaccgg ccacagcaca    91560
caaggcaaag gagcttgtga tggccctccc aggtcctgat agactctggt agcttggtca    91620
aaagcttgta caaaaggcac ctggtatggg tcaggtgtaa attttacatc ttcagaagtc    91680
gagtttgggt ccatcatctt cagcaaagat agcaaggtg gccggcaagg tgcaatgttt     91740
agtgagttac ctgtctaaca tctcccctt aaagccaagg caccagcctc ctctgtgatg     91800
tcatggtttg ggacgtgcta aatttaggtg tgtctctgag gcacattagc aatgcctgtg    91860
gctcatgcat agtttccaaa agaggaggag gcagttttca gaagtgtcta aaataagctg    91920
gtgtcaaaaa tagacagccc agttgaaata tgcatggcat gcagcagaca ttcatcattt    91980
agaaatgtat ccaagatttc attaagttcg ggggtcaggg gggagtccag attcaaatcc    92040
tctgtcatgg actctagtgt tgtggtcagt tcgtccaaat ggccacgagg gggcgggtgg    92100
ttcaggtcca tctgtccaca tatggctgct tcctccttct ggggaataac agtgtcagcc    92160
atctccctta gggccttcac ggcctgactg gtttcctcat cagggtcctc caacagatga    92220
cttgcctcgg gggttactgc gggggccggg tcaagtggcc ggggcactgg ggctggcgtt    92280
agggatccga ccggttcatg gacaggtcct gtggggtgg gagccaaaga ggcaggcagg     92340
ggccggttgg cccacgggga tccggtgga tggaagggcc tgatcctctt tggctgacac     92400
acctctcgcc cctcgaacac gtcagatatg gcactgcccg cttccggctt tggcaggaac    92460
ataccttccc ggctatccct gaggcccttc ttcctttaa cgggaggaag aaaggtgggc     92520
tttgaggggt gggggaatat gggtctctca tcgctctctt ggtggaccgc tgctatccaa    92580
ggctgttcag gttcctccgc gttggaagga catggagttt gaccacggtt gggcctggat    92640
gtccggcgcg actttggggc ccgcaggcgc ggggcctcgg ccctggcctc ttcccgctcg    92700
ctctgctcgg tgtcactgtt gcccgagtca ctgctgctgg aactgctgtc accgcagtcg    92760
gcgctttggg caccgggctt caggggcatg gtcgggctcg ggagactttc gagttcatct    92820
gtaaaagcat gaaactgtcc ggactccgag tagcgggcct cggtgtgaga ggcaccccca    92880
tcattcccca tgagctcctc gtccatcctg tcggctccgg acacgaggat aggagtttcc    92940
actgccttgg acttggttga cagcaggcac gcgggaagca cgccgctcac gtagctcctc    93000
tgtccggcgt ggctggagta ggaggccgg ggcagtgtct taatcagagc cctgacatcc      93060
ttaacatcgt ccgtcagatg gcctgtcttg gacgagacca tagtctggaa catctcctcg    93120
aggacgggat aggtgaacac ccacttgcaa aaggccttga acttggagct taggaggcct    93180
tccttctcca tcctgttcag gtgttccact acctgcttgc cggaggccat gatggccgcg    93240
cggtccacgc ccagcacctt gctgtaggtg taggcccgca cccgactgtg ttttaggagc    93300
ttgtacatag cggtgcctat ggtggcagga atcatcaccc ggttgctggg ggcctggatg    93360
aagaatctgt cagtgaccac tatcaggtgg tctaacacgt agcgcatcac tatagggcac    93420
gcgatggaac atgcgtcgtt gccggcattc tcagcccgtc ttcttaccct gttgtttcgg    93480
agaatggccc aaaaattgca gatgttgagc gtggccatta gcccgcccca ttctcgcccg    93540
tgggccttgg cctcatttat aaatgccttg catattttgt aggatctcag agtaatctcc    93600
acactcccgg ctgtaaattc cttgttgagg acgttgcagt agtcagagac cagagagccc    93660
```

```
agctgctttt tgatttcagg agttagcctc agaaagtctt ccaagccatc cttttttaggc   93720 ctcatggcta gtagtaacag aggaaatgcc cgaccattaa aatctttcct ccatgagctt   93780
tacctgaaac actatcccga agtgggggat gtggtgcatc tactgaacac catcggggtc   93840
gactgcgacc tcccacctag ccacccactc ctgacagccc agagggggct gttcctggca   93900
agagtcttgc aggctgtaca gcagcacaag ctgctggaag acaccatcgt ccccaagatc   93960
ttaaagaagc tggcttattt cttagagctg ctaagctact actcccccaa ggatgaacag   94020
cgtgacatcg ccgaggttct tgaccacctc aagacgaatc gggacctggg gctggacgac   94080
agactctggg ccctgattag gaaactgcgc caagacagac accatgcctc tgtaaatgtc   94140
ctcatgccag gaagcgacta cacagccgtg tcgctgcagt actacgacgg catctccata   94200
ggtatgagga aggtaatcgc ggatgtctgc cgcagtggct atgcctccat gcctccatg    94260 acggccacgc acaacctctc ccaccagctc ttgatggcgt ccgggcccag tgaggaaccg   94320
tgcgcctggc gcgggttctt taaccaggtc ctcctctgga ctgtggccct ctgcaagttt   94380
cgcagatgca tttactataa ctacattcag ggatctatag ccaccatctc ccagcttctg   94440
cacctcgaga tcaaggccct ctgcagctgg ataatatccc aggatggcat gcgcctcttt   94500
caacacagca ggcctctcct caccctctgg gagagcgtgg ccgcaaatca ggaggtcacg   94560
gatgccatta ccctgcctga ctgcgctgaa tacatagacc tactaaagca cacaaaacat   94620
gtcttagaaa actgttctgc catgcaatac aaataaattt ctcttacctg cgtctgtttg   94680
tgtagtgagg tgttgtgtcc tgtatggtat tctactttaa aaatgccggc tgacatggat   94740
tactggtctt ttatgagcca ttggcatggg cgggacaatc gcaatataaa accctgacca   94800
tcacatgggg cattaggcga ctctgcatca gcatcgctta agtatgagtg ggcagcagag   94860
aggctcggtt attttggttc ctgaacatct ggctggggca ttaactaagc ttatgagcga   94920
ttttatcaca ggacaagatg tcactctttc tggaggaaat attgcagtca aaattcgcga   94980
tgctataaac cagaccccg ggggtggtga tgtagctata cttcttccc tgtttgcttt    95040 atggaatgcc ctcccaacat ctggtagaca atcctccagg gacgatttaa tcccagccgc   95100
cgtgcaggcc ttaaccacgg cccacaactt atgtctgggt gttattccag gtgagacctc   95160
acacaaggac acacccgagt cattgctccg ggctatcgtg acgggtctcc aaaaattgtg   95220
ggtggattcg tgcggatgtc cagagtgcct acaatgtctt aagggattga aggcaattaa   95280
gcccggcctt tatgaaatcc ctaggataat accacacact aagcagtgta gtcctgtcaa   95340
tctcctgaac atgttggtcc acaagcttgt ggctttacgt ggtcatgtgc agcttgcata   95400
cgacgcccgt gtcctgacgc ctgactttca cgaaatccct gacctcgatg actccgatgc   95460
tgttttcgca cgcaccttat tggcagcctt atttcacctc aatatgttct ttattctcaa   95520
agattacata acacaagact ccatgagctt gaagcaggcc ctcagtggtc attggatgtc   95580
tgccacgggc aacccctgc ctgcagcacc ggaaaccctg cgagactact tggaagcttt    95640
ccgaaattcg gataatcact tttatctccc gacgacaggg cctttaaaca ccttcaaatt   95700
tcccgaagag cttctggggc gcgttgttgt gattgattcc tctttgtgtg ccgccagtca   95760
cgttcaggac gttatcaccc gtggtgttgg ggcgggtgtt cctcgtcctc agttttttggc   95820 cctgcctccg gccccatccc gtaagcccca gcagacatgc tctcagttaa cgagcagagg   95880
aaatgaaagc tcacggcgaa acttgggcca gccccggggg acctcccctg ctgttccccc   95940
agtttgcccc atcgtttccc tgacggcctc aggggccaag caaaaccgcg ggggcatggg   96000
gtccttgcac ttagccaagc ctgaggaaac ctcccccgcc gtctccccag tatgcccat    96060
```

```
cgcttcccca gcggcctcca ggtccaagca gcactgcggg gtcactggat cctcacaggc   96120
cgcacccagc tcttcttccg ttgccccagt agcatctctg tctggtgacc ttgaagagga   96180
agaggagggg tcccgagaat ccccatccct accgtccagc aaaaaggggg ccgatgaatt   96240
tgaggcctgg cttgaggctc aggatgcaaa ttttgaggat gttcagcgag agttttccgg   96300
gctgcgagta attggtgatg aggacgagga tggttcggag gatggggaat tttcagacct   96360
ggatctgtct gacagcgacc atgaagggga tgagggtggg ggggctgttg gaggggggcag   96420 gagtctgcac tccctgtatt cactgagcgt catctaataa agatgtctat tgatctcttt   96480
tagtgtgaat catgtctgac gagggaccag gtacaggacc tggaaatggc ctaggacaga   96540
aggaagacac atctggacca gacggctcca gcggcagtgg acctcaaaga gagggggggg   96600
ataaccatgg acgaggacgg ggaagaggac gaggacgagg aggcggaaga ccaggagctc   96660
cgggcggctc aggatcaggg ccaagacata gagatggtgt ccggagaccc caaaaacgtc   96720
caagttgcat tggctgcaaa ggggcccacg gtggaacagg agcaggagga ggggcaggag   96780
caggaggggc aggagcagga ggggcaggag caggaggggc aggagcagga ggggcaggag   96840
caggaggggc aggagcagga ggggcaggag caggaggggc aggagcagga ggggcaggag   96900
caggaggggc aggagcagga ggaggggcag gagcaggagg ggcaggagca ggaggggcag   96960
gagcaggagg aggggcagga gcaggaggag gggcaggagc aggaggaggg gcaggagcag   97020
gaggaggggc aggagcagga ggaggggcag gagcaggagg aggggcagga gcaggaggag   97080
gggcaggagc aggaggaggg gcaggagcag gaggaggggc aggagcaggc ggggcaggag   97140
caggcggggc aggagcagga ggaggggcag gagcaggagg aggggcagga gcaggaggag   97200
gggcaggagc aggaggaggg gcaggagcag gaggaggggc aggagcagga ggaggggcag   97260
gagcaggagg aggggcagga gcaggaggag gggcaggagc aggaggaggg gcaggagcag   97320
gaggaggggc aggagcagga ggaggggcag gagcaggagg aggggcagga gcaggaggag   97380
gggcaggagc aggaggaggg gcaggagcag gaggaggggc aggagcagga ggaggggcag   97440
gagcaggagg aggggcagga gcaggaggtg gaggccgggg tcgaggaggc agtggaggcc   97500
ggggtcgagg aggtagtgga ggccggggtc gaggaggtag tggaggccgc cggggtagag   97560
gacgtgaaag agccagggggg ggaagtcgtg aaagagccag ggggagaggt cgtggacgtg   97620
gtgaaaagag gcccaggagt cccagtagtc agtcatcatc atccgggtct ccaccgcgca   97680
ggccccctcc aggtagaagg ccatttttcc accctgtagc ggaagccgat tattttgaat   97740
accaccaaga aggtggccca gatggtgagc ctgacatgcc cccgggagcg atagagcagg   97800
gccccgcaga tgacccagga gaaggcccaa gcactggacc ccggggtcag ggtgatggag   97860
gcaggcgcaa aaaggaggg tggtatgaa agcatcgtgg tgaaggaggt tccagccaga   97920
aatttgagaa cattgcagaa ggtttaagac ttctcctggc taggtgtcac gtagaaagga   97980
ctaccgagga tggaaattgg gtcgccggtg tgttcgtata tggaggtagt aagacctccc   98040
tttacaacct caggcgagga attggccttg ctattccaca atgtcgtctt acaccattga   98100
gtcgtctccc ctttggaatg gcccctggac ccggcccaca acctggccca ctaagggagt   98160
ccattgtctg ttatttcatt gtcttttttac aaactctata atttgctgag ggtttgaagg   98220
atgcgattaa ggaccttgtt ttgccaaagc ccgctcctac ctgcaatatc aaggtgactg   98280
tgtgcagctt tgacgatgga gtagatttgc ctccctggtt tccacctatg gtggaagggg   98340
ctgccgcgga gggtgatgac ggagatgacg gagatgaagg aggtgatgga gatgagggtg   98400
```

```
aggaagggca ggagtgatgt aacttgttag gagacgccct caatcgtatt aaaagccgtg  98460 tattccccg cactaaagaa taaatcccca gtagacatca tgcgtactgt tggtgtattt   98520
ctggccacct gtcttgtcac cattttcgtc ctcccaacat ggggcaattg gcatacccca  98580
tgttgtcacg tcactcagct ccgcgctcaa caccttctcg cgttggaaaa cattagcgac  98640
atttacctgg tgagcaatca gacatgcgac ggctttagcc tggcctcctt aaattcacct  98700
aagaatggga gcaaccagct ggtcatcagc cgctgcgcaa acggactcaa cgtggtctcc  98760
ttctttatct ccatcctgaa gcgaagcagc tccgccctca cgggccatct ccgtgagttg  98820
ttaaccaccc tggagactct ttacggttca ttctcagtgg aagacctgtt tggtgccaac  98880
ttaaacagat acgcatggca tcgcggggc tagacctctg gctggatgag cacgtgtgga   98940
agaggaaaca ggagattggt gtgaaaggag aaaatctcct tctccccgac ttatggctag  99000
atttcctaca actcagcccc atcttccagc gcaagcttgc tgccgttatt gcctgtgtcc  99060
gacgactgcg gacacaggcc accgtctacc cggaggagga catgtgcatg gcctgggccc  99120
gcttttgcga cccctctgat attaaggtgg ttatttgggg ccaggacccc tatcacgggg  99180
gtcaagcaaa cggcctggca ttcagcatcg catacggctt tccagtcccc ccagcctga   99240 ggaacatcta cgcggagctg caccggagtc tgccggagtt ttctccccca gatcacggct  99300
gtctagacgc gtgggcctcc caggggtgt tgctactcaa caccatcctg accgtgcaaa    99360
agggcaagcc cggctcgcac gcagacattg gctgggcgtg gtttactgac cacgtaattt   99420
cattgctctc tgagcggtta aaagcgtgcg tgtttatgct gtggggtgcg aaggcgggag   99480
acaaagcttc actaatcaac tccaagaagc atctggttct gacctctcag catccctctc   99540
ccctggccca gaacagcacc cgaaagagtg cccagcagaa gttcctgggc aacaaccact   99600
ttgtcctcgc taacaacttt ttgcgtgaga aggggctcgg tgagatagat tggaggctgt   99660
agaggggtca tcactatggc catgtttctg aagtcgcgtg gggtccggtc ttgcagggac   99720
cggcgcctct tgtcggacga ggaggaagag acttcacaga gcagcagcta cactctgggg   99780
tctcaggcct cccagtctat ccaggaggag gacgtgagtg acactgatga gtctgactac   99840
tcagatgaag acgaggagat tgatttggag gaagagtacc ccagtgacga agacccatct   99900
gagggcagtg atagcgaccc ctcgtggcat ccttcagatt cagacgagtc tgactacagc   99960
gagagcgacg aggatgaagc aaccccccggc tctcaggcct cacgatcttc aagagtctgc  100020
ccatctaccc aacagtcttc aggtctgaca cccacgcctt cgttctcccg accacgcacc  100080
cgggcacctc cgaggccgcc ggctcccgcg ccggtcaggg gacgggcctc agcacctccc  100140
aggccaccag ccccagttca gcaatccacc aaagacaagg gtccccatag acctacgcga  100200
cctgtactta gaggcccagc tccacgccgc ccccctccac cttcaagtcc aatacatac   100260 aataaacaca tgatggaaac caccccccc attaagggca ataacaacta caattggcca   100320
tggctgtaaa taaatgtca taacctggag tctgcatgtc tgttgtttta ttcagtaaac    100380
cagtagtgcg cgtgagttct ttagggcatc cacgatgtag ccgctcgcgg ggttccctc   100440 cccagtgatc atctcggata ggggattcct gtccatgacc acgcaattag agtgccgggc  100500
ccgggacagc gccacataca catggccggg tttgatgttt ctgtggctgc cgaagcagat  100560
ggcgactttg tttagggaca gaccctgggc cttggctatg gtcatggcca gctttgagct  100620
aatgccatag tcacggatgc tgcagaggtt cagggacttg tcctctatcg tctcatacag  100680
cttgttagta ttgtgttcca ggcagcacac gaagcctgcc tcatccttga ccattagcct  100740
gggcatgcgt gaactgccag cgtcctgagg ctgctgcttt cctcggatgc caaagaagac  100800
```

-continued

```
gttgagatgc gtgtagccca gaagcgtgta gttctcggtg gtggaggcgt agtccaggag   100860
gccgtgaagg agaggctcgt ctgaggtgaa ctctatgttg tcgcgaatca gcatgttgtt   100920
ggtaaatgtg cagaagggga ggtccctgaa ctcccttctg ccatagcgga cggccacatc   100980
caggcattgc ctgaaatagg ccctgaggtc attatatatg tttaacaggg agcagagggg   101040
ggcagaattt gcggccgggg gagccagtac tcgggcatag aagacagcgg cggggctccg   101100
ctccccatcc caggcaacct ccagcggcag ttcacccagc tccatcccag cagtcacctc   101160
cggatcccac gtacgcccgg gcaggggcac agcaccaagc tccgccacgt attccccgtt   101220
ttcacagaga gaatgtcctc cgtggctaaa agcgtagatg ccgccgtaga tgagtcgggc   101280
caggaagctg tagacatact cgggctgctc atgcccgtgg gcctccacga agctgtccgc   101340
ctcgagcgtg tccataaagt ccccgaaggt gccggtatag ccacagatgg acttttggt    101400 cttgcagttg accgacactg agctgtgctt cacgtaggtg acattgtagg tgaccttgac   101460
ccgttcttca tcctgctcgg ttcccaccgg gaccatgtct tggtcggcga actgcgagta   101520
gttaccgagg cgtgcataat tcttttggag ccaggtgtgg gccgtgaggc ccggaagacc   101580
gaccagggtc ttgtactggg ccaggggctc gaggaagacc tcgcactcca ccgggcaggt   101640
aaacatggtc accccgcccc catctccccc agttcccgc gcggcgcgcc cctgcccggc    101700
agtcttgagc gtggcgtgga gggtggtgag gaaggtcttg acctcggcgt gggagaggaa   101760
gagccgggtc cagcccacgt actgcgtggg gtccattatg gccgccctgg ggacgacgaa   101820
gcggtcgacg taggccagga tgtccggcga gagctcgagg ccgtactcga gggtcttcat   101880
gaggtgtcca aactggacgt cggtgcagcg cttgttgttg atgaagaggg cccagttgcg   101940
ggccacgtcc acgtaggtcg cggccctggg gttgcccacc aggaaggtga ggatgttgtc   102000
gcactcgcga atcttgttta cctgggtctc gtggctaaag gaggactgaa aggcgtctgt   102060
ctgggtggga gagcccacgc agacgatgca gggaatgcgg cccggcggt agagtggggt    102120 gcgcagccag gcgttgaaga accagtagca aaagaccacg gctgttagaa tgtgcacgga   102180
aagcgttcca gcttcgtcca ccacgatcac attggtggtc catagctgcc cctggtgcat   102240
gtctctcagg acctcaaagg cggggccaga gactcccgag tatagccccc tgggcttggt   102300
tcgcctgaac tcggcggcaa tgtcggagag taccggccag tatttggcca tgtcccgccg   102360
ctggagttcc tctagggcgg cgtccgtaga gcgaccatga ctgctgaccc gctgcgtcat   102420
atttatgtgg cggctcttga acccaaaggc gctatagacg gttgggcagt aggctcggag   102480
tgtctgggag aggttctgtg cggccacggt tgtggctccc gtgaccaggc agtccatcgt   102540
gtggtggagg cagctaacgc tggtgctctt gccagccccc gccgttcccg taattacata   102600
ggctgaaaag ggcaggaagg ggggctccga gatctccggg tcaaactcgg gggagaacgt   102660
ctccatatcc gggagttgtt ggacgcggcg cttagccagg gtccctatcc tcctgactat   102720
acgcctcacg gaggcgtctg aggtcatgtt caacatgaac gtggacgaga gcgcctctgg   102780
cgctctcggc tcctcggcca ttcctgtgca ccccacgccg gcctcggtcc gactttttga   102840
gatcctgcag ggaaagtacg cctacgtcca gggacagacc atctacgcca acctccgtaa   102900
ccccggagtc ttctcgaggc aggtgtttac ccatttgttt aaacgagcca tctctcattg   102960
cacgtacgat gacgtgctac atgactggaa caagttcgag gcctgcatcc agaagcgatg   103020
gccgagcgat gactcgtgtg cgagccggtt tcgtgagtcc accttcgagt cgtggtccac   103080
gaccatgaag ctgaccgtgc gtgacctgct gaccaccaac atctaccgag tgctacacag   103140
```

```
ccgctccgtg ctctcctatg agcgttatgt ggactggatc tgcgccaccg gcatggtgcc    103200
cgccgttaag aagcccataa cccaagagct ccactccaag ataaagagcc tgagggacag    103260
gtgcgtctgt cgggaattgg ggcatgagag gaccatcagg agtatcggga cggaattata    103320
tgaggcaacg agggaaataa tagagtcgct caactccacg ttcatccccc agtttacgga    103380
ggtgaccatc gagtaccttc cggggagcga cgagtatgtg gcctactact gtggccgccg    103440
catcaggctg catgtgctct tccccccggc catctttgcc ggaacggtga ccttcgacag    103500
cccggtgcag cgcctatacc agaacatttt catgtgctac cgcacgctgg agcatgccaa    103560
gatctgccag ctcctgaaca cggcccctct caaggccatc gtgggccacg ggggcgaga    103620 catgtacaag gacatcctgg cccatctgga gcagaactca cagcgcaagg accccaagaa    103680
ggagctgctg aacctgctgg tcaagctctc ggagaacaag accatcagcg gggtcacgga    103740
cgtggtggag gagttcataa cggatgcctc caacaacctg gtggaccgca accgtctatt    103800
tggccagccc ggggagacgg ctgcgcaggg cctaaagaaa aaggtctcca acacggtggt    103860
caagtgtctg actgatcaga taaacgagca atttgaccag attaatggcc tagagaagga    103920
gagggagctc tatctaaaga agatccgctc catggagtct cagctgcagg cctccctggg    103980
tcccggcggc aacaacccag cggcgtcagc ccccgccgca gttgcggcag aagccgcgtc    104040
tgtagatata ctgacgggca gcaccgcctc cgcaatcgaa aagctgttca actcccgtc    104100 cgccagcctg ggtgccaggg tgtctggtca caatgaaagc atcctaaaca gtttcgtttc    104160
tcaatacatc cccccttcgc gggaaatgac taaggatctg actgaactt gggaaagcga    104220 gctgtttaac accttcaagt taacacccgt ggttgataat caggggcagc gtctctacgt    104280
cagatactcg tcagacacga tctctatatt attgggcccc ttcacctatc tggtggcaga    104340
gctttcaccg gtggaactcg tgacagatgt ctacgccacc ctaggcatcg tggagatcat    104400
cgacgagctc taccggagca gtcgcctggc catctacatc gaggacctcg gtcgaaaata    104460
ctgccccgcg agcgcgaccg ggggagatca tggcatccgg caagcaccat cagcccgggg    104520
ggacgcggag cctgaccatg caaaaagtaa gcctgcgcgt gaccccccgc ctggtgctgg    104580
aagttaaccg ccataacgcc atctgcgtgg ccaccaacgt ccctgagttc tacaatgcca    104640 gggggggacct taacatccga gacctccggg cccacgtcaa ggcccggatg atctcgtccc    104700
agttttgcgg ctacgtcctc gtgagtctgc tggactccga ggaccaggtc gaccacctca    104760
acatattccc ccacgtgttc tccgagagga tgatcctgta caaacccaac aatgtgaacc    104820
ttatggagat gtgcgccctg ctctcgatga ttgagaatgc caagagcccc tccataggcc    104880
tctgccggga ggtgctgggt cgcctgaccc tcttgcactc caagtgcaac aatctggact    104940
ctctgttcct gtacaatggg gccaggacgc tgctgtccac cctggtcaag taccacgacc    105000
tggaggaggg ggctgccacc cccgggccgt ggaatgaggg cctgagtctc tttaagctgc    105060
acaaggagct gaagcgcgcc ccatccgaag cccgggacct catgcagagc ctctttctga    105120
cctcggggaa gatgggtgc ctggccaggt cacccaagga ttactgcgcg gatctaaaca    105180
aggaggaaga tgccaactcg ggcttcacat ttaacctgtt ttatcaagat tctttattga    105240
ccaagcattt ccagtgccag accgtcctcc agaccttgag acgcaagtgc ctcgggagtg    105300
acacggtctc aaaaataatt ccctagaata aactgagaac agtcatcagt aaatctgtct    105360
ctcgcgtgat ttccatagga atggtgtagc cggggtggag ggccgatatc acatcaagca    105420
gaaaggccat aatctctcga aagtaggcgg tggggctgag accatgctca gtggccgtct    105480
ggcagggggc cgggcgcgct ccgtccttgt ccaggagaca cacgtggctt ccagagaggc    105540
```

```
gcagcccagc cctccgcagc cgctgaagcc aggctcgcgg aagagcccaa aacctgtttc 105600
ggcgccgccc gggggccagt ctccgggtca ggtcgcggac cagggtcaac aggtggtcgt 105660
gggatggcgg ggccttgtct gcctcgggtc tcgccgctag ttggtccagg gtccaggaga 105720
aggcttcgtg ccaaaccaaa aagggccccg agtgctccct acatccaccc acgtaaagat 105780 cccccctgaaa gatggccatc agtaggcacc cgggcccgcg tcgagccttc acccgaatgt 105840
gtctgcgggc cacggtggcc tctccaccca tcacatcccg gtcgagccgg ctggcatcct 105900
ccgagtcttt cacgccttgc aggaaagcct aggagataca gcaacagaaa gctattagcc 105960
ggtggttccc ccaccatcat tcttcctgtt aacgggaaga ataagagttg gcaaacccc 106020 gggggccgcg ctctcccacc cagccccgct tctcacctgt gctagtggct cctctgaagg 106080
atgggcggag gttggtgcca caaagcccag gatgaactcg tctgcataag cccaggtcag 106140
tcctaggtca gcggccgcgt gtaggagaac ccgggtgacg gcggtgtaga ggcccccgag 106200
tgcccgtcgc gtgtctgagg tgccatagcg gtgaagggcc cgcagccagg tttgcgcgtc 106260
ccgcgcctgc cctccgccat caggcgttcc cacgggggcg cccctggcag agaggtggca 106320
gcgggccaat tcgtagagcc accaagtggc atcagcctca aggatggctg tggcctccgc 106380
gcgcccgacc accgtcgtct cgtcctcccc ccctccctcg ccgccttccc gcgtgcaaac 106440
gtggcgaggg ttaatctcct ttcgggtcgg gggccagatt tgttgtagga gcagcgagcc 106500
gcgtcgttgc cctgaccgcg cgtcgaggcc caggagggcg tctgccaggg gcgtcccaga 106560
gactcccagt tcaggtcca gtagcaggag accctgctg tgtggcgccc ggtgccagaa 106620
ggccggcctc gcccgtccca cataatggat gggcaggaag ggaaagcccg ggacataggg 106680
ctggaaatct gagcccccctg gcagagttc ggggtccagg aggtagaaga tgggcttggt 106740
gcctctgtgg ttggcgtagc aggaggcata gatactgcgg aggaaggcgt agagcccgcc 106800
cccggccata ctccaagagt tgacaagcca ggactcgaat ccccccagccg gctcaagaat 106860 tttcaggctg acgcggtgcc gtcgggcgtc cccaccacgg ccggtggccc cgtcggacga 106920
caccagatct acttcataag tgaccggtcg caggatgtcc ctaaagggga cgggagaggg 106980
gtcgtcggga gtctcggtgg aataggtgaa aacatcccca cgcggtgtcc tgatgtatac 107040
gtccaactgt ccgggagact cagagtgcct ctgagcatgg gggcatgtct gttccccctc 107100
catctcggac ccgaagccat caacaggtgg gggttgttgg tcccgcccat catccccga 107160 gcagctttgg cagaccacct gtgctggaaa gagaggctgg aagatgaggc cctgctcatc 107220
ctccaccctg gcggcggaca agagtctgcg gtctcgggtt ctaaatgaaa ggtcaaatag 107280
gtccttctcg gcggcatcgg cgagcatagc aatgagcccc ccgctgcgcc tgagctcccg 107340
ctcccatcgc aaaaagttga gttcggtagt cgagggcgcg ttgaccacgg ggggctccag 107400
ggagcctcca agcggcggct ggcaggcctg caccacgatc agagtctcaa cgtcctccct 107460
tttgatgggc acgatgccca cgacccaaat cgcccaccac cgccctgcgg tctgggtgac 107520
attataaaag gtaaccgagc tgacgcgggc cctgacgctc tccgcgggtg tttccatcat 107580
tgtttgagat ctgaggagga ctggacccctt aaaacatcc ggtcacgccc tttgcaaatt 107640
atttaaaagg tgaatgctca actgagacca tcgcaatcat gaagtcctcc aagaatgaca 107700
cgttcgtcta tagaacgtgg ttcaaaacgc ttgttgtgta cttttgatg tttgtcatgt 107760 cggcggtggt ccccatcacc gccatgttcc ccaacctggg gtaccctgc tactttaacg 107820 cactggttga ttacggggca cttaacctga ccaattacaa cctggcccac cacctgaccc 107880
```

```
ccacgctcta tctggagccg ccggagatgt ttgtctacat cacactggtc tttatcgcgg  107940
actgcgtggc tttcatctac tacgcctgcg gcgaggtggc gctaatcaag gcccgaaaaa  108000
aggtctcggg tcttacagac ctctcggcct gggtctcggc agtgggctcc ccgaccgtgc  108060 tgttttggc catcctcaag ctctggtcca tacaggtctt catccaggtc ctttcctaca  108120
agcacgtctt tctctcggcc tttgtgtact ttttgcactt tctggcctca gttctacacg  108180
cctgcgcatg tgtgactcgc ttctccccgg tctgggtggt caaggcccag gacaactcta  108240
ttccccagga caccttcttg tggtgggtgg tcttctacct gaagcccata gttacaaacc  108300
tgtacctggg gtgccttgcc ctggagacgc tggtcttctc gctcagcgtg ttcctggccc  108360
tgggcaacag cttttacttt atggtggggg acatggtgct gggagccgtg aacctcttcc  108420
tcgtcctgcc catattctgg tacattctga cggaggtgtg gctggcctcc ttcctgcggc  108480
acaactttgg cttctactgc ggcatgttca tcgcctccat catcctgatc ctgcccttgg  108540
tcaggtacga ggccgtcttt gtctccgcca agctgcacac cactgtggcc atcaatgtgg  108600
ccatcatacc tatcctgtgc tcagtggcca tgctcatcag gatatgccgg attttcaaaa  108660
gcatgcgcca gggcactgac tatgtccctg tctcggagac ggtggaactg gagctagagt  108720
cagagccgag gcctaggccc tcgcgcacgc catcacccgg gcgcaaccgc cgccgctctt  108780
ctacgtcctc atcttcctcc aggtcaacca ggagacagag gcccgtctct acccaagccc  108840
tcatctcctc cgttttaccg atgacgacg acagcgagga ggagatcttc ccctaatgca  108900
ataaaaactt aaaacactga ggttactttc ccgtcattct ttcgggggaa cgagggagg  108960 cgggaattgg gttaagatag gggcgaaggg tggggtggg tgcaagaatt ggggctggga  109020
atggagaggg gagtgggcta ggtgccgaca ccggggtgcc aagataatgg attgagtaag  109080 catgggctc tgatcgggtc cgccgggttc tcaggggtgt agtgggtggg cattgcatat  109140
ttttgccgcg gtgctgttgg gccttggact cggggtgatc atccgtacca tcacccgcac  109200 ccgcaccca gtccacagcc accggccaag gtcctgggcc tcccaccacc gttatgcctc  109260 ccccttacc cattaattac aagagatgtt agtttggttt tttatttggc aaaaacagca  109320
attcatcatt tcagagtcc tcatcatatt cgagcccctc gttggtttcc ccgcaggccc  109380
tcccttcttc ggccgctatt agcttagtag tctccaggtt aaactcctca tagtcattat  109440
acaggttgat tattccccg tccacgtcgc ctatggagtt gactcgtcgt cggcaaagag  109500
accagagggc acccatggcg cggtgtcaaa agtattgtct gcgtacgctt tccaggagcc  109560
agccgcggtg ctcaaggtct tacggatgac agagtccggc aggaccacgg gtgtcaccag  109620
caccgccacg ggaatctcca ccgaggcgtc cagaagcagg tctgagccga gcgtgcaggt  109680
cgccgggtct agaggcgacc gttttcgaaa gaaggccgtc acaatgttca cccgggggtga  109740 gcagtctctc ccgggcttgc cacccccact gtggcggacg tagtctccaa caattttgta  109800
ttggaggagc acctggtaga agtagttgtg ccgtggattg atgaagatgt tgactgggac  109860 ccggtctta ataccaatgc gccccgcatt ttcgcttggg tccgtcatta cgtagagcat  109920
agactccacc ccctgttgg cagctaggct gtctgccacc aggtcatgac cggggcccag  109980
tttgcgctta cggacatctt taagattcca ggcctcatcc tgcgtcaaca gatagtcacc  110040
ctccgagggc aaccgcccat ccgggacgta ctccacggta ggacgagcta tagaattgat  110100
aaatctgata aatgacctct tgcatggcct cttgtaaagc gcagtgtagg atgggtagat  110160
ggggtcaaat tctgacttgg aaaagaggta cttgaagcgg cacttaatct cataaatgca  110220
gctccggtcg gtgaacagta taaagtctcc ctgtgactcc acattgacgc aaagatccag  110280
```

```
agacacccca aaaatgccat ccgtgggact aatcataaag ccaaattgac ggttggcgga   110340
tgcgtccccg cagatgagct tacagacaat gtccttgacc gtgtcctcac accgcaggcc   110400
aaaggccaca ggtcccccaa agtagtgatt tgtggagatg ggagctggct caaacacctt   110460
ggtgggtcca ttcttaatgg tggagagcag cttggaagag gaaattatgc catttcgcaa   110520
tatgtcccac atcaggttct cagactgccc cctggtcatg gactccacgt acgagcagag   110580
aacagtcctc tgctcgtcgg tggcctcctg tagcccccag taaatggatt tcagggaggg   110640
accgtcctgg ctgtcattct cttggactaa cgaggagaca aagtcacaga agccagtttc   110700
accagagaac tcttgtattt gttcacagag gcaatagaga tagacatagc gcatggccgg   110760
catctgaggt ggacggtcaa ggttacggac aaaggcctca gtctccggac tgcggaggaa   110820
gcgggcaaac gtgtaggagg tcatctcctc catgggatcc tcgagctcat ccacgtcggc   110880
catctggacc aaagaagtcg tctgccaaga gttcagctac cagacctgga agatgagggt   110940
gctcaaaccg tgggcgacag ttgaagaagt agctctcctt gaacctcttt ttaaggctcc   111000
ggcaccactg caagaattga ctcatatgct ccgccgtgac atccacgcac ggactctcgc   111060
cacacgaggt caggcccatg tctaagttca ggttccacat ctgcgacagc acctccaaca   111120
gcaccacctt tggggctgca aattgcaaaa agtagagcgg gtcggatcgg tcaaatccca   111180
tgtcagggtt ggggtagggg attttgtggg tggagtcagc gaggtgcatg ataccataga   111240
gcagcgagta gccgagcgac tgcagatcca ggcgaagggc cgtctgcgcc cccacggggc   111300
cacacgccga ggggtcaggg atgtgcccag ccccccctcaa gatgtagcac ttgctcaaaa   111360
ggcagagggg cttataggtg tccttggcta tagaaaatgg ttccctctgg caatagaggc   111420
gatagagctg ccggcccctta gaagactta gccgcacatc cagcatcttg ttgcggtcgt   111480
ggagggaagc agtcccataa tcagtcagga ccagcctacc catgccccac atggtgtctg   111540
tgaaatccac caggatgttg ctggggctaa tgtccgaatg gaagaggccg cagtgccgat   111600
tcagaaagta aacggcatct ttgaggccct gaaagccccg caccaggggc tcaatactac   111660
catcatgcca gtggccataa tcctggagac tgcatctgaa ctggggcata aacagggcgt   111720
ggcaggacgt gcaggccgac aggtagtcca ccagggcctt gtcctgccca tcctcggccg   111780
tggccttccc aatctgaatc atgtcacaca ccatgagctc gtgatacagc tccgtcacag   111840
agtcatagag tttgaccgtg gcattatctg catgtgcata cacggccccg tagctccccc   111900
gccccagcag atactcgcag gtaatgggga ggtgatcaca gcgcgtcatg ttctccggca   111960
gctttacata gagggtctcc gtcatgtcat caatgttggt caccttcagg tgtttgtgct   112020
gaaaggtgaa gtaatcaatg acagtcacct tccccaaaaa ggcctgggtc tctcgagggg   112080
gttctgggga gacactcaac tcgccactgc tggaggagtt cgtcgggctc aactccgcag   112140
ccatattcac atccatgttc ctcaaatggc tcgagggcct gtcgcagctc gtctctggcc   112200
tcaagctcct gctcacggag ctcctccacc cgctctagct gcttgtagtt gatttttgga   112260
aattgagtct tggtcgcggt gaccaccctc tgataggtag aaattagctg tttggactca   112320
aacgtctccc ttgcgcggcg cagggactct aaggcacccc gagcagatgt aaactgtgtt   112380
tcaaacagag cgtggtccct cccaaatctg tcacgtgcgc tcacagccgc tctcttttct   112440
accgaggctc ttagttgctg ggccaccaga tctcgcttag aactactcat cttcataagt   112500
caccatgtcc gcaactatgg agcccagatc atacgtgggg tagagtacgg tagttccagt   112560
ggaggcttcc cggtaatttc ccacagcgtc caccatatat ctttctgcct ctcccgttag   112620
```

```
aattaggcaa ggatcatacg tgtccaccgg ccttttatac tgagcgttta ggttttgttt   112680
atgtagcaag cacaaaaggc acacacgagt gatgcaaaag ggttcctgag gcagcaggca   112740
gagctgtttt gccattttat tcaggcggct aacgtcaaag ggaggagcta tatcctcacc   112800
cttccagtca cgcacgtcca agtacagggc atacacacac ctggtgaggt gtgccaggaa   112860
tgcctctatg ttggcacatg gtgtataaac cgcagtgggt agcagaatag ggcccctctt   112920
gccccgtgct gcagcgtaaa cacagtgacg ctcttcgcag tgggacctgg ggccgtagaa   112980
gagggcccac atccaaggga gtgggtcttc aggcaccagg gaggtccagg tatgggagtg   113040
ggccaatatt tgcaaggcct gacctataac ctcatctttg ttccaggcca gcgcaattcg   113100
cataaggtcc ccatcaaaca cctcaaaaca cagacccatg cccatttcag gctgagaggg   113160
ctccatccgg ctcgaccacc cttgtccacc aaactgccat tcttctggta acgggattt   113220 gaggggcaag agctccaaag ccaggctcga gaagtcatag tcatcctcgg ccacacggcc   113280
ggagctccgg gcctcgtgcc agggcctgtt gtcctggggg aggatattgg acacgagcag   113340
gaagctcttg agtggcgtct ccaccagctt aaattgctcg ggcgtgtcct ggcaggcctc   113400
cagtgccagt tccagacact gcccatacct gcgggcgagc atcgggtcat cgggcatatc   113460
ggccttgacc gcgttgaaca tgctgtatgc ctcgcagcgc ggccgtctga ccgagaacct   113520
aagaaacgcc ctgcagcagg atagcaccac gcaaggctgc ctgggtgccg agacccgag    113580 tattatgtac acggggcca agtcagacag gtgggctcac cctctggtgg gcacaattca   113640
cgccagtaat ttatattgcc caatgcttcg agcatactgc cgccactatg gccccaggcc   113700
cgtgtttgta gcttctgatg aatcattacc catgttcggt gcgagccccg cccttcacac   113760
cccagtccag gtccagatgt gcctactacc agagctacgc gacacgttac agcgcctgct   113820
gcccccaccc aatcttgaag actccgaggc cttgacggaa ttcaagacca gcgtgtcctc   113880
tgcccgtgcc atccttgagg accccaactt tttggagatg agagagtttg tcaccagcct   113940
ggccagcttc ctgagtggtc agtacaagca caagcccgcc cgcctagaag cattccagaa   114000
acaagtagtg ttacattctt tttattttct gatctcaatc aaatctttag agattacaga   114060
caccatgttt gacatctttc aaagtgcttt cgggttggaa gaaatgacgc tggagaagct   114120
gcacattttt aagcaaaaag ccagcgtgtt tcttatcccc aggcgccacg gcaagacctg   114180
gatagtcgtg gccatcatca gcctcatcct ctcgaatctc tccaacgtgc aaataggcta   114240
cgtggctcac cagaaacatg tcgcgtccgc cgttttcact gaaattattg acaccttgac   114300
caagagcttc gactccaagc gtgtagaggt caacaaggag accagcacca tcacgtttag   114360
gcacagtggg aaaatctcca gcaccgtaat gtgtgccacc tgcttcaata agaatgtaag   114420
acctgacgtt tcagtacttg gcaattgtag agcatagccc ggctgtaaag gtcagaaaat   114480
cgcagcaggg tccaaggttg tgctgtacat gggacctctt tcccattagc aagaacccc    114540 tgcaggacgc gtgacatgtc cgggtgcatt ttgggtgggt taaatctcag tcccaccaca   114600
aagggggcat cctccggttt gaacatcaga cccaacaaag cccgatgccc agttatgggt   114660
acgtagtcgt tgttcagggc cgtgcatggt agcagacaag gacaggtgcc agatgtgcct   114720
gggctatcgt cctccgtcca gccacgcagg atgttcacgt gggccccggc accatagcat   114780
gtcacacatt ccccgttatc acatctggtt agcaggttga taaaatgggt cagtgatgga   114840
aaggttggca tattggggca gcacatcagc atgtccatgt taacgaaaaa catgtacagg   114900
gccccttctg cataccaggc accacccgt cccagtggga tgatctccga gggtgtgata    114960
tcttgcagtt cttctactgt tttaacggcg gttgaggtgg taaagacgtg gccgtggtc    115020
```

```
agatctgtgc aggtgactac agggtttccc ctaatctcca caggcaccgc ctcacccacg  115080
gcatctgaga ataccccaaa gtacatgaga gtcaggctgt gtggcccctg gactgcctta  115140
gtgaagagaa cctcgggcct ggccacggtg gctagggttc cattgatgta gacggtcaca  115200
taggtgggct tcttcttggg cttcagcaca atgagggtaa cattcatgta ggttttagga  115260
ggtccggcta tctgaggcac gtacacagct gacacggcgg ttgtggccgt atagactttc  115320
atctggggcg tagaggcatc gctcagcacc cagaggcact ccttgttgag gaacttgcga  115380
agctgttccc ggctactgtt cgcggcggat gccatgacgt gccagaatat atcccctctc  115440 ctcggggtg agtgccaatt ggcctttaat aacaaagccc ccaggcagca ccaaaaatgc  115500
ctgcccgtcc gatgtggtgg ccaggtggac gcagtgcccg tcagttccaa gggctactag  115560
ctgggaagca gccccaacca gcccaccggg gggcctggag tcgatcacct taccccaggc  115620
cgaggcccct tcctcataca gcgggtggct atctatccat aggcaggcat ccggcgtctt  115680
tggtgcattg gagatagctt tcacccaaca actttcccaa ctaacccgtg tctggacagt  115740
gaagaacgct tccctgatca ggtctgaatt tttatagata cgggagtagg aggtgggaat  115800
aacaactggg atttcttgtt gtgctgtcca ggcctgcatg gccagttttt ccctgaagct  115860
agcagaaatt ctgagggcca ctgaaatgag gaagcgaaac tccctctctg gagctcccaa  115920
aattgaaacc tcagcaagat ctgttgctgg ggaggcatgg gtgacagctg tcatcctgtg  115980
cagtctgccc tgggcactca gctctggata tgtgacaaca tagagagcgt gggggctaaa  116040
aatatgagca attcccctga ccagggccct ggactcacga atgcccgac gggtcttaga  116100 gaaagaaaca ggcaccctcg agagtgcccc cgacccgacc cccacagtgc cgccagtccc  116160
tgctcggcct ccgccgcctt ccccaccggc gctgccccgg atgttgctgg ggttctcgag  116220
ggctgggtgg tgcttggaca cagaggtctc agcagccgcc ttggtctcgg ccccggccct  116280
aagtctgagc cccaggcaaa gggccggact cccagcgtgg cccaacctct gctcccctct  116340
attctcctct tgcgttatct ccaatagaat ttgcttgagg tcatacgttt tagggtgctc  116400
gacctgggcc gcggccatcg gcatatgctc tatacccgcc cctccggggg gcccaggatc  116460
tataggtatg ggctgcatag ccgcagcaga ctcctggacc ccagaggcct ctctgatcag  116520
atgcccgtcg gtcagagccc ttttggcccc ctcaaagaga gacaggtaat aaatctgtag  116580
ctccccaacc agccctcctt catcgtaaaa tcgaagggcg gccacgtgga agggttgta  116640 gagctctgga aggccctcct cgcagtacac tggcacactg gtaaacgtgc cccgatggct  116700
aggccgtccg ggcagcatgc cccgagcagc aaacacgcgg cagaccctcg tgagaccgt  116760 ccggtcactg aagagagtct ggcaccaggc cccctcgcag tttggcacgc gattggggca  116820
aagctctgcc ataaccgtgt cgggaacaaa taggtgcacg aggagggggg tcccgaggcc  116880
actcaacact tggttgtcaa tgtggacatc catagctctc tcatgcgttt ggctacagca  116940
tcatagcgct tgtttctggt ggatttaaat aacagggccc cgtagacagt cttttgtgag  117000
taaatagaga tgatgacatg gatgtagaga ctgaggacca catccaccac cttctcggag  117060
gaggcccccc taaacagcat caggcagcaa gggaacacaa aggaaaccag gccgggatg  117120 tgaggcctca gcgcccctc ctgatcaaag agggcctcgc tgaccccgga gatgacattc  117180
tcattcagaa agtagtgata gaggtgattg accacagtct taaccaggcc ctggacttgt  117240
tcaggctccc acttgtcccg ctggtcctgt gtgtcttgtc ggatctcggt ccagggcctc  117300
agcgccggct ggaaatgcgg ccccatgtag ttgcctgtaa gggcgcacac cactccctca  117360
```

```
tgggtctcaa tcagggtgca ctcgctggat ccatcacata cgtggtactc gccacagccc  117420
cagcaggcaa acacggaggc catgctctca ggtaacggga gatggaactc cagcttacta  117480
tacgagcaca ggtggcgagg attgggctca tccgtgcccc cctcccccg cgggaggctc   117540 aatcggcctt ggtctgacat tccaccccgg ccaggtccag gagggtgcaa atattctcca  117600
ggcgctgcac ctcagagacc tcctgctcaa agaggcctcc caccgccacg tagacgcggg  117660
ccaccgtccg gggaaggtca gtggggtccc agctcagcaa ttgtccaaat tctgtctccc  117720
caatagtgac tcgcttctta tcctgtcttt cagagcatcc gggggcagac atttcacctc  117780
ttgtttgtgg acgaggctaa ctttatcaag aaggaggccc tgccggcgat cctgggcttt  117840
atgcttcaga aggatgccaa gattatcttc atctcgtctg tgaactcggc tgaccaggcc  117900
accagctttc tttataagct gaaggatgct caggagcggc tgctgaacgt ggtaagttat  117960
gtgtgtcagg agcatcggca agattttgac atgcaggaca gcatggtctc atgcccctgc  118020
tttcgcctgc acatcccgtc ctacatcacc atggacagta acatccgagc aaccaccaac  118080
ctctttctgg acggggcctt tagcaccgag ctgatgggtg acacctcctc gctgagccag  118140
ggtagcctga ccgcactgt gcgtgacgat gccatcaacc agctggagct ctgccgggtt  118200
gacaccctca accccgagt agccggacgc ctagcctcct ccctctacgt gtacgttgat  118260
ccggcctata ccaacaacac atccgcatca ggcaccggaa tcgccgccgt gactcacgac  118320
agggcggacc ctaacagggt catcgtcctg ggcctggaac acttcttcct caaggaccta  118380
acaggggacg ctgccctcca gatcgccacc tgcgtcgtgg ccctcgtctc ctcgatcgtc  118440
accctgcacc cccacttgga ggaggtgaag gtagccgtgg agggcaacag cagtcaggac  118500
tctgcggtgg ccattgcctc aatcattggg gaatcctgcc ccctcccctg cgccttcgtg  118560
cacaccaagg acaagacgtc cagcctgcag tggcccatgt acctcctgac taatgagaag  118620
tcaaaggcct ttgagaggct catctacgca gtgaacacgg ccagcctttc tgccagtcag  118680
gtcaccgtct ccaacaccat ccagctctcc ttcgatccgg tcctctatct catctcccag  118740
atcagggcca tcaagcccat ccctctccgc gacggtacct acacctacac cggcaagcag  118800
cgcaacctct ctgacgacgt gctggttgcg ctagtcatgg ctcatttcct cgcaacaaca  118860
cagaagcaca cgttcaagaa agttcattaa actttattga ctacaccagt cccttgtaaa  118920
gcgacgggtc tcgcgtgacg gcattcgtga gcagggcttc gtccagggc ttgttcttgg   118980 cggacatcat tagcccagcc gcaaatatca gaattagcat cagaaaagtg agccccacaa  119040
acaccagtgt ccagagagga agaccgtaag ataaagatgg ctgcctctca tctgaacgg   119100 tgggaagctc agcagttgtt tttgtggcat tggacgtccc tttggaggac agcgtggggg  119160
ccaaggtggt agcgttggta atacgggtag tagcactggt ggtggtggag gacctggtgg  119220
tgacattgct agtcacaccc gtggaggttc ctgttccggc ctcggtggca gtgatgttct  119280
gtgcagtaac cttagtggtg acattgatgg tggatgcgtt ggaagttgtt gggactggtg  119340
tgacagttgt cccagtggat gtcaccgtgg ttgtgttggt gctcaggata gcagttgtgg  119400
ttataggggc gctggtcgtg gtcaaggtcg tagactggtt tgtgctagga cccgatgccg  119460
acggtgatgg tgtagtcaca gccgttgtgc ctgtcacgtt ccccgccgag gccgtcgaac  119520
tgccactaga tgtccagata aggcttgtct cacagatgag tatcatggcc aggacagcgc  119580
ctgccttgtc tctggcgtgt gccatcgcgt ctggacgcag aaggcctccc ggcctctttt  119640
atagctagtc tccacaccca atactctact gaaccatcac atacatgacc tcctcgaggt  119700
atgcagggaa tgagcggtcc gtgagccggt caacacgaca ttgcttccgt ttcatgcctc  119760
```

```
cagctgcccc tgaccagtta ggacccttga cggatgtctt taacggcgcg gtgcagttgg   119820
tcaccaatga cggcctaaag gccaacacat ccttgaagca gggcgtagga atggtaccaa   119880
actcggggcc caccccatca aagacataat atgtctcata gtggcagtga tgatgcatca   119940
ccaccacagc actcgccagg accctctgca tatcttgtac aaggcgcctt tcaactcggc   120000
cactggctct ggtgacgtta aatgtcctgt tcctattagt cacagcctgt agatttgggc   120060
acccagactc aaaaagtgca gctacatgaa gggcagccgc ctcaaatcca ccatgacccc   120120
catggctgtc cgtgttgttg gggtaataag tcacattgtt aatgaccacg gccgggataa   120180
gggtgtaaac cttgcagaat ggattggtcg gacacccata agacagggc accccaaaat   120240 cacgcccctt accccgaagc accttggccc ccaccggcat aaagctgggc aaaaagagtg   120300
ggttaaaacc aaaggcgagt agggccagga acgccaaata gcagcagtaa tagatgaaaa   120360
caaagctcag catgaaacag cgtggaggct cagctagggt ctctgcctct ccatcataga   120420
catcttcctt gaatctcatt ctctcaccgc atacctcgct cttcatccag gaggggggcca  120480 tggctgccat tctaccagtt aacgaggaga gagagagtag gtccgcggaa attggtgccc   120540
ctctctgccc tcctgacgag gccatggtgt catccatctc cgcagtccgt tcttcagctt   120600
tggcattggt ccgggtccgg gtggtctgat tttgattctg atcctgggta ttggtcttgg   120660
tctctcctcc cccattggca tggattggca taggtgggtg tggctcaggc tcaggttccg   120720
gccctgggac ggcagcagcc gccgggacgg tgaagtcgtg gaaggtagag gcccgtccct   120780
cccgaggtcg tggggccgga gccttataaa agacttccac cctctccccg ctggccaaga   120840
cacgccgctc gtggaccacg ccatcttcct cccggctgat tgtgtggctg acggtgccgt   120900
gttccaccgc cacttgttca tcgaccatgg taccccttt atcttaacca gcaagtggcc   120960
gtcagggtct cttgagagta tgccgctgtg gccaagcgag gccccaaatt aaatagtgat   121020
gccaaagact gtaggtaggt catcatcaca cgcatgcgtg ataaatcatc cgccactgac   121080
aggtcatcca ggtctatccg ggctatctca tccggcacca tttcctggaa gagattcaag   121140
aggtcgtaat gctcatgccg gataaggcct cggaccaggc gcatactggc cctgggcagc   121200
agggtcacca tgatgcaaaa gtagagactc agattgtcca gcagggccaa gccaagggc   121260 cctggcacct ccgggagggc caactcgtag tggtgcccca ggtatgaaac agagccaaga   121320
tgcatgtgta catcgagcat gtctgcgttc ccgggagcct gcatgacaac ccgggagtac   121380
acgttaaaca ggagaatctt ctgcagcacc tcctctgcta tgggcgtagg cagcaccatg   121440
gggaaaacaa tgtccacatc attggactct aacttcacgg tggcatgctc tcgtccaaat   121500
accgggggca taacactgag gctcccggtc ccatgccact ggaaaaaggg ctggtacttg   121560
ttcttaatgg cgtaggtctg acctggaaca atccttggtga gtatcaaact gtccacgcta   121620
acctcatcca gcacggccag ggtgcaatca gacaggtagt tgtacatgga cacgtagtcc   121680
gggaccgtct ctagagagta cacctgaccc aagcccaatc cctgcacatt ctgcgtcccg   121740
tgagtggaag ccaggggtaa gatgcagcca atcctctgtt gcatcttggc aatctcatcg   121800
gtatacagac gagaggagag agacactacc actttcaaat ccatctttat tgacaattat   121860
caaaaaacca ccttatttcc aaactttaat attcttcgta ccggcgccac ctcttcaatt   121920
atatagtgtc cgtaatggat gggggcgtgg gtctgtttga cagacataaa ctcatcgatg   121980
agtgcccggg aggaggctga gagtgcgggg aatgcctcct gcagaaagct gcagggctgc   122040
tccagaaaca cgtcagtgcc agcaatcact acaaactgca cctctgtgtt gctggtggct   122100
```

```
gggtgccctc caagtcgctg gctgtactcg ttgaccatgt tgtagagtcc cctgttgttg   122160
cgcagaagct cctccttgtt gaaaaatgcc cggcaggggc tgtagaggcc cgggacggcc   122220
gtctggcgat aggaggagtt gtacatgatg tcacccagag aacccagctg agatgcccag   122280
ggattcacag tgctccggta ttcataggcg gcatccgggc gagaatggtc atagatgagc   122340
ccctcggcaa cctcctgatt gtagttttca caggagacca cacaggcggc ccgtcccctt   122400
ggagagttgg acttttgaaa ataagccacg tctgccgtga ccggtgttac gataatctca   122460
caggtggcct gctggccgtg gcagagtcct ggagctccat taacattagt catacctgcc   122520
aggtatgtcc tggggtcccg aagcagcgtc ccattgcgct gagcgcccac cttggccttg   122580
atgtagtcat tgacttgctg gttgccaaag gcctcggccg gaaagacgct aaagaagtct   122640
tgggtgtgga tacccatgtc agtagtgatg gccgccaccc tggccggcgt catggtcgag   122700
ctataactaa gcccggtgtc gatggaggcc atctcgtgat gcacctcaaa ggttaccgcg   122760
tccaccctgg cctccggcg gctaacattt ggggtcccaa tgaacatgga tgttgaggcc   122820
ctggagctaa acaatatgtt ttcagagagg atctcatcgg tcctgaccac ggtcatggcc   122880
acccctgggt ggatcttgag cttggcctgg gcaatatagg ccatggggga catcttgatg   122940
tgcatggcgg tcattccact gattgaaacg agggaaggaa gacattcggc cgcgtatttg   123000
cccatgggcg agcggtgcca ctcccggtac tctgcaaaga gctgctctgg ccggttgaag   123060
gcttccacgg cccgctgctg aggattgcgc ataacaaagg tggcaacatc ctggtgcatg   123120
gtggcagcca ctcgcgggtc cccgtaaaac atatggaaag gaatggcgtg aaagagacac   123180
tgggtgacgg cccgggtcct ctcggagaag gcaaaggcca ccagcccgtt caccaaaaca   123240
gtctgctctg tccgcttgtc ggcgggattc ggggccagct gctgcgtaac gtcattgtcc   123300
accgacacgc gcacggtgcg ggtgaaagtg gggcaggtca tgaatgaggc gctgaggtcc   123360
ctgatcatgc ccacggtggg gcggaggtcg gagatctcca gcagatccct gagcgtccca   123420
ttctccaaat tgtcgagtat gtcctcgtcc ctggtaaaat gatggctgaa ggctggcccg   123480
ttgtaggcca gggtctgggc cacgtgctga aagtccaccc cgaggccgca catgtgggca   123540
ttggtgcagg tcgggaggaa aacgtagtaa aagatctttt ccagcacatc cgcatgcccc   123600
tcatctacat aagggcctag gtgcagacgg aaatcgtggt cgtggtctcc gttaacccgg   123660
tagccgtaca aggccacaaa ttgggcagcc atctcatcca tgtttccaac cctctcaata   123720
aactggggcg cggccagggt gtcagcgtaa acctcatttc cgataataat ctgggggcc    123780 cggtcactaa cggtgagaag atgggtgaaa atgtctgtgt aggccaccgg ggggagcagg   123840
ttagggtcca ggagtgcgca gacatactga cccacgctct catcccccac aacatctgac   123900
ccggccaggc gcatcagggc ctgctctagg gctataagtt ccccatagat ttttctatac   123960
atggaatagg cctccttgga gatggcgtta tttcccaggt ggcggcagat gaacttgatc   124020
atggaaaagc tgttcacaaa ggcaagcctc cctgcccgtt cccagtaggt gttgatgcac   124080
agggacacca aaggcacgtt catgacaaac ttttcctcaa acccgtggat catagcctcg   124140
actacgtaga agaaggctgg ataggcagtg tcataggcag tatcctgcac agtctcaata   124200
acggcctgat ccaccacgtg ggccagagat gtggcggtct caaactgctg cccccgggcc   124260
tcttggaatg cagctggggc caggggagtc ggcaggttac ccaccattag ccggtgcacg   124320
gccctgtgcc tggccctctc cccggcatcc ctgccaatgt aaatatcata aggggggtgc   124380
agctccagcc gcagcaggtc ataattggac gggtggagga agtcttcggt gggcagcccg   124440
cacttgagag ctatatctgt cacgggggct gcatacttgt tatcatagaa ctcgtccaca   124500
```

```
ataacaagca cattcatgtg attgggcctc ctgtgttgca gggagtaggt ctcgcgcctg 124560
tctcgcgggg ccggggccgc gttgaggctg tttagggtat gggcgggtgt gtggagtcgg 124620
gggtgacaga gaaccttgag agcattctgt aggttaaacg cgaggagaag gttattcttg 124680
tttacgatcc atgcctccac cggtagctgc tgtgtgggt tgtccagcat tttgatggcg 124740
gcggaggtcg tgtacttggg attgggcata aacaggccca ctgggaaata gtagctgtac 124800
tgcattcttc tgttgagggg gtatgggac tgagtgtcat tgtacatctt ttgcaggctt 124860
tccacggcca ccgcgtggtt gcccagcttg atgacggcgg ctgagatcgg cacccggggc 124920
tgatcctcga cccctgcggc cacagccggc aggtcagact tggtgcttcc ggcttttcc 124980 ggtgagtcca cgatcctagc catgaaatgc tcaaacgtac gcatcacgcg cccgtagctc 125040
acggcagtga ccaggttctc cccccgtacc acaaaagaag catagctcga gggcccatg 125100 atctggttgt cggcctcctc acccaggaag gtcaagagct ggcgcagaac gttgtcggtg 125160
acaataaaca ccccccccac tggctctccc cccttggcgg tcgtgtaggt actgacccc 125220 ttgagcacgc tctccccgga cacggccgct accatctcag agagacggct tcgcacgtac 125280
tgagaaaacc cggagcccat gttctcggcc cggtccagga agaaggagtg ctccagcaga 125340
tgcctcttga acatggcaat gaggtcagac ttgacagtct tggagaaccc cctctcagtg 125400
aaggtaggat ccgccagggt ctgcaggata aacatgggag gggcgtggcg aagcttcaca 125460
ctcaggacgg tgttaatgag gccctctcc agggcatcga cccaaactg tagggccgag 125520 gccacggtct tgacagcccc cacgtactct gcgtactcga ccggggtctc ggggatacta 125580
tgcaggatct ccagatccag catggacagt tccatttccg tactaatgtg gtgtttgtgg 125640 caattttga ccacaatgaa tgtccgctgc ttgctgggtc tccttccgtc cccgtgagca 125700
atggtgggga cggagattcg aaattgaatc ttgccatccg tcatacgact caggtctttg 125760
aattccgtgt tcacacagga cacggccagt gccgtctcca ggaagcgaac atattggatg 125820
gcgttcgtgt agaccccgag tagcacctca aacttgatgc ccgcctctct ggcatccttg 125880
cccaccagca ggtcaaagct atgaaacagc ccctcggccg ctgactgccg caggttcgag 125940
agcaggtcgg catccaccgt cagataggg aagggtctgt tttccacacc ctcatttgag 126000
gccatgacac aagtaagag ggagatgggg ggaggtctcg agggcttctc ttcacagctg 126060
ggtctctttt acgccctggc ctgcaaccgc agcccaccg cacttcccga ggatgctacc 126120
cttctaatca aatggttgga cacggccctg gcagggagg ccaccttta cgcgtgtcgg 126180 gctatgcgtc gtcttctact cggcgttatc cgaataaatg actgccagga gctgccacct 126240
ggtttaataa ttctgagtcc gggcaccgtc cctggccccc ttggagtcca gagtctggag 126300
catacagact gcgaaatatg gtcctctgcc caccctgacc acgctgccca cctcccggtg 126360
cccagggtca tcacatacac cgactgcccg ggttccataa gcacgagctc aatgtttcgc 126420
cttatcatcc gctacttgtc tcatcaccaa tttgagcgct gcttcgagca gttctgccgc 126480
gtggtcccgc gtcgcttcct agggacctgt aagcaaaact ctgcaaagat gctggctcat 126540
ctgaagcagg ttaccaggat ccccccctgt ccgcccttca gcgggcggga ggccagactc 126600
aagttccact tcttctcctg gagcacattc atgctgtcat ggccaaacaa tgccacactc 126660
cgggagatca ggacgagggc cgccaccaac ctcacccacc acccacatct agtggacact 126720
ctgtaccacg cctctccgca gaccccattt ctgacacgca gcggtgctct ataccgcttc 126780
gtcacctgtt gcaactgcac cctgcccaat atctccatcc agcagtgcaa ggccggggac 126840
```

```
agaccgggggg acctggagat cattctacag agtaacggcg agggaggcc tgcgagcttc   126900
cagttcccct cctccccaac cggcgcccta ttgcgatgca tagttgctgc ggccctgctg   126960
ccagaggtgt ccgtggggca ccaggagctg tctccgctca tgtccagaag ccatggaggg   127020
cagacggatg tcaggtcggg cccggacccg gccggaggc tggtggccct cctgcgaagg   127080
gaagatgggg cacctaagga ccccctctg ggaccgtttg gacaccccg ggggcccggc   127140
ccggccaaga gcgaagacga ggagtctgag cgtcgagacg cccctccacc cccgctcgat   127200
ttcagcttcc aagcttcccg gttggtgccc gtggggcctg ggtttcgcct gcttgtgttc   127260
aacaccaatc gggtgatcaa cactaaattg gtgtgctcag agccctggt gaagatgcga   127320
gtttgcaatg tcccccgcct catcaacaac tttgtagccc gcaagtacgt ggtgaaagag   127380
acggcgttca ccgtcagtct attctttacg gacgggtgg gggccaacct agccatcaat   127440
gtcaatatca gtggcaccta tctgagcttc ctattggcca tgacgtcact gcggtgcttc   127500
ctgcctgtag aggctattta tcccgcggcc gtgtcaaact ggaactcgac tctagatctc   127560
catgggctgg aaaatcagag cctagtcaga gagaaccgaa gcggggtctt ttggactacc   127620
aactttccct cggtggtgtc ctgccaggac ggtctcaacg tgtcctggtt aaggccgca   127680
actgccacca tatctcgagt gcacgggcgg acattggagc agcacctgat ccgtgaaatc   127740
accccccatcg tgacgcatcg agaggcaaaa atctcccgga ttaaaaaccg gctctttacc   127800
ctgctagagc tacgcaatcg gagtcagatt caagtgctgc acaagcgttt cctggaaggc   127860
ctgctagact gcgcctccct cctgcgcctg gatcccagct gtatcaaccg aatcgcctcc   127920
gagggcctgt ttgatttctc caagagaagc atcgcccact ccaaaaaccg acacgagtgc   127980
gcgcttctgg gtcacagaca ttcggcgaac gtgacaaagc ttgtggtaaa cgagcgcaag   128040
acccgcctgg acatactggg ccgtaacgct aactttttaa cgaggtgtaa gcatcaggtt   128100
aatctaagac agtcacctat tttcctgacc ctcctgaggc acatccgccg acgtctgggc   128160
ctgggccgtg cttccgtaaa acgagagatt accttctcc tggcccacct gcgcaaaaag   128220
acagccccca tccactgccg tgatgctcaa gtgtaagcag cccggggccc gcttcattca   128280
cggggccgtg cacctgccat cgggacagat tgtcttccac accatccaca gccccactct   128340
tgcctcggcg ctgggactgc ctggggaaaa tgtacccatc ccggccctct tccgtgcctc   128400
gggcctcaac gtccgtgaga gcctgccat gaccaacatg agagcaccga tcatctcgct   128460
ggctcgcctc atcctggccc ccaaccccta tatcctagag ggacagctga cggtgggcat   128520
gacacaggac aacggcattc ccgtgctttt tgccaggcct gtcattgagg taaaaagcgg   128580
gcctgagtcc aacattaaag cctcctcgca acttatgata gcagaagact cctgcctgaa   128640
tcagatcgcc ccctttttccg catcagagca ccccgccttc tccatggttg agtccgtaaa   128700
acgagtccgg gtcgatgagg gagcaaacac ccggcgcacc atccgggata ttctggagat   128760
ccccgtgact gtgctctcat ccctgcaact gtctcccacc aagtccatcc tgaaaaaggc   128820
accggagccc ccacctccgg agcccaagc caccttcgat gccgcccct atgcccgcat   128880
cttttacgac atcgggcgac aggtgcccaa gctgggcaat gccccgccg cgcaggtcag   128940
caacgtgctc atcgccaacc gctcccacaa ctctctaagg ctggtgccca atccggactt   129000
gctgcctctc cagcatttgt acctcaagca cgtagtgcta aagagtctga atctggagaa   129060
tatagtgcag gactttgagg ccatcttcac ctccccgtct gataccatca gtgaggctga   129120
aaccaaggcc tttgagaagc tggtggagca agccaaaaac accgtagaga acatagtctt   129180
ttgcctcaac agcatctgtt ccacctctac actcccagat gtcgtccccg atgtcaataa   129240
```

```
cccaaacatt agcctggctc tagagaagta ttttctcatg ttccctccct caggcaccat   129300
tatgagaaat gtcagattcg ccaccccat cgtccggctc ttgtgccaag gggctgagct    129360
tggcaccatg gcacagtttc taggaaagta catcaaggtc aagaaggaaa ctggaatgta   129420
cacactggtc aagctttatt acctgctgcg catctaaagg aaaaacataa caatcttgtg   129480
aaccagaaag atacccagag caaaagcaat aaagtacagg attattgcca aaacaacgtg   129540
tgctctttct tcatacaggc ccgcaatttc catgacagtc ccgttggtgg tcagcagcag   129600
atagtgaacg tggaggttgt caaaatcaaa gtagttggag ctcaagatgg agttttggac   129660
ttcctgggag gtgatgtagg ttgtagtttc caggccttcc ttttcatcat aactgagcag   129720
ggcaaagcca caaaaaatgc aggatttctg cgtcctggta aaattctgga tctttggaat   129780
ctggcggggc tccccagcca cagcaccctg cgaacattta ttcattataa cgggggagag   129840
aaagagagag ctgctgagat aggtggtgct ggcctcgtat agcgccgagc tcggacctc    129900 acggtcacta gagattatga atgtcacgtt gatgagcggg ataatcatca gaactttgtc   129960
gagcctgtcc acgcatttgt aggcggggag atgccacgca tccctgtctt ctcgctccaa   130020
agagagacgc ccaagaaacc catccacagc atttgaaacg gccgcctggt ccagcattgc   130080
ctcctggggg gccatgctca gcagcttgtc tcgtgtgagg tcaaatcgta ggctgaggta   130140
gcacggtgag aagagcccgc tctccgtccc cagggctagc ccccgcaaaa cctcccaat   130200 ctctagggcc gagcacaggg cggtggacag cagttggtat agggcaaggt tgggcccctg   130260
ggtagtcacg ttcagccgca actcgcgtag caccacgtgg ctgccgataa acagggtctc   130320
tctcatcacg gtatgcaggg gctggaaaag ggggtggcgg ttgtaggccg agagaagcac   130380
agatgtggcg cctccaatga ggccactgta aaccccggcc ttggggtagc cgacggtggc   130440
taacctcagc gcgtactcct gtttctcagt cgtcaggtga ccaagctcct ccatcttgac   130500
cgtggccatc agcacggcgg ccaagcgctc cagcccgtag gattgcatgc ccttgacagt   130560
ggccccataa catatgccga tgatgtcttt caggacagtc agctcaaaga agctcttggc   130620
caaccagcgg aggtccacgc agccattgcc agtctcaccc acggcatgac ccaccttaaa   130680
gaaggccaca gaaacctcaa acatggtagt cagcgtttcc gtgtccagtt ctggctcccg   130740
gcagcctccc ttcatctcca gcaggaccag tttctggaga acgtagcgag cgtagctggc   130800
ggctgtcatg gtgacggctc gggaaaaacat atccttcagg ttgggtacaa agtagttgtg   130860
aaagttggca taatgcacaa aggttgtaac aatcaccagg gaatagtccc cgctttgggc   130920
actggttaag gatgggtaac taaaaggccc cctcagatcc ggcaggtcct tcgtcttgcc   130980
aaagatcagg ctcaacacat gctcatctcc cttctcggtc actcgcttgt aggtgcccat   131040
cagaaattta gaagtcatgg cccccgtgta ctgaaacttg tccccgttga tggacagggc   131100
cacataagac aagtgacagc gcagctgata aaagacatag ctgtgtggcc gcgtgttggg   131160
cagcatggtg ccaatatagt agaagagctg cttctcaagg ggggcactaa gcatgcaggc   131220
aggggaattc aggccgctaa tgactccggg atggaccta gatgcatcca cttgcatgga   131280
tccttcagag acagcaggga tatcgacagg ctcggccagc gcaataccaa gggtaccaga   131340
cgtcttgtaa attaacttgt agcggttaag catagacgcc aaatcttcgg tgacatttgc   131400
ctctctccac agcgcctctg ggctaaggcc tgggaccttt gccatcagtt cggtccatgg   131460
gatggtgtaa tgcgaagcat gcccctctat gtccaggtgc agcttaacct cgctgagact   131520
ggcagccccc acctcccata gcaacaccag gcaaaaaaca cagagcaact gcatcctagt   131580
```

```
cccgatttcc cctctcaaaa tcagagatca ccttgctcag accagcccaa tcgaaaaact   131640
gagatcgtat tgccggattc ttcaatgcct gcatgtaaat ctccgtccag catccaggta   131700
aatcgtcctg aaactctgag aggtccacaa gcacaaactg aaggtaggct agcgttcggg   131760
tgaacgcaag acaaacttcc aacaacaccg cgtcggctcg aaaggctgt atgacttcct   131820 taagtacact aaagatgctg ttcttataca gcttctcggc cacaccactt cgaattatgg   131880
gggtgtggct ttgatgacat actgtcgtga ttgttgttag accggcacat accttcacaa   131940
tgtcctcggg ggcaaaatac tgtgttagga gccaggcaca gtaaacggcg tgatatgcat   132000
cgttgacact cttcaggtag ccagcatcca gtcctgactc atgtttcctc cctcgcttct   132060
tcaggcggcg catgttctcc tccacgttta acttcatcca gactatggtg tccccgggt   132120 ctgcggtaaa cgtggccaaa acttgaataa agtcactata ggagagaagc tggctccgga   132180
gcagcattag agggaaaacc acggaggccg acagcaaatg gcgatcatgc aaaatccaac   132240
aatccagggg cgcgactgac ctggcaccag actcggtaac cagcaagctc cgcttcctag   132300
aggccaagac tctgaaaggg gtagtaaatt tcatctggca tgctaaaacc tcagccgacg   132360
tgtcttccct tccatgcctc gcccgagtca cattcttgtg catggcctta atggcatttt   132420
catacacatg agtccagtac cgcatcggtt cagggactac aatggtcagg tccccaaaga   132480
cagccttcaa atgattcagc atagtagtct ttcccacacc aggggcacct tccaaaaata   132540
gggaacaggc aggtttgatt actggtacat gatttgtcag gtgggtcaca attggaaccc   132600
gcgtgctctc cttcctctga gccttggcct ggcgggtgtc ttgggcatca tccagattca   132660
gaacattcat cacactccca cttagccgct tcagctgggc agcatgcttg gataacttac   132720
taaactcacg cccatgggcg gccaggtgtt cgaagagacc agaaggctta cccttgccac   132780
cattcttttg ttttaacgcg gaatgagaag agggcctgcg gaaattagac tcatcctcag   132840
actcacagtc agatttgtca tcaagcccaa ggccggccag gccctcctca agccttttct   132900
ggtacatgaa gctccggctc gtggagtccg cacctccttc tgtgcacgaa gtttgcgga   132960 accaggagaa ggggtctggc gtcttgctgg ggccacactc ccggctacgt ggcttcgggg   133020
taggggcagt aggcttttgg tgtgcgggtg ctggtggctg ggctcccctg ggtagggtaa   133080
aggggcacga tgtgtgccgg ctacccggag agtttccagt attagatgtc acggcagcct   133140
gggtccggca cggcaccctc tccccagaca gtccggtcgg agccatcaag gggggccagt   133200
gggtgggcac ctggtagagt ccgtcatcat cttcctcacc tgcccctgag tcactgccgg   133260
ttggggtaag aactgagggg gcaaagtcat caatctcagc gtaaaagttt tcgtgtcttt   133320
cgttttcagg ggactcatcc tcctgacatt ttcgccagcc gccgggcggg ccggcctcct   133380
ttcctggaaa tccagccatg gatcccaccc gaggtctgtg tgccctctcc acgcacgacc   133440
tggcaaaatt tcacagtctc cccccggcta gaaaggcggc aggtaagcga gcgcacctta   133500
ggtgttactc caagctgctc tctcttaaga gctgggagca actagcctct ttttgtctc   133560 tgcccccggg acccacgttt acggacttta gactattttt cgaagtcacc ctgggtcgga   133620
gaatcgcaga ttgcgttgtg gtagctctgc agccttcccc ccggtgttat attgtagaat   133680
ttaagacggc catgagcaac acggccaacc cgcaaagcgt tactcgcaag gcacagaggc   133740
tagagggcac cgcccagttg tgtgactgtg ccaattttct tcgcacgtcc tgccccccg   133800 tgctgggcag tcagggcctg gaagtcttgg cggcgttggt atttaaaaac cagcgatccc   133860
tgagaacgct ccaggtagag tttccagccc tgggccaaaa gaccctcccc acctccacca   133920
ccggcctgct aaacctcctc tcccgctggc aggatggcgc tctccgggca cgtcttgata   133980
```

```
gaccccgccc gactgcccag ggacacaggc cccgaactca tgtgggcccc aagccttcgc   134040
aactcactgc gcgtgtcccc cgaagcgctc gagctggcag agcgggaggc cgaaagggcc   134100
aggtcggagc ggtgggacag gtgtgcccag gtgctcaaaa ataggctgct ccgcgtggag   134160
ctggacggca tcatgcgtga ccacctggcc agggcggagg agatccgcca ggacctggat   134220
gctgtagtgg ccttctctga tggcctggag agcatgcagg tcaggtcccc ctccacggga   134280
gggcgctctg cgccagcccc gccctcccca tccccagccc agccgttcac tcggctcacc   134340
gggaacgccc agtatgcagt ctcaatctct cccacggacc cccctctgat ggtggccggc   134400
agcctggctc aaacgctgct tggtaatctg tacgggaaca tcaaccagtg ggtaccgtcc   134460
ttcggaccct ggtacaggac catgtcggct aatgccatgc agcggcgcgt gttccctaag   134520
cagctgaggg gcaacctgaa ctttaccaac tccgtctccc taaagctgat gacagaagtg   134580
gtggcggtgc ttgagggcac cacccaagac ttttctcag acgtcaggca cctgccagac   134640
ctccaggctg ccctgatcct ctcggtggcc tacctgctac tccaggggg ctcctcacac   134700 cagcagcgcc cctccctgc ctcacgggaa gagctgctgg agctgggccc ggagagccta   134760
gagaaaatca tcgccgacct caaggccaag tcacccggcg gaaattttat gattttaaca   134820
agcggaaaca aggaagcgcg ccagtcaata gcccctctca accgacaggc ggcatatcca   134880
cccggcacat tcgcggacaa taagatttac aacctgtttg tgggagcggg actactgccc   134940
acgacggccg cgctgaacgt gcccggggcg gcgggtcggg accgagacct ggtgtaccgg   135000
atcgccaacc agatctttgg ggaggacgtg cccccctct catctcacca gtggaacctg   135060
cgcgtaggtt tagccgcact cgaggccctg atgctcgtct acacgctctg cgagaccgcc   135120
aacctggccg aggcggccac ccggcgtcta cacctatcgt ccctgctccc ccaggcaatg   135180
cagcggcgca agcctgccat ggcgtcagct ggtatgccgg gcgcctatcc agtccagacg   135240
cttttccgcc atggggagct cttccgcttc atctgggccc actacgtgag gcccacggtg   135300
gcggcagacc cccaggcctc catcagctct cttttccccg gctggtttt gctggccctg   135360 gagctgaagt tgatggatgg gcaggctccc tcccattatg ccataaacct gaccggacaa   135420
aagtttgaca ccctctttga gattatcaac cagaagcttt tatttcacga cccggctgcc   135480
atgctggcgg cacgcacaca gctgcgtcta gccttcgagg acggcgtcgg tgttgccctg   135540 gggcgccct cgcccatgct tgcggcgcgg gagatcctgg agcgtcagtt ctcagcctcg   135600
gatgactacg accggctgta cttcctgacg ctgggctacc tggcctcccc ggtggcccca   135660
agctgagcca gttcctcgca ctggagtggg tcattggcaa aaaggtaaat aaagtcatcg   135720
cacgggggtt ttgcctcctt ctcgtctctt gtttcgggta ggggagtaag gccgtgccag   135780
gccgccatgc tcagggccac ggcgtgccag aggccctcgt agtcgtgcgc atccgagagg   135840
atggcacggt ccagaagcag atagccggcc aggcagagga aggccacgaa gaggggggcga   135900 aggcgtgccc gaaccggggt tcatgctcg tctgcacccc agtggacaag gcagtagagg   135960
acacccacca ccaggcggtt agggaggaca ctgccaaggt tgaagagcag atttccgtca   136020
gccagggtga cctggctcag gtccggcgcc ctgcgcagtc caagctgcgc ccacacacat   136080
gcacagacgg cccctgtgac atcaggcggg tcatgcaaaa acagacaaag agaccgtgag   136140
cggttaccgg ggcgcagggc ctctgccggg aagcccaccc gggccagggc ccggtaaagc   136200
aggtaccagt attcatccgg caccttcgcg gccagcacac gattcgtgcg gttttccagta   136260 tttatcacgg cttcccgcca caggtaaaag ttaacactta gggtcagcag cttggtcagg   136320
```

```
gataggtgca aaaacctgag ctcgtcctcg cgcagagcgc aaagcggcca gttctttagc   136380
atcttcagga ggagcccgtg aatcccaggt gtcattcgcg cgtcatcccc gcgcaccccc   136440
agtcccatta acatagcggg cacaatggtg caggcaccgt ctgtatacgt ctgcggcttt   136500
gtggagcgcc cggacgcccc acccaaggac gcctgccttc acctggatcc cctcaccgtc   136560
aagagccagc tccctctgaa gaagcccttg ccactcacgg tggaacacct gccggatgct   136620
ccggtcggct cagtctttgg cctttaccag agccgagcgg gtctctttag cgcagcctcg   136680
attacctctg gggtcttcct gtccctgctg gactcaattt accacgattg cgatattgca   136740
cagagtcagc gcctgcccct ccctcgagaa cccaagttgg aggctctgca cgcctggctc   136800
ccctcactgt cactggcctc cctccaccca gacataccccc aaaccaccgc agatggaggc   136860
aagctgtcct tctttgacca cgtgtctatc tgtgccctgg gtcgtcggcg cggcaccacg   136920
gcagtctacg gtacagacct tgcgtgggtc ctgaagcact ttagtgacct ggaaccgtct   136980
atcgccgccc agattgagaa tgacgccaat gccgcaaagc gtgaatccgg atgcccggaa   137040
gaccaccctc tgcccctcac gaagctcata gctaaggcca tcgatgctgg atttctgaga   137100
aaccgcgtgg agactctgag gcaggacagg ggtgtggcca atatcccagc cgagtcgtat   137160
ttaaaggcca gcgatgcccc ggacctacaa agccggaca aggcacttca gagcccacca   137220
ccggcctcca cagacccaga caccatgcta tcaggtaacg caggagaagg agcaacagcc   137280
tgcggaggtt cggccgccgc gggccaggac ctcatcagcg tcccccgcaa caccttatg    137340
acactgcttc agaccaacct ggacaacaaa ccgccgaggc agaccccgct accctacgcg   137400
gccccgctgc ccccctttc ccaccaggca atagccaccg cgccttccta cggtcctggg   137460
gccggagcgg tcgccccggc cggcggctac tttacctccc caggaggtta ctacgccggg   137520
cccgcgggcg gggacccggg tgccttcttg gcgatggacg ctcacaccta ccaccccac    137580
ccacaccccc ctccggccta ctttggcttg ccgggcctct ttggcccccc tccaccgtg    137640
cctccttact acgatcccca cttgcgggca gactacgtcc ccgctcctc gcgatccaac    137700
aagcggaaaa gagaccccga ggaggatgaa gaaggcgggg ggctattccc ggggaggat    137760
gccaccctct accgcaagga catagcgggc ctctccaaga gcgtgaatga gttacagcac   137820
acgctacagg ccctgcgccg ggagacgctg tcctacggcc acaccggagt cggatactgc   137880
ccccagcagg gccctgcta cacccaccccg gggccttacg gatttcagcc tcatcaaagc   137940
tacgaagtgc ccagatacgt ccctcatccg ccccccaccac caacttctca ccaggcagct   138000
caggcgcagc ctccaccccc gggcacacag gcccccgaag cccactgtgt ggccgagtcc   138060
acgatccctg aggcgggagc agccgggaac tctggacccc gggaggacac caaccctcag   138120
cagcccacca ccgagggcca ccaccgcgga aagaaactgg tgcaggcctc tgcgtccgga   138180
gtggctcagt ctaaggagcc caccaccccc aaggccaagt ctgtgtcagc ccacctcaag   138240
tccatcttt gcgaggaatt gctgaataaa cgcgtggctt gaaagtaaac tttattgcgt    138300
gttagtacct gtccattcac aggggtatcc agcccttgcg ccgcctcccc cagcccgcca   138360
gccaccccag acaggagatg ataatgatga ggagcaccgg agccaccaca gcacaagtga   138420
ttaggagcag ggcccagtgc acccaggtgg tcttagggcg ccaggatcg attggaaaag    138480
ggcccagggt cactggctta tgcgtgggac gtttagaaac aggccgccta tggggcctgt   138540
gactggtgct tgtggtgtgg gagactaatg tggtggggc tatggtagtg ctgggataa    138600
cagtaagatg catacgctga gtgagcgtcc ggttggcatg gtattggtcg tcttcttccc   138660
ctgcagagta attgcagtgg accccggagg ccacactgca atttctcagc gtcacattgc   138720
```

```
acgtgtagta acctgcatgc gcaagggtca cattggggat tatcagagag acggaggtgt  138780
tggagtcatt tacccattct agggtaaggc tataattgta accccgtta gttatatgag    138840
ttccgttgtt ggaagtagct acggccaagg gcagttgtcc atccccggga gtgtatcccc  138900
ggcccaactc gatccgagag accgactcat tgctaggaac gctgcaggtg agattcactc  138960
tagcacctgc atgggcggtg acattttcaa atttaaccag atctgagaaa aatgcacaaa  139020
cagaccccac acagcagcac aatagaagca ctaaatgagt cattcctaaa ctgtcagttt  139080
taaaactccc tgcttctcag gcctaaatac gtggtggggt gtgcttagga tcactttcat  139140
attctgcaac aacagccata cccggaagag gagctgccgg ttgccatttt tcaagctgct  139200
aaaccacgag tggcagcagg cctaagaagc tcctcagcaa catggagacc tcgaagggaa  139260
actggcagga gcagggagtc acgtaggcac tagcctcttc atgtgaggta agatcgct    139320
aaaaatggga tcagggtatg taaaccgagt tttgcggggg atggtgagcc agacacggcg  139380
ggtgggggga aggagctgac acgagtgcgt agaaagggcc aaaaatacac cagctataag  139440
gaattgctca gaccaaagtt gttcctcagg tggctttagg cctaatgtag gcaattgcgt  139500
gcctagaaca ttgctaatgt gccctgtgtt tcctgccttc atgcaaatat cctacctccc  139560
ccggcctggt gcaaaatgtc tgcctcagaa tactaacagc taatccaagc taacattcta  139620
tcagtaaacg ggcagaaaac tgataaggac gcgggagttt ggccctccgc ggtgtccggt  139680
ggtcctcaca cgtgccctcc ccccccggg ccgatggctg aggcccggaa tatgcaagtg  139740
catctttcta accagtaggg gcctccacct aggtgctttg ttaatcttta gtgggaacta  139800
gtgggagtgc tgtgcctagg gtaccctat cctataggtc ctaccggagc tccttgcctt   139860
gataatccct gtaaacacac accacctaag aacaaggcat cgttaacctt tggtggaacc  139920
tagtgttagt gttgtgctgt aaataagtgt ccagcgcacc actagtcacc aggtgtcacc  139980
ggaggctact tgcctcagtg ccacttttac cttctcaaat ctatacgggg gggggcctc   140040
tgtaacattt ggtgggacct gatgctgctg gtgtgctgta aataagtgcc tagcacatca  140100
cgtaggcacc aggtgtcacc agggctactt gcctcggcat ctcctcaccg gagaaggggt  140160
taacaaaccc gtgggggtc ttagtggaag tgacgtgctg tgaatacagg tccatagcac   140220
cgctatccac tatgtctcgc ccgggctata tgtcgcctta cctccctat atagtcacga   140280
ccccaccgaa ccaggcatga tgtagaataa aattttatgc atcatcttct aatctgtgcc  140340
gcttggaggg aaacatgacc acctgaagtc tgttaaccag gtcagtggtt ttgtttcctt  140400
gatagagaca caaggactgc cagccccgtt ggggagggg tggtgggtac gggagagttt   140460
gggctcgtct aaacaaagcc tcctctgatg ctctgtggca cctcaaggtg aatatagctg  140520
cccatcgacg tatcgctgga aaccggtggg ccgctgttca cctaaagtga cgcaaggtct  140580
gtcagccgcc agggtccgtt taccaggctt tcaggtgtgg aatttagata gagtgggtgt  140640
gtgctcttgt ttaattacac caagatcacc accctctatc catatcccac aattgataaa  140700
cctccgcatg tccaaccacc acgttgaaca ggatgtggca ccctaagagg acgcaggcat  140760
acaaggttat tacccagtcc ttgtatgcct ggtgtcccct tagtgggacg caggcctagg  140820
tagcatcatt tacactaaaa gcagtgacct tgttggtact ttaaggttgg tccaatccat  140880
aggcttttttt gtgaaaaccc ggggatcgga ctagccttag agtaactcaa ggccaagcat  140940
ttcacacctg caaatgcacc atgtaaccac agatctaaac tgaaagttgc agctttagat  141000
ggcaaggaaa cttgggtttc aggcatagaa agcctggctc actatagcag cccatgtttg  141060
```

```
ttccagggtg ggggaaaggc acgtgccctt agaaaactta gctgcaaaaa ttctattgtg   141120
ttgggagagc ctctatatct aaaggccttt cctcccaata caaatgttac taacatctgc   141180
cctctggaga cctgctatgt ggctagactt atggcctacc caagacgttg ggggtctcgg   141240
gtaggccgat tcttccaggc ataggttaca accagtcact gctatcaagc ctactcagtt   141300
cccaacgcag cacataccc cgcctctcc tgccatgagg actcatggca gtgtttactg    141360
ttctgctttt actcttggac caggccgtca ttctatcaga ataacagggg aagcaatgcc   141420
ccctgcgtca gcgggacacg tgtttctaga atctcggagc caataactac ctgcccctct   141480
aatctgtacg ctgcatgaaa aaccacatac acgtgatgta agtttagcca gtttattgtt   141540
acaccaatgc cccgaaagtc ccccctgtc cctttgggtc tcaggaccca gccctggagc   141600
tcggggggcg gccgggtggc ccaccgggtc cgctgggtcc gctgccccgc tccggtgggg   141660
ggtggccggc tgcagccggg tccggggttc cggccctgga gctcgggggg cggccgggtg   141720
gcccaccggg tccgctgggt ccgctgcccc gctccgcgg ggggtggcc ggctgcagcc    141780
gggtccgggg ttccggccct ggagctcggg gggcggccgg gtggcccacc gggtccgctg   141840
ggtccgctgc cccgctccgg cgggggggtgg ccggctgcag ccgggtccgg ggttccggcc   141900
ctggagctcg ggggcggcc gggtggccca ccgggtccgc tgggtccgct gccccgctcc   141960
ggcggggggg tggccggctg cagccgggtc cggggttccg gccctggagc tcggggggcg   142020
gccgggtggc ccaccgggtc cgctgggtcc gctgccccgc tccggcgggg gggtggccgg   142080
ctgcagccgg gtccggggtt ccggccctgg agctcggggg gcggccgggt ggcccaccgg   142140
gtccgctggg tccgctgccc cgctccgcg ggggtggc cggctgcagc cgggtccggg    142200
gttccggccc tggagctcgg gggcggccg gtggcccac cgggtccgct gggtccgctg    142260
ccccgctccg gcgggggggt ggccggctgc agccgggtcc ggggttccgg ccctggagct   142320
cggggggcgg ccgggtggcc caccgggtcc gctgggtccg ctgccccgct ccggcggggg   142380
ggtggccggc tgcagccggg tccggggttc cggccctgga gctcgggggg cggccgggtg   142440
gcccaccggg tccgctgggt ccgctgcccc gctccggcgg ggggtggcc ggctgcagcc    142500
gggtccgggg ttccggccct ggagctcggg gggcggccgg gtggcccacc gggtccgctg   142560
ggtccgctgc cccgctccgg cggggggtg gccggctgca gccgggtccg ggttccggc    142620
cctggagctc ggggggcggc cgggtggccc accgggtccg ctgggtccgc tgccccgctc   142680
cggcgggggg gtggccggct gcagccgggt ccggggttcc ggccctggag ctcggggggc   142740
ggccgggtgg cccaccgggt ccgctgggtc cgctgccccg ctccggcggg ggggtggccg   142800
gctgcagccg gtccggggt tccggccctg gagctcgggg ggcggccggg tggcccaccg    142860
ggtccgctgg gtccgctgcc ccgctccggc ggggggtgg ccggctgcag ccgggtccgg    142920
ggttccggcc ctggagctcg ggggcggcc gggtggccca ccgggtccgc tgggtccgct    142980
gccccgctcc ggcggggggg tggccggctg cagccgggtc cggggttccg gccctggagc   143040
tcggggggcg gccgggtggc ccaccgggtc cgctgggtcc gctgccccgc tccggcgggg   143100
gggtggccgg ctgcagccgg gtccggggtt ccggccctgg agctcggggg gcggccgggt   143160
ggcccaccgg gtccgctggg tccgctgccc cgctccggcg ggggggtggc cggctgcagc   143220
cgggtccggg gttccggccc tggagctcgg ggcggccg gtggcccac cgggtccgct    143280
gggtccgctg ccccgctccg gcggggggt ggccggctgc agccgggtcc ggggttccgg    143340
ccctggagct cggggggcgg ccgggtggcc caccgggtcc gctgggtccg ctgccccgct   143400
ccggcggggg ggtggccggc tgcagccggg tccggggttc cggccctgga gctcgggggg   143460
```

```
cggccgggtg gcccaccggg tccgctgggt ccgctgcccc gctccggcgg ggggtggcc    143520 ggctgcagcc gggtccgggg ttccggccct ggagctcggg gggcggccgg gtggcccacc    143580
gggtccgctg ggtccgctgc cccgctccgg cggggggggtg gccggctgca gccgggtccg   143640
gggttccggc cctggagctc gggggcggcc cgggtggccc accgggtccg ctgggtccgc   143700
tgccccgctc cggcgggggg gtggccggct gcagccgggt ccggggttcc ggccctggag   143760 ctcgggggc ggccgggtgg cccaccgggt ccgctgggtc cgctgccccg ctccggcggg    143820
ggggtggccg gctgcagccg ggtccgggt tccggccctg agctcgggg ggcggccggg     143880 tggcccaccg gtccgctgg gtccgctgcc ccgctccggc ggggggtgg ccggctgcag     143940 ccgggtccgg ggttccggcc ctggagctcg ggggcggcc gggtggccca ccgggtccgc    144000
tgggtccgct gccccgctcc ggcgggggg tggccggctg cagccgggtc cggggttccg    144060
gccctggagc tcggggggcg gccgggtggc caccgggtc cgctgggtcc gctgccccgc    144120
tccggcgggg gggtggccgg ctgcagccgg gtccgggggtt ccggccctgg agctcggggg  144180
gcggccgggt ggcccaccgg gtccgctggg tccgctgccc cgctccggcg ggggggtggc   144240
cggctgcagc cgggtccggg gttccggccc tggagctcgg ggggcggccg ggtggcccac   144300
cgggtccgct gggtccgctg ccccgctccg gcggggggggt ggccggctgc agccgggtcc  144360
ggggttccgg ccctggagct cggggggcg ccgggtggcc caccgggtcc gctgggtccg    144420
ctgccccgct ccggcggggg ggtggccggc tgcagccggg tccggggttc ggccctgga    144480 gctcggggg cggccgggtg gcccaccggg tccgctgggt ccgctgcccc gctccggcgg    144540
gggggtggcc ggctgcagcc gggtccgggg ttccggccct ggagctcggg gggcggccgg   144600
gtggcccacc gggtccgctg gtccgctgc cccgctccgg cggggggtg gccggctgca    144660 gccgggtccg gggttccggc cctggagctc ggggggggg gcgctcccag gccggaccct    144720
ggtgccaggc agggaccccg cgccaccgc ttcatggggg gggaggccgc cgcaaggacg    144780
ccgggccggc tgggaggtgt gcaccccccg agcgtctgga cgacgctggc gagccgggcc   144840
agctcgcctt cttttatcct gttttttggg gtctctgtgc aatacccttaa ggtttgctca  144900 ggagtggggg cttcttattg gttaattcag gtgtgtgatt ttagcccgtt gggttacatt   144960
aaggtgtgta accagctggg tggtacctgg aggtcattct attgggataa cgagaggagg   145020
aggggctaga ggcccgcgag aattgggggta ggcggagcct caggagggtc ccctccatag   145080
ggttgaacca ggaggggag aatcgggctc cgccccgata tacctagtgg gtggagccta    145140
gaggtaggta tccataggggt tccattatcc tggaggtatc ctaagctccg ccctatata    145200 ccaggtgggt ggagctaggt aggattcagc taggttccta ctggggtacc cccctaccct   145260
accttaaggt gcgccaccct tcctccttcc gttttaatgg tagaataacc tataggttat   145320
taacctagtg gtggaatagg gtattgcagc tgggtatata cctataggta tatagaacct   145380
agaggaaggg aacccctatag tgtaatccct cccccccta ccccccccctc ccttacggtt   145440 gcctgagccc atcccccacc ccagcacccc ggggtgacgt ggcacccccgc gtgccttact   145500 gacttgtcac cttttgcacat ttggtcagct gaccgatgct cgccacttcc tgggtcatga   145560
cctggcctgt gccttgtccc gtggacaatg tccctccagc gtggtggctg cctttgggat   145620
gcatcacttt gagccactaa gccccgttg ctcgccttgc ctgcctcacc atgacacact    145680
aagcccctgc taatccatga gccccgcctt taggaagcac cacgtcccgg ggacggaagc   145740 tggatttttgg ccagtcttaa attttgggga gtggttttgt gtgagccgga agttggcaat   145800
```

```
ggggtgaggg tggcgctggt taagctgacg acctcccaag gtctctcacc ctgggtacac   145860
aggtggggcg gcagcctcta actttggctg tggcctctat ttcctccctt tcctagccag   145920
ggccatgtgt tcctgcatgt ctacttgcct cctgtggtgg cagagcttgg ccctgggccc   145980
aacccccgcc ttgggagcct gtaggggcca acacccttgg tttgtttgtg ttcctgtttg   146040
ctggcaactt actggcagcc gagcagattc taatgggcgc ccgccttctt tctctcttgt   146100
tttattaata gaatctcagc caggacctat acctgagact tcaaagtctg gtcctggggtt  146160
ctgagacccc caagatttgt catgcacacc tgcacacctg ttggtattgg gtttctattc   146220
ttgagtgtga aagtttgtaa aaaaattcat aaaatgtcac taattcctct tacctgttta   146280
gagtattgtg caattcttca gcctgcctat tttcaatttg cctaaggtgg caatttaaga   146340
tgtggttaat taaccatttt cctgtctgac accactgcat gggcaaccgg gttccatggc   146400
acatttacag ataaacatag atgtcttgtc ttgctcatgt gcagaggagg gggtgttggt   146460
gtgcaatata gtttctggat tccaaaatga gttgggggtg ctattttcac tatggaatta   146520
aattactgac attagacagt ggacaccggg ctatatgtgg ggatgtctgt ggcttgtcat   146580
ttcctcttag aaggtaatcc cccatcttaa cttcccttta aattgtgatg caagccctgg   146640
gttatttata gaatgattat ctaggtttga tagtctgaag gctgggcaga gaatgtttgt   146700
aattttatt caccttctt accccccacg agtatccagt tctagaaaat ctcctgatat   146760
cccgggctgc cattattccc ttgagtgtta tagcttcctc ttaacttaag caagagctcc   146820
aggatgttag ctttttggt ggggctggtt gtcaggaaga ggttccagtg ttgtccttta   146880
tttttagatg ttagctttgt gttgggttag tatgggctgg gtattcacta gtgaaggcaa   146940
ctaacacagc tagacgtgct agttgtgccc actggtgttt atccggtccc aaatgtcaca   147000
acagaacaca ggaggctgga tttggcagca gcacgtgtgc ttttgttgat ttttacccct   147060
gtatcagagt gggggatgct tctggttcct ggtcttctct gtgcacaaaa agggccaat   147120
ggccacggcc ccgcggcttt ttgtgccggt gcggagccaa tttagcttcc cctcccctta   147180
gcggggggtc tcgcggggtg ccaattgtcg cctgccttcc cctgcttccc cttgttaact   147240
tatagcatga taggtaggtc acctaacgtg gaagcctggt gggtgatcct tcctcggtag   147300
ggagcgctta gggctgttga gctcaacagc cccacctggg taaaatgtat gttctaaaga   147360
gttacccaat tataacaaaa ctgttgtagg gtaacgaaga cctgatggaa gtggtattgt   147420
tgccgttgaa agacgggtgt cctggctcaa gttcgcactt cctatacagt gttaaagcct   147480
tgtatcggaa gtttgggctt cgtcccagtg tactcaataa tgtcgactgc tgcgaaggtt   147540
tggaccgtct tccagtaggt gttggggtc ccaaatcacg aggttaggca ggtgcactta   147600
gctctttagg agggacccctt aagccaggca atgtagtgcc cctttttttt gcaaattggc   147660
cttattatta aattcttgtt aacactaatt ctgttctatg accctgtgtt tttcagatgc   147720
cgttggacgt gtcactgagc tgattttgga cgcagctact tgacctttgc ccccgtgcct   147780
ccaacgccga taagtgctgc ttccactttg tgttacaggt gggccaaacc tccagaatat   147840
caagtggtgg ggccttggtg ggctgcataa ggcagtaggt tttaggtgac ctacttggac   147900
catgtggatc cagtgtcctg atcctggacc ttgactatga aacaattctt aaaaaatgca   147960
tcatagtcca gtgtccaggg acagtgcact cggaagtctc atcatctccg tttgtgtgtt   148020
tagtgtggcc agtacggcca ctcctgtgcc acgccctggc atgctgctga catctgggcg   148080
ccaatttcag cgggcccttt tccccttgt tcaccccata gcaagaaggg taggttacat   148140
gggtattttc ccatcagcac ctgactggcc ggtgtaatta gaggagaggg caacaacgca   148200
```

```
aggctgttgt tttatttggg ttacaagagc tgcggtggtc gatgggttca ctgattacgg 148260
tttcctagat tgtacagatg aactagaact gtcacaatct atggggtcgt agacagtgtg 148320
cttaccagac ttccatggaa gatgtgaatt tgctgctagc tatatgggtg gtgctatggg 148380
ctccctaggg actcatgtag tggggctttg tgatagctaa tgaatgtggc agctgttgtt 148440
tgtactggac cctgaattgg aaacagtaac ttggattctg taacacttca tgggtcccgt 148500
agtgacaact atgctgaata tcttgaatat gggaggaggg gggctttggg ttccattgtg 148560
tgccctttcc tggccaacgt gagggtccta gtgttatagg gcgtggcagt tttcttgagg 148620
gctaataacc cgggtgaggc ggttgtcaca ggtgctagac cctggagttg aaccagtacc 148680
actcggttac aaagtcatgg tctagtagtt gtgaccctgc aaagctacgt ggggatgagc 148740
agccagggac tttggttggc aagcagacag gcggcgcatt ggaacccccag aggagtgtcc 148800 cggggccacc tctttggttc tgtacatatt ttgttattgt acataaccat ggagttggct 148860
gtggtgcact ccatctggta aggggctgg tgcggacgcc tgtgtttagt ctatgccaat 148920
gtttacctgc cttgggttac tattccaaac gaccacacct ttgaggacac ctggagccct 148980
gatcattctc ggcttttact gccacctggc ttctgttggg tcagacagtt tggtgcgcta 149040
gttgtgtgct tagcagcaac gcacaccagg ctgactgcct tagcagtgtg gccctttatt 149100
gtggcatcct aaggagggat tctggagtgc ctttcgcgtg aagcatgccc tgagacgtac 149160
tcgagttagg acttaatcgc tcctgtgccg ctggatgagg gagcgccaat ttgtacatcc 149220
tagctctggc catagagtta gcccacccct tgtgtctccct ttggcctttg cggtgccaat 149280
ttccggtggt ttccctttttc cgcccgttta tccaatagca tgtaagagag gttgcctaga 149340
tttggcaact ttgagggaac gttccgtgta gctggtgacc taacacccgc ccatcaccac 149400
cggacagatt ctgaacttgt cctgtggtgt ttggtgtggt tttggggtac gcaggagtac 149460
gttggaatgc tttggagccg agagggatgg gcccgcttgt gcgcttatgt gttacacggt 149520
gccaataacc ggcccggtgc ggctgccccg tgacccgtgg gccttacctt cctggccatc 149580
gggggaccct ggtgctaggg tcccttgtgt tgctttctgc cataggggggg aaagcatcgc 149640 cttcagaatt ggctgctccg ttggaacatt tgaggcctac tgtatccgtg tcctgacaac 149700
attccccgca aacatgacat gggttaattt aaacatgttt tgtttgcttg ggaatgctct 149760
tagggcctgg aagcttgtca ttggattcat cgtttcctga actacaggcg tagggcctat 149820
tgtagcaggc atgtcttcat tcctgcgtac cgaatggcat gaaggcacag cctgttacca 149880
ttggcacctt ttttccatgt aaacctccgt gatcctgggt cctttggaga ctcaagtgtg 149940
aatttgtttt ggtgttcggc gccagggcat ctcgacgttg gaatgtcaac tcaacttggg 150000
cacctcgata accggctcgt ggctcgtaca gacgattgtt tggctctgta acttgccagg 150060
gacggctgac gatgtgttta gtctgccact tgcatccggc gctttggtta cacgggagac 150120
taatgggggg tgtggtatgg cacaggctgg gggtgagtct ggggatgtcc ctgggcgttg 150180
ctgcagccca ttcgccctct ggggatgaga tgttcagggg tggccggtac cctacgctgc 150240
cgatttacat aatataaatt gtaaatgctg cagtagtagg gatctggacg cgcgacctgc 150300
tactcttcgg aaacgccaac ccaggagcgt cgcctctggc cccatactcc cgccatgcga 150360
ctgctcgccc cctccaggc ctccctggtg agcccttgcc gctccccgca ttcctgcttt 150420 cggcgccccct gcggatcccg atgacagcag gcctttcctt cccccgttaa tgaaaagaat 150480
gacagtgagg ttgtgacaga aggacagctt tattcagttt acagagtgcc ctcggaggct 150540
```

```
acgatattcc cgttaaatgt cttgttgatt ctctcaaagg tggggaggga ggagctctcc   150600
acaacaatgt tccctggcag cgtgagcgcg cagccctgcc gttggatgta tcttctcatg   150660
atggtgctga tagaggggtc tccggcgtag atgaaaaagg cctgggccat gctctggccg   150720
gtcacgatcg ttatggggtt gttggaaatg ttccggaccg tcagcttgag ggtctggccc   150780
ggcttccact cctgtgggta gacgtagaag accgggttgg aggagtggga cacgacaacg   150840
gccgtaatct tggagctcag gggggcctcg taggtgttgt tgtattccag ctccgtgatg   150900
aaattaggag gaataatcac aggggagcca agtagcgga tgtctgtgga ttccccgtcc    150960
cagcgccagt ggctcttagg gtaggggttg taacggaagg caataatcac atcatccaat   151020
agggtcatgc ccaccttgac gttcagcggg ccctctcgtt tcaggtccgg cgtgtccacg   151080
gagactcgga cgtagccctt accgcggcgt atggcgttga ccggacacac cttcccggg    151140
aatgtgtgaa tacgggcgta tgactttaga aatgggggcg tgtgctgcgc cagcaggtaa   151200
ggcaggcact cgtcctggct ggtgacggga gagccactga ggaagatctg gggctcgctg   151260
gtgtttagct tgtccccact ctgggtgcag gagcgtgtca gctgaatgtc gctctgcccg   151320
ggcagaatct gcaggtagag gtaggggttc ttgaccaatc tgatgggcac aatgtaccag   151380
gtaaacttcc ctttctctat gaacaggctg cgcggattca ggacgcttag cacgatgtcc   151440
tggtcagagt gcataacgaa gaagggcttg aggaatacct cgttgtcttc cgctccaaag   151500
aacaagaacg caaccgtaaa gtagcggctg ccgtaggtgg tcgtgttgaa ggagaaagaa   151560
ggtaacttga agctgagtat ctggcccacc gaggggcagg gaggcagctc ttggcactgc   151620
gcgtccagct gcaatacctg cttgttggtg acgcgaacgt atgaggggaa gatctcgtac   151680
ttccacacgc ctctcatgaa cgacgtgtct ggttttcag tgggccgcag gcggcggagg    151740
ctgttcctga acgacgagcg ccgggacgct agtgctgcat gggctcctcc ggggtaagct   151800
tcggccatgg ccggagctcg tcgacgggca aggtgagagt cggggggcgg gcgacggtgc   151860
ggccccaata caactctccg ctcgttagct ggtagaatat ccgcccggcg tctaggttgt   151920
cacttcgctc ggccggccag aagagcgcaa gtccaagtct ggtgctgggg ccgatgtgca   151980
gcggtttgtg cccgcagttg tagactgtca tttttatggg cgagtgggcg gtccacacgc   152040
gcgggcgcag cacccattgg tcgcacgccg cctcctggaa tgtaaacccc cagagagagg   152100
gcgtgccgcc ctggagatgg ccctgtgcca tcacatgtat ttcctccttg ggtgaacga    152160
cggcgtcgtg ctccgggtgg aggggaata gcgtccaggc atctttcagg gtcacgagac    152220
cggggtccat gcttagaaaa cagccctccc gggcggtggg cggcccgggc tccagcagaa   152280
cgtcgcagac ccagccctcc tcggccctgt ccacctgtat gtccaggtgc acggacccgg   152340
aggctgcgtc tcgtgacatg gccaggcctg gtgccagccg accacgtccc gtgtcccagc   152400
cgaggccgcg ccagagcaga gcccgggact gactcagggc cacatcccct cggcccgcgg   152460
acgctgcctc gccagccccc gggccttcat gggcccgctt tctacctctc tccggcaccc   152520
cagcctggtc agccgcagag gaagcatgac cttggggtgg gacggggcag gcgtgatcct   152580
gggcgcaatc tttaccgatc cccacacctt cactccttgt tagtttgata gaatgtcggt   152640
accacgccac ggggggcggg cccgcatagg gaaaagccag ggagagcgat atgggcgagg   152700
atgggctcag gcggccccag acacgcaatt tgcccccctg ggcggccgca gcctgcccct   152760
cggcggcccg tgcccagct ccgtcacggg gggcgcatag gaggggtata tctaggatag   152820
ccgcacctac acaaatgaga cacagacaca ggtcgtgagg atttaggcaa cgcaggcttg   152880
tcttttatagt tacaaacatg ggagcgtgca cctggaagat gcagctgggg tagatcttta  152940
```

```
catctttaca gggcgcagcg gccgccagac actgaagggc agagttcacg gcgggcacct  153000
cccagaggga gcccaccagc ccgtacctgg ccacggccag ggcctcgtag gccgagacgg  153060
gcagccggag cttgtggtac tgtccctccg gcaggtggag tgggacacag ttagagaaca  153120
ttagtcccct ggtccctatc tccacccgcc aggcatgtgt gtcagtttgc agggccatcc  153180
tcgcgctcag gtggactggc taggcaccct tctgaagtat ctggcggtga ctgtcacctg  153240
gttcttgaga gagtccataa aatggctgaa gctccaggcg tatagtataa tgagcaacag  153300
ggccagacag gcggcgggc ctgggtagta gcgggcaacg agagactctg tgcaatcaaa  153360
ccccaggctc ccggcctcac ccaggaagag cagcggcagg acagcataa accaggagaa  153420
ggcgcagatg agtccggtga aggtgacgtt gcatatcagg cgcggcttcc ttccgaattt  153480
tgtgcgcaaa agtttccaga tgatgatgac tgtgaggagg acgatcagga ctgccgccag  153540
taggtagcag ccggctttca gtccttggac ggccgtgtgc atgcctttgg tggggccttc  153600
cctgcacatg ttggggcctc tgttgagatt ggcgtcgggg cccatggtaa tgaggaggat  153660
gataatcagc aggagtacca gacaaaacac gcccatcagg tacaggcaca catttctgtg  153720
ggaggttcgc ttgggcgttc ggctgaacaa tgctagggtc ttctccaacg ccatacccaa  153780
gtgagtccat acggagcaca tcaggcccaa gaacatcatg ttctgggtca aaggcagag  153840
accggtagac gagaactcct gaatcatttt tcccagcacc cagagcagca gttctatgag  153900
aagagctatc agccagacat ccattcggtg aaccaatttt cttacaaaga tgataaacaa  153960
gatgccagcc agtgttagca gaatcagcag gacgagcagc aggcttgtca tgccgctgag  154020
gaaggcgctg taggatttag tgcacgcatc ttccgttgca ttgacggaag tcatgttggc  154080
caccagggtc cccacagtgg acccgggggc catggtggag agcatcttgc tggtcagagc  154140
cagactgggt ggtgtctgca gcaaaagagg aacttgccca ggcagtcagt tattttgcat  154200
gccacctccc tgcctggtgg acttccagac tattttctgc attcgccctt gcgtgtccat  154260
tgttgcaagg agcgatttgg agaaaataaa ctgtgagttt cacagatcca cgggccacgc  154320
tccccctgggg gcttcatgat cccaccgcct ttccgatga tgatgacaac cgcggctgtc  154380
tgaagcggct gacgaaatcg gttgagattc tgatgagagg cttgggggg tctttgccct  154440
caaggcgagg ctccttctcc taggaatgcc gagcccctg cactagcttc gctccactgg  154500
ggatctttgc cagccttcat actagattca gcgatccccc ggttgggaat cttcgccagc  154560
cccccgtcct gctatcccgc tcgtcgccgc gcctcccatg ctaagggccc ccttcctttc  154620
ccttgacttt ggggatattc ggagtctgct ctcgccgctc tcttctctcg tttaaacgag  154680
agaatagtag tagggtccag tctcaggccc cctcactttg ggtcttagaa tggtggccgg  154740
gctgtaaaat tctggaggac ggagagggcg gccccggagt tgttatcaaa gaggcactgg  154800
aggatgttgg ccgctccttg gagcagcttg tcgaaataat gatccacggc cacgggaacg  154860
ccgtgccgct cggcgtaggc cgggtcctcg gccatctccg tctttctcgc cccttcact  154920
cccccttgg gctccacaaa gacgtactgg atgcggtcgt ggatctgggg cagttcctcg  154980
ttgcgctcga cgaacttctg gtagacggcc aggtgaggca tctgggtgct cttgtaggct  155040
gagagcttgc ggctgagctc cgttgaaaag cagagctccc ccatgggac cctgccttca  155100
cggaggtctg tgtaggcctg gtttaggatg tcaatgacgg gcaaaaagcc cacaggtagc  155160
ccttgtgtaa atgactcttg gaagggccgg tgggagagga ggctgccgc ctcctttacc  155220
cgggcatccg ccagcaccag gtcgagcacg cgccggcagc gtgtctgcac aaacttgcag  155280
```

```
gccgtcttcc ggacgagctc cacccccttc atcagggtct tgccgtccgt cagcaccccc   155340
acatatctct tctttgtaat cagcatcagg caggagaagg tcttctcggc ctccaggag   155400 atgggggcca caaacaggct ccgggtggtg tgggcggcca gggcctcggc aaagcgcagg   155460
gtctcgctct ctgaaaaccc ccggcactcg ataaacagcg agtccgtgtc cccgtagatg   155520
actcgaagct ggccctcggg gttgaggggc gcccaggcgt ctggggaggg ggccagggcc   155580
tgcaggttgg cggggctcag ggcctccacg aaggccttgg cccgctccaa catcgtgcgg   155640
ccctgcagcg tcaccgtctc ggcgatggag aggcagggaa agaggccgtt ggccaccccg   155700
gtgaagccgt agacgcgtt gcacgtgcac ttgatggcca gctgctgctt gtcgaggatg   155760
gtcctttggc gcggatcctc gcaggccgcc agcagcttct tgatggcctt gcgcttggcc   155820
agccaggagg tcaacagact agccaagaag gactcgtgca cgtgcttctt cacaaagtgg   155880
tagacgcccc ccgtgagcct gaaggactca tagtcttctc ccgggcgcag gccggctagc   155940
ctgtgctctt ctcccggcgt tatcatggta gaataacaga gattatgagc ctgaatgatg   156000
ctcgggtaga ggctggcaaa gtccaccacc agaaccgggg agttgtagaa tccgacagg   156060 ggctggatga cggtggcccc ctggtagccg tcccggtcag aggccgaggg catgggcagg   156120
ataaagtttt ccttttgggc ggccgccagg aggcaggaga acacgcggat ctgctgccca   156180
tcgtccagca cccgcctgca ggggatgtga gcgatcttgg caatctctgc cacctccacg   156240
tggatcacga aatggtttag cagatccatg accaggccg agtcctgcac gcagtacatg   156300
ccgagccgcc tgcgcccctc ggggcccgct gcaaagaggc gaggaatctc cttgtaatgc   156360
acatcctcct tcttggcccc cagtaggtgc ctggctactg tgtccagctt gtagtctgag   156420
agactgagct tgtcccggca cacggcgtac atgtctatgg ggatgaggcc ggtgatgcgg   156480
accttggtgt tggcccgcaa gaagcccttg cccgcatcat ggggtcgcct gacctcgcag   156540
acgcccccag ccctaatttt gcccagagag gctgggttga tgctgtagat gtgcctggct   156600
ctgtccagaa tgtagggcca gtcaaagttg gccacgttgt agccggtcac aatctccacg   156660
ctgaggtctc tgatgagctg gaagaaggcg tagagcatgt ccagctccga tgggaactcg   156720
tagacctcaa cccctctat gtcttcgcag gtgcccagcg tcagcaggat gcgcctatag   156780
cgcccggcct cctcccctgt cgaccagaga acgcaggata tctgcaggat caggtcagcc   156840
tcgttggtgg ccgtggggaa gccctcctcc cctagacact cgatatcgaa ggccagggcc   156900
tggtaggagg gccaggagct gtcttcacgc cggaccgaga ggtcgcccac ctcacagtcg   156960
tactcgagct cggcgtacga gtccggtgc tggaggcggg ggatggcgcg gcggcagctg   157020
taccagccaa aggtgacaaa gtcattgtcc aggacaaagc ggcgcgtggc atccacgttg   157080
gcctcaaaga tccgacaccc gtgcttgtct tgcagccacg tggccacgtg acacacactg   157140
ttgggatggg agagggtgat cttgtggtag tcgccggcat ggttgccgta gcccataatg   157200
gaacggcgcg tgaccttctc caccgagacc cggcaggggg tcctgcggtc gaaggtgctg   157260
gccttgaggg cgctgaggac tgcaaactcc acgtccagac cctgaggcgc gctggcgtag   157320
aagtaggcct gctgcccaaa cacgttcaca cacacgctgg ccccatcggc cttgcgccgg   157380
cccagtagct tgatgacgat gccacatggc accacatacc cctgtttatc cgatggaatg   157440
acggcgcatt tctcgtgcgt gtacaccgtc tcgagtatgt cgtagacatg gaagtccaga   157500
gggcttccgt gggtgtctgc ctccggcctt gccgtgccct cttgggcacg ctggcgccac   157560
cacatgccct ttccatcctc gtcaccccc accaccgtca gggagtcttg gtagaagcac   157620
agggggggct gaggccccg cacatccacc acccctgcgg cgcctggtgt ctggaaacac   157680
```

```
ttgggaatga gacgcaggta ctccttgtca ggcttttca gaaggccttt attaggtctt 157740
aggaaagggt tatagaagag tcccccagac atggttaaaa ctcagtctct gcctcccaa  157800 gcagtgcggc ggcggtctct ggatcgtgat agcgtcttct gcgtaggcct ggaaaacggt 157860
ccctggctgc ctgcaatgct ctgctggcca ctgagggtcc ggccgccctc tgagctgctc 157920
tcttttgctc ctggttttgc tcatgcagcg ctaacatgat ggcttgtaat tctgtcttac 157980
taatgggatt aatgcctgga ccctcaccag aggcatgttg ctgagcgagc tcgtcgatcc 158040
cggggtagag catctgcacc ggctgctgcg acatctggcg cgtgcgcctc gtgagggaaa 158100
taaccaggat caccaccccc gccaccagga ccagaatgag catgccgccg aaggggtttt 158160
tgaagaagga gatgaaacca gagaccaggc tgctaaacaa accccccacc gtgctgacta 158220
ggttggtgat ggactgaccc acgctaccca gactgtccat aagttccccc aggccgtcca 158280
cgaattgatt tcttccgttt gacactgcat tgtccaaatc cttccgcagg ccggcgatgt 158340
tttgcgcctg gaagttgtac tcccggaaga tgccctccag gtcaaagacg ttggaggcac 158400
gctgttcgtc ccgtgagtac agctccaggg aggcaaagtc aatgttctcg atgagggagg 158460
tgtttagtga gatgaaggtc tgcagggtgg caatgccgtc cagctcgatg gttttaaagt 158520
ggtggtagtc gttgtagacg tggatctcgt tgccggactg gaagtagtac tggctggtcg 158580
cctggcacac ctccgtcatc ttttttgtga ggaagatctc gttgtcggtg cccagctgtc 158640
cctcgtaggt cttggtgtcg ttgataaagc tgaaggacac caggggcgc gagtagcaca 158700 tggtctcgga gccagggacc ctcatgctct tgcgcagggt gacggtggcc tggttaacgg  158760
gcacgcactg ggagactgag atgacatccc ccaggcgctt ggccgccacc gccttaccgt 158820
agatgctgga catgacggtg gtgggattaa tcttggttag ttctctcagc accatgttct 158880
gcctcttctg ctccaggcac caggcccgcg cgaggtctcc cagcatgcgg ttgatctggc 158940
ggcgcaggga atcgtaggca aattggatct ggacggtggc gggattgttg agggtgccca 159000
gggacttccc gggggccgcg gggggcaccg gtgtggtggc attccccgca tcccgcctcc 159060
ggcgcctcag aacggcggcg gaggtgctcc cgcgggccgc gggtgggcg ggggcgatg  159120 gactgctggg gggtgaggaa gtcggagtgg taagctccgt caggttcttg acggtggcca 159180
acgagcgcgg ggtcagaggt agccaagcta ataacaatcc tccgctcgtt ataaatatg  159240 taatggcttc ctggcccttc gtgtaacgat cctggacggc ctcgtacttc tcatgcatgg 159300
tcttgttcac ctgctcttcg atgcacttga aggcgtccgg gagctctatg cccacggttg 159360
tgttggtcac gaagctagag gtgccctcgt cagtcacaaa atgtattgac ttccctgttt 159420
ctgtggcgat ggtcgagtca aaggtttgcc agtgttgaag cgggcagtag ctgtcctgt  159480 tctcgagctt ccaagatagg gtgtaagtgc ccttgtccag gaaggctcgg cgttcgcctt 159540
gcgggttcgt ccctcggttg tcgtagtcca ctatcttgta gttagttctc acgtggaagg 159600
agtctgcccg ctcatggaag gttcctttat tttcccgtc atagaaaggg gacatttcca  159660
cagtctgccc ggtggtggtc acaaagaagt cgaaggggct gttggacttg gccatcatgt 159720
cagttatcag gcagttgacg gtagttcttg ttctgtaagt ccatatcaac caccggggg  159780 cgtcatagag ctccgtctgg ctggcgtagc ggcgcacccc gttggccagg cccccggtgg 159840
gctttaggtt gacggtgatg ttaactccgt cgcggtctac atacacgcgc gtcagcccat 159900
cttttgtcat cttgaccgcg ttgtagcact ggtagatggt atccatctgg tcagtttcgt 159960
agctgtcaac ggagaacttc tcctcgtgcc ggttggtcac ggagtccgcg taccagccat 160020
```

-continued

```
tgtagatgag aatgttggtc actatcttgg tgtaggagcg gaccttaaac gagtagggaa  160080
taatgttgtc tttaaacacc atcaacaggc cctccgtgtg attctcccgc gtgccaaacg  160140
agggacactg gatgtccgag gagaagcgga acaggtcgcc gtggctggag agctcgcaga  160200
ctcggaaagg aaagctggtt tgctgacgcg tggcggtagg ctgcaccgtg gtggcggggg  160260
gtgcgggctg ctctggggtc tgcgcaccga ggcggcacgc cagggcggct agcagcacga  160320
ccacgcttag caccctacgc cgagtcatct ctcatttgga ggtgcaggta gagaagggca  160380
tatagatcct taaatacccc acccctgccc ttatacagaa gaattagggg ccggtcagag  160440
tcgtacgtga ggtaaagccc atccgggggc agggcctggc cggggctgac cgcgtccgcc  160500
cggcgcagga tcaaggaccg cccccaggtc ttgttgtaga gggacacggt taggacggcc  160560
tcgcgcagcg cccggcacag aatttgctgg ctagatgcca gtgagccccc gggtacgctg  160620
tagaagctgt tgaaggaggt ctctatccag tcgctcggct cgatgcctgg ccatatcagg  160680
gaagtcagga acgccttctg gtgaggcagc gtacctgcgg cgtcacagca gcgagccagg  160740
gccacgttgc tgggtggggg aaagagcccg ctctcctccg ccaggggccc cgtgatgaag  160800
gtgtacaggc tgtgcgtcag cgcgtgcagg tgctccgagc tcagggtctg ggtaaacagg  160860
tgtgttttga tgtacttgga attctcaaag gcggcaccct cgccgcgcg cctgtcctcc  160920
cagggacccg agacgaaggc ccgtctgtag aggaagtggt tgcgcatgcg ggccagctcc  160980
cagtagacca cgtcccccca gacgcgcagg cacagggtct cggtcagggt ctcgctctgt  161040
tgcgccaggc aggactgcag cttggccaga ccctcggtgg ccacctggcg caggtactgc  161100
tccttgcgct tgagcgcgtc cgagagggcg ccggacgggc cgggctctcg tgccccagcc  161160
ggccggggca cctccgggct ctccgggac gcctcctcct cgcctcggcc caaccgctgc  161220
atggctcggt tgagccgcgt gtagagctcg ttcctctttt gcaggatggc ccggtactgg  161280
gggtgcgccg tgaaggcggc ggcgcagtcc gccttcagcg cctccaccgc gtcgcccgag  161340
gagctgtaga ccccgccgca gaagagccgc tccgtggccc cggagccac ggcatcaaac  161400
aggtgagtca gccttgcccc cgccagcgcc tcctcgcagg cccgccgcac cagggccagg  161460
cgacgctccc gggcaaacag ggcagagagg cgggaatggc cgccaccctc ccctgcccc  161520
gttgcaccga tagcatggcc gccagagttc caatagagga gctccgagag ttccgccacc  161580
tccgggggca ctgtcgagaa gacgttgtag gtgtccagcg ctctggtcgc cccctctgcc  161640
tccggccgcc ccgggcccgg gaccgcgccc tcctctgggc cgcccggcct cgccttctcc  161700
tcagcctcca acaggtgccc gagcccagcc tgccggactt cattctcaaa cagtcccgag  161760
accggctccg gattcaccgg caccgccagg tggttacagg agacgtgggt cccctctgcc  161820
gtggaagggt tgccgtggtt gggcagaacc atcagctcgc ccacacacgc ccagcagggc  161880
acagaggtga tgtagaggcg cgggtctggg atgggactta cgccccgaaa gcggcccagc  161940
agatccaggg cccgttccag gctctccagc cccatggtgt gagacatgca ataaacacg   162000
ctattgattc tcttcattaa aatctctatg tcatttatta ggcacaaact acatcgact   162060
ttatgccccc cgtaaaactc cacagagtac gcgactgagg gggtgcggag aggcgggacc  162120
cgggtaccct ttctaccagg ggcgagcagc gcggcagagg cctctctcga gttctctagc  162180
aggtgcacca gctccaggga cagggcgctg catgcacggt cattctgccg tctcaaacgg  162240
ggaaggagga tggcctccag ctcggccagc aggccggcgt tgcgcactac cgcagccacg  162300
tccagactcc gggggtccag ccgggcgcac acgtcagct caaccgccag ggcgtacacc  162360
tggctgtacg ccgccgccag cagccccgac atcgccgccc caggggtctc tagacctcga  162420
```

```
gtccggggag aacggtggcc agacggcgct tgcgtctgcc cccggagccc tgccctcctc 162480
cacccagcag cagcccggcc gaggcctgcg acgcggtgct gaccggctcg gccacgctga 162540
taaagttgtc ctgggctgcc ccgggccac cccacactcc ctccagaaag tcccgagcgg 162600
cccccgccgt ccactctatc ccgctggagg caatggtcgc cagggtttct aggacgctgt 162660
ccgccaggac ggagaagcgg cccaataagt actccgcgtc gtccctagtc agcgaggcgc 162720
atgcctcgcc catggcatcc acaaggttgc acaccacatc aaacacacag tcttcctcct 162780 gttttttgtga tataatggcc tccaggccag ccctgatgtt ctcaatctca tatgtggtcg 162840
cggcttgggt ccggcgcttc acggtcaacc ctagggtggg ggtggcaaag acaaacttct 162900
tccgcatgga agagccccg gcctgcttgc gcagcccagc cccgggggcc tgcagcaggt 162960
tcctgtccac gccccggccc ataaagtatc ccaggttccc ggcctggaat atctggttgt 163020
tgccgttgac ccccgtgtac ttgttgatgg tcactggcag cgtgacaacc ggacgggcct 163080
tgcagacctg gctaagacag tctgtggccg cgcagaccac cgtagtcgca gtaagggagg 163140
aggtggcctc cgcgtaggcc gctgccgact ccaccgcccg cgtgcccagt acgtggggt 163200 agtcacgggc gggcaccgac tgcgtcctcg gcaccagtcc ctgaatcagg ctgatgtaga 163260
actgggtctg gccgcacgcc ttcaggatgg cgttgttgag cctctgcttg gcgtaagtga 163320
ccaggttgcc aggcaccaca tctatgacgt tgctctcttc gtgggcccgg gagccccgt 163380 ccacaaagag ggccaggtca gagtactcct ccgcgctggc cccgctgggg acagggaccg 163440
agcgccgcct ggaaaagttg tgccacaggt acaggcttga gagcttagtg tccgggaata 163500
gggtcttgtg gtaggtgttg aggaatttca tgtagggccc gttgatgatg tagttctccc 163560
tcctggtagt ggacttgatg aagctgttct ggagggcggc attctccccc gtgaagacca 163620
ccctgttctt gatcttgatg ttcctggggc acagcatcag caccttggac atgcgcacag 163680
gcagccgccg gccgtacacc cggccctgca gggccgcgtc caggtctggc aggtcgcagg 163740
tgggctcccc atgcaccacc ttggcctcct tggccgtgag gaccccctg tcgatggcca 163800 ggctcctaaa gttggtgcac agcgtctggt agtgacccctt tagccactct gggggctct 163860 ggccaagccc ggggttgtca ttctcatagc acatacagat gggcagggag atgtcctgca 163920
ggatggtcag cagtgagcgg taaaacagct gggtgaagat ggggcaggcg ggctgcgcaa 163980
aggggttgca cgagtactgc atcacgtggt agcagctctt gaccaggtcc ttgtaggtga 164040
tgttgttctt ggccatgctg ttcataaact ggaccacttc ggcgtccacc gccgcatcca 164100
cgtccttgaa catcttgaca aagtcacgcg ggccatgggg ctccttctct agctttccct 164160
cagcgtctat gcccagccga gacagccgct ccagcaggtt ctggttcagc tgccagtagg 164220
tgtagcgggg ctcgtcgtcc ggccgctgcc cgtcgtcctc cttatcgatg aagttgagaa 164280
agttgcccaa aaagtccgtc tcgttgtagg agcccgaggc ccccgagatc acatagggt 164340 ccctccgctg cgtggacatg acgggggaa agcggtccct cagcctaaag aagagcgtgt 164400
tcaggcacac ggccggggcc cggccctcgc agagcgagca catgggctg gcggccgccc 164460 ccgccacgta gctgcccgtc tccggcaccg gggtcagaga gctcttctgt ccctggcaaa 164520
actgcaggta gtaggcatag cgggcaagaa ggttgggcga gaaggaggcc gcatagacca 164580
ggtgctccac agcgtagttt cccggaccgt tggttccggt cacgtctggc ccaccccagc 164640
ccgagaagca gggtcggcgg cagggtccc aggtcccctc ctgcagggtc cccaggccgt 164700
gggtcatgta gaaactgtta aagagactct ccttgccctg accggttgac ttcgagaccc 164760
```

```
ccgagacgta gaggacggaa ttggtggcaa agatctgcgt ggacacgtgg ggggccaggc  164820
tggcattata tcggtgtaac gcagccacac gggcctctgg accctcacag tcggcaaaca  164880
ggggccacga gtcgtagttg aggctggccg gggtctcgtg cgaggcctcc agcatggcgg  164940
gcgcgtagct caccgccagc tcgcaggccg cgctgtccac aatcattaag gctcccgagt  165000
ccgggtgact gatggttgag gctgggaact ccttgagggg ggccaccttg gccaccttgg  165060
cctggtcctg caggctctgc ttctccagca gctccaccag cttgcccacc cgtcggacgc  165120
gcagcgcctg cgccagcccg gtgtacagcg cctcgtgcat gcagcggctg aggtccgagt  165180
tgtaaaactg gcggagctgg ggcacgccct ctgggaacac ctccttgtcg tagagcggga  165240
ccctaacgct cgcagactgc cccaccgcta cctcctgttt taacgatgga atggccacca  165300
ggtttccgct gtagagtcgc tccttgaagg cctcggttat tgccaccgcc caaggtagg  165360 cagagggatc tagcccttcg gggaagaagt cccccggctc ggagctttcc ctcggtaggg  165420
cgctgtaggc gtcgtatcca aacacctccc tggtctcgcc acagagggcc tcgagacccg  165480 gccccctcaaa gatgggggga accatatggg cattgtggaa cacgtagatg tccctgtgat  165540
aggaggtagc gcgtaggagc cgcagttgg ggtcgggcct cctgtgcaga gccttgacat  165600
tgatgctgaa gcccggctcc acggtgatgc cacaaaggag cggcaccgtc aggcacctgt  165660
ggcccgcgta gccggtcccc agtgtggcca cctccctaag agggtaggtg gccaggggt  165720 aaaagtagat gtagccgcac ggacccggct ggctctggct gcccagatta tcctcgctag  165780
tctgtgcacc ctgcatgatg cccaaggtat cgccccggcc tcccagtccc acattaaatg  165840
ttacacttta ctcatcacgc aacacccact gtttattcat ttacaaagat ttcaggaagt  165900
cagtcaggct ggccagggcc cacgtcacgg ggaactgacg tctcagcgat cttggcatgc  165960
cgcccagcct cgcaaaccag agtctgcgat agagggccag gtagtgggcg attgccccca  166020
gcacgaaggc ggcgctcttg tggtcatcca ggtagtttcg caccgcaaac accactgtgt  166080
agcacagcac caccctgagc cgcgaccagt agtcgtagtg gtcgttgtac actgcgcgca  166140
ggacgctgat gatgagccgt acgtgcgtgt ctttgccccc gatgtcggct gtcctgcagg  166200
ccagctccgc gtacagcttc ctatccttcc tcagggaggc cttgatgagc cggcagagga  166260
ccagggctgg caaaggcagg tcttttctcat cccgggtgaa caccgcgtac atggccctga  166320
acatgaggta gctggactca gccacccttgt cgtccggcgg cgaggcgcg acccacgcct  166380 cgaccggggt cctcacaaac acagaatctg tagacttggc tggcctcatg gtctcgtcag  166440
gccagctcac gggcttcagg cttatatgat aaaatgggcg tggcagaata gtataagacg  166500
cgaggcctgg gtgaggagag tccagagcaa tggccaggtt catcgctcag ctcctcctgt  166560
tggcctcctg tgtggccgcc ggccaggctg tcaccgcttt cttgggtgag cgagtcaccc  166620
tgacctccta ctggaggagg gtgagcctcg gtccagagat tgaggtcagc tggtttaaac  166680
tgggcccagg agaggagcag gtgcttattg ggcgcatgca ccacgatgtc atctttatag  166740
agtggccttt caggggcttc tttgatatcc acagaagtgc caacaccttc tttttagtag  166800
tcaccgctgc caacatctcc catgacggca actacctgtg ccgcatgaaa ctgggcgaga  166860
ccgaggtcac caagcaggaa cacctgagcg tggtgaagcc tctaacgctg tctgtccact  166920
ccgaaaggtc tcagttccca gacttctctg tccttactgt gacatgcacc gtgaatgcat  166980
ttccccatcc ccacgtccag tggctcatgc ccgagggcgt ggagcccgca ccaactgcgg  167040
caaatggcgg tgttatgaag gaaaaggatg ggagcctctc tgttgctgtt gacctgtcac  167100
ttcccaagcc ctggcacctg ccagtgacct gcgttgggaa aaatgacaag gaggaagccc  167160
```

```
acgggcgttta tgtttctgga tacttgtcgc aataaacgca cttgcctatt tcaccttgtc 167220
ttagtgtggc atgggggggg tggcattgcg ggtggatagc ctcgcgactc gtgggaaaat 167280
gggcggaagg gcaccgtggg aaaatagttc caggtgacag cagcagtgtg tgaagattgt 167340
cacagctgct ggtttggaga aaacgggggt gggcggtgat cagggagaac aattccccgg 167400
ggacacctgc acgagacccc tgcgctctca ggaacttcgc ccaggtctcg ccaattgggg 167460
tgatcctgta gcgccgcggt ttcagcatca caggttattt tgcctgaagc ttgctggggc 167520
gtaaatccct ctcgccttgt ttctcagaga gcatttcagg ccggttttgc agtcgctgct 167580
gcagctatgg ggtccctaga aatggtgcca atgggcgcgg gtcccctag ccccggcggg 167640 gatccggatg gggacgatgg cggaaacaac tcccaatatc catctgcttc tggctcttct 167700
gggaacaccc ccaccccacc gaacgatgag gaacgtgaat ctaatgaaga gccccaccg 167760 ccttatgagg acccatattg gggcaatggc gaccgtcact cggactatca accactagga 167820
acccaagatc aaagtctgta cttgggattg caacacgacg ggaatgacgg gctccctccc 167880
cctccctact ctccacggga tgactcatct caacacatat acgaagaagc gggcagagga 167940
aggtaagagt gccatctatc tgtactttta tttattgcat cacaagtcac atcaataata 168000
agggcgccat ctagcgggag atgttatcca caccatccca attcacatct cagggacaac 168060
aggtcaaagt tctttgttga cacccccagc gctggctcca gggggtggca gcgttggatg 168120
cagtcctccg catcggggcg gacgcctcct cccaacgcgt ttctgcggat cagtcgctgg 168180
ctggtgggca tcggagtcgg tgggcggtcc tccacgggga cacgctcctt cttggccttg 168240
ttctttgacc ttttggacat tcttctgaag gaacggcgga gagtagcgta gaatccagcc 168300
agtggtctac ccggtcgcat ggtggcttct tagatgagga gcaggcataa aagtccaaac 168360
aggacacaga gtaccaccag gagtagtctt agtctgctga cgtctgggtc ctcggggcag 168420
gggtggctag gcctggtctc cgtagaagag ccgggcaggc cgcaggcaga ggactgctgc 168480
tctagcaaag cacgctccag gacgtgtacc atctcgagag tgaggcacag ctgttttcgt 168540
ggacttttat acagtaagga caaggaaaga aggccagagg aatgtggaaa gatgagcgag 168600
gacaggtgtg gaggttttgg gctagctctt agtttctggg tgtgagagag ggattaaagt 168660
gcttatgcgc aaagaatgtg tcaacaacag gtgttcctgc atctgctggc atgagttagg 168720
tgtggcttgg gctgaatcca aatgtgtatt ggcacaagat ggaaagcaaa gttgctggag 168780
ttactgggtg ggagacaggg atgtatgtgg tcccccgctg gtatgccagt accctgtgga 168840
agtaaggggc ctcatctgcc cggtagttgt gttgtgcaga ggtctgatgt gtgtaggagg 168900
ggtgggttca acgcaggggc gttggtggcg gagtctggca acgcccgggt cctcttgcta 168960
cctgtgtggt gtgtgaaggg ctgggtaaag gtgtctgcca attctcgcat gtcctccttt 169020 cccttgttt tgaaatagaa tatgaatgtg gcttttcagc ctagacagac agtgtggcta 169080
agggagtgtg tgccagttaa ggtgattagc taaggcattc ccagtaaatg gagggagagt 169140
cagtcaggca agcctatgac atggtaatgc ctagaagtaa agaaaggtta gtcatagtag 169200
cttagctgaa ctgggccgtg ggggtcgtca tcatctccac cggaaccaga agtacccaaa 169260
agcagcgtag gaaggtgtgg atcaccgccg ccaccgtctg tcatcgaagg cgggcccgg 169320 tcacctcctt tgttttcaac ctcttccgtc aaatttggtg ggcctccatc atttccagca 169380
gagtcgctag ggttatgagg cagcgggtca tgtgggccat tgtcagcagt gttgtcaggg 169440
tcctgtgggc cattgtcatc agtgttgtca gggtcctgtg ggccattgtc atcagtgttg 169500
```

```
tcagggtcct gtgggccatt gtcatcagtg ttgtcagggt cctgtgggcc attgtcagga   169560
ccacctccag gtgcgcctag gttttgagag cagagtgggg gtccgtcgcc ggctccagtc   169620
acgagcaggt ggtgtctgcc ctcgttggag ttagagtcag attcatggcc agaatcatcg   169680
gtagcttgtt gagggtgcgg gagggagtca tcgtggtggt gttcatcact gtgtcgttgt   169740
ccatggtaat acatccagat caaaatcgcc agaaacagga ggagccaaag gagatcaacc   169800
aatagagtcc accagttttg ttgcagatag agagcaataa tgagcaggat gaggtctagg   169860
aagaaggcta ggaagaaggc caaaagctgc cagatggtgg caccaagtcg ccagagaatc   169920
tccaataagt agatccagag acctaagact gcgttgaaaa aagagtgtta gggttggaaa   169980
agtgggggtg tggtaaataa ttcccaggga atgttagatc ttaccaagta agcacccgaa   170040
gatgaacagc acaattccaa ggtacaatgc ctgtccgtgc aaattccaga gagcgatgag   170100
caggaggtg actgggaaa gaggagaaag tgcgttagag aaggaagagt aagggaaagg    170160
gggtgtgggg caaagggtgt aatacttact catcagtagg agtagacaaa gggctccaag   170220
tggacagaga aggtctcttc tgaagataaa gatgatcaaa attataatta taagtatgag   170280
agcaaaggaa tagaggacaa ggagggctcc tccagtccag tcactcataa cgatgtacag   170340
ccaaaacagt agcgccaaga ggaggagaag gagagcaagg cctagggaag aggagagggg   170400
gggtcctcga gggggccgtc gcgggcccgg tgggcccctc tcaaggtcgt gttccatcct   170460
cagggcagtg tgtcaggagc aaggcagttg aggaaagaag ggggcagagc agtgtgagag   170520
gcttatgtag ggcggctacg tcagagtaac gcgtgtttct tgggatgtag ggccgggggg   170580
atttgcgggg tctgccggag gcagtacggg tacagatttc ccgaaagcgg cggtgtgtgt   170640
gtgcatgtaa gcgtaaaaag gggaagtaga aagcgtgtgt tagtgttaga aaagcgggtc   170700
cccgggggc aagctgtggg aatgcggtgg gcaagtgcaa caggaaatgg aaaggcagtg    170760
cggcaatcag aaggggagt gcgtagtgtt gtgggaagcg gcagtgtaat ctgcacaaag     170820
aggcgtgggg cgcgcaacgt tgggaggtcg ttggcggcag gcgggaggcc gtgctttagg   170880
ggggttcagg tgaggcaagg ctgtggggta accgtagggg aggcgggtga ggcggctaag   170940
agggctaagg gtcggcgggt gacgaagcag cagacggcgg atatgggaat ttcagaatga   171000
ggtggcggat tcaggcgaaa agggtgtggg ctgtgcgagt gtcatgaggc aggcgcggaa   171060
agtcgctgcg gcttgctggg gccatgggcc gcgcattcct ggaaaaagtg gaggggggcgt  171120
ggcctgcccc ccgcggcccc ctagccccc cgcacagagc ggcgcaacgg cgggcgggcg    171180
gcgggggtc gggtccgcg ggctccgggg gctgcgggcg gtggatggcg gctggcgttc      171240
agggggaacgg ggggtcggg gggcgcagcg gccgcgcagc catgcgtgac cgcgaggagg   171300
ggacagggtc gcagggggcg tgtctggtgg gggcgggagc gggggcggc gcgggagcct    171360
gcacgccgtt ggagggtaga atgacagggg ggcggggaca gagaggcggt cgcgccccc    171420
gccgcggcag ccaagccccc aagggggcg gggcgcgggc agcggagcgt gacgaagggc    171480
cccagggctg accccggcaa acgtgacccg gggctccggg gtgacccagc caagcgtgac   171540
caagggccg ctgggtgaca cagacaaccc tgacaaaggc ccccaggaa agaccccgg      171600
ggggcatcgg ggggtgttgg tgggccatg ggggtgggc catgggccgc gcattcctgg     171660
aaaaagtgga ggggggcgtgg cctgcccccc gcggcccct agccccccg cacagagcgg    171720
cgcaacggcg ggcgggcggc gggggtcgg ggtccgcggg ctccggggc tgcggcggt     171780
ggatggcggg tggcgttcag gggaacgggg gggtcgggg gcgcagcggc cgcgcagcca    171840
tgcgtgaccg cgaggagggg acagggtcgc agggggcgtg tctggtgggg gcgggagcgg   171900
```

-continued

```
ggggcggcgc gggagcctgc acgccgttgg agggtagaat gacagggggg cggggacaga    171960
gaggcggtcg cgcccccccgc cgcggcagcc aagcccccaa ggggggcggg gcgcgggcag    172020
cggagcgtga cgaagggccc cagggctgac cccggcaaac gtgacccggg gctccggggt    172080
gacccagcca agcgtgacca aggggccgct gggtgacaca gacaaccctg acaaaggccc    172140
cccaggaaag accccggggg ggcatcgggg ggtgttggtg gggccatggg ccgcgcattc    172200
ctggaaaaag tggaggggggc gtggcctgcc ccccgcggcc ccctagcccc cccgcacaga    172260
gcggcgcaac ggcgggcggg cggcgggggg tcggggtccg cgggctccgg gggctgcggg    172320
cggtggatgg cggctggcgt tcaggggaac ggggggggtcg ggggggcgcag cggccgcgca    172380 gccatgcgtg accgcgagga ggggacaggg tcgcagggggg cgtgtctggt gggggcggga    172440 gcgggggggcg cgcgggagc ctgcacgccg ttggagggta gaatgacagg ggggcgggga    172500
cagagaggcg gtcgcgcccc ccgccgcggc agccaagccc ccaagggggg cggggcgcgg    172560
gcagcggagc gtgacgaagg gccccagggc tgaccccggc aaacgtgacc cggggctccg    172620
gggtgaccca gccaagcgtg accaagggggc cgctgggtga cacagacaac cctgacaaag    172680
gccccccagg aaagaccccc ggggggcatc ggggggtgtt ggtggggcca tgggggtcg    172740 gatttcgccc ttattgccct gttt    172764
```

<210> SEQ ID NO 16
<211> LENGTH: 706
<212> TYPE: PRT
<213> ORGANISM: Epstein-Barr virus

<400> SEQUENCE: 16

```
Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
                20                  25                  30

Ala Ser His Tyr Thr Ile Pro Trp Thr Glu Leu Met Ala Lys Val Pro
            35                  40                  45

Gly Leu Ser Pro Glu Ala Leu Trp Arg Glu Ala Asn Val Thr Glu Asp
        50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
                100                 105                 110

Ser Gly Leu Asn Ser Pro Ala Cys Met Leu Ser Ala Pro Leu Glu Lys
            115                 120                 125

Gln Leu Phe Tyr Tyr Ile Gly Thr Met Leu Pro Asn Thr Arg Pro His
        130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
                180                 185                 190

Val Leu Ser Leu Ile Phe Gly Lys Thr Lys Asp Leu Pro Asp Leu Arg
            195                 200                 205

Gly Pro Phe Ser Tyr Pro Ser Leu Thr Ser Ala Gln Ser Gly Asp Tyr
```

```
              210                 215                 220
Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Val Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Met Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640
```

```
Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Val Val Leu Ala Ile Ile Leu Tyr Phe
        675                 680                 685

Ile Ala Phe Ala Leu Gly Ile Phe Leu Val His Lys Ile Val Met Phe
690                 695                 700

Phe Leu
705

<210> SEQ ID NO 17
<211> LENGTH: 137
<212> TYPE: PRT
<213> ORGANISM: Epstein-Barr virus

<400> SEQUENCE: 17

Met Arg Thr Val Gly Val Phe Leu Ala Thr Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly
    130                 135

<210> SEQ ID NO 18
<211> LENGTH: 857
<212> TYPE: PRT
<213> ORGANISM: Epstein-Barr virus

<400> SEQUENCE: 18

Met Thr Arg Arg Arg Val Leu Ser Val Val Leu Leu Ala Ala Leu
1               5                   10                  15

Ala Cys Arg Leu Gly Ala Gln Thr Pro Glu Gln Pro Ala Pro Pro Ala
            20                  25                  30

Thr Thr Val Gln Pro Thr Ala Thr Arg Gln Gln Thr Ser Phe Pro Phe
        35                  40                  45

Arg Val Cys Glu Leu Ser Ser His Gly Asp Leu Phe Arg Phe Ser Ser
    50                  55                  60

Asp Ile Gln Cys Pro Ser Phe Gly Thr Arg Glu Asn His Thr Glu Gly
65                  70                  75                  80

Leu Leu Met Val Phe Lys Asp Asn Ile Ile Pro Tyr Ser Phe Lys Val
                85                  90                  95

Arg Ser Tyr Thr Lys Ile Val Thr Asn Ile Leu Ile Tyr Asn Gly Trp
            100                 105                 110
```

```
Tyr Ala Asp Ser Val Thr Asn Arg His Glu Lys Phe Ser Val Asp
            115                 120                 125

Ser Tyr Glu Thr Asp Gln Met Asp Thr Ile Tyr Gln Cys Tyr Asn Ala
130                 135                 140

Val Lys Met Thr Lys Asp Gly Leu Thr Arg Val Tyr Val Asp Arg Asp
145                 150                 155                 160

Gly Val Asn Ile Thr Val Asn Leu Lys Pro Thr Gly Gly Leu Ala Asn
                165                 170                 175

Gly Val Arg Arg Tyr Ala Ser Gln Thr Glu Leu Tyr Asp Ala Pro Gly
            180                 185                 190

Trp Leu Ile Trp Thr Tyr Arg Thr Arg Thr Thr Val Asn Cys Leu Ile
            195                 200                 205

Thr Asp Met Met Ala Lys Ser Asn Ser Pro Phe Asp Phe Phe Val Thr
        210                 215                 220

Thr Thr Gly Gln Thr Val Glu Met Ser Pro Tyr Asp Gly Lys Asn
225                 230                 235                 240

Lys Glu Thr Phe His Glu Arg Ala Asp Ser Phe His Val Arg Thr Asn
                245                 250                 255

Tyr Lys Ile Val Asp Tyr Asp Asn Arg Gly Thr Asn Pro Gln Gly Glu
            260                 265                 270

Arg Arg Ala Phe Leu Asp Lys Gly Thr Tyr Thr Leu Ser Trp Lys Leu
        275                 280                 285

Glu Asn Arg Thr Ala Tyr Cys Pro Leu Gln His Trp Gln Thr Phe Asp
        290                 295                 300

Ser Thr Ile Ala Thr Glu Thr Gly Lys Ser Ile His Phe Val Thr Asp
305                 310                 315                 320

Glu Gly Thr Ser Ser Phe Val Thr Asn Thr Thr Val Gly Ile Glu Leu
                325                 330                 335

Pro Asp Ala Phe Lys Cys Ile Glu Glu Gln Val Asn Lys Thr Met His
            340                 345                 350

Glu Lys Tyr Glu Ala Val Gln Asp Arg Tyr Thr Lys Gly Gln Glu Ala
        355                 360                 365

Ile Thr Tyr Phe Ile Thr Ser Gly Gly Leu Leu Leu Ala Trp Leu Pro
        370                 375                 380

Leu Thr Pro Arg Ser Leu Ala Thr Val Lys Asn Leu Thr Glu Leu Thr
385                 390                 395                 400

Thr Pro Thr Ser Ser Pro Pro Ser Ser Pro Ser Pro Ala Pro Pro
                405                 410                 415

Ala Ala Arg Gly Ser Thr Ser Ala Ala Val Leu Arg Arg Arg Arg
            420                 425                 430

Asp Ala Gly Asn Ala Thr Thr Pro Val Pro Ala Ala Pro Gly Lys
            435                 440                 445

Ser Leu Gly Thr Leu Asn Asn Pro Ala Thr Val Gln Ile Gln Phe Ala
        450                 455                 460

Tyr Asp Ser Leu Arg Arg Gln Ile Asn Arg Met Leu Gly Asp Leu Ala
465                 470                 475                 480

Arg Ala Trp Cys Leu Glu Gln Lys Arg Gln Asn Met Val Leu Arg Glu
                485                 490                 495

Leu Thr Lys Ile Asn Pro Thr Thr Val Met Ser Ser Ile Tyr Gly Lys
            500                 505                 510

Ala Val Ala Ala Lys Arg Leu Gly Asp Val Ile Ser Val Ser Gln Cys
            515                 520                 525
```

-continued

```
Val Pro Val Asn Gln Ala Thr Val Thr Leu Arg Lys Ser Met Arg Val
        530                 535                 540

Pro Gly Ser Glu Thr Met Cys Tyr Ser Arg Pro Leu Val Ser Phe Ser
545                 550                 555                 560

Phe Ile Asn Asp Thr Lys Thr Tyr Glu Gly Gln Leu Gly Thr Asp Asn
                565                 570                 575

Glu Ile Phe Leu Thr Lys Lys Met Thr Glu Val Cys Gln Ala Thr Ser
                580                 585                 590

Gln Tyr Tyr Phe Gln Ser Gly Asn Glu Ile His Val Tyr Asn Asp Tyr
            595                 600                 605

His His Phe Lys Thr Ile Glu Leu Asp Gly Ile Ala Thr Leu Gln Thr
        610                 615                 620

Phe Ile Ser Leu Asn Thr Ser Leu Ile Glu Asn Ile Asp Phe Ala Ser
625                 630                 635                 640

Leu Glu Leu Tyr Ser Arg Asp Glu Gln Arg Ala Ser Asn Val Phe Asp
                645                 650                 655

Leu Glu Gly Ile Phe Arg Glu Tyr Asn Phe Gln Ala Gln Asn Ile Ala
                660                 665                 670

Gly Leu Arg Lys Asp Leu Asp Asn Ala Val Ser Asn Gly Arg Asn Gln
            675                 680                 685

Phe Val Asp Gly Leu Gly Glu Leu Met Asp Ser Leu Gly Ser Val Gly
        690                 695                 700

Gln Ser Ile Thr Asn Leu Val Ser Thr Val Gly Gly Leu Phe Ser Ser
705                 710                 715                 720

Leu Val Ser Gly Phe Ile Ser Phe Phe Lys Asn Pro Phe Gly Gly Met
                725                 730                 735

Leu Ile Leu Val Leu Val Ala Gly Val Val Ile Leu Val Ile Ser Leu
                740                 745                 750

Thr Arg Arg Thr Arg Gln Met Ser Gln Gln Pro Val Gln Met Leu Tyr
            755                 760                 765

Pro Gly Ile Asp Glu Leu Ala Gln Gln His Ala Ser Gly Glu Gly Pro
        770                 775                 780

Gly Ile Asn Pro Ile Ser Lys Thr Glu Leu Gln Ala Ile Met Leu Ala
785                 790                 795                 800

Leu His Glu Gln Asn Gln Glu Gln Lys Arg Ala Ala Gln Arg Ala Ala
                805                 810                 815

Gly Pro Ser Val Ala Ser Arg Ala Leu Gln Ala Ala Arg Asp Arg Phe
                820                 825                 830

Pro Gly Leu Arg Arg Arg Arg Tyr His Asp Pro Glu Thr Ala Ala Ala
            835                 840                 845

Leu Leu Gly Glu Ala Glu Thr Glu Phe
    850                 855

<210> SEQ ID NO 19
<211> LENGTH: 223
<212> TYPE: PRT
<213> ORGANISM: Epstein-Barr virus

<400> SEQUENCE: 19

Met Val Ser Phe Lys Gln Val Arg Val Pro Leu Phe Thr Ala Ile Ala
1               5                   10                  15

Leu Val Ile Val Leu Leu Leu Ala Tyr Phe Leu Pro Pro Arg Val Arg
            20                  25                  30

Gly Gly Gly Arg Val Ser Ala Ala Ala Ile Thr Trp Val Pro Lys Pro
        35                  40                  45
```

```
Asn Val Glu Val Trp Pro Val Asp Pro Pro Pro Val Asn Phe Asn
     50                  55                  60

Lys Thr Ala Glu Gln Glu Tyr Gly Asp Lys Glu Ile Lys Leu Pro His
 65                  70                  75                  80

Trp Thr Pro Thr Leu His Thr Phe Gln Val Pro Lys Asn Tyr Thr Lys
                 85                  90                  95

Ala Asn Cys Thr Tyr Cys Asn Thr Arg Glu Tyr Thr Phe Ser Tyr Lys
                100                 105                 110

Glu Arg Cys Phe Tyr Phe Thr Lys Lys Lys His Thr Trp Asn Gly Cys
            115                 120                 125

Phe Gln Ala Cys Ala Glu Leu Tyr Pro Cys Thr Tyr Phe Tyr Gly Pro
        130                 135                 140

Thr Pro Asp Ile Leu Pro Val Val Thr Arg Asn Leu Asn Ala Ile Glu
145                 150                 155                 160

Ser Leu Trp Val Gly Val Tyr Arg Val Gly Glu Gly Asn Trp Thr Ser
                165                 170                 175

Leu Asp Gly Gly Thr Phe Lys Val Tyr Gln Ile Phe Gly Ser His Cys
            180                 185                 190

Thr Tyr Val Ser Lys Phe Ser Thr Val Pro Val Ser His His Glu Cys
            195                 200                 205

Ser Phe Leu Lys Pro Cys Leu Cys Val Ser Gln Arg Ser Asn Ser
    210                 215                 220
```